(12) United States Patent
Li et al.

(10) Patent No.: US 11,957,682 B2
(45) Date of Patent: *Apr. 16, 2024

(54) **COMPOUNDS AND METHODS FOR REGULATING, LIMITING, OR INHIBITING *AVIL* EXPRESSION**

(71) Applicant: University of Virginia Patent Foundation, Charlottesville, VA (US)

(72) Inventors: Hui Li, Keswick, VA (US); Zhongqiu Xie, Charlottesville, VA (US)

(73) Assignee: University of Virginia Patent Foundation, Charlottesville, VA (US)

( * ) Notice: Subject to any disclaimer, the term of this patent is extended or adjusted under 35 U.S.C. 154(b) by 48 days.

This patent is subject to a terminal disclaimer.

(21) Appl. No.: 17/809,145

(22) Filed: Jun. 27, 2022

(65) Prior Publication Data

US 2023/0018590 A1 Jan. 19, 2023

Related U.S. Application Data

(63) Continuation of application No. 16/759,210, filed as application No. PCT/US2018/057697 on Oct. 26, 2018, now Pat. No. 11,369,608.

(60) Provisional application No. 62/577,749, filed on Oct. 27, 2017.

(51) Int. Cl.
| | | |
|---|---|---|
| *A61K 31/506* | (2006.01) | |
| *A61K 31/40* | (2006.01) | |
| *A61K 31/454* | (2006.01) | |
| *A61K 45/06* | (2006.01) | |
| *A61P 35/04* | (2006.01) | |

(52) U.S. Cl.
CPC ............ *A61K 31/506* (2013.01); *A61K 31/40* (2013.01); *A61K 31/454* (2013.01); *A61P 35/04* (2018.01); *A61K 45/06* (2013.01)

(58) Field of Classification Search
CPC ........ A61K 31/506; A61K 31/40; A61P 35/04
See application file for complete search history.

(56) References Cited

U.S. PATENT DOCUMENTS

| 9,556,170 B2 | 1/2017 | Vankayalapati et al. |
|---|---|---|
| 2007/0208074 A1 | 9/2007 | Bonni et al. |
| 2009/0186910 A1 | 7/2009 | Bacus |
| 2010/0035863 A1 | 2/2010 | Raphy et al. |
| 2010/0179141 A1 | 7/2010 | Belanger et al. |
| 2014/0378430 A1 | 12/2014 | McCarthy et al. |
| 2015/0353553 A1 | 12/2015 | Cammarano et al. |

FOREIGN PATENT DOCUMENTS

| WO | 2013040044 A1 | 9/2012 |
|---|---|---|
| WO | 2019084395 A1 | 5/2019 |

OTHER PUBLICATIONS

European Office Action dated Apr. 14, 2023.
Database Registry [Online] Nov. 13, 2011 (Nov. 13, 2011), Anonimous: "1331986-18-5", XP093037319, retrieved from STN Database accession No. 1331986-18-5.
Database Registry [Online] Chamical abstract Service; Sep. 13, 2011 (Sep. 13, 2011), Anonimous: "1332069-62-1", XP093037321, retrieved from STN Database accession No. 1332069-62-1.
Database Registry [Online] Chemical Abstracts Service; Sep. 14, 2011 (Sep. 14, 2011), Anonimous: "1332084-64-6", XP093037323, retrieved from STN Database accession No. 1332084-64-6.
Database Registry [Online] Chemical Abstract service; Sep. 14, 2011 (Sep. 14, 2011), Anonimous: "1332132-84-9", XP093037324, retrieved from STN Database accession No. 1332032-84-9.
Database Registry [Online] Chemical Abstract service; Sep. 14, 2011 (Sep. 14, 2011), Anonimous: "1332142-15-0", XP093037325, retrieved from STN Database accession No. 1332142-15-0.
Database Registry [Online] Chemical Abstracts service; Sep. 14, 2011 (Sep. 14, 2011), Anonimous: "1332165-29-3", XP093037327, retrieved from STN Database accession No. 1332165-29-3.
Database Registry [Online] Chemical Abstracts service; Sep. 14, 2011 (Sep. 14, 2011), Anonimous: "1332170-23-6", XP093037330, retrieved from STN Database accession No. 1332170-23-6.
Database Registry [Online] Chemical Abstracts service; Dec. 16, 2011 (Dec. 16, 2011), Anonimous: "1351059-00-1 ", XP093037333, retrieved from STN Database accession No. 1351059-001.
Database Registry [Online] Chemical Abstracts service; Jun. 13, 2012 (Jun. 13, 2012), Anonimous: "1377769-25-9", XP093037335, retrieved from STN Database accession No. 1377769-25-9.
Database Registry [Online] Chemical Abstracts service; Jun. 13, 2012 (Jun. 13, 2012), Anonimous: "1377882-03-5", XP093037336, retrieved from STN Database accession No. 1377882-03-5.
Database Registry [Online] Chemical Abstracts service; Jun. 5, 2013 (Jun. 5, 2013), Anonimous: "1434659-35-4", XP093037337, retrieved from STN Database accession No. 1434659-35-4.
Database Registry [Online] Chemical Abstracts service; Jun. 30, 2013 (Jun. 30, 2013), Anonimous: "1442538-60-4", XP093037339, retrieved from STN Database accession No. 1442538-60-4.
International Search Report issued for PCT/US2020/031212, dated Sep. 4, 2020.
Pubchem. CID 97151041, Mar. 4, 2013, pp. 1-11 [online], [retrieved on Nov. 26, 2018] Retrieved from the Internet <URL:https://pubchem.ncbi.nlm.nih.gov/compounds/70778823#section=Chemical-Vendors>; p. 2, formula; p. 10.

(Continued)

*Primary Examiner* — Kamal A Saeed
(74) *Attorney, Agent, or Firm* — Thomas | Horstemeyer, LLP

(57) ABSTRACT

In one aspect, the disclosure relates to compounds useful to regulate, limit, or inhibit the expression of AVIL (advillin), methods of making same, pharmaceutical compositions comprising same, and methods of treating disorders associated with AVIL dysregulation using same. In aspects, the disclosed compounds, compositions and methods are useful for treating disorders or diseases in which the regulation, limitation, or inhibition of the expression of AVIL can be clinically useful, such as, for example, the treatment of cancer. This abstract is intended as a scanning tool for purposes of searching in the particular art and is not intended to be limiting of the present disclosure.

19 Claims, 79 Drawing Sheets

Specification includes a Sequence Listing.

(56) References Cited

OTHER PUBLICATIONS

Lin et al., A cytokine-mediated link between innate immunity, inflammation, and cancer, J Clin Invest.; 117(5):1175-1183, 2007.
European Search Report for EP Application No. 18869916.9 dated Jun. 14, 2021.
Su WT et al: "Positional gene expression analysis identifies 12q overexpression and amplification in a subset of neuroblastomas", Cancer Genetics and Cytogenetics, Elsevier Science Publishing, New York, NY, US, vol. 154, No. 2, Oct. 15, 2004 (Oct. 15, 2004), pp. 131-137, XP027168932, ISSN: 0165-4608.
European Search Report and Written Opinion dated Nov. 24, 2022.

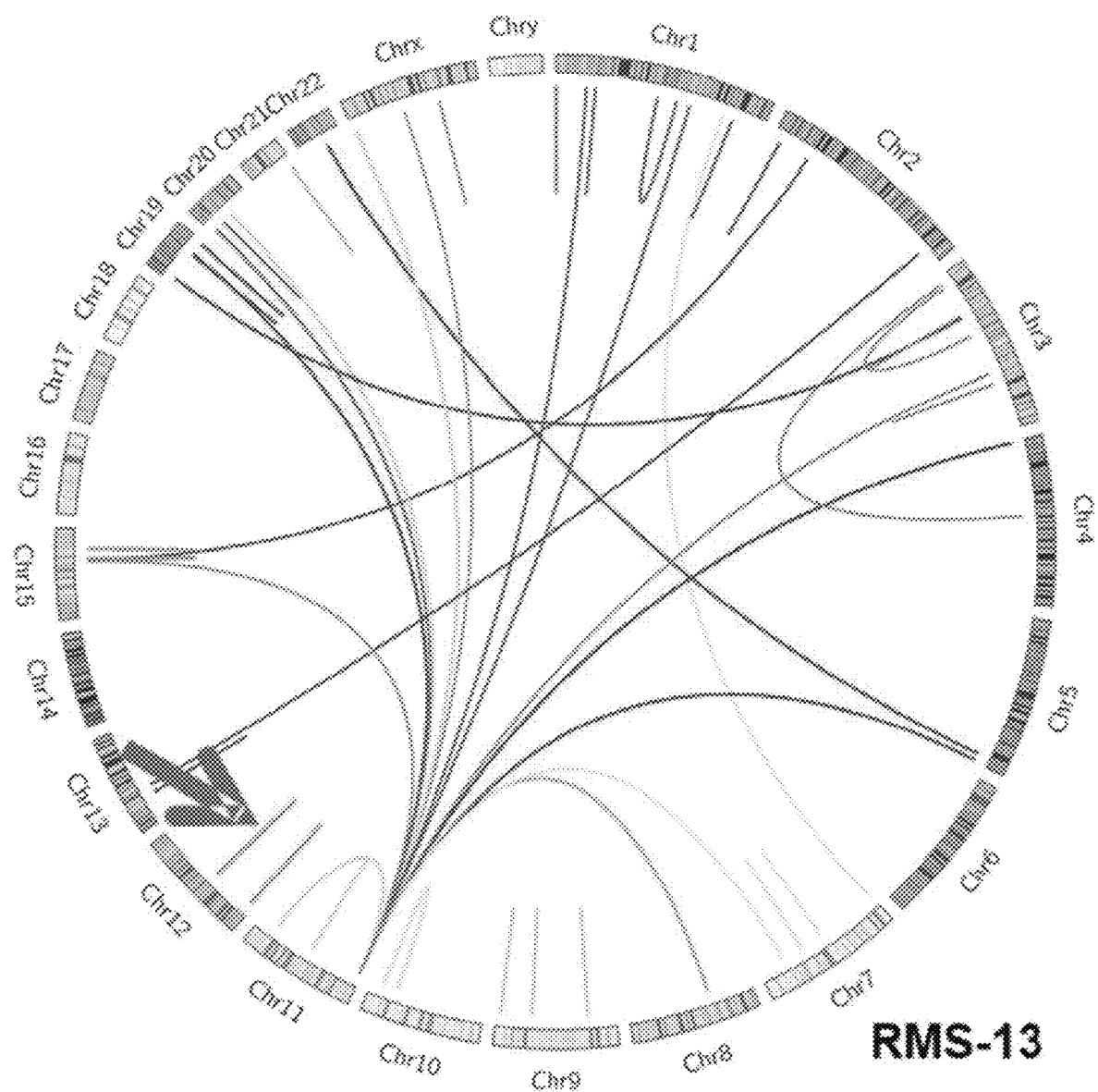
FIG. 1A, continued

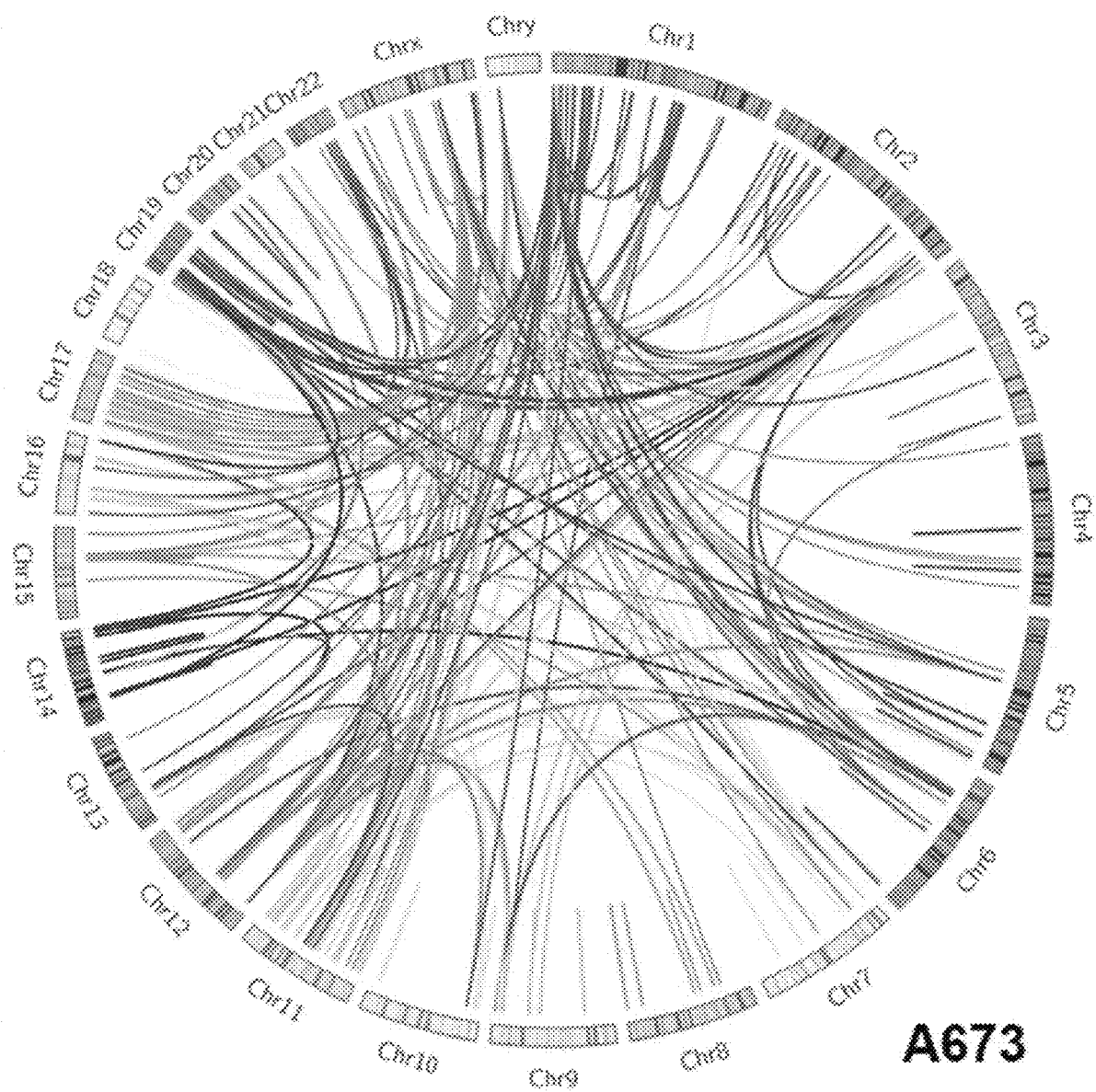
FIG. 1A, continued

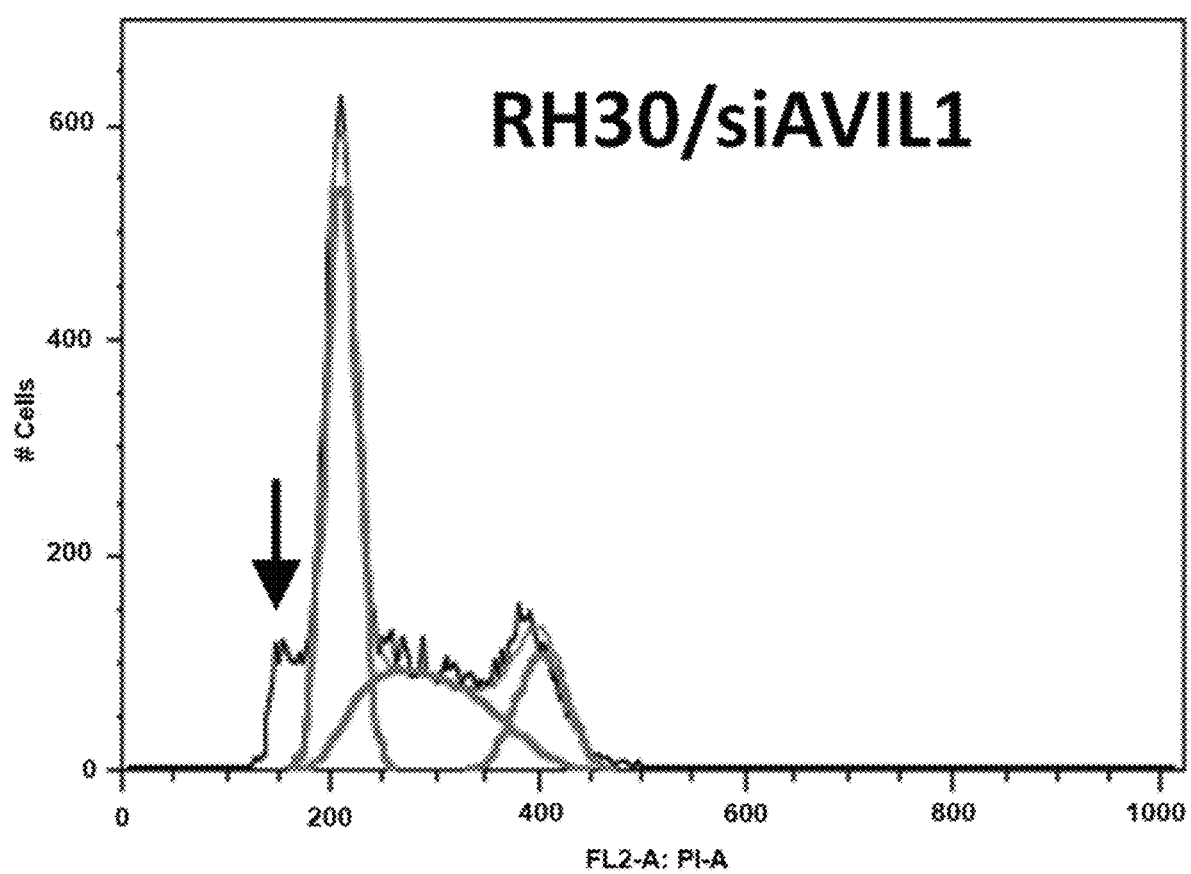
FIG. 2A, continued

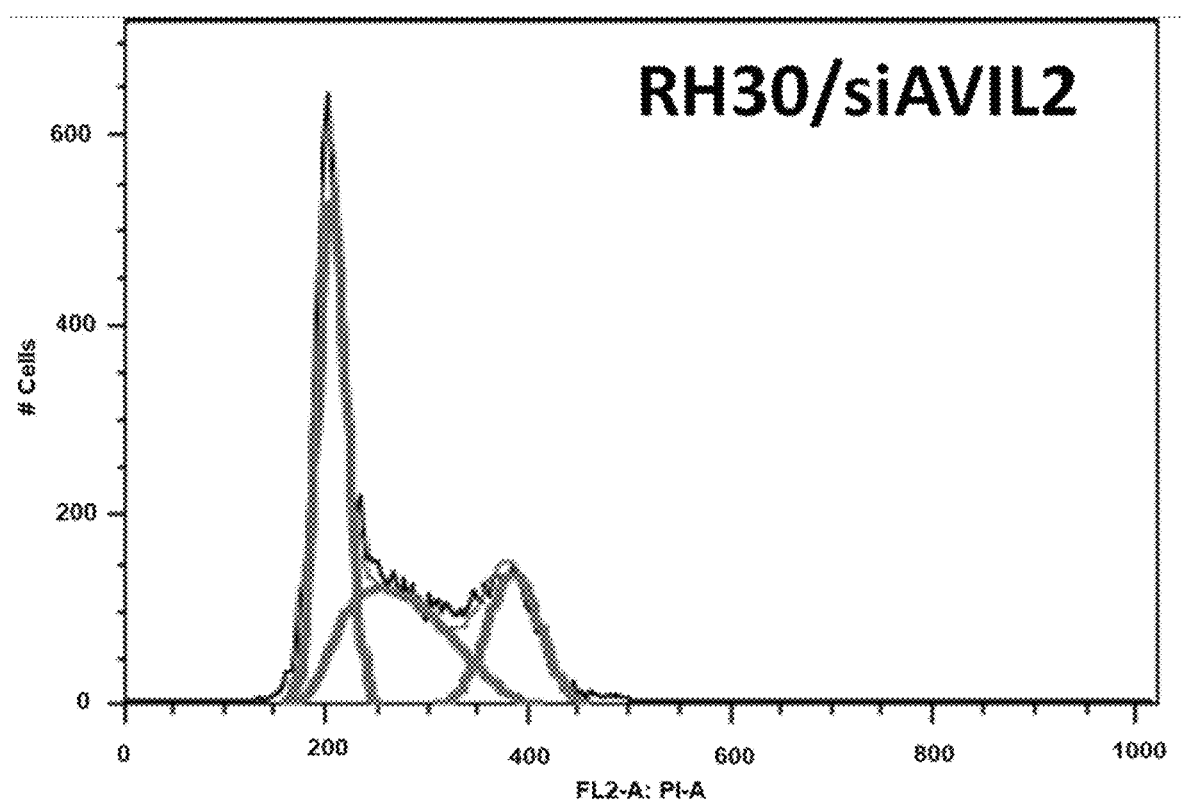
FIG. 2A, continued

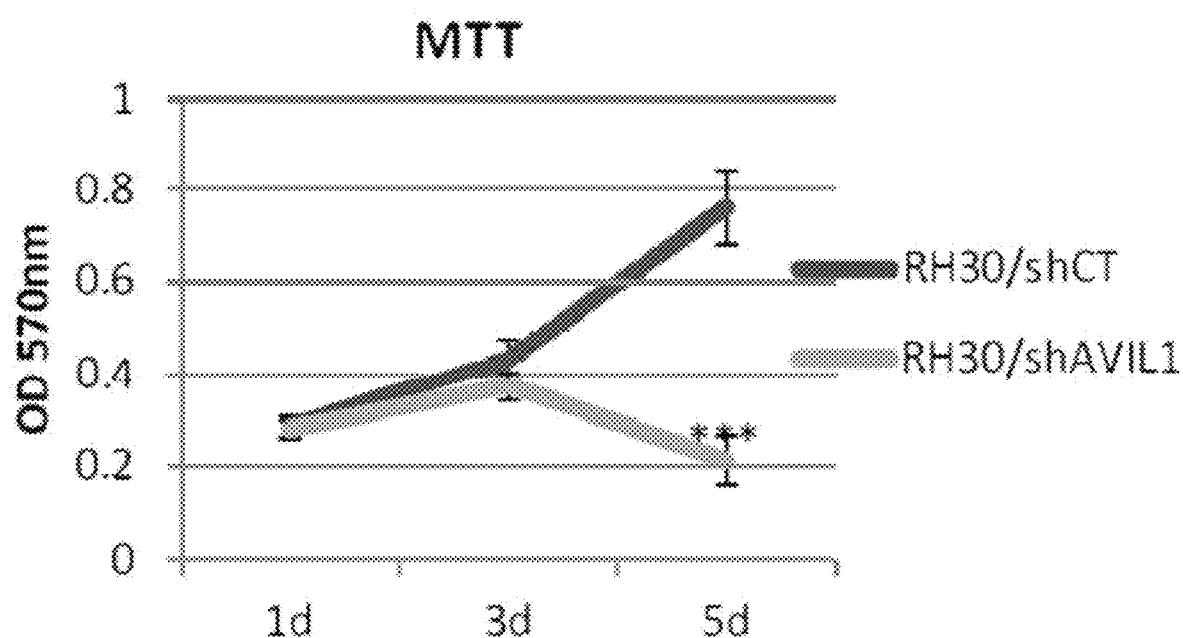
FIG. 2D, continued

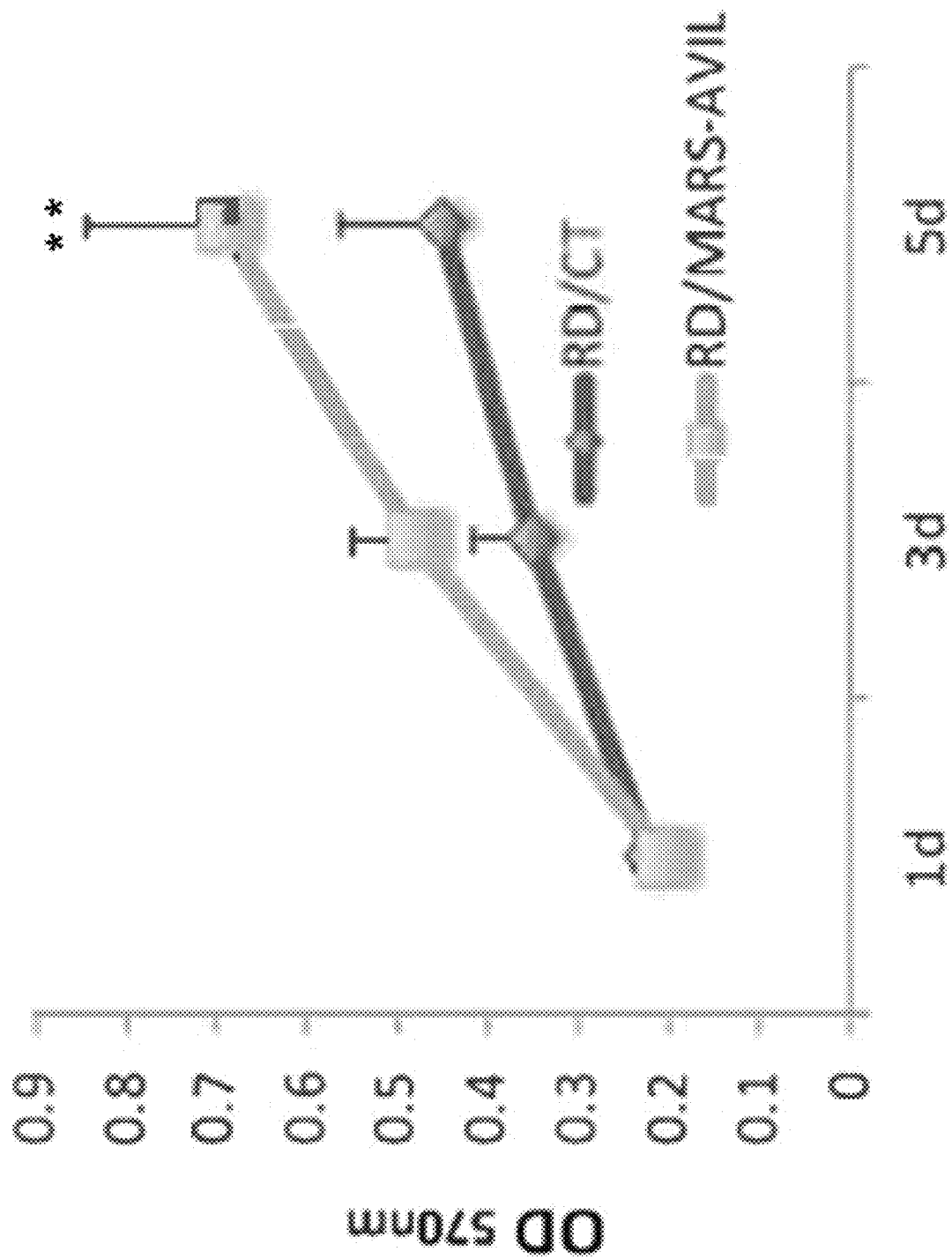
FIG. 2E, continued

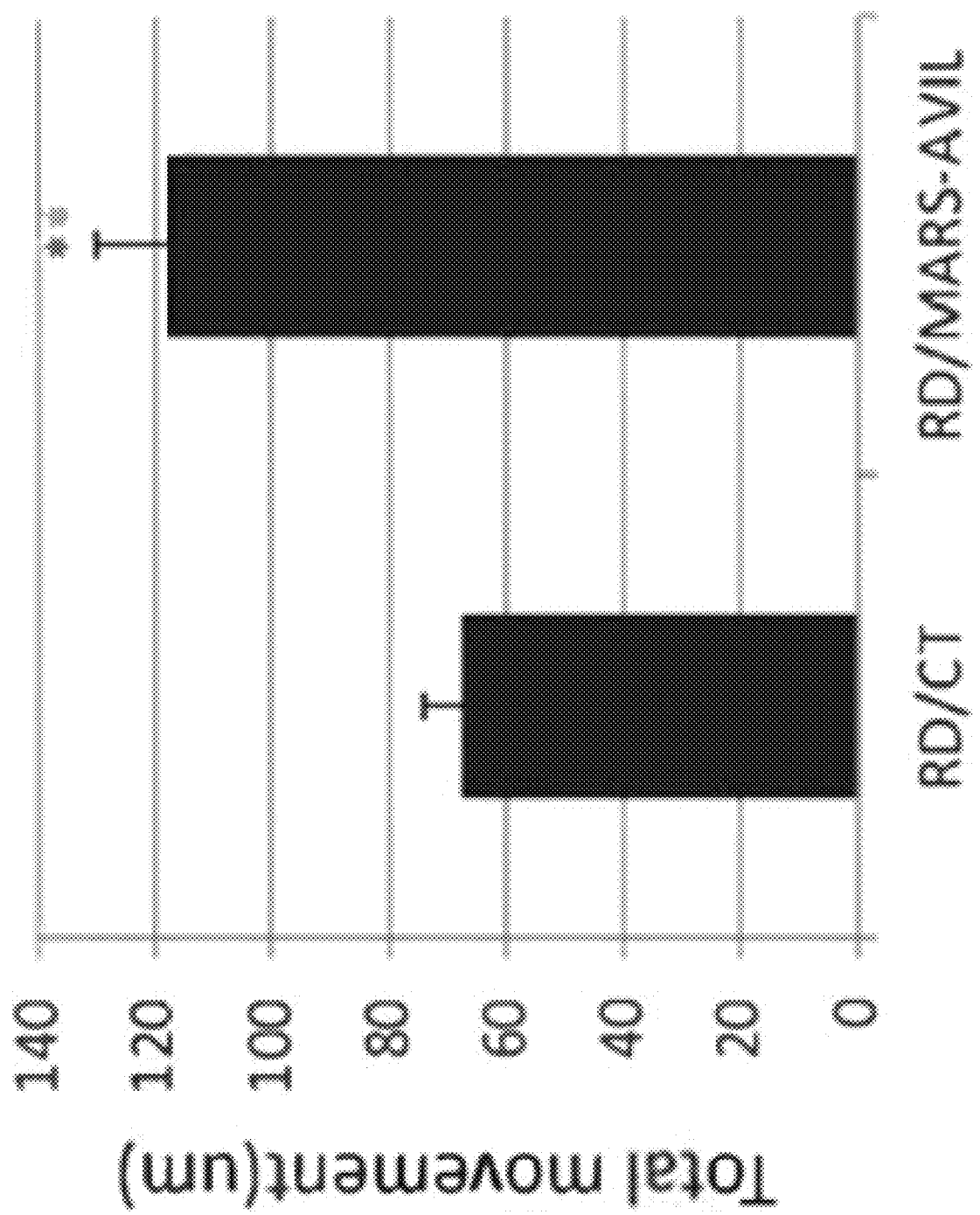
FIG. 2E, continued

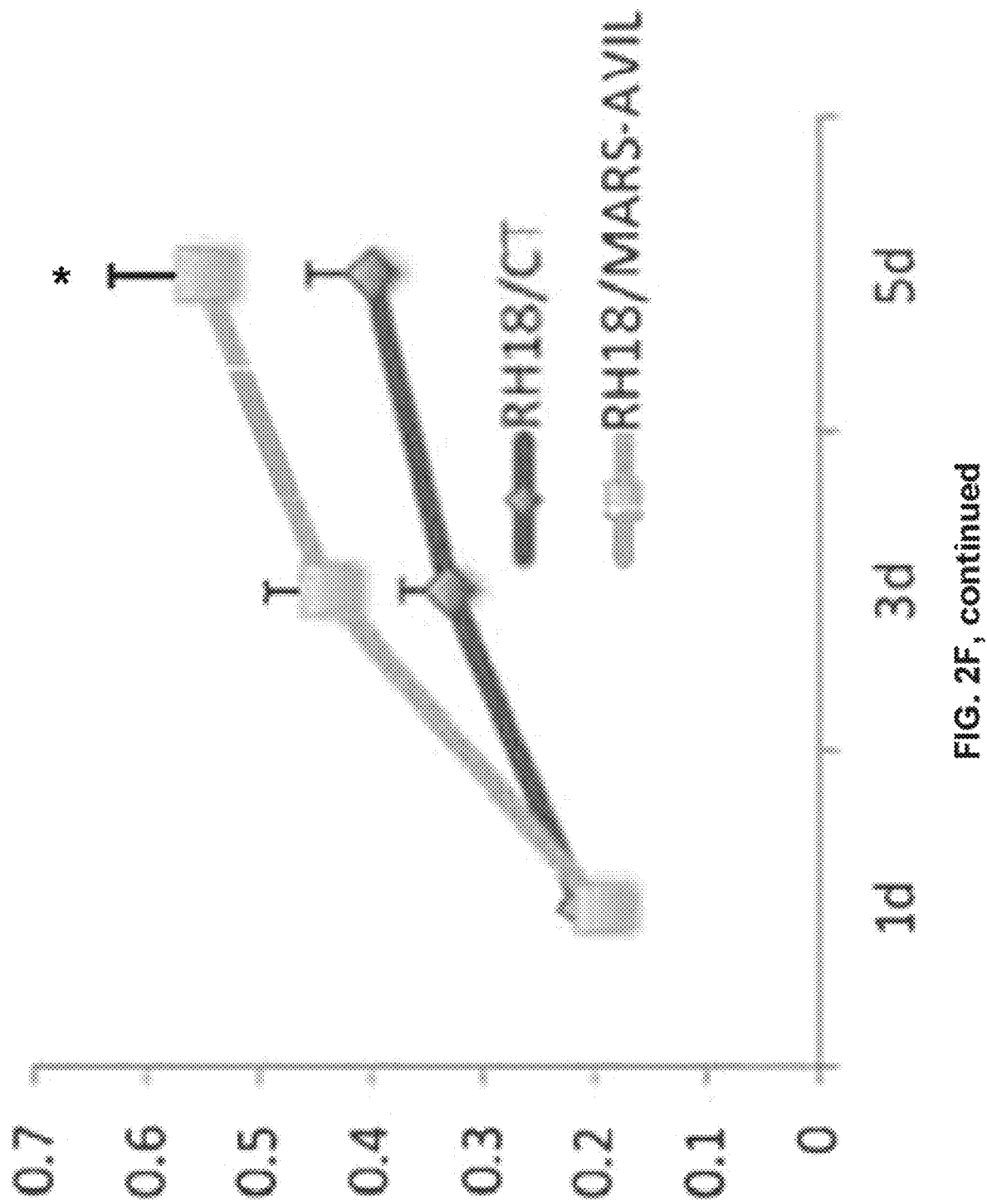
FIG. 2F, continued

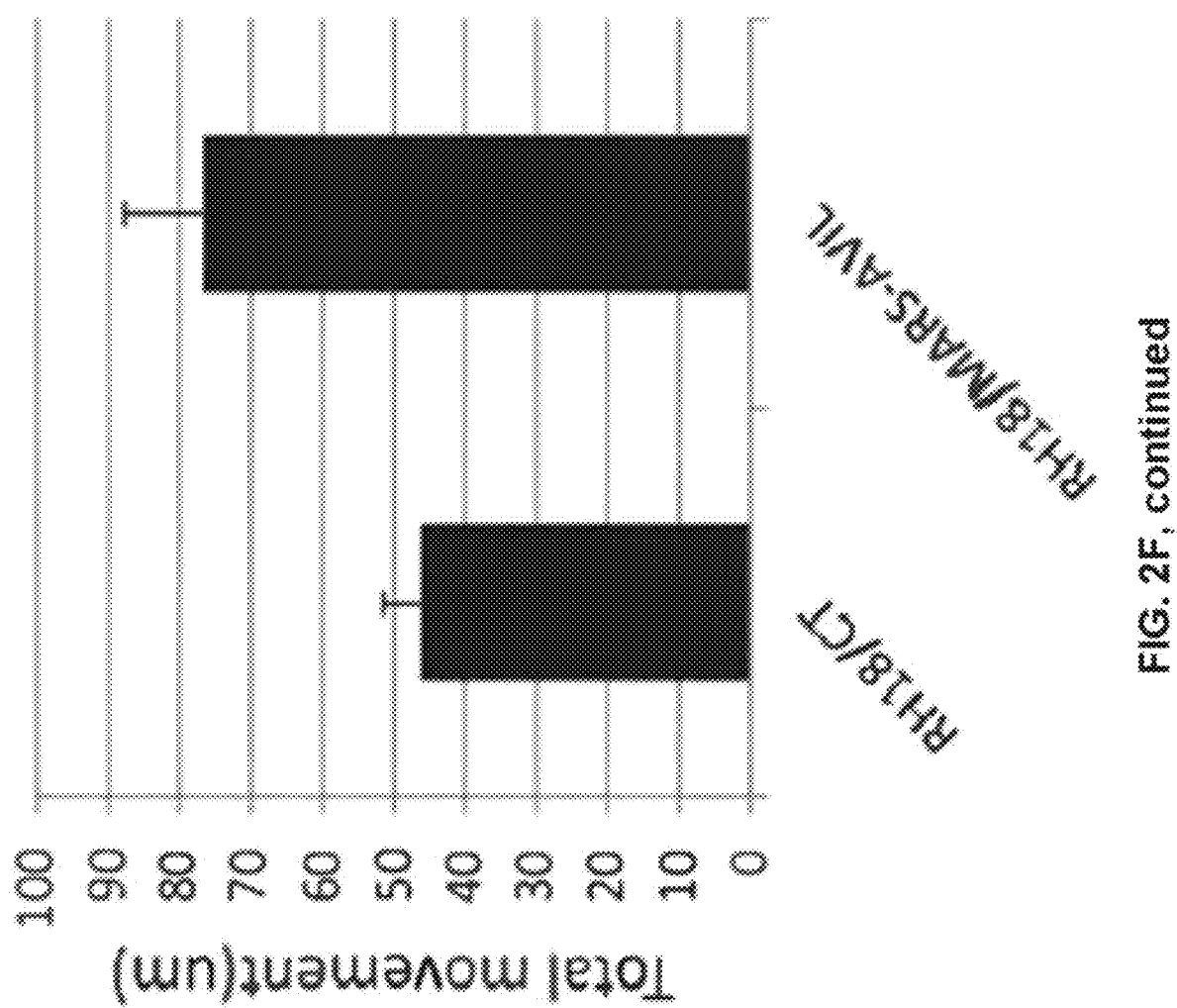
FIG. 2F, continued

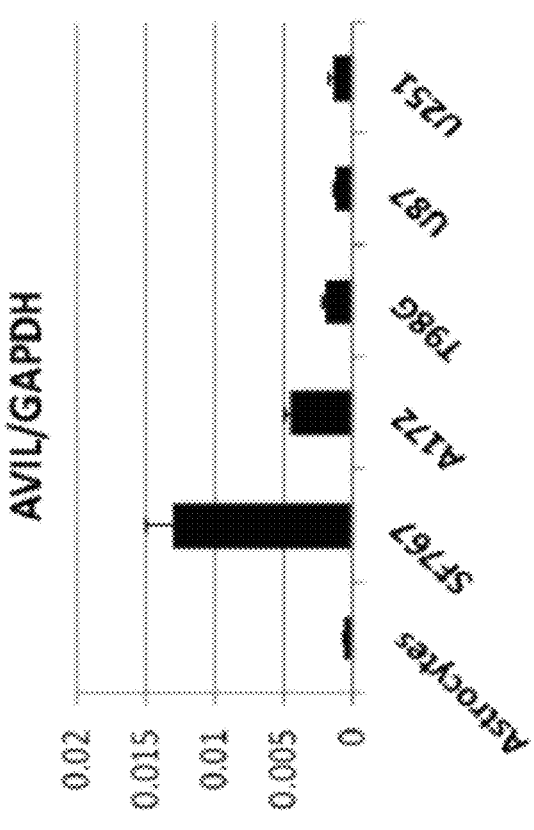
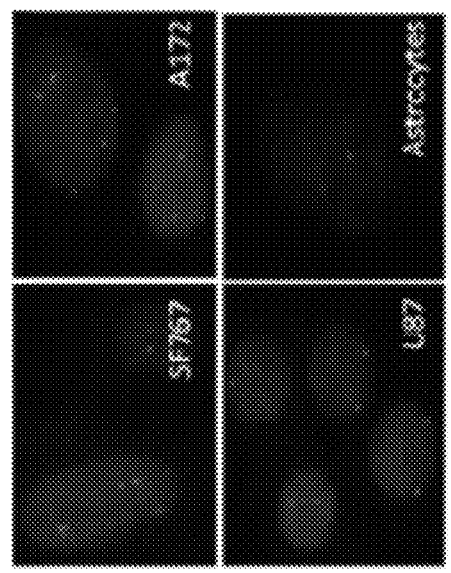
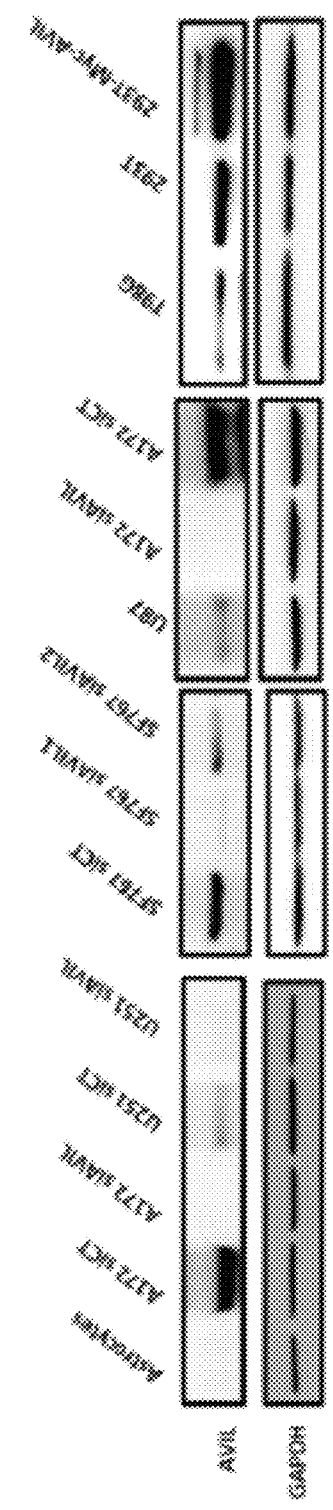

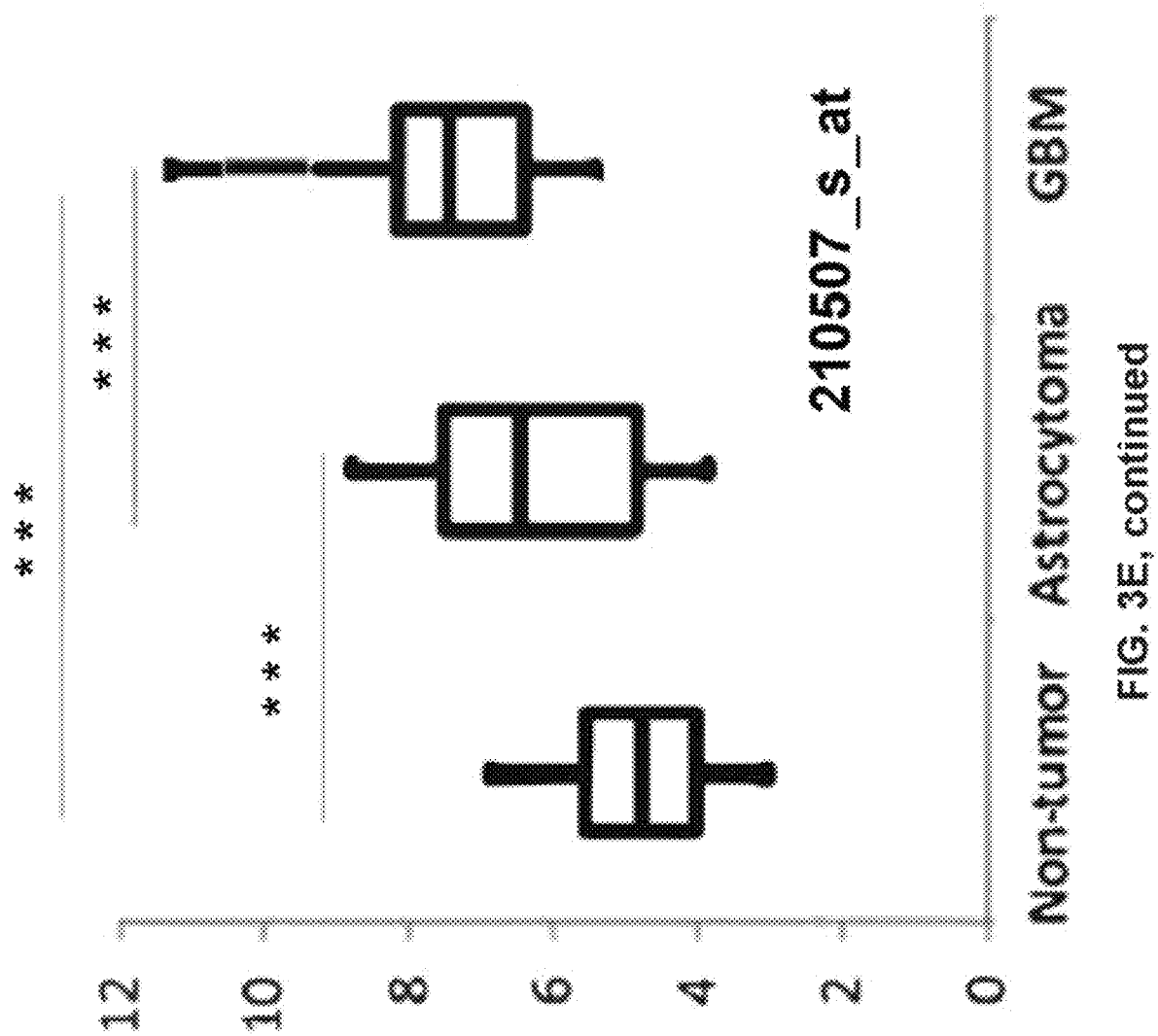
FIG. 3E, continued

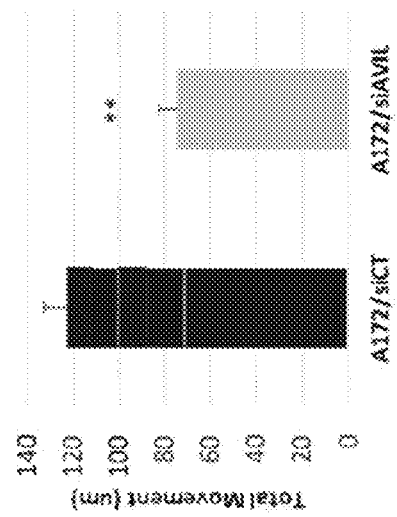
Fig. 4B
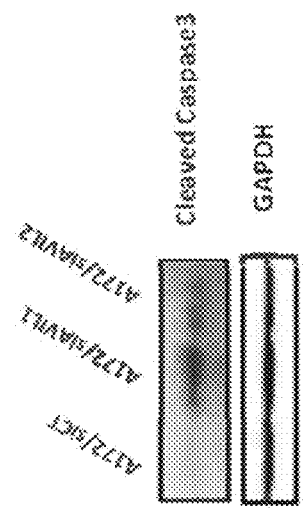
Fig. 4D
Fig. 4A
Fig. 4C

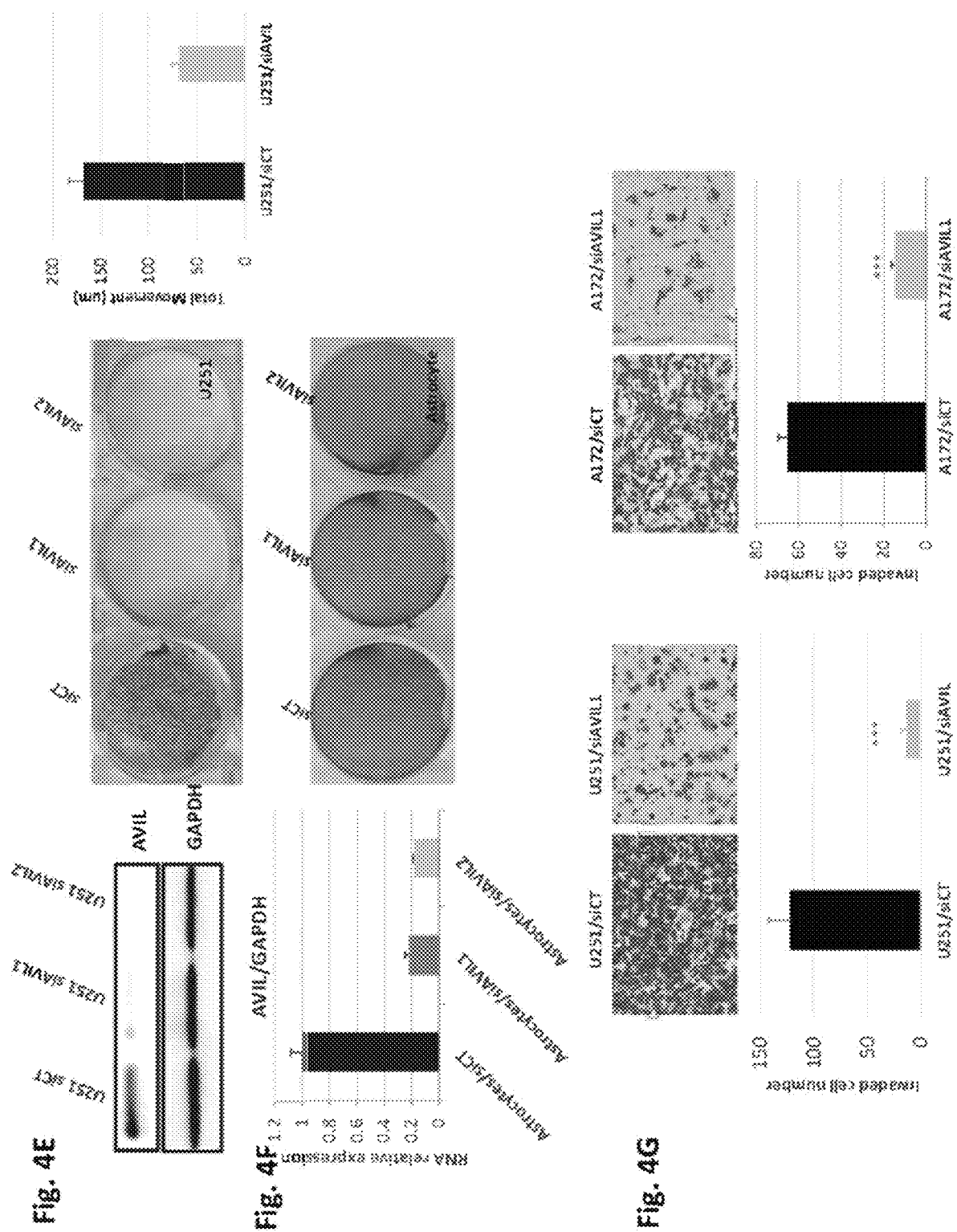

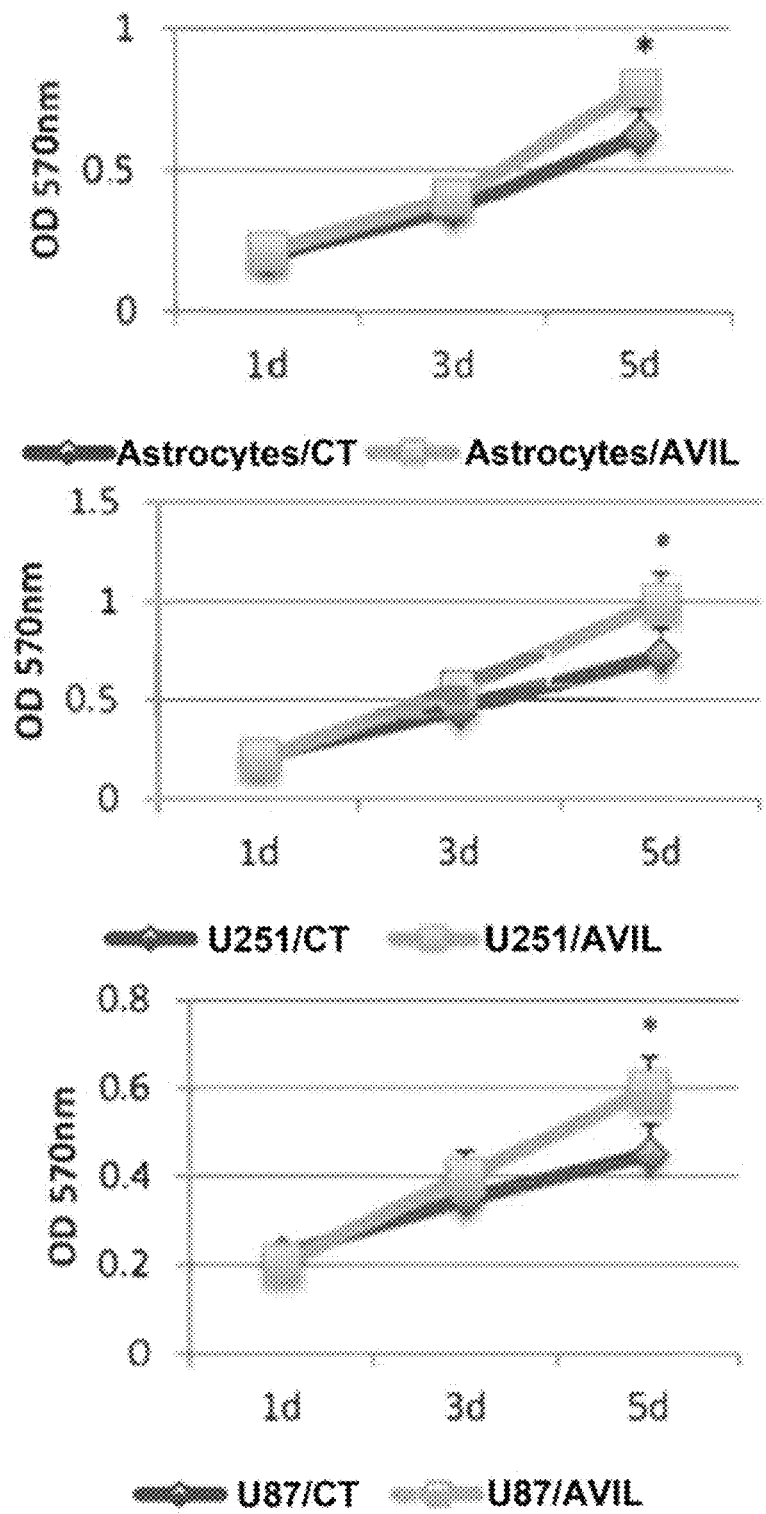
FIG. 4H, continued

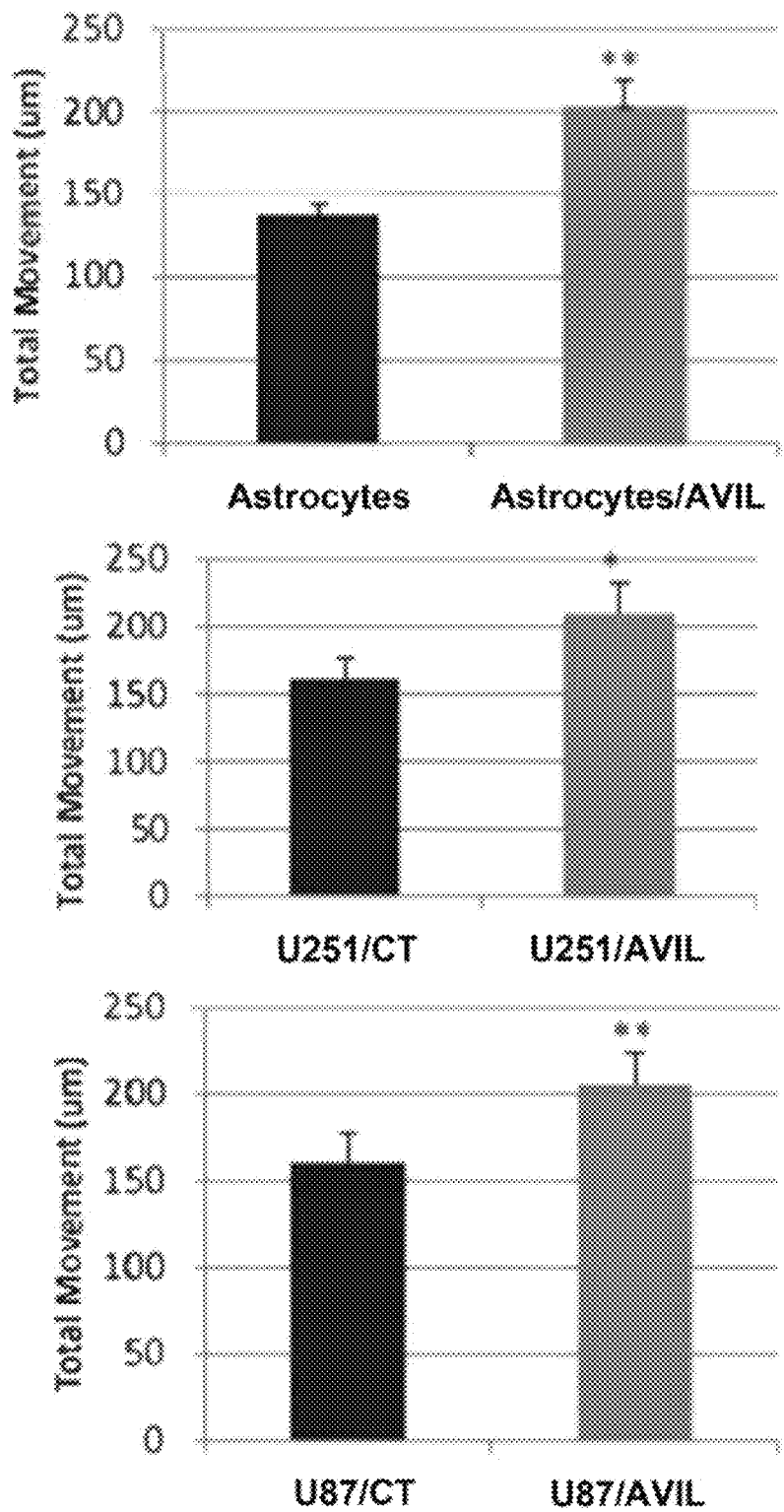
FIG. 4H, continued

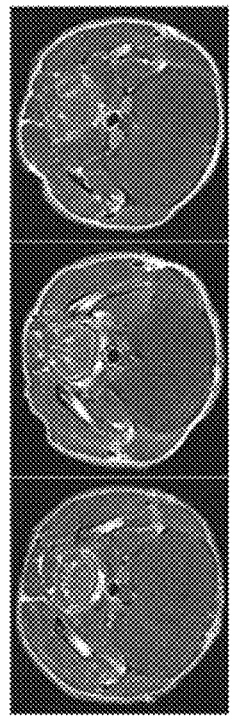
Fig. 4I
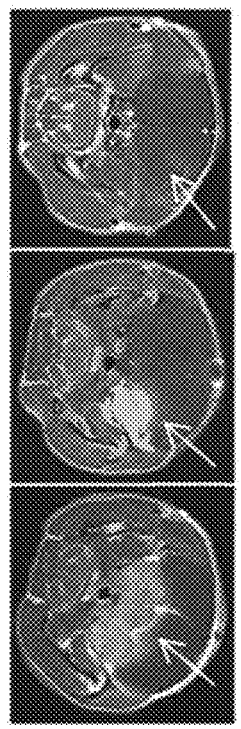
Fig. 4J
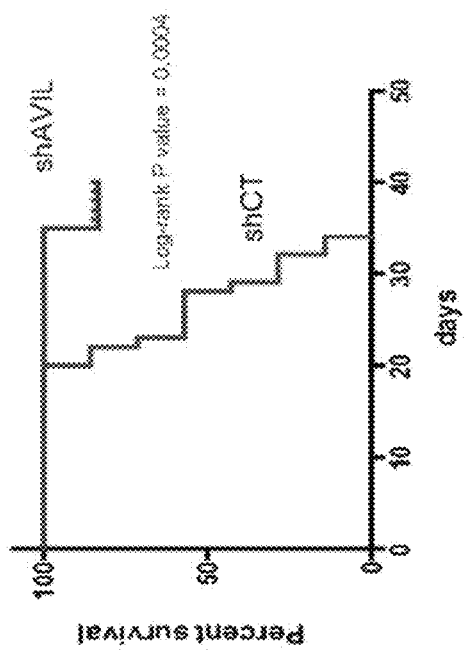
Fig. 4K
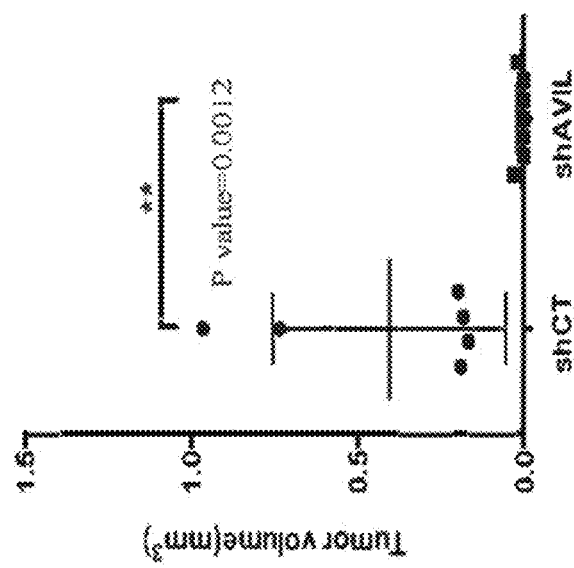

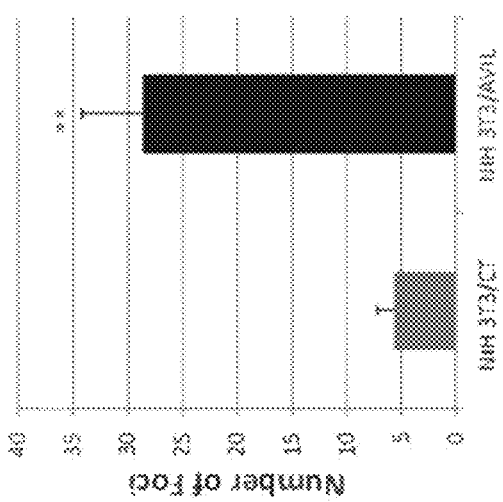
Fig. 4M
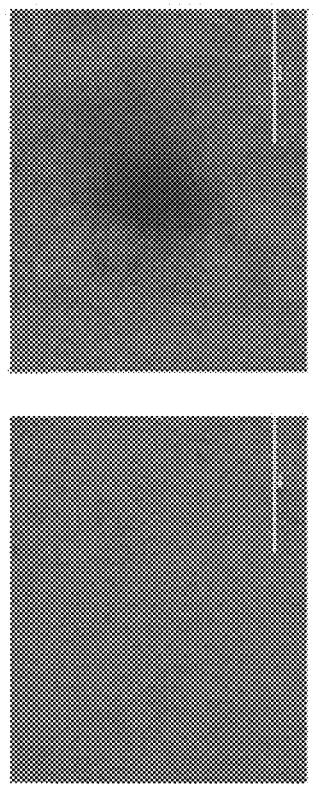
Fig. 4L
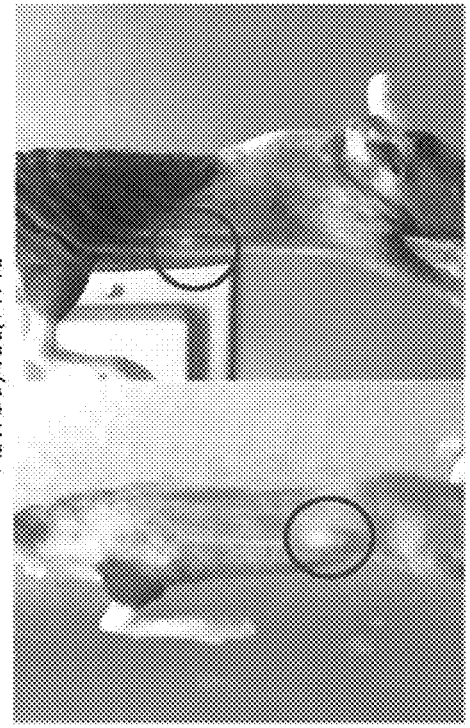
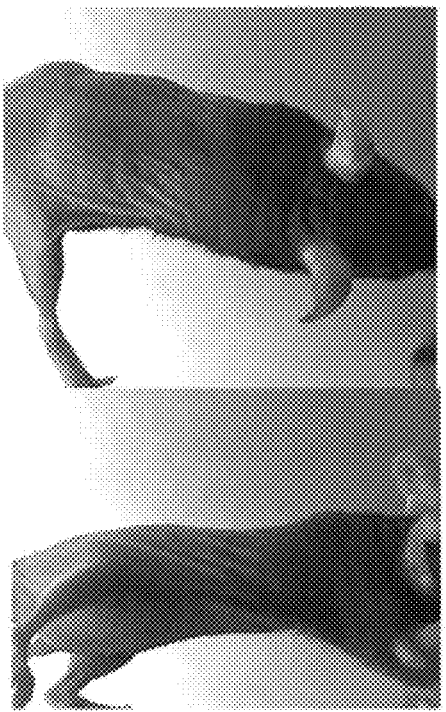
Fig. 4N

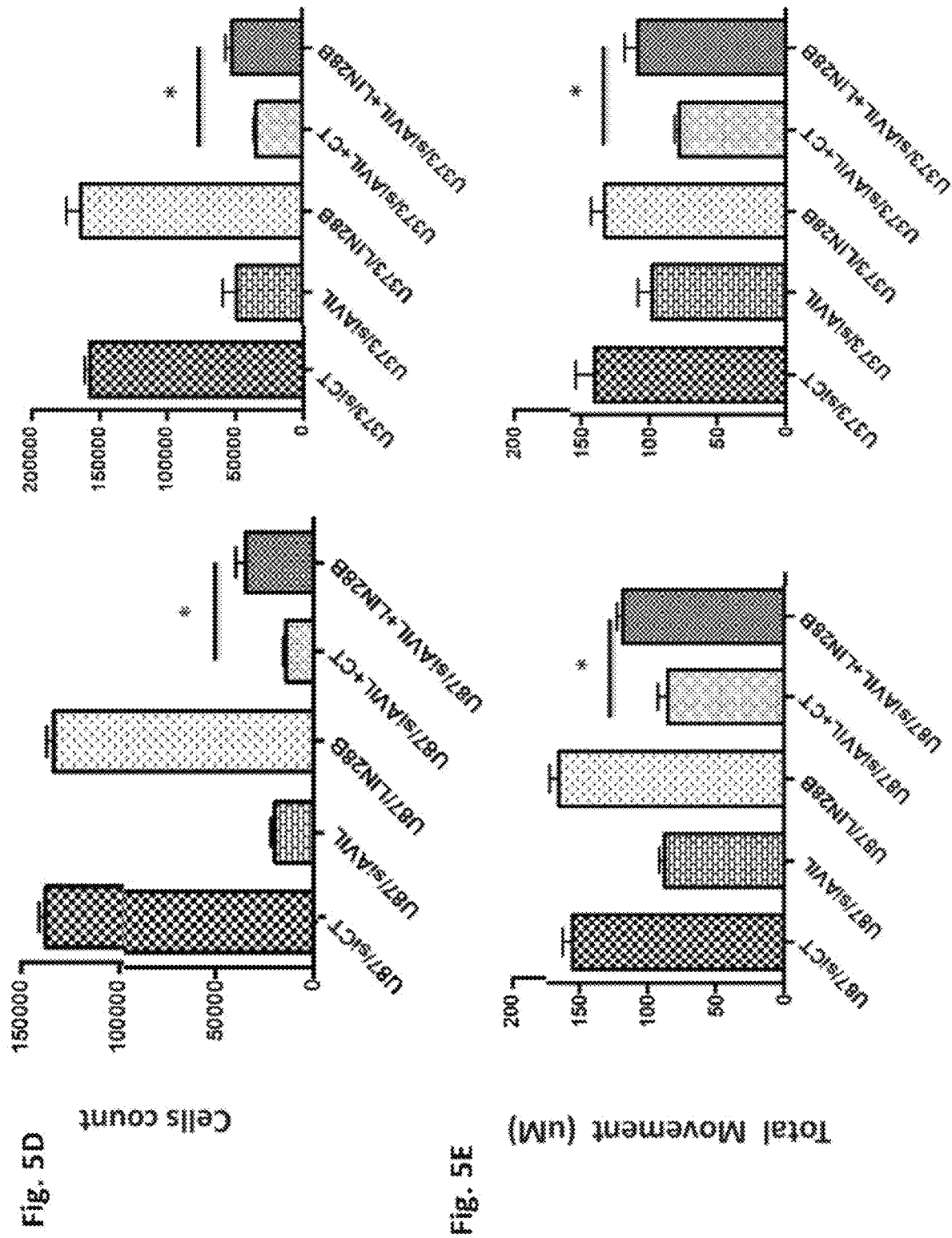

Fig. 5H
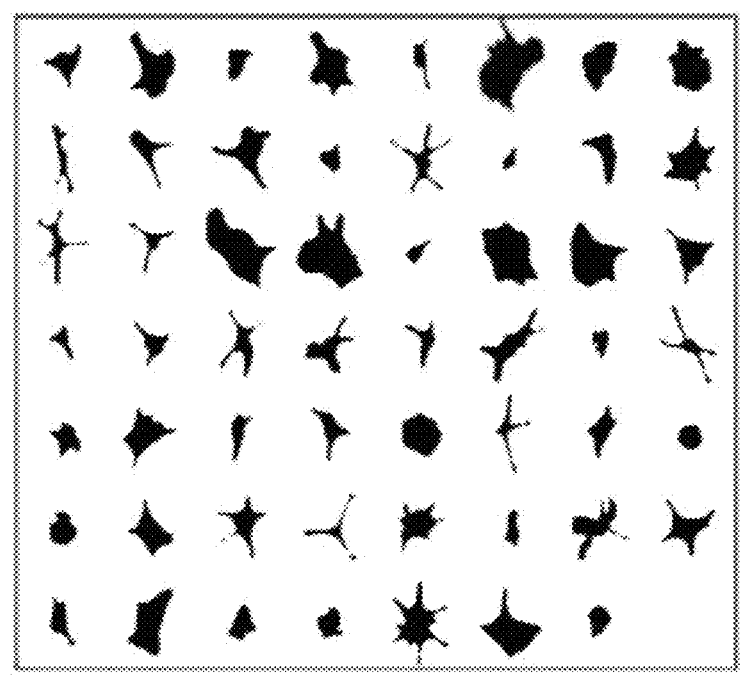
A172/siCT
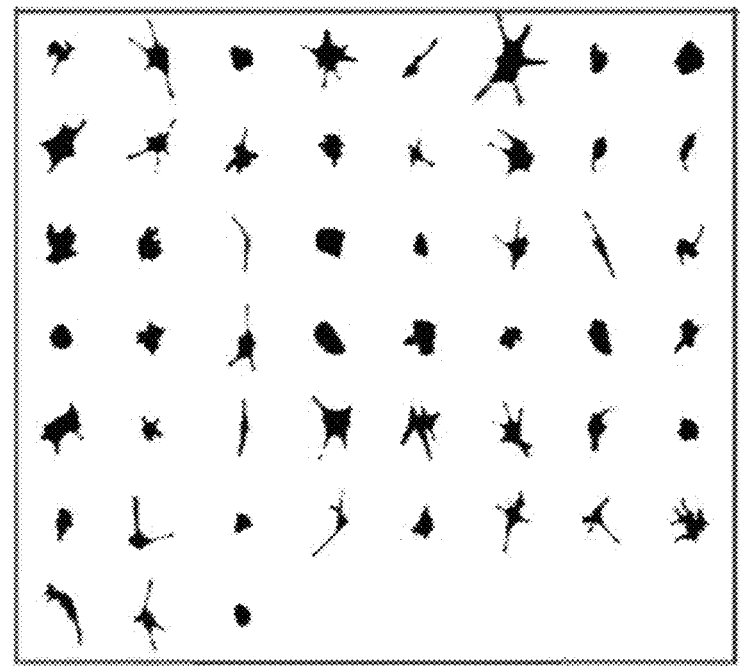
A172/siAVIL1

| 1-10 | 11-20 | 21-30 | 31-34 |
|---|---|---|---|
| SEPT7P2 >> PSPH | EEF1D>>NMRT1 | SETD5>>NUDT9 | PAX3>>FOXO1 |
| BSDC1>>FAM229A | MA01L1>>MROH3P | TIMM23B>>LINC00843 | LINC00545>>MEOAG |
| WARS2>>TBX15 | METTL21B>>TSFM | FXBO11>>MAP2K5 | C12orf76-AS1>>BCL10 |
| NAOK01>>SOX2 | B3GALNT2>>GNG4 | SLIRP>>LINC00545 | MARS>>AVIL |
| TMEM56>>RWDD3 | COMMD10>>AP3S1 | ENO1>>EDARADD | |
| SYNE3>>LINC00341 | U1SOAPfuse7 >>SOAPfuse >>KLF7P1 | RRM2>>c2orf48 | |
| TBCEL>>TECTA | ROBO1>>XPC | MEGF11>>TIPIN | |
| RPLP1>>RBM15B | POLR2J3>>DNAJC2 | TMEM190>>RPL28 | |
| TEAD2>>SLC6A16 | POLR2I2>>DNAJC2 | MCM8P>>POX011 | |
| THSD4>>SERHL2 | POLR2I2SOAPfuse2SOAPfuse >>DNAJC2 | KLRO1>>LINC00545 | |

FIG. 8A, continued

DNA

CCCTTCTGTGGCTATGAGGAGGCTCGGGGTGACCAGTGTGACAAGTGTGGCAAGCTCATCAATGCTGTCGAGCTTAA
GGTAAGAGGAGGGTCTCCATGGGAGCCCGGAAGGAGACAGTCCTTATTCTTAAGGGACGCCCTTGCTGTCCCATTTA
GGATTTTTATTTTAGCATTCTAGACCTTTAACCAGTGGCCCTTTCTGCCCCATCTCAGCAACTCGTCATTTAGTTCATTT
GAAAAATACTCCCTGAGCACTTACTATGTGCTGAGCACTGTGCTAAGAAACAGACAAGTTGAGTTTATATTTCCCAACC
TTTGGTCTTGCATCACACCACCTGATCTACATTTGTTTAGATCCTTCTCTCTTCTTTAAATATCTTCTCTTCTAGCCATTT
GTTAATTTATTTCTTCATTCATTTATTCAACATACATTTTTTTGAATCCTTAGAATAGGCCAATTACAATTCTGCGTGCTGG
GGGTATGGCAATGAATAAGACAGATTTTATTTAGTATGGTCAGGAGACCAACACTAACTAAGGAAATGATATAGAATAA
ACTGCCAGGAAAATGTGACAGAGAGTGACTTCTGGGGGAAGATCTAACTTAGGTAGATAGGGAAGGCCTTTCAGAGG
CAGTAACATTTGAACTGAGAGTTTAACCAAAGAATTAGGAGCAAGCCAGGCAATAAGAGGTTAAGAATGTTCTAAGCG
GAAGGACTAGGAAATGCAAAGGCCATGAGGCAGCTAAGAGCTGAAAAGGCAGAATTGGCAAGGCCAGTATAGCACTA
GCACAGTGAGTGAGGAGGAGGGTAGACTGAGATGAGGTGAGAGAGATGGCAGGGGCCAGATCACCAGGGCCTGTG
AAGCCATTGTGGGAATTTAGATTTTATTCTGGTGAATGACAAGCTGCTCTGTGGAAAATGGATGGCAGGGAAGCAAGA
AATAAAGTATGTTGAAGGGGCTGGGGCATTGGTGGCTCATACCTATAATCCCAGCACTTTGGGAGGCCAAGCTGGGTG
GATCACTTGAAGCCACGAGTTTGAGACCAGCCTGGCCTGTAACATGGCAACCCTGTCTCTACTGAAAATACAGAAATG
GCTAGGTGCGGTGGCTCACGCCTGTAATCCCAGCACTTTGGGAGGCTGAGGTGGGCAGATCACTTGAGGTCAGGAG
TTTGAGACCAGCCTGGCCAACATGGTGAAACCCTGTCTCTACTAAAAAAATACAAAAATTAGCTGGGTGTGGTGGCGG
ACCCCTGTAATCCCCGCTTCTTGGGAGGCTGAAGCTTGAGAATCACTTGAACCTGGGAGGCAGAGGTTGCAGTGAGC
TGAGATTGCGCCACTGCATTCCAGCCTGGGTTACAAAGTAAGACTCTGTCTAAAAAAAAAAAAAACCACAAAAATTAT
CCAGGCCGTGGTGGCGCACACCTGTAATCCCAGCTACTTGGGAGGCTGAGGCAGAAGAATTCTTGAACCTGGGGAAG
CGGAGGTTGCAGTGAGCCAAGATTGCCACTGCATTCCAGCCTGGGTGACAGAGCAAGACTGTTCCCCCTCCACCAAA
AAAAAAAGTATGGAGAAGGATTTGGAGGCAACAAGGCTACAACCCAGAAATGGGATAATGGTGGCTTGCACTAGGTTA
GTAGCACTAGAAATGGAAAAGAAAAAATAGACTTGAGGTATATTTTTGGAGGTAAACTCCACGGAGTTGGATAGACTG
GAATTTGGGATGGTGCAGAAAAAGATGCCTTGTAAGTTTTTGGCCTGAGTAGATGGTAGTACCATCTGTGAACGTGAG
TGAGGAGAACAGGCTTTCAGGTGGGATGCAGCCATACTGTTTGGGTTTGTTAAGCTTGAGATGCCTGTTAGATAGCCA
GGCAGAGAAGTCAGGTAGACAGTTGGATATTAGGCATATGGAGTTCAGGAGAGAGGTCCTGAGGAATTATAATTTCTC
ACCTTCAAAAACTCAGATCAAAACTCACTTGGGGCCAGGTGTGGTGGCTCACGCTTGTAATCCCAGGACTTTGGGAAG
<ins>CTGAGGGACCAAGGTTCAGATCCGGGGTGATGCAAGCAGAGCTCACAGAAGCCAGAGGGATGGCCACGTTAACCCT
GTGGCTGGCAGCCTCACATCCTGTAAGGTCATTGAGAACATCTCCCCTCCTTCTCCCCACCACCTGCACCGAATGACA
GAGAGGAGAGGGAGGCTCATGGGGAAGGGAGGTGGGAGGGGATGTAGCCTATACCCACCCCTTGTCCTTCCAGAAA
ATGGAGCTGGCGCTGGTGCCTGTGAGCGCCCACGGCAACTTCTATGAGGGGACTGCTACGTCATCCTCTCGGTGA
GCACCCTCCTGCCCACTCCTGTGAGCCTCTCCCCTGGGCCAGTTCTTGGGCTGTACTGGGAGATGTGCTGGTGAG
GGAAGGTAGTCAGTCCCTGGTATCGGTCTCAATGGTTCCTCAGTGCTATGCAGAGCAGACCTCCAGTCTGACTATCAA
AGGCCATCATTAAGCCTGGGTTTTTAATGCTGCATAAGAGGATGGGGGTAGGACCCTCAGTCTGAACCCTCAGTGAGC
CACCCACAAGCAGCACTTCTCCCGGGGCCTAGGCCCCACATTAAAGTGGTGTGGAAGAAGGCCTGATAAATGCAAGGC
CTGTCTCTAGCCTCAAAGTGCTATTCTCATGGAGGAGACTCACATGAACCGTGCTGACAGGGTCGTGCAGGTGTACA
GATGAGCATGTGCTGCCAGCTGTGTGAGTGCAAGGCACCAAGGGGACCTGTGAGGTAAGGCTGCAACCCGGCTGGGAA
AAGATCCCCGTTGGTATCTATTTATTTGGGGAACAACAGCTGTCAACTTTCCCCAAATGCGGGGGAGGAATTTGGGCT
GCCAAAGTTTATGCCATGATCGGCAGGTCTGCTCGGGGGCCAGGGCAGCTCCCACATCCACTGGGAGAGAGGGCC
CTCAGTCTGCCAAGGGCATGCAGATGTGCTGCATTCTCCCCATAACAGGGGCCAGCAGCAAAGGGGAGGTGAGCTG
GCCTCTGACCTGATCTCTCTGACTACGTCCCAGACCCGGAGAGTGGCCAGTCTCCTATCCCAGGACATCCA</ins>

RNA

CCCTTCTGTGGCTATGAGGAGGCTCGGGGTGACCAGTGTGACAAGTGTGGCAAGCTCATCAATGCTGTCGAGCTTA
<ins>AG/AAAATGGAGCTGGCGCTGGTGCCTGTGAGCGCCCACGGCAACTTCTATGAGGGGACTGCTACGTCATCCTC
TCGACCCGGAGAGTGGCCAGTCTCCTATCCCAGGACATCCA</ins>

Fig. 8B

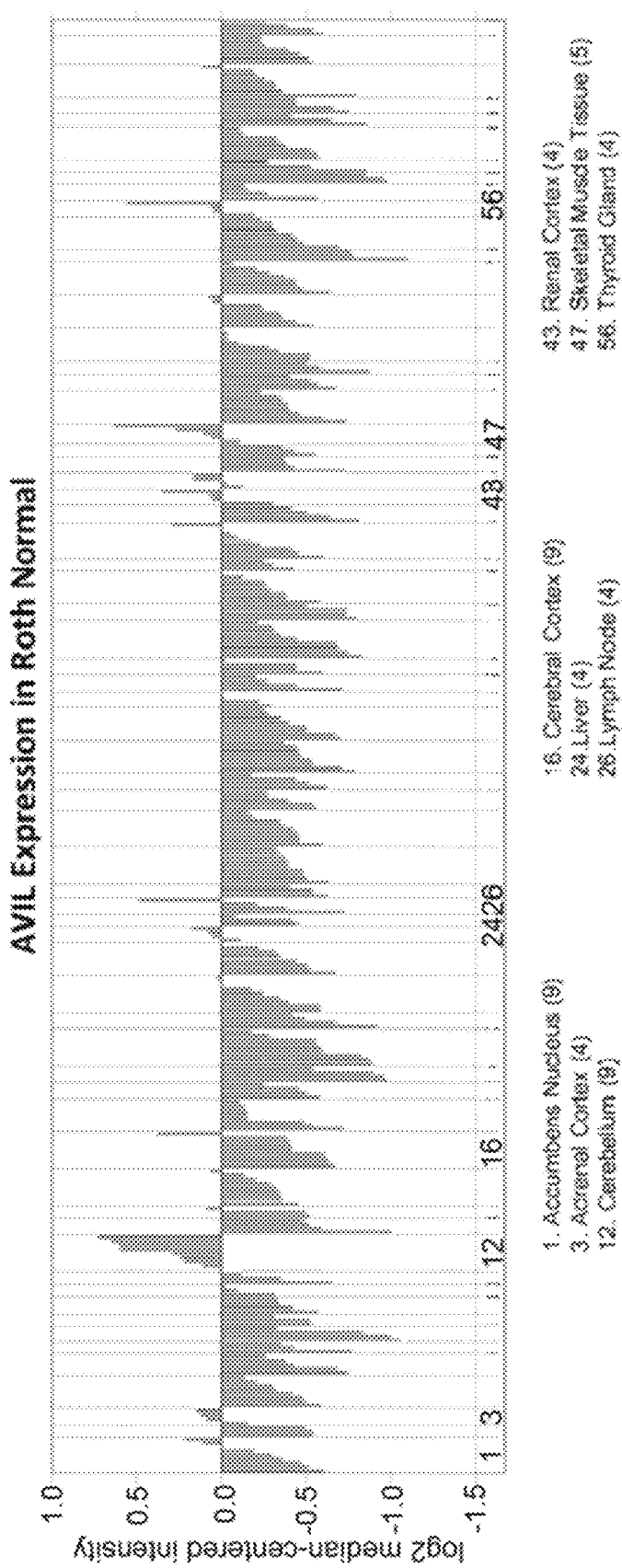
FIG. 8H, continued

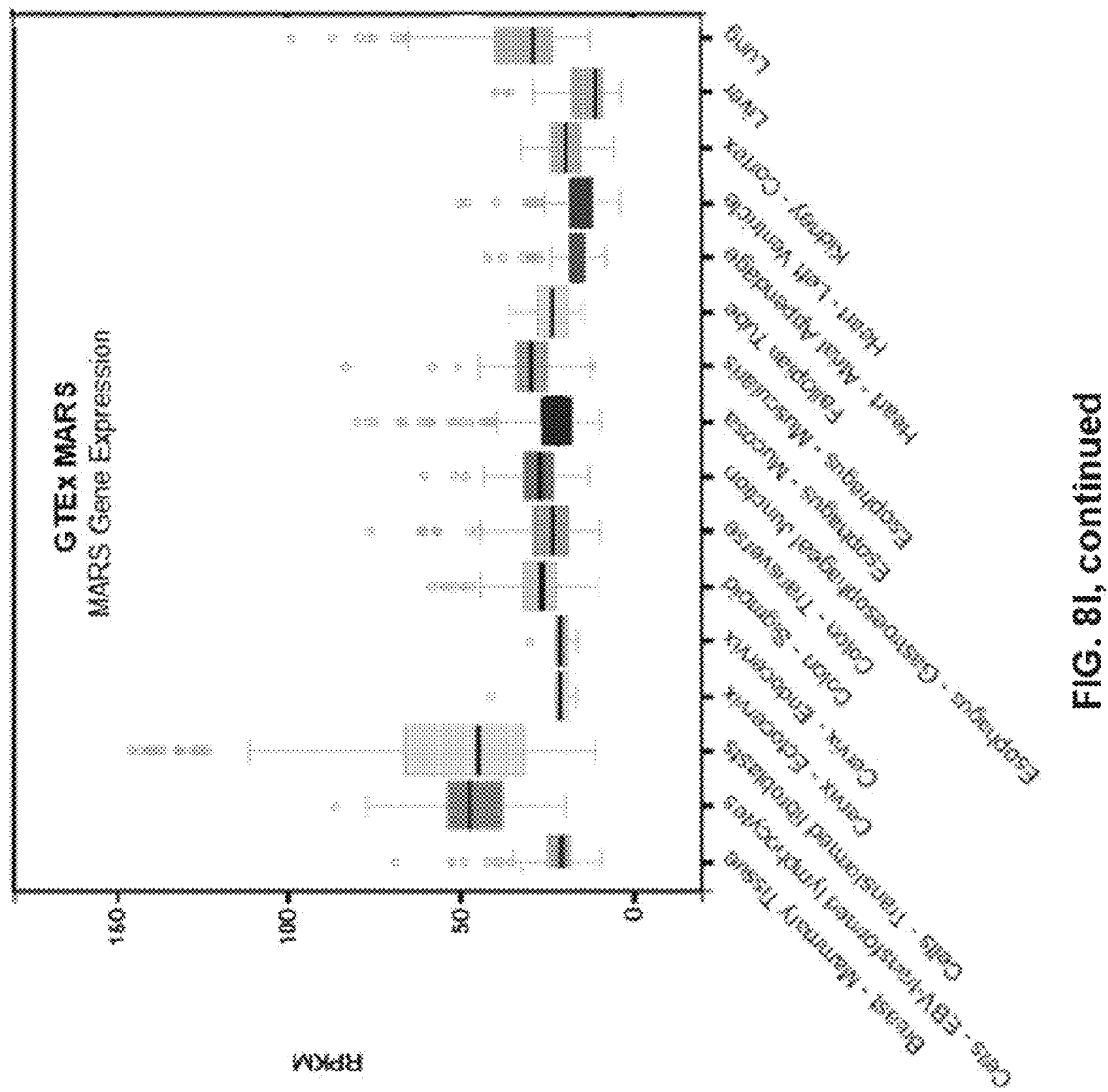
FIG. 8I, continued

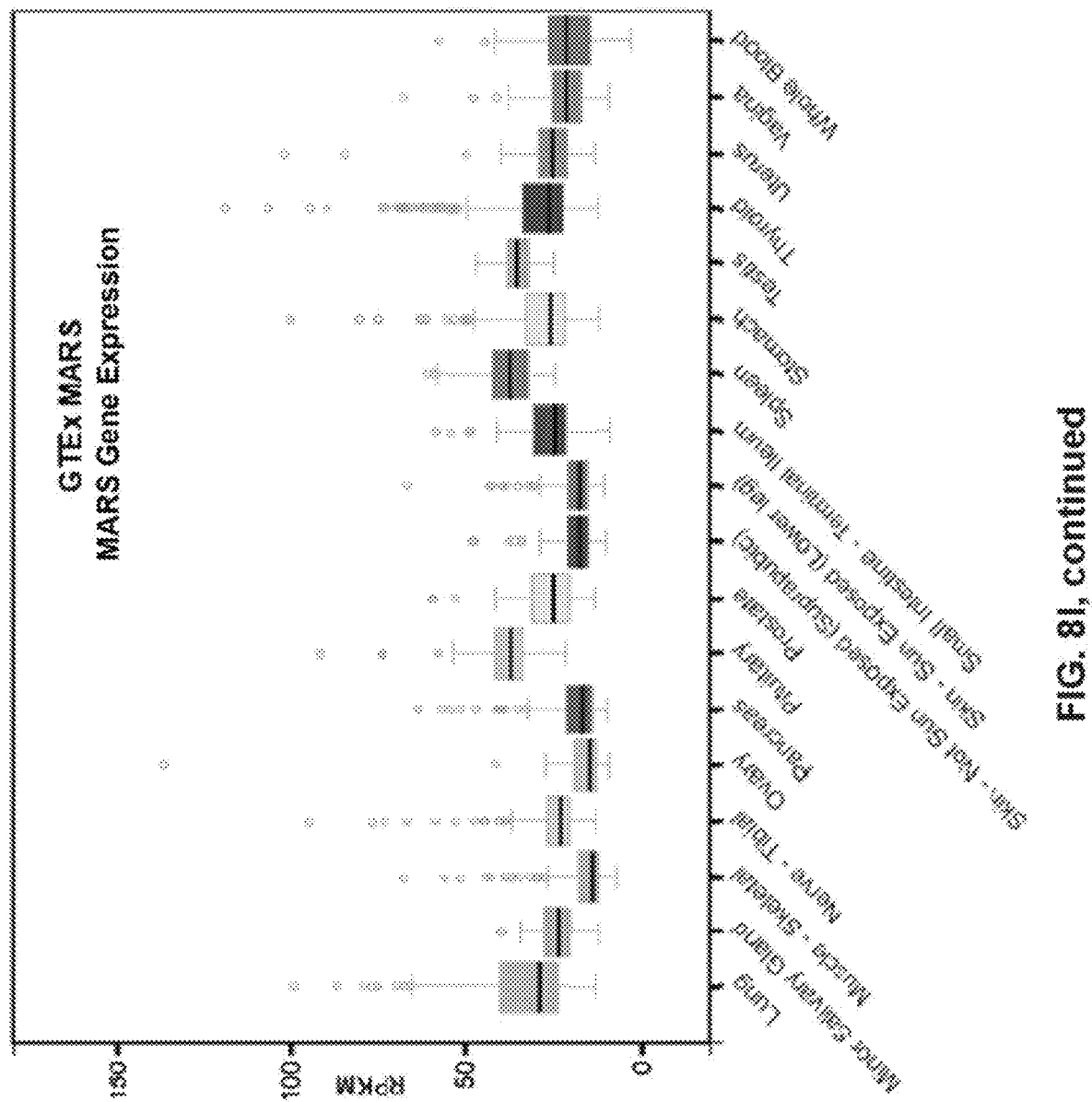
FIG. 8I, continued

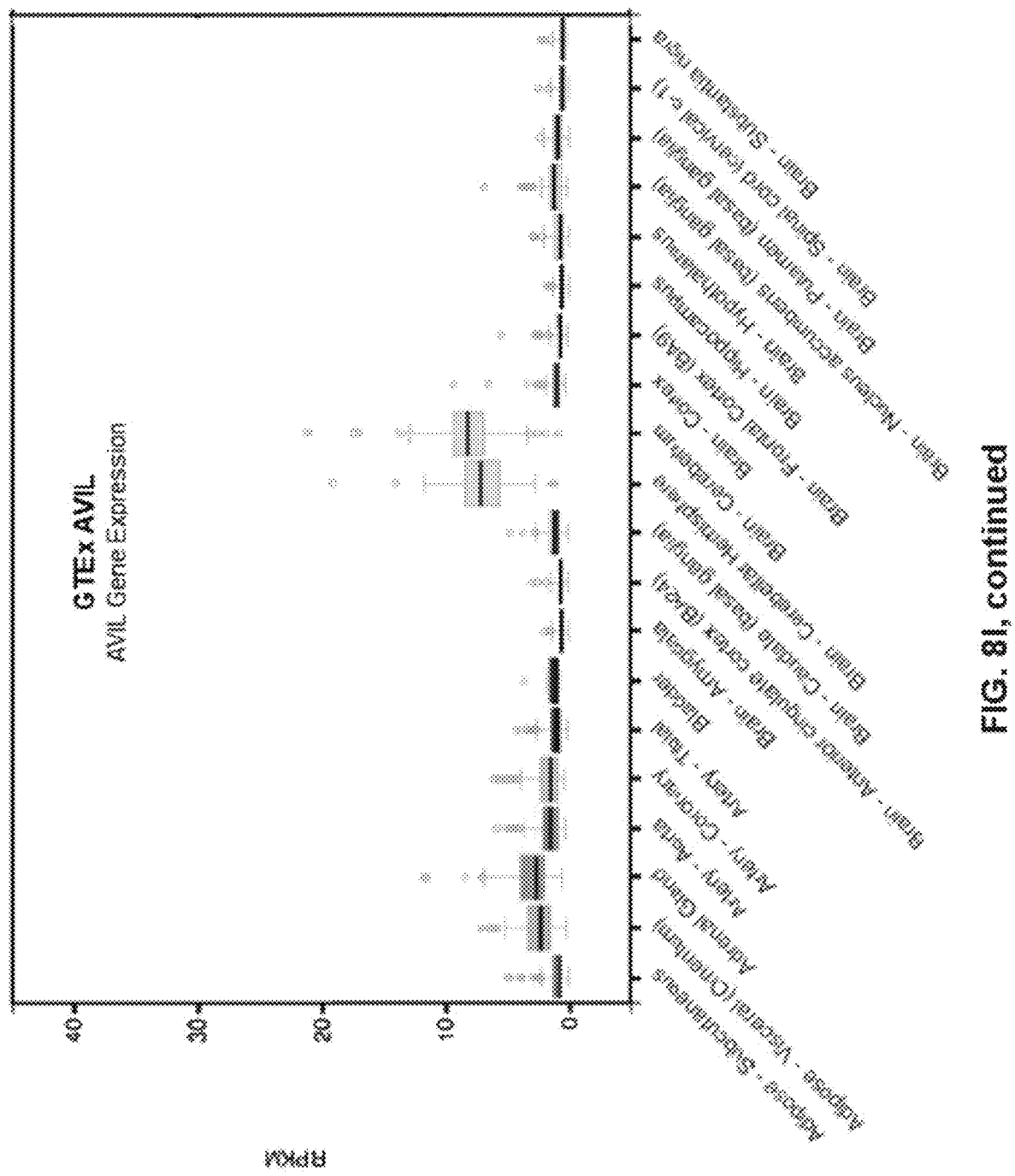
FIG. 81, continued

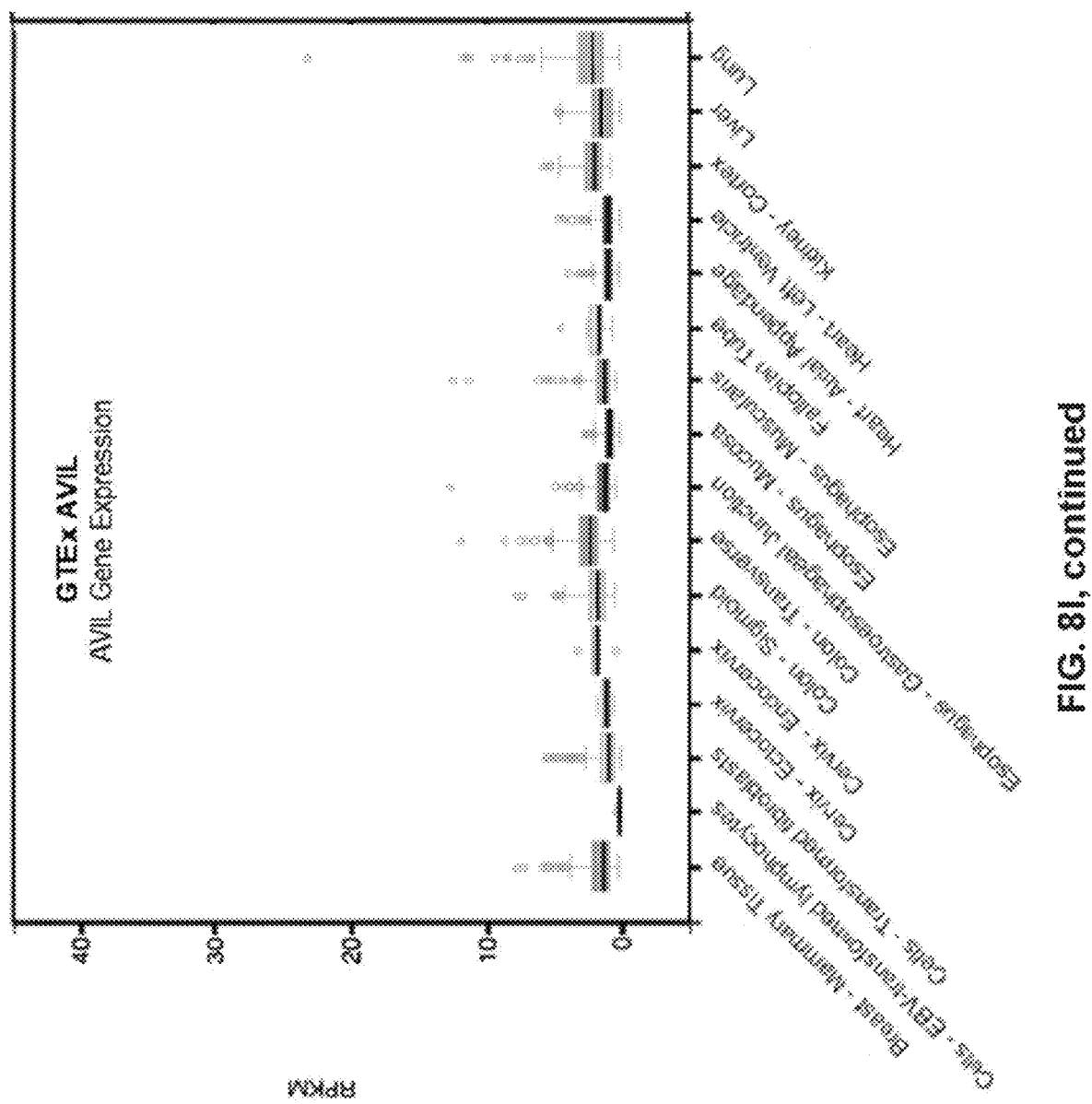
FIG. 8I, continued

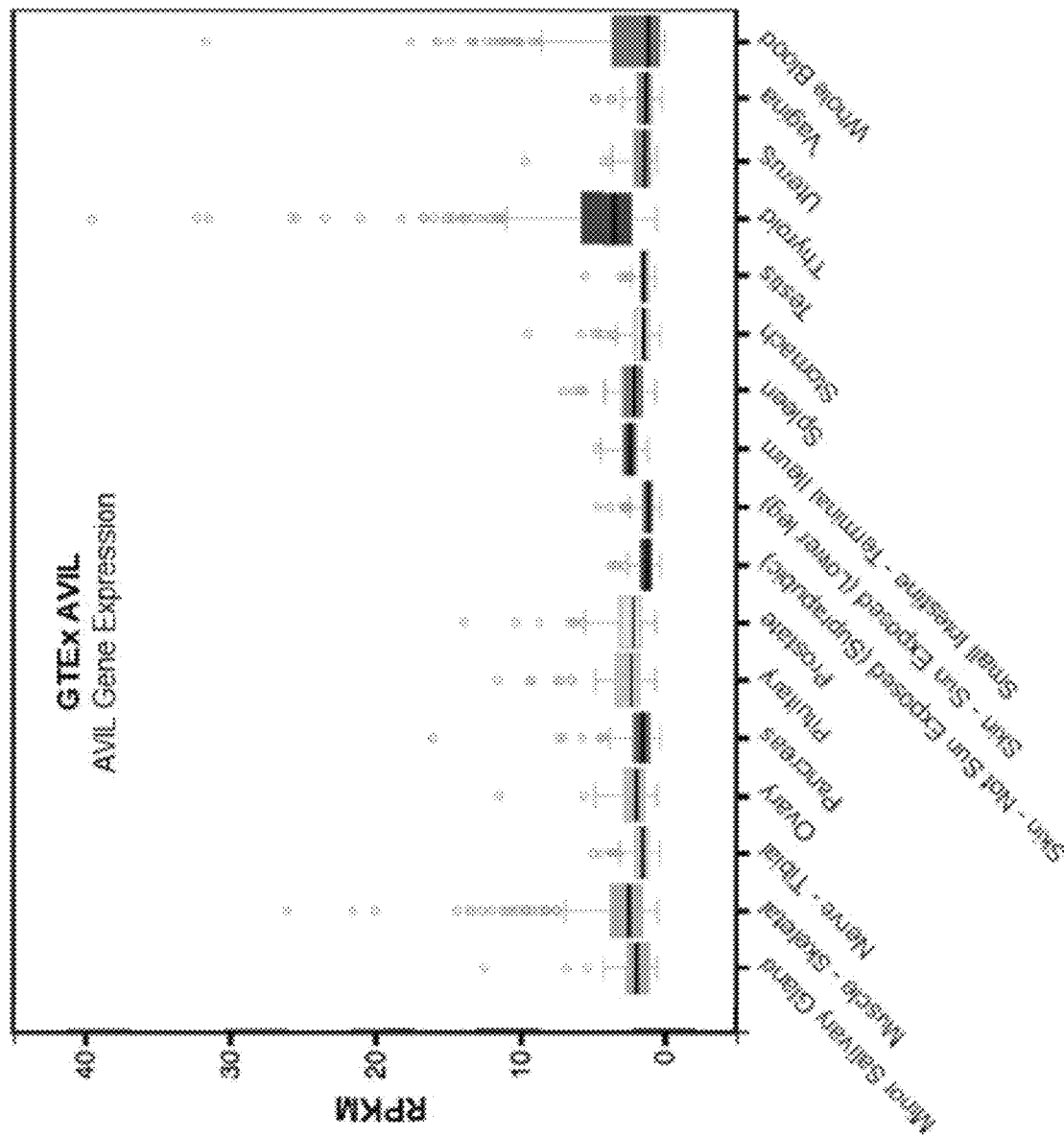
FIG. 8I, continued

▌AVIL Up-Reg. >=2.0x ▌AVIL Intermediate

View Clinical Reports

Upregulating Samples   Intermediate Samples

Statistical Report:

AVIL

Reporter: 1568706_s_at

Number of samples in group:
Up-Regulated: 49
Intermediate: 55

Log-rank p-value (for significance of difference of survival between group of samples)
Up-Regulated vs. Intermediate: 2.12474lE-4

FIG. 8L, continued

SEQUENCE LISTING

```
<160> NUMBER OF SEQ ID NOS: 9

<210> SEQ ID NO 1
<211> LENGTH: 3687
<212> TYPE: DNA
<213> ORGANISM: Homo sapiens

<400> SEQUENCE: 1
atgagactgt tcgtgagtga tggcgtcccg ggttgcttgc cggtgctggc cgccgccggg      60
agagcccggg gcagagcaga ggtgctcatc agcactgtag gcccggaaga ttgtgtggtc     120
ccgttcctga cccggcctaa ggtccctgtc ttgcagctga atagcggcaa ctacctcttc     180
tccactagtg caatctgccg atatttttt ttgttatctg gctgggagca agatgacctc     240
actaaccagt ggctggaatg ggaagcgaca gagctgcagc cagctttgtc tgctgccctg     300
tactatttag tggtccaagg caagaagggg gaagatgttc ttggttcagt gcggagagcc     360
ctgactcaca ttgaccacag cttgagtcgt cagaactgtc ctttcctggc tggggagaca     420
gaatctctag ccgacattgt tttgtgggga gccctatacc cattactgca agatcccgcc     480
tacctccctg aggagctgag tgccctgcac agctggttcc agacactgag tacccaggaa     540
ccatgtcagc gagctgcaga gactgtactg aaacagcaag gtgtcctggc tctccggcct     600
tacctccaaa agcagcccca gcccagcccc gctgagggaa gggctgtcac caatgagcct     660
gaggaggagg agctggctac cctatctgag gaggagattt ctatggctgt tactgcttgg     720
```

```
gagaagggcc tagaaagttt gcccccgctg cggccccagc agaatccagt gttgcctgtg    780
gctggagaaa ggaatgtgct catcaccagt gccctccctt acgtcaacaa tgtccccac    840
cttgggaaca tcattggttg tgtgctcagt gccgatgtct ttgccaggta ctctcgcctc    900
cgccagtgga cacccctcta tctgtgtggg acagatgagt atggtacagc aacagagacc    960
aaggctctgg aggagggact aaccccccag gagatctgcg acaagtacca catcatccat   1020
gctgacatct accgctggtt taacatttcg tttgatattt ttggtcgcac caccactcca   1080
cagcagacca aaatcaccca ggacattttc cagcagttgc tgaaacgagg ttttgtgctg   1140
caagatactg tggagcaact gcgatgtgag cactgtgctc gcttcctggc tgaccgcttc   1200
gtggagggcg tgtgtccctt ctgtggctat gaggaggctc ggggtgacca gtgtgacaag   1260
tgtggcaagc tcatcaatgc tgtcgagctt aagaaaatgg agctggcgct ggtgcctgtg   1320
agcgcccacg gcaacttcta tgaggggggac tgctacgtca tcctctcgac ccggagagtg   1380
gccagtctcc tatcccagga catccacttc tggatcggga aggactcctc ccaggatgag   1440
caaagctgcg cagccatata taccacacag ctggacgact acctgggagg cagccctgtg   1500
cagcaccgag aggtccagta ccatgagtca gacactttcc gtggctactt caagcagggc   1560
atcatctaca gcaggggggg tgtcgcctct gggatgaagc acgtggagac caataccac   1620
gacgtgaagc ggctgctaca tgtgaaaggg aaaagaaaca tcagggctac cgaggtggaa   1680
atgagctggg acagtttcaa ccgaggtgat gtcttcttgc tggaccttgg gaaagtcatc   1740
atccaatgga atggcccaga gagcaacagt ggggagcgcc tgaaggctat gcttctggca   1800
aaggatattc gagacaggga gcgaggggc cgtgctaaaa taggagtgat cgagggagac   1860
aaggaggcag ccagcccaga gctgatgaag gtccttcagg acacccttgg ccgacgctcc   1920
attatcaagc tacagtcccc tgatgagatc atagatcaga agcagaaatc aactatcatg   1980
ttgtatcata tctcagattc agctgggcag ctggcagtca cagaggtagc aacaaggcct   2040
ctggtccagg acttactgaa ccatgatgac tgctacatcc tggaccaaag tggaaccaaa   2100
atctacgtgt ggaaaggaaa aggagccaca aaggctgaaa acaggcagc catgtctaaa   2160
gcgctgggct tcatcaagat gaagagctac cccagcagca ccaatgtgga gaccgtcaac   2220
gatggtgctg agtcggccat gttcaagcag ctgttccaga agtggtcagt aaaggaccag   2280
accatgggcc tggggaaaac gttcagcatt ggtaaaattg ctaaagtttt ccaggataaa   2340
tttgatgtga ctctgctaca caccaagcca gaggtagctg cccaggaaag aatggtcgat   2400
gatggcaacg gaaaagttga ggtctggaga attgagaacc tggagctggt ccctgtggag   2460
tatcaatggt atggcttctt ttatggggga gactgttatc tggtcctcta cacatacgag   2520
gtaaatggga agccacatca catcttgtac atctggcagg gccgccacgc ctcacaggat   2580
gagctggcag cctcagcata ccaggcagtg gaggtggatc ggcagtttga tggggctgct   2640
gtgcaggttc gagtcaggat gggaacggag ccacgccact tcatggccat cttcaaaggg   2700
aagctagtta tctttgaggg tgggacttcc aggaagggaa atgccgagcc tgaccctcca   2760
gtaagactct tccaaattca tggaaatgac aaatctaaca ccaaagcagt ggaagttcca   2820
gcctttgcct cctccctaaa ctccaatgat gtctttctgc tgcgaactca ggcagagcac   2880
tacctgtggt atggcaaggg gtctagtggg gatgagcggg caatggctaa ggagctggcc   2940
agccttctct gtgatggcag cgagaacact gtggccgagg gccaggagcc agccgagttc   3000
tgggacctac tgggagggaa aactccctat gccaatgata aaagacttca gcaggaaatc   3060
ctagatgtcc agtctcgtct ctttgaatgt tccaataaga ccggccaatt cgttgtcact   3120
```

| | |
|---|---|
| gagatcacag acttcaccca ggatgacctg aaccctactg acgtgatgct cctagatacc | 3180 |
| tgggaccagg tgttcttgtg gattggggct gaggccaatg ccacggagaa ggagagtgcc | 3240 |
| cttgccacag cacagcagta cctgcacact cacccccagcg gccgagatcc cgacacacca | 3300 |
| atcctgatca ttaagcaggg gttttgagcct cccatcttca caggctggtt cctagcctgg | 3360 |
| gaccctaaca tttggagtgc aggaaaaaca tatgaacaat taaaagaaga gctgggagat | 3420 |
| gctgctgcta tcatgcgaat cactgctgac atgaagaatg caaccctctc cctgaattct | 3480 |
| aatgacagtg agccaaaata ttaccctata gcagttctgt tgaaaaacca gaatcaggag | 3540 |
| ctgcctgaga atgtaaaccc tgccaaaaag gagaattacc tctctgaaca ggactttgtg | 3600 |
| tctgtgtttg gcatcacaag agggcaattt gcagctctgc ctggctggaa acagctccaa | 3660 |
| atgaagaaag aaaaggggct tttctaa | 3687 |

<210> SEQ ID NO 2
<211> LENGTH: 2460
<212> TYPE: DNA
<213> ORGANISM: Homo sapiens

<400> SEQUENCE: 2

| | |
|---|---|
| atgcctctga ccagtgcctt cagggctgtg acaacgacc ctgggatcat tgtctggaga | 60 |
| atagagaaaa tggagctggc gctggtgcct gtgagcgccc acggcaactt ctatgagggg | 120 |
| gactgctacg tcatcctctc gacccggaga gtggccagtc cctatcccca ggacatccac | 180 |
| ttctggatcg gaaggactc ctcccaggat gagcaaagct cgcagccat atataccaca | 240 |
| cagctggacg actacctggg aggcagccct gtgcagcacc gagaggtcca gtaccatgag | 300 |
| tcagacactt ccgtggcta cttcaagcag ggcatcatct acaagcaggg gggtgtcgcc | 360 |
| tctgggatga agcacgtgga gaccaatacc tacgacgtga agcggctgct acatgtgaaa | 420 |
| gggaaaagaa acatcagggc taccgaggtg gaaatgagct gggacagttt caaccgaggt | 480 |
| gatgtcttct tgctggacct tgggaaagtc atcatccaat ggaatggccc agagagcaac | 540 |
| agtggggagc gcctgaaggc tatgcttctg gcaaaggata ttcgagacag ggagcgaggg | 600 |
| ggccgtgcta aaataggagt gatcgaggga acaaggagg cagccagccc agagctgatg | 660 |
| aaggtccttc aggacaccct tggccgacgc tccattatca agcctacagt ccctgatgag | 720 |
| atcatagatc agaagcagaa atcaactatc atgttgtatc atatctcaga ttcagctggg | 780 |
| cagctggcag tcacagaggt agcaacaagg cctctggtcc aggacttact gaaccatgat | 840 |
| gactgctaca tcctggacca aagtggaacc aaaatctacg tgtggaaagg aaaaggagcc | 900 |
| acaaaggctg aaaacaggc agccatgtct aaagcgctgg gcttcatcaa gatgaagagc | 960 |
| tacccccagca gcaccaatgt ggagaccgtc aacgatggtg ctgagtcggc catgttcaag | 1020 |
| cagctgttcc agaagtggtc agtaaaggac cagaccatgg gcctggggaa aacgttcagc | 1080 |
| attggtaaaa ttgctaaagt tttccaggat aaatttgatg tgactctgct acacaccaag | 1140 |
| ccagaggtag ctgcccagga agaatggtc gatgatggca acggaaaagt tgaggtctgg | 1200 |
| agaattgaga acctggagct ggtccctgtg gagtatcaat ggtatggctt cttttatggg | 1260 |
| ggagactgtt atctggtcct ctacacatac gaggtaaatg gaagccaca tcacatcttg | 1320 |
| tacatctggc agggccgcca cgcctcacag gatgagctgg cagcctcagc ataccaggca | 1380 |
| gtggaggtgg atcggcagtt tgatgggget gctgtgcagg ttcgagtcag gatgggaacg | 1440 |
| gagccacgcc acttcatggc catcttcaaa gggaagctag ttatctttga gggtgggact | 1500 |

```
tccaggaagg gaaatgccga gcctgaccct ccagtaagac tcttccaaat tcatggaaat   1560
gacaaatcta acaccaaagc agtggaagtt ccagcctttg cctcctccct aaactccaat   1620
gatgtctttc tgctgcgaac tcaggcagag cactacctgt ggtatggcaa ggggtctagt   1680
ggggatgagc gggcaatggc taaggagctg gccagccttc tctgtgatgg cagcgagaac   1740
actgtggccg agggccagga gccagccgag ttctgggacc tactgggagg gaaaactccc   1800
tatgccaatg ataaaagact tcagcaggaa atcctagatg tccagtctcg tctctttgaa   1860
tgttccaata agaccggcca attcgttgtc actgagatca cagacttcac ccaggatgac   1920
ctgaacccta ctgacgtgat gctcctagat acctgggacc aggtgttctt gtggattggg   1980
gctgaggcca atgccacgga gaaggagagt gcccttgcca cagcacagca gtacctgcac   2040
actcacccca gcggccgaga tcccgacaca ccaatcctga tcattaagca gggggtttgag  2100 cctcccatct tcacaggctg gttcctagcc tgggacccta catttggag tgcaggaaaa    2160 acatatgaac aattaaaaga agagctggga gatgctgctg ctatcatgcg aatcactgct   2220
gacatgaaga atgcaaccct ctccctgaat tctaatgaca gtgagccaaa atattaccct   2280
atagcagttc tgttgaaaaa ccagaatcag gagctgcctg aggatgtaaa ccctgccaaa   2340
aaggagaatt acctctctga acaggacttt gtgtctgtgt ttggcatcac aagagggcaa   2400
tttgcagctc tgcctggctg gaaacagctc caaatgaaga agaaaagggg cttttctaa    2460

<210> SEQ ID NO 3
<211> LENGTH: 19
<212> TYPE: RNA
<213> ORGANISM: Artificial Sequence
<220> FEATURE:
<223> OTHER INFORMATION: Synthetic Construct

<400> SEQUENCE: 3
gcuucuggca aaggauauu                                                 19

<210> SEQ ID NO 4
<211> LENGTH: 19
<212> TYPE: RNA
<213> ORGANISM: Artificial Sequence
<220> FEATURE:
<223> OTHER INFORMATION: Synthetic Construct

<400> SEQUENCE: 4
ccacacagcu ggacgacua                                                 19

<210> SEQ ID NO 5
<211> LENGTH: 19
<212> TYPE: RNA
<213> ORGANISM: Artificial Sequence
<220> FEATURE:
<223> OTHER INFORMATION: Synthetic Construct

<400> SEQUENCE: 5
gcaaaggaua uucgagaca                                                 19

<210> SEQ ID NO 6
<211> LENGTH: 19
<212> TYPE: RNA
<213> ORGANISM: Artificial Sequence
<220> FEATURE:
<223> OTHER INFORMATION: Synthetic Construct

<400> SEQUENCE: 6
gcaccaaugu ggagaccgu                                                 19
```

```
<210> SEQ ID NO 7
<211> LENGTH: 19
<212> TYPE: RNA
<213> ORGANISM: Artificial Sequence
<220> FEATURE:
<223> OTHER INFORMATION: Synthetic Construct

<400> SEQUENCE: 7
ggaaagaaug gucgaugau                                              19

<210> SEQ ID NO 8
<211> LENGTH: 19
<212> TYPE: RNA
<213> ORGANISM: Artificial Sequence
<220> FEATURE:
<223> OTHER INFORMATION: Synthetic Construct

<400> SEQUENCE: 8 gcauccuug cuuguuaua                                               19

<210> SEQ ID NO 9
<211> LENGTH: 19
<212> TYPE: RNA
<213> ORGANISM: Artificial Sequence
<220> FEATURE:
<223> OTHER INFORMATION: Synthetic Construct

<400> SEQUENCE: 9
gagcuuaaga aauggagc                                               19
```

COMPOUNDS AND METHODS FOR REGULATING, LIMITING, OR INHIBITING *AVIL* EXPRESSION

CROSS-REFERENCE TO RELATED APPLICATIONS

This application is a continuation application of U.S. nonprovisional application Ser. No. 16/759,210 filed on Apr. 24, 2020, which is a US national phase application under 35 USC § 371 of international application no. PCT/US2018/057697, filed Oct. 26, 2018, which claims the benefit of U.S. Provisional Application No. 62/577,749, filed on Oct. 27, 2017. Each application is incorporated herein by reference in its entirety.

CROSS REFERENCE TO SEQUENCE LISTING

The genetic components described herein are referred to by sequence identifier numbers (SEQ ID NO). The SEQ ID NOs correspond numerically to the sequence identifiers <400>1, <400>2, etc. The Sequence Listing, filed in electronic form as an ASCII.txt file entitled 222117_1061_sequ_list_ST25.txt in written computer readable format (CRF) having file size 9.59 kilobytes, created on Jul. 8, 2022, is incorporated by reference in its entirety.

BACKGROUND

Understanding the molecular mechanisms involved genesis and maintenance of cancer, as well as developing therapies which may help prevent or manage cancerous growth continue to be active areas of research. Work over the last decade is providing evidence that at least certain kinds of cancers may depend on a single oncogene or oncogenic pathway for growth, proliferation and survival. Oncogene addiction describes a phenomenon according to which tumor cells become reliant on the activity of a particular oncogene and die once this activity is inhibited. (Vivanco, 2014; Weinstein, 2002; Weinstein and Joe, 2006). Many recent targeted cancer therapies exploit this concept (Lord and Ashworth, 2013; Luo et al., 2009). It is perhaps best exemplified by the successful use of imatinib in the therapy of chronic myelogenous leukemia (CML) (Druker et al., 2001). In CML, the major driver of tumorigenesis is the BCR-ABL fusion oncogene; imatinib inhibits the constitutively active BCR-ABL protein kinase, to which leukemic cells become addicted. Other successful examples include trastuzumab targeting ERBB2 addiction (Paik et al., 2008), and vemurafenib targeting BRAF addiction (Bollag et al., 2010; Chapman et al., 2011; Davies et al., 2002). The challenge is to find such key oncogenes. Even though large sets of genome and transcriptome data are available to facilitate the identification of driver mutations in cancer, true signals are often buried in a large number of passenger events.

Despite advances in cancer research, better treatment options, and identification of novel therapeutic targets are needed. These needs and other needs are satisfied by the present disclosure.

SUMMARY

In accordance with the purpose(s) of the invention, as embodied and broadly described herein, the invention, in one aspect, relates to compounds useful to regulate, limit, or inhibit the expression of AVIL (advillin), methods of making same, pharmaceutical compositions comprising same, and methods of treating disorders associated with AVIL dysregulation using same. In aspects, the disclosed compounds, compositions and methods are useful for treating disorders or diseases in which the regulation, limitation, or inhibition of the expression of AVIL can be clinically useful, such as, for example, the treatment of cancer.

According to various aspects, the compounds comprise one of Compounds A-L:

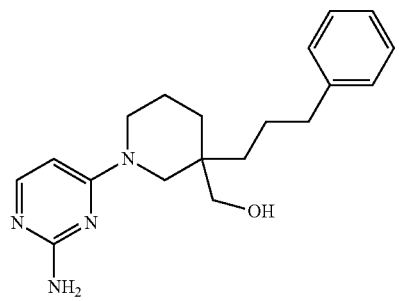

Compound A:
(1-(2-aminopyrimidin-4-yl)-3-(3-phenylpropyl)piperidin-3-yl)methanol

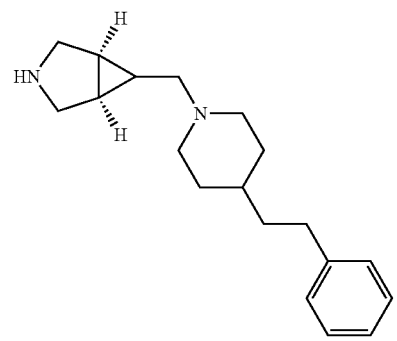

Compound B:
(1R,5S)-6-((4-phenethylpiperidin-1-yl)methyl)-3-azabicyclo[3.1.0]hexane

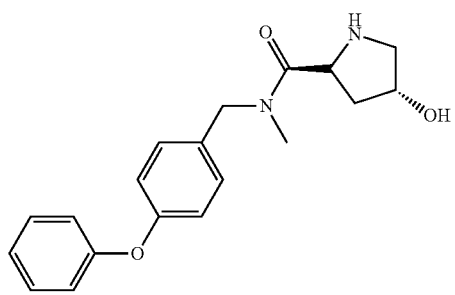

Compound C:
(2S,4R)-4-hydroxy-N-methyl-N-(4-phenoxybenzyl)pyrrolidine-2-carboxamide

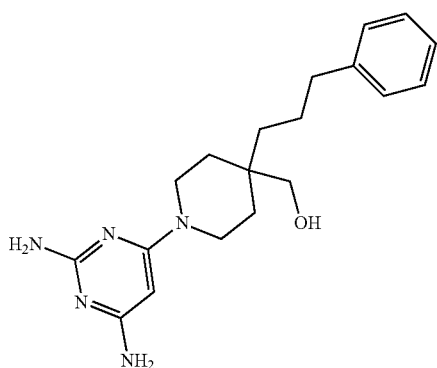

Compound D:
(1-(2,6-diaminopyrimidin-4-yl)-4-(3-
phenylpropyl)piperidin-4-yl)methanol

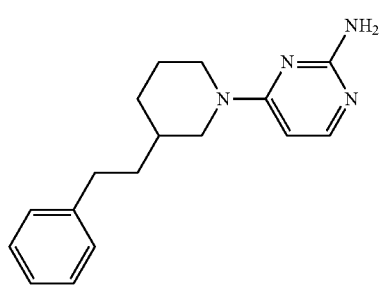

Compound E:
4-(3-phenethylpiperidin-1-yl)pyrimidin-2-amine

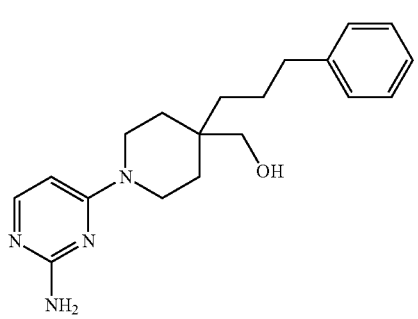

Compound F:
(1-(2-aminopyrimidin-4-yl)-4-(3-
phenylpropyl)piperidin-4-yl)methanol

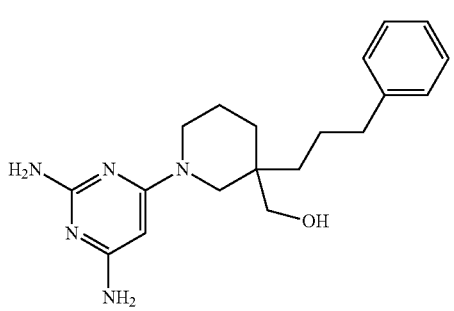

Compound G:
(1-(2,6-diaminopyrimidin-4-yl)-3-(3-
phenylpropyl)piperidin-3-yl)methanol

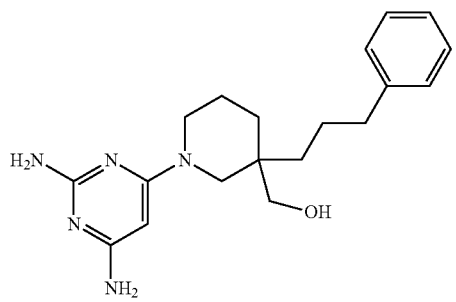

Compound H:
(1-(2,6-diaminopyrimidin-4-yl)-3-(3-
phenylpropyl)piperidin-3-yl)methanol

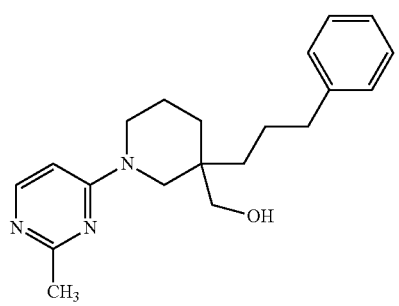

Compound I:
(1-(2,6-methylpyrimidin-4-yl)-3-(3-
phenylpropyl)piperidin-3-yl)methanol

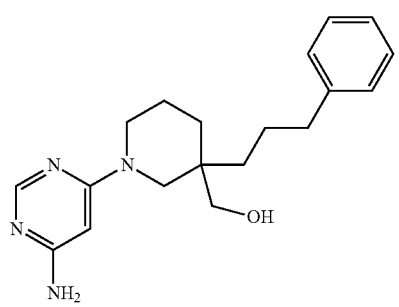

Compound J:
(1-(6-aminopyrimidin-4-yl)-3-(3-
phenylpropyl)piperidin-3-yl)methanol

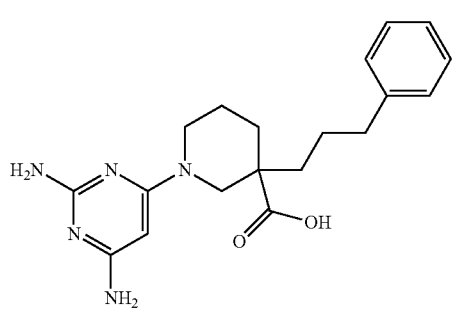

Compound K:
1-(2,6-diaminopyrimidin-4-yl)-3-(3-
phenylpropyl)piperidine-3-carboxylic acid

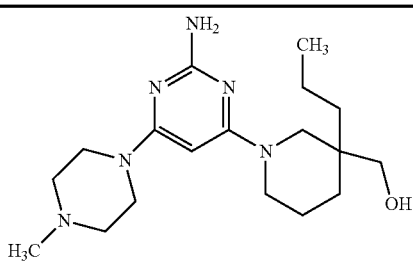

Compound L:
(1-(2-amino-6-(4-methylpiperazin-1-yl)
pyrimidin-4-yl)-3-propylpiperidin-3-yl)
methanol In each case, the compound can include a pharmaceutically-acceptable salt, solvate, or polymorph thereof.

Also disclosed are pharmaceutical compositions comprising a therapeutically effective amount of one or more disclosed compounds, or pharmaceutically acceptable salt thereof, and a pharmaceutically acceptable carrier.

Also disclosed are methods for the treatment of an oncological disorder or disease associated with dysregulation of AVIL in a mammal comprising the step of administering to the mammal a therapeutically effective amount of at least one disclosed compound or pharmaceutically acceptable salt thereof.

Also disclosed are methods for regulating, limiting, or inhibiting AVIL expression in a mammal comprising the step of administering to the mammal a therapeutically effective amount of at least one disclosed compound or pharmaceutically acceptable salt thereof.

Also disclosed are methods for regulating, limiting, or inhibiting AVIL expression in at least one cell, comprising the step of contacting the cell with an effective amount of at least one disclosed compound or pharmaceutically acceptable salt thereof.

Also disclosed are uses of a disclosed compound, or a pharmaceutically acceptable salt thereof; a disclosed product of making, or a pharmaceutically acceptable salt thereof; or a disclosed pharmaceutical composition.

Also disclosed are uses of a disclosed compound, or a pharmaceutically acceptable salt thereof, in the manufacture of a medicament for the treatment of a disorder associated with dysregulation of AVIL in a mammal.

Also disclosed are methods for the manufacture of a medicament to regulate, limit, or inhibit AVIL expression in a mammal comprising combining at least one disclosed compound, or a pharmaceutically acceptable salt thereof with a pharmaceutically acceptable carrier or diluent.

Also disclosed are kits comprising at least one disclosed compound, or a pharmaceutically acceptable salt, hydrate, solvate, or polymorph thereof, and one or more of: (a) at least one agent known to regulate, limit, or inhibit AVIL expression; (b) at least one agent known to treat cancer; and (c) instructions for treating cancer and/or for administering the compound in connection with cancer therapy.

While aspects of the present disclosure can be described and claimed in a particular statutory class, such as the system statutory class, this is for convenience only and one of skill in the art will understand that each aspect of the present disclosure can be described and claimed in any statutory class. Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

BRIEF DESCRIPTION OF THE FIGURES

The accompanying figures, which are incorporated in and constitute a part of this specification, illustrate several aspects and together with the description serve to explain the principles of the disclosure.

FIGS. 2A-2I show representative data demonstrating that MARS-AVIL is important for rhabdomyosarcoma tumorigenesis, as described further in Example 1. (A) RH30 cells were transfected with siAVIL1, siAVIL2, or siGL2 as control (siCT). Cell cycle analyses were performed with PI staining and FACS. Arrow points to a sub-G1 peak, indicating the population of apoptotic cells. (B) Western blot using MARS, PARP, cleaved Caspase3, and GAPDH antibodies. (C) Crystal violet staining of RH30 and RH18 cell cultures, transfected with the same set of siRNAs as in (A). (D) Cell counting and MTT assays of RH30 cells stably expressing shAVIL1, or shCT. (E) and (F) Ectopic expression of MARS-AVIL in RD and RH18 cells. The level of the transgene is similar to that of RH30 cells (left). MTT assay was used to measure cell proliferation of cells stably infected with MARS-AVIL or control viral plasmid (middle). Wound healing assay was performed to measure cell motility (right). (G) Xenografts of RH30 cells expressing shAVIL1, or control (shCT). The tumors were harvested at the end of the experiment, and pictured (n=10). (H) Tumor volume (right) and tumor weight (left) comparison between the two groups. (I) Percent survival of the animals was plotted according to Kaplan-Meier analysis. (* p<0.05,  p<0.01, * p<0.001).

FIGS. 3A-3G show representative data demonstrating that AVIL is frequently up-regulated in glioblastomas, as described further in Example 1. (A) Cross-cancer analysis of mutations and copy number variation from cBioPortal. The AVIL locus is amplified in about 15% (TCGA GBM provisional), or 18% (TCGA GBM 2008 study) of GBMs. (B) FISH analysis using a probe covering the AVIL locus in GBM cell lines SF767, A172, U87, and an immortalized astrocyte culture. (C) qRT-PCR measuring AVIL mRNA level in GBMs, and control astrocytes. AVIL RNA expression was normalized against that of GAPDH. (D) Western blot measuring AVIL protein expression in GBM cells, astrocytes, siAVIL treated GBM cells, and 293T overexpression cells. GAPDH was used as an internal loading control. Arrow points to Myc-AVIL. (E) AVIL expression in REMBRANDT database with microarray data of 28 non-tumor brain tissues, 148 astrocytomas (WHO grade II or III), and 228 GBM (WHO grade IV) cases. Results from two microarray probes are shown. (F) qRT-PCR summary of our own collection consisted of 8 non-tumor brain tissues, and 36 GBM cases. AVIL level was normalized against that of GAPDH. (G) Western blot measuring AVIL protein in 12 non-tumor (N1-N12), and 14 GBM (T1-T14) samples. P value is calculated by standard two-tailed t-test. (* $p<0.05$,  $p<0.01$, * $p<0.001$).

FIGS. 5A-5J show representative data demonstrating that AVIL regulates LIN28B, cell shape, and spreading, as described further in Example 1. (A) Microarray analyses of U87 cells transfected with siAVIL vs. siCT, and stable AVIL overexpression cells vs. empty vector control (CT). (B) Candidate targets were validated by qRT-PCR. Their relative expression level was plotted against that of siCT or CT. (C) Let-7 family members that are expressed in U87 were measured by qRT-PCR. Their expression levels were plotted against that of siCT, or CT. (D) LIN28B mediates at least some of the AVIL effect. U87 (left), or U373 (right) cells transfected with siAVIL or siCT were further transfected with LIN28B expression vector, or control plasmid (CT). Cell proliferation was measured by cell counting. (E) Cell motility was measured by wound-healing assay. (F) AVIL protein colocalizes with F-actin. GFP-AVIL plasmid was transfected in 293T (upper), or Hela (lower) cells. Rhodamine-phalloidin was used to stain actin filaments (F-actin). Confocal microscopy was used to confirm colocalization of the signals. (G) Silencing AVIL resulted in cell shape change, and actin ruffling. U87, U251, A172, and astrocyte cells were transfected with siAVIL1, or siCT. Rhodamine-phalloidin was used to stain F-actin. (H) Silencing AVIL resulted in reduced ability of A172 cells to spread. Silhouettes of cells were imaged 1.5 hrs after the cells were plated on fibronectin-coated slides. (I) Cell area was plotted for A172 cells transfected with siCT, or siAVIL1. Significant difference ($p<0.002$) was observed by the Rank-Sum test (non-parametric test for non-normally distributed data). (J) Electro microscopy confirmed advillin binding to F-actin. Recombinant advillin was incubated with F-actin filaments. Arrows point to the representative bindings of advillin with F-actin. (* $p<0.05$,  $p<0.01$, * $p<0.001$).

FIG. 8B shows representative data demonstrating Sanger sequencing results from long-ranged PCR (top) and RT-PCR (bottom). Regions belonging to MARS are represented by normal font. Regions belonging to AVIL are represented by underlined font.

FIGS. 8H-8I show representative data demonstrating that MARS is expressed ubiquitously, but AVIL is more tissue-specific. (H) Oncomine data. (I) GTEx data.

Figure 1A:
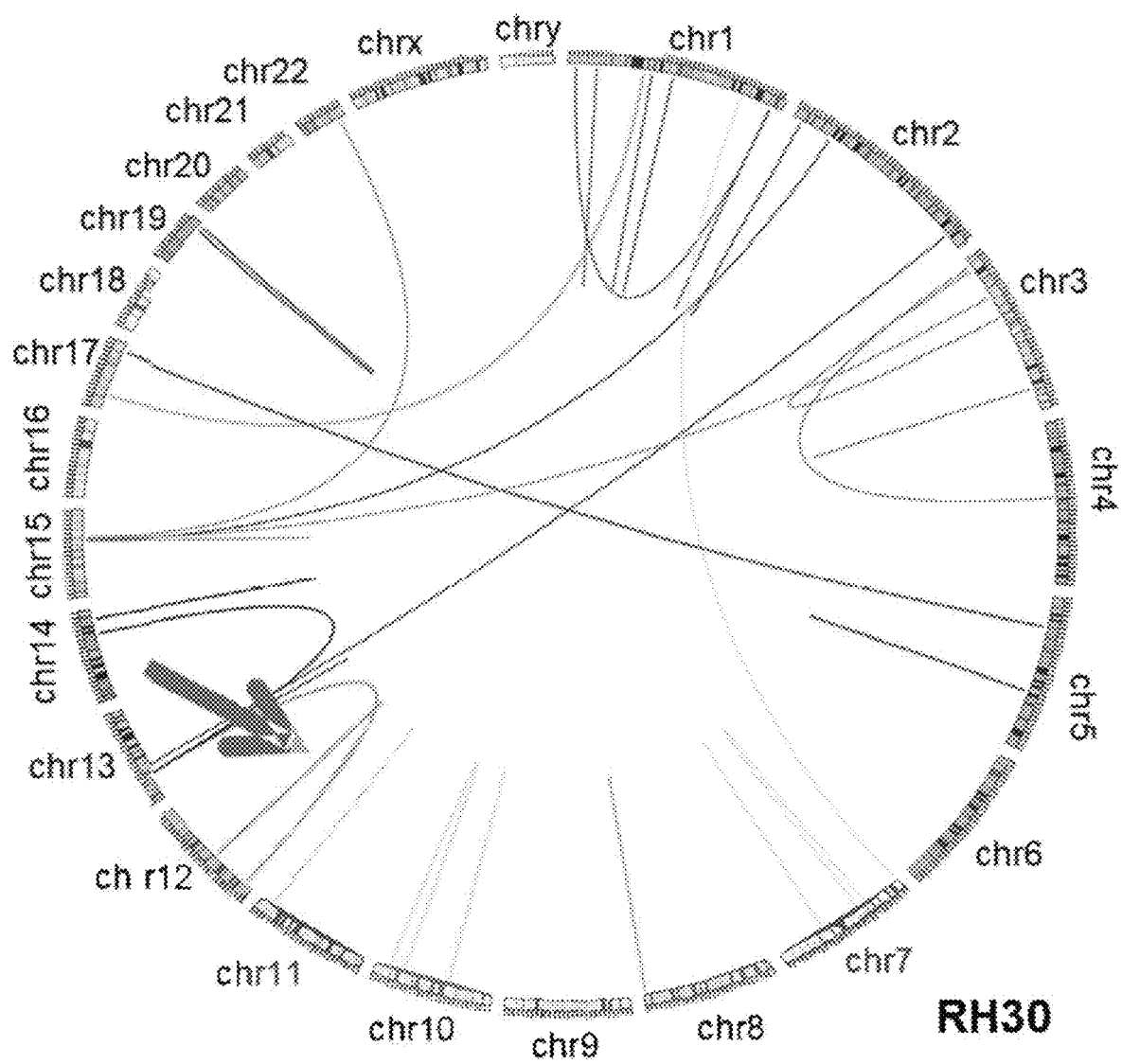
FIGS. 1A-1E show representative data demonstrating the MARS-AVIL fusion in rhabdomyosarcoma, as described further in Example 1. (A) Circos plots showing chimeric fusion transcripts from the RNA-sequencing of RH30, RMS-13 and A673 cells. Lines connect the parental genes. Arrow points to the MARS-AVIL fusion. Due to the closeness of the two genes, the pin collapsed into a half line. (B) The fusion is composed of the first 10 exons of MARS and last 18 exons of AVIL. Lower panel is a Sanger sequencing result for the chimeric RNA. Dotted line indicates the junction site. (C) Long range PCR with genomic DNA from RH30, RH18, and mesenchymal stem cells (MSC). The same primers for RT-PCR were used. (D) The fusion transcript encodes an in-frame chimeric protein. Western blot using MARS antibody. siAVIL1 targets both wild type AVIL and the fusion. 293T cells expressing exogenous Myc-tagged fusion was also included as control. (E) Detection of the fusion in clinical samples. RT-PCR of 14 clinical cases of rhabdomyosarcomas; MARS-AVIL was found in eight of them.

Additional advantages of the disclosure will be set forth in part in the description which follows, and in part will be obvious from the description, or can be learned by practice of the disclosure. The advantages of the disclosure will be realized and attained by means of the elements and combinations particularly pointed out in the appended claims. It is to be understood that both the foregoing general description and the following detailed description are exemplary and explanatory only and are not restrictive of the disclosure, as claimed.

DETAILED DESCRIPTION

Many modifications and other embodiments disclosed herein will come to mind to one skilled in the art to which the disclosed compositions and methods pertain having the benefit of the teachings presented in the foregoing descriptions and the associated drawings. Therefore, it is to be understood that the disclosures are not to be limited to the specific embodiments disclosed and that modifications and other embodiments are intended to be included within the scope of the appended claims. The skilled artisan will recognize many variants and adaptations of the aspects described herein. These variants and adaptations are intended to be included in the teachings of this disclosure and to be encompassed by the claims herein.

Although specific terms are employed herein, they are used in a generic and descriptive sense only and not for purposes of limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure.

Any recited method can be carried out in the order of events recited or in any other order that is logically possible. That is, unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

All publications and patents cited in this specification are cited to disclose and describe the methods and/or materials in connection with which the publications are cited. All such publications and patents are herein incorporated by references as if each individual publication or patent were specifically and individually indicated to be incorporated by reference. Such incorporation by reference is expressly limited to the methods and/or materials described in the cited publications and patents and does not extend to any lexicographical definitions from the cited publications and patents. Any lexicographical definition in the publications and patents cited that is not also expressly repeated in the instant application should not be treated as such and should not be read as defining any terms appearing in the accompanying claims. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

While aspects of the present disclosure can be described and claimed in a particular statutory class, such as the system statutory class, this is for convenience only and one of skill in the art will understand that each aspect of the present disclosure can be described and claimed in any statutory class.

It is also to be understood that the terminology used herein is for the purpose of describing particular aspects only and is not intended to be limiting. Unless defined otherwise, all technical and scientific terms used herein have the same meaning as commonly understood by one of ordinary skill in the art to which the disclosed compositions and methods belong. It will be further understood that terms, such as those defined in commonly used dictionaries, should be interpreted as having a meaning that is consistent with their meaning in the context of the specification and relevant art and should not be interpreted in an idealized or overly formal sense unless expressly defined herein.

Aspects of the present disclosure will employ, unless otherwise indicated, techniques of molecular biology, microbiology, organic chemistry, biochemistry, physiology, cell biology, blood vessel biology, and the like, which are within the skill of the art. Such techniques are explained fully in the literature.

Prior to describing the various aspects of the present disclosure, the following definitions are provided and should be used unless otherwise indicated. Additional terms may be defined elsewhere in the present disclosure.

Definitions

As used herein, "comprising" is to be interpreted as specifying the presence of the stated features, integers, steps, or components as referred to, but does not preclude the presence or addition of one or more features, integers, steps, or components, or groups thereof. Moreover, each of the terms "by", "comprising," "comprises", "comprised of," "including," "includes," "included," "involving," "involves," "involved," and "such as" are used in their open, non-limiting sense and may be used interchangeably. Further, the term "comprising" is intended to include examples and aspects encompassed by the terms "consisting essentially of" and "consisting of." Similarly, the term "consisting essentially of" is intended to include examples encompassed by the term "consisting of.

As used in the specification and the appended claims, the singular forms "a," "an" and "the" include plural referents unless the context clearly dictates otherwise.

It should be noted that ratios, concentrations, amounts, and other numerical data can be expressed herein in a range format. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. Ranges can be expressed herein as from "about" one particular value, and/or to "about" another particular value. Similarly, when values are expressed as approximations, by use of the antecedent "about," it will be understood that the particular value forms a further aspect. For example, if the value "about 10" is disclosed, then "10" is also disclosed.

Where a range is expressed, a further aspect includes from the one particular value and/or to the other particular value. Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure. For example, where the stated range includes one or both of the limits, ranges excluding either or both of those included limits are also included in the disclosure, e.g. the phrase "x to y" includes the range from 'x' to 'y' as well as the range greater than 'x' and less than 'y'. The range can also be expressed as an upper limit, e.g. 'about x, y, z, or less' and should be interpreted to include the specific ranges of 'about x', 'about y', and 'about z' as well as the ranges of 'less than x', less than y', and 'less than z'. Likewise, the phrase 'about x, y, z, or greater' should be interpreted to include the specific ranges of 'about x', 'about y', and 'about z' as well as the ranges of 'greater than x', greater than y', and 'greater than z'. In addition, the phrase "about 'x' to 'y'", where 'x' and 'y' are numerical values, includes "about 'x' to about 'y'".

It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a numerical range of "about 0.1% to 5%" should be interpreted to include not only the explicitly recited values of about 0.1% to about 5%, but also include individual values (e.g., about 1%, about 2%, about 3%, and about 4%) and the sub-ranges (e.g., about 0.5% to about 1.1%; about 5% to about 2.4%; about 0.5% to about 3.2%, and about 0.5% to about 4.4%, and other possible sub-ranges) within the indicated range.

As used herein, "about," "approximately," "substantially," and the like, when used in connection with a numerical variable, can generally refers to the value of the variable and to all values of the variable that are within the experimental error (e.g., within the 95% confidence interval for the mean) or within +1-10% of the indicated value, whichever is greater. As used herein, the terms "about," "approximate," "at or about," and "substantially" can mean that the amount or value in question can be the exact value or a value that provides equivalent results or effects as recited in the claims or taught herein. That is, it is understood that amounts, sizes, formulations, parameters, and other quantities and characteristics are not and need not be exact, but may be approximate and/or larger or smaller, as desired, reflecting tolerances, conversion factors, rounding off, measurement error and the like, and other factors known to those of skill in the art such that equivalent results or effects are obtained. In some circumstances, the value that provides equivalent results or effects cannot be reasonably determined. In general, an amount, size, formulation, parameter or other quantity or characteristic is "about," "approximate," or "at or about" whether or not expressly stated to be such. It is understood that where "about," "approximate," or "at or about" is used before a quantitative value, the parameter also includes the specific quantitative value itself, unless specifically stated otherwise.

As used herein, the terms "optional" or "optionally" means that the subsequently described event or circumstance can or cannot occur, and that the description includes instances where said event or circumstance occurs and instances where it does not.

As used herein, "advillin" and "AVIL" can be used interchangeably, and refer to a protein encoded by a gene in humans with a cytogenetic location of 12q14.1 and a molecular location of base pairs 57,797,376 to 57,818,704 on chromosome 12 (*Homo sapiens* Annotation Release 109, GRCh38.p12). The protein encoded by this gene is a member of the gelsolin/villin family of actin-regulatory proteins. AVIL has also been referred to as Actin-binding protein DOC6, DOC6, P92, ADVIL.

As used herein, "administering" can refer to an administration that is oral, topical, intravenous, subcutaneous, transcutaneous, transdermal, intramuscular, intra-joint, parenteral, intra-arteriole, intradermal, intraventricular, intraosseous, intraocular, intracranial, intraperitoneal, intralesional, intranasal, intracardiac, intraarticular, intracavernous, intrathecal, intravireal, intracerebral, and intracerebroventricular, intratympanic, intracochlear, rectal, vaginal, by inhalation, by catheters, stents or via an implanted reservoir or other device that administers, either actively or passively (e.g. by diffusion) a composition the perivascular space and adventitia. For example a medical device such as a stent can contain a composition or formulation disposed on its surface, which can then dissolve or be otherwise distributed to the surrounding tissue and cells. The term "parenteral" can include subcutaneous, intravenous, intramuscular, intra-articular, intra-synovial, intrasternal, intrathecal, intrahepatic, intralesional, and intracranial injections or infusion techniques. Administration can be continuous or intermittent. In various aspects, a preparation can be administered therapeutically; that is, administered to treat an existing disease or condition. In further various aspects, a preparation can be administered prophylactically; that is, administered for prevention of a disease or condition.

As used herein, "therapeutic agent" can refer to any substance, compound, molecule, and the like, which can be biologically active or otherwise can induce a pharmacologic, immunogenic, biologic and/or physiologic effect on a subject to which it is administered to by local and/or systemic action. A therapeutic agent can be a primary active agent, or in other words, the component(s) of a composition to which the whole or part of the effect of the composition is attributed. A therapeutic agent can be a secondary therapeutic agent, or in other words, the component(s) of a composition to which an additional part and/or other effect of the composition is attributed. The term therefore encompasses those compounds or chemicals traditionally regarded as drugs, vaccines, and biopharmaceuticals including molecules such as proteins, peptides, hormones, nucleic acids, gene constructs and the like. Examples of therapeutic agents are described in well-known literature references such as the Merck Index (14th edition), the Physicians' Desk Reference (64th edition), and The Pharmacological Basis of Therapeutics (12th edition), and they include, without limitation, medicaments; vitamins; mineral supplements; substances used for the treatment, prevention, diagnosis, cure or mitigation of a disease or illness; substances that affect the structure or function of the body, or pro-drugs, which become biologically active or more active after they have been placed in a physiological environment. For example, the term "therapeutic agent" includes compounds or compositions for use in all of the major therapeutic areas including, but not limited to, adjuvants; anti-infectives such as antibiotics and antiviral agents; analgesics and analgesic combinations, anorexics, anti-inflammatory agents, anti-epileptics, local and general anesthetics, hypnotics, sedatives, antipsychotic agents, neuroleptic agents, antidepressants, anxiolytics, antagonists, neuron blocking agents, anticholinergic and cholinomimetic agents, antimuscarinic and muscarinic agents, antiadrenergics, antiarrhythmics, antihypertensive agents, hormones, and nutrients, antiarthritics, antiasthmatic agents, anticonvulsants, antihistamines, antinauseants, antineoplastics, antipruritics, antipyretics; antispasmodics, cardiovascular preparations (including calcium channel blockers, beta-blockers, beta-agonists and antiarrythmics), antihypertensives, diuretics, vasodilators; central nervous system stimulants; cough and cold preparations; decongestants; diagnostics; hormones; bone growth stimulants and bone resorption inhibitors; immunosuppressives; muscle relaxants; psychostimulants; sedatives; tranquilizers; proteins, peptides, and fragments thereof (whether naturally occurring, chemically synthesized or recombinantly produced); and nucleic acid molecules (polymeric forms of two or more nucleotides, either ribonucleotides (RNA) or deoxyribonucleotides (DNA) including both double- and single-stranded molecules, gene constructs, expression vectors, antisense molecules and the like), small molecules (e.g., doxorubicin) and other biologically active macromolecules such as, for example, proteins and enzymes. The agent may be a biologically active agent used in medical, including veterinary, applications and in agriculture, such as with plants, as well as other areas. The term therapeutic agent also includes without limitation, medicaments; vitamins; mineral supplements; substances used for the treatment, prevention, diagnosis, cure or mitigation of disease or illness; or substances which affect the structure or function of the body; or pro-drugs, which become biologically active or more active after they have been placed in a predetermined physiological environment.

As used herein, "kit" means a collection of at least two components constituting the kit. Together, the components constitute a functional unit for a given purpose. Individual member components may be physically packaged together or separately. For example, a kit comprising an instruction for using the kit may or may not physically include the instruction with other individual member components. Instead, the instruction can be supplied as a separate member component, either in a paper form or an electronic form which may be supplied on computer readable memory device or downloaded from an internet website, or as recorded presentation.

As used herein, "instruction(s)" means documents describing relevant materials or methodologies pertaining to a kit. These materials may include any combination of the following: background information, list of components and their availability information (purchase information, etc.), brief or detailed protocols for using the kit, trouble-shooting, references, technical support, and any other related documents. Instructions can be supplied with the kit or as a separate member component, either as a paper form or an electronic form which may be supplied on computer readable memory device or downloaded from an internet website, or as recorded presentation. Instructions can comprise one or multiple documents, and are meant to include future updates.

As used herein, "attached" can refer to covalent or non-covalent interaction between two or more molecules. Non-covalent interactions can include ionic bonds, electrostatic interactions, van der Walls forces, dipole-dipole interactions, dipole-induced-dipole interactions, London dispersion forces, hydrogen bonding, halogen bonding, electromagnetic interactions, π-π interactions, cation-π interactions, anion-π interactions, polar π-interactions, and hydrophobic effects.

As used interchangeably herein, "subject," "individual," or "patient" can refer to a vertebrate organism, such as a mammal (e.g. human). "Subject" can also refer to a cell, a population of cells, a tissue, an organ, or an organism, preferably to human and constituents thereof. Thus, the subject can be a human, non-human primate, horse, pig, rabbit, dog, sheep, goat, cow, cat, guinea pig or a rodent. The term does not denote a particular age or sex. Moreover, adult and newborn subjects, as well as fetuses, whether male or female, are intended to be included. A "patient" refers to a subject afflicted with a clinical condition, disease or disorder.

As used herein, the terms "treating" and "treatment" can refer generally to obtaining a desired pharmacological and/or physiological effect. The effect can be, but does not necessarily have to be, prophylactic in terms of preventing or partially preventing a disease, symptom or condition thereof, such as cancer, or a disease or disorder associated with increased, aberrant, or dysfunctional levels of AVIL. The effect can be therapeutic in terms of a partial or complete cure of a disease, condition, symptom or adverse effect attributed to the disease, disorder, or condition. The term "treatment" as used herein can include any treatment of cancer, or a disease or disorder associated with increased, aberrant, or dysfunctional levels of AVIL, in a subject, particularly a human and can include any one or more of the following: (a) preventing the disease from occurring in a subject which may be predisposed to the disease but has not yet been diagnosed as having it; (b) inhibiting the disease, i.e., arresting its development; and (c) relieving the disease, i.e., mitigating or ameliorating the disease and/or its symptoms or conditions. The term "treatment" as used herein can refer to both therapeutic treatment alone, prophylactic treatment alone, or both therapeutic and prophylactic treatment. Those in need of treatment (subjects in need thereof) can include those already with the disorder and/or those in which the disorder is to be prevented. As used herein, the term "treating", can include inhibiting the disease, disorder or condition, e.g., impeding its progress; and relieving the disease, disorder, or condition, e.g., causing regression of the disease, disorder and/or condition. Treating the disease, disorder, or condition can include ameliorating at least one symptom of the particular disease, disorder, or condition, even if the underlying pathophysiology is not affected, e.g., such as treating the pain of a subject by administration of an analgesic agent even though such agent does not treat the cause of the pain.

As used herein, "dose," "unit dose," or "dosage" can refer to physically discrete units suitable for use in a subject, each unit containing a predetermined quantity of a disclosed compound and/or a pharmaceutical composition thereof calculated to produce the desired response or responses in association with its administration.

As used herein, "therapeutic" can refer to treating, healing, and/or ameliorating a disease, disorder, condition, or side effect, or to decreasing in the rate of advancement of a disease, disorder, condition, or side effect.

As used herein, "effective amount" can refer to the amount of a disclosed compound or pharmaceutical composition provided herein that is sufficient to effect beneficial or desired biological, emotional, medical, or clinical response of a cell, tissue, system, animal, or human. An effective amount can be administered in one or more administrations, applications, or dosages. The term can also include within its scope amounts effective to enhance or restore to substantially normal physiological function.

As used herein, the term "therapeutically effective amount" refers to an amount that is sufficient to achieve the desired therapeutic result or to have an effect on undesired symptoms, but is generally insufficient to cause adverse side effects. The specific therapeutically effective dose level for any particular patient will depend upon a variety of factors including the disorder being treated and the severity of the disorder; the specific composition employed; the age, body weight, general health, sex and diet of the patient; the time of administration; the route of administration; the rate of excretion of the specific compound employed; the duration of the treatment; drugs used in combination or coincidental with the specific compound employed and like factors within the knowledge and expertise of the health practitioner and which may be well known in the medical arts. In the case of treating a particular disease or condition, in some instances, the desired response can be inhibiting the progression of the disease or condition. This may involve only slowing the progression of the disease temporarily. However, in other instances, it may be desirable to halt the progression of the disease permanently. This can be monitored by routine diagnostic methods known to one of ordinary skill in the art for any particular disease. The desired response to treatment of the disease or condition also can be delaying the onset or even preventing the onset of the disease or condition.

For example, it is well within the skill of the art to start doses of a compound at levels lower than those required to achieve the desired therapeutic effect and to gradually increase the dosage until the desired effect is achieved. If desired, the effective daily dose can be divided into multiple doses for purposes of administration. Consequently, single dose compositions can contain such amounts or submultiples thereof to make up the daily dose. The dosage can be adjusted by the individual physician in the event of any contraindications. It is generally preferred that a maximum dose of the pharmacological agents of the invention (alone or in combination with other therapeutic agents) be used, that is, the highest safe dose according to sound medical judgment. It will be understood by those of ordinary skill in the art however, that a patient may insist upon a lower dose or tolerable dose for medical reasons, psychological reasons or for virtually any other reasons.

A response to a therapeutically effective dose of a disclosed compound and/or pharmaceutical composition, for example, can be measured by determining the physiological effects of the treatment or medication, such as the decrease or lack of disease symptoms following administration of the treatment or pharmacological agent. Other assays will be known to one of ordinary skill in the art and can be employed for measuring the level of the response. The amount of a treatment may be varied for example by increasing or decreasing the amount of a disclosed compound and/or pharmaceutical composition, by changing the disclosed compound and/or pharmaceutical composition administered, by changing the route of administration, by changing the dosage timing and so on. Dosage can vary, and can be administered in one or more dose administrations daily, for one or several days. Guidance can be found in the literature for appropriate dosages for given classes of pharmaceutical products.

As used herein, "$IC_{50}$," is intended to refer to the concentration of a substance (e.g., a compound or a drug) that is required for 50% inhibition of a biological process, or component of a process. For example, $IC_{50}$ refers to the half maximal (50%) inhibitory concentration (IC) of a substance as determined in a suitable assay. For example, an $IC_{50}$ for the activity of a compound disclosed herein can be determined in an in vitro or cell-based assay system using the methods described herein. Frequently, an assay, including suitable assays for AVIL, can make use of a suitable cell-line, e.g. a cell line that either expresses endogenously a target of interest, or has been transfected with a suitable expression vector that directs expression of a recombinant form of the target such as AVIL. For example, the $IC_{50}$ for the compounds disclosed herein can be determined using appropriate cells lines, e.g., glioblastoma cells (U87) and astrocyte cells (non-cancer control).

As used herein, the term "prophylactically effective amount" refers to an amount effective for preventing onset or initiation of a disease or condition.

As used herein, the term "prevent" or "preventing" refers to precluding, averting, obviating, forestalling, stopping, or hindering something from happening, especially by advance action. It is understood that where reduce, inhibit or prevent are used herein, unless specifically indicated otherwise, the use of the other two words is also expressly disclosed.

The term "pharmaceutically acceptable" describes a material that is not biologically or otherwise undesirable, i.e., without causing an unacceptable level of undesirable biological effects or interacting in a deleterious manner.

The term "pharmaceutically acceptable salts", as used herein, means salts of the active principal agents which are prepared with acids or bases that are tolerated by a biological system or tolerated by a subject or tolerated by a biological system and tolerated by a subject when administered in a therapeutically effective amount. When compounds of the present disclosure contain relatively acidic functionalities, base addition salts can be obtained by contacting the neutral form of such compounds with a sufficient amount of the desired base, either neat or in a suitable inert solvent. Examples of pharmaceutically acceptable base addition salts include, but are not limited to; sodium, potassium, calcium, ammonium, organic amino, magnesium salt, lithium salt, strontium salt or a similar salt. When compounds of the present disclosure contain relatively basic functionalities, acid addition salts can be obtained by contacting the neutral form of such compounds with a sufficient amount of the desired acid, either neat or in a suitable inert solvent. Examples of pharmaceutically acceptable acid addition salts include, but are not limited to; those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like.

The term "pharmaceutically acceptable ester" refers to esters of compounds of the present disclosure which hydrolyze in vivo and include those that break down readily in the human body to leave the parent compound or a salt thereof. Examples of pharmaceutically acceptable, non-toxic esters of the present disclosure include C 1-to-C 6 alkyl esters and C 5-to-C 7 cycloalkyl esters, although C 1-to-C 4 alkyl esters are preferred. Esters of disclosed compounds can be prepared according to conventional methods. Pharmaceutically acceptable esters can be appended onto hydroxy groups by reaction of the compound that contains the hydroxy group with acid and an alkylcarboxylic acid such as acetic acid, or with acid and an arylcarboxylic acid such as benzoic acid. In the case of compounds containing carboxylic acid groups, the pharmaceutically acceptable esters are prepared from compounds containing the carboxylic acid groups by reaction of the compound with base such as triethylamine and an alkyl halide, for example with methyl iodide, benzyl iodide, cyclopentyl iodide or alkyl triflate. They also can be prepared by reaction of the compound with an acid such as hydrochloric acid and an alcohol such as ethanol or methanol.

The term "pharmaceutically acceptable amide" refers to non-toxic amides of the present disclosure derived from ammonia, primary C 1-to-C 6 alkyl amines and secondary C 1-to-C 6 dialkyl amines. In the case of secondary amines, the amine can also be in the form of a 5- or 6-membered heterocycle containing one nitrogen atom. Amides derived from ammonia, C 1-to-C 3 alkyl primary amides and C 1-to-C 2 dialkyl secondary amides are preferred. Amides of disclosed compounds can be prepared according to conventional methods. Pharmaceutically acceptable amides can be prepared from compounds containing primary or secondary amine groups by reaction of the compound that contains the amino group with an alkyl anhydride, aryl anhydride, acyl halide, or aroyl halide. In the case of compounds containing carboxylic acid groups, the pharmaceutically acceptable amides are prepared from compounds containing the carboxylic acid groups by reaction of the compound with base such as triethylamine, a dehydrating agent such as dicyclohexyl carbodiimide or carbonyl diimidazole, and an alkyl amine, dialkylamine, for example with methylamine, diethylamine, and piperidine. They also can be prepared by reaction of the compound with an acid such as sulfuric acid and an alkylcarboxylic acid such as acetic acid, or with acid and an arylcarboxylic acid such as benzoic acid under dehydrating conditions such as with molecular sieves added. The composition can contain a compound of the present disclosure in the form of a pharmaceutically acceptable prodrug.

The term "pharmaceutically acceptable prodrug" or "prodrug" represents those prodrugs of the compounds of the present disclosure which are, within the scope of sound medical judgment, suitable for use in contact with the tissues of humans and lower animals without undue toxicity, irritation, allergic response, and the like, commensurate with a reasonable benefit/risk ratio, and effective for their intended use. Prodrugs of the present disclosure can be rapidly transformed in vivo to a parent compound having a structure of a disclosed compound, for example, by hydrolysis in blood. A thorough discussion is provided in T. Higuchi and V. Stella, Pro-drugs as Novel Delivery Systems, V. 14 of the A.C.S. Symposium Series, and in Edward B. Roche, ed., Bioreversible Carriers in Drug Design, American Pharmaceutical Association and Pergamon Press (1987).

As used herein, the term "derivative" refers to a compound having a structure derived from the structure of a parent compound (e.g., a compound disclosed herein) and whose structure is sufficiently similar to those disclosed herein and based upon that similarity, would be expected by one skilled in the art to exhibit the same or similar activities and utilities as the claimed compounds, or to induce, as a precursor, the same or similar activities and utilities as the claimed compounds. Exemplary derivatives include salts, esters, amides, salts of esters or amides, and N-oxides of a parent compound.

The term "contacting" as used herein refers to bringing a disclosed compound or pharmaceutical composition in proximity to a cell, a target protein, or other biological entity together in such a manner that the disclosed compound or pharmaceutical composition can affect the activity of the a cell, target protein, or other biological entity, either directly; i.e., by interacting with the cell, target protein, or other biological entity itself, or indirectly; i.e., by interacting with another molecule, co-factor, factor, or protein on which the activity of the cell, target protein, or other biological entity itself is dependent.

As used herein, nomenclature for compounds, including organic compounds, can be given using common names, IUPAC, IUBMB, or CAS recommendations for nomenclature. When one or more stereochemical features are present, Cahn-Ingold-Prelog rules for stereochemistry can be employed to designate stereochemical priority, E/Z specification, and the like. One of skill in the art can readily ascertain the structure of a compound if given a name, either by systemic reduction of the compound structure using naming conventions, or by commercially available software, such as CHEMDRAW™ (Cambridgesoft Corporation, U.S.A.).

It is understood, that unless otherwise specified, temperatures referred to herein are based on atmospheric pressure (i.e. one atmosphere).

In various aspects, the present disclosure pertains to certain compounds and methods that are useful to regulate, limit, or inhibit the expression of AVIL (advillin) in tissue of a mammal, particularly where there are increased, aberrant, or dysfunctional levels of AVIL. It has been found that AVIL expression, or over-expression, is associated with the genesis and growth of certain forms of cancerous tumors. For example, it has been found that AVIL is overexpressed in the vast majority, if not all of human glioblastomas (GBMs). It has been found that GBM cells depend on the overexpression of AVIL for increased survival and migration. Silencing AVIL induced GBM cell death in vitro, and prevented GBM xenograft formation and growth in animal models.

Silencing AVIL also dramatically changed cell morphology, and reduced cell migration/invasion ability. In contrast, normal astrocytes express very low levels of AVIL, and silencing AVIL had no obvious effect on cell growth or morphology of normal astrocytes. Clinically, higher expression of AVIL has been correlated with worse patient outcome in GBMs as well as in lower-grade gliomas. In addition to gliomas, lung cancer, bladder cancer, and renal cancer patients with high level of AVIL expression also had worse prognosis. Therefore, in various aspects of the present disclosure, certain compounds are provided, and methods useful for targeting AVIL as an oncogene and a therapeutic target. Other compositions, compounds, methods, features, and advantages of the present disclosure will be or become apparent to one having ordinary skill in the art upon examination of the following drawings, detailed description, and examples. It is intended that all such additional compositions, compounds, methods, features, and advantages be included within this description, and be within the scope of the present disclosure.

Compounds.

In various aspects, the present disclosure pertains to certain compounds that are useful to regulate, limit, or inhibit the expression of AVIL (advillin) in cells of a mammal having increased, aberrant, or dysfunctional levels of AVIL, which will have use as therapeutic agents in a variety of clinical conditions such as cancer.

In aspects, the compound comprises one of Compounds A-L:

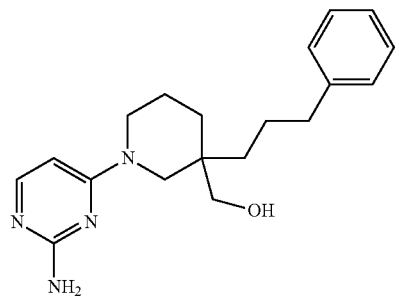

Compound A:
(1-(2-aminopyrimidin-4-yl)-3-(3-phenylpropyl)piperidin-3-yl)methanol

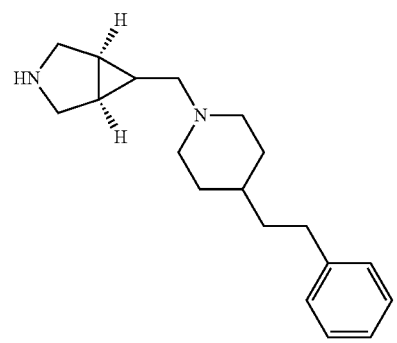

Compound B:
(1R,5S)-6-((4-phenethylpiperidin-1-yl)methyl)-3-azabicyclo[3.1.0]hexane

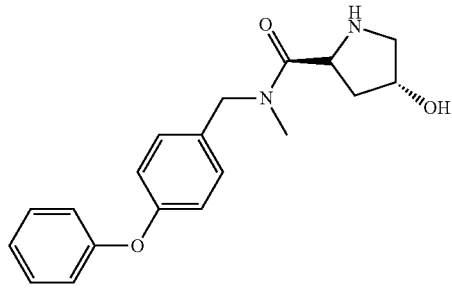

Compound C:
(2S,4R)-4-hydroxy-N-methyl-N-(4-phenoxybenzyl)pyrrolidine-2-carboxamide

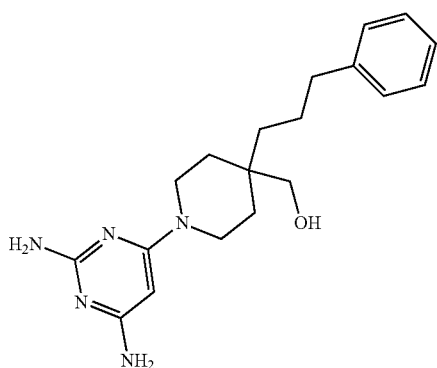

Compound D:
(1-(2,6-diaminopyrimidin-4-yl)-4-(3-phenylpropyl)piperidin-4-yl)methanol

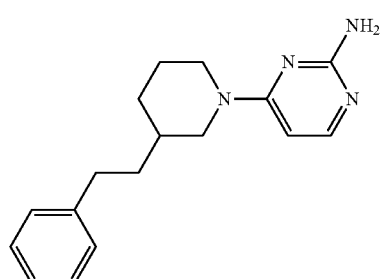

Compound E:
4-(3-phenethylpiperidin-1-yl)pyrimidin-2-amine

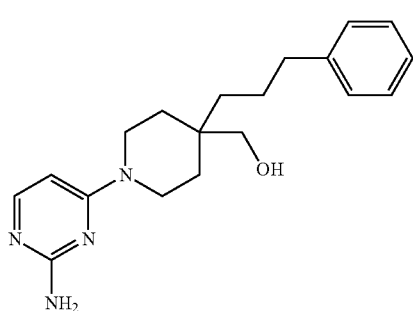

Compound F:
(1-(2-aminopyrimidin-4-yl)-4-(3-phenylpropyl)piperidin-4-yl)methanol

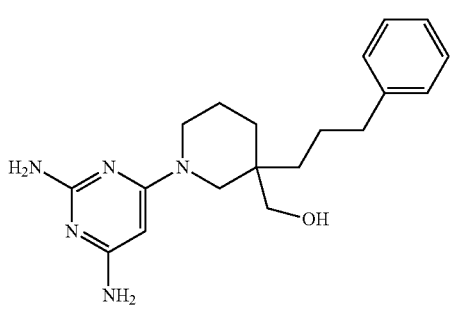

Compound G:
(1-(2,6-diaminopyrimidin-4-yl)-3-(3-phenylpropyl)piperidin-3-yl)methanol

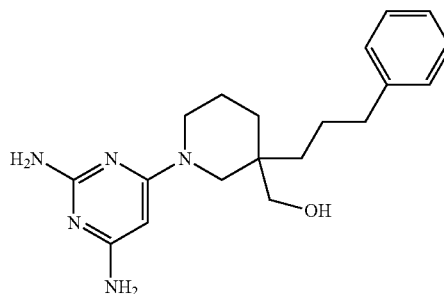

Compound H:
(1-(2,6-diaminopyrimidin-4-yl)-3-(3-phenylpropyl)piperidin-3-yl)methanol

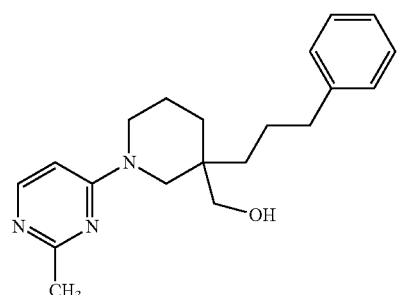

Compound I:
(1-(2,6-methylpyrimidin-4-yl)-3-(3-phenylpropyl)piperidin-3-yl)methanol

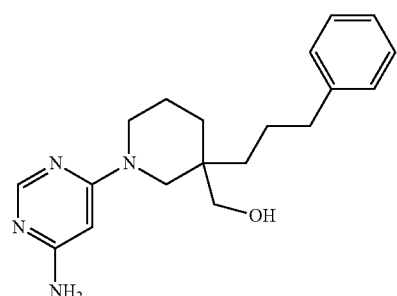

Compound J:
(1-(6-aminopyrimidin-4-yl)-3-(3-phenylpropyl)piperidin-3-yl)methanol

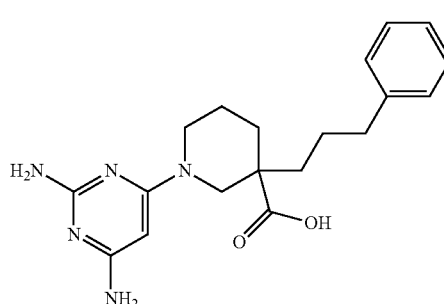

Compound K:
1-(2,6-diaminopyrimidin-4-yl)-3-(3-phenylpropyl)piperidine-3-carboxylic acid

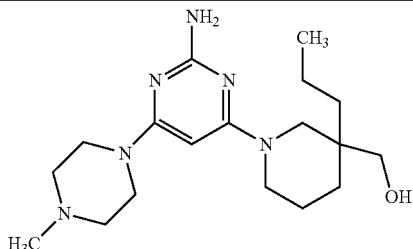

Compound L:
(1-(2-amino-6-(4-methylpiperazin-1-yl)
pyrimidin-4-yl)-3-propylpiperidin-3-yl)
methanol It has been found that Compounds A-L interact with the AVIL protein. In cellular assays using glioblastoma (GBM) cell lines and immortalized astrocytes, it was found that these Compounds A-L provide significantly different $IC_{50}$ in GBM lines, as compared to astrocytes.

In various aspects, it is contemplated herein that the disclosed compounds further comprise their bioisosteric equivalents. The term "bioisosteric equivalent" refers to compounds or groups that possess near equal molecular shapes and volumes, approximately the same distribution of electrons, and which exhibit similar physical and biological properties. Examples of such equivalents are: (i) fluorine vs. hydrogen, (ii) oxo vs. thia, (iii) hydroxyl vs. amide, (iv) carbonyl vs. oxime, (v) carboxylate vs. tetrazole. Examples of such bioisosteric replacements can be found in the literature and examples of such are: (i) Burger A, *Relation of chemical structure and biological activity*; in Medicinal Chemistry Third ed., Burger A, ed.; Wiley-Interscience; New York, 1970, 64-80; (ii) Burger, A.; "Isosterism and bioisosterism in drug design"; *Prog. Drug Res.* 1991, 37, 287-371; (iii) Burger A, "Isosterism and bioanalogy in drug design", *Med. Chem. Res.* 1994, 4, 89-92; (iv) Clark R D, Ferguson A M, Cramer R D, "Bioisosterism and molecular diversity", Perspect. *Drug Discovery Des.* 1998, 9/10/11, 213-224; (v) Koyanagi T, Haga T, "Bioisosterism in agrochemicals", *ACS Symp. Ser.* 1995, 584, 15-24; (vi) Kubinyi H, "Molecular similarities. Part 1. Chemical structure and biological activity", *Pharm. Unserer Zeit* 1998, 27, 92-106; (vii) Lipinski C A.; "Bioisosterism in drug design"; *Annu. Rep. Med. Chem.* 1986, 21, 283-91; (viii) Patani G A, LaVoie E J, "Bioisosterism: A rational approach in drug design", *Chem. Rev.* (Washington, D.C.) 1996, 96, 3147-3176; (ix) Soskic V, Joksimovic J, "Bioisosteric approach in the design of new dopaminergic/serotonergic ligands", *Curr. Med. Chem.* 1998, 5, 493-512 (x) Thornber C W, "Isosterism and molecular modification in drug design", *Chem. Soc. Rev.* 1979, 8, 563-80.

In further aspects, bioisosteres are atoms, ions, or molecules in which the peripheral layers of electrons can be considered substantially identical. The term bioisostere is usually used to mean a portion of an overall molecule, as opposed to the entire molecule itself. Bioisosteric replacement involves using one bioisostere to replace another with the expectation of maintaining or slightly modifying the biological activity of the first bioisostere. The bioisosteres in this case are thus atoms or groups of atoms having similar size, shape and electron density. Preferred bioisosteres of esters, amides or carboxylic acids are compounds containing two sites for hydrogen bond acceptance. In one embodiment, the ester, amide or carboxylic acid bioisostere is a 5-membered monocyclic heteroaryl ring, such as an optionally substituted 1H-imidazolyl, an optionally substituted oxazolyl, 1H-tetrazolyl, [1,2,4]triazolyl, or an optionally substituted [1,2,4]oxadiazolyl.

In various aspects, it is contemplated herein that the disclosed compounds further comprise their isotopically-labelled or isotopically-substituted variants, i.e., compounds identical to those described, but for the fact that one or more atoms are replaced by an atom having an atomic mass or mass number different from the atomic mass or mass number typically found in nature. Examples of isotopes that can be incorporated into compounds of the invention include isotopes of hydrogen, carbon, nitrogen, oxygen, phosphorous, fluorine and chlorine, such as $^2H$, $^3H$, $^{13}C$, $^{14}C$, $^{15}N$, $^{18}O$, $^{17}O$, $^{35}S$, $^{18}F$ and $^{36}Cl$, respectively. Compounds further comprise prodrugs thereof, and pharmaceutically acceptable salts of said compounds or of said prodrugs which contain the aforementioned isotopes and/or other isotopes of other atoms are within the scope of this invention. Certain isotopically-labelled compounds of the present invention, for example those into which radioactive isotopes such as $^3H$ and $^{14}C$ are incorporated, are useful in drug and/or substrate tissue distribution assays. Tritiated, i.e., $^3H$, and carbon-14, i.e., $^{14}C$, isotopes are particularly preferred for their ease of preparation and detectability. Further, substitution with heavier isotopes such as deuterium, i.e., $^2H$, can afford certain therapeutic advantages resulting from greater metabolic stability, for example increased in vivo half-life or reduced dosage requirements and, hence, may be preferred in some circumstances. Isotopically labelled compounds of the present invention and prodrugs thereof can generally be prepared by carrying out the procedures below, by substituting a readily available isotopically labelled reagent for a non-isotopically labelled reagent.

In various aspects, the disclosed compounds can possess at least one center of asymmetry, they can be present in the form of their racemates, in the form of the pure enantiomers and/or diastereomers or in the form of mixtures of these enantiomers and/or diastereomers. The stereoisomers can be present in the mixtures in any arbitrary proportions. In some aspects, provided this is possible, the disclosed compounds can be present in the form of the tautomers.

Thus, methods which are known per se can be used, for example, to separate the disclosed compounds which possess one or more chiral centers and occur as racemates into their optical isomers, i.e., enantiomers or diastereomers. The separation can be effected by means of column separation on chiral phases or by means of recrystallization from an optically active solvent or using an optically active acid or base or by means of derivatizing with an optically active reagent, such as an optically active alcohol, and subsequently cleaving off the residue.

In various aspects, the disclosed compounds can be in the form of a co-crystal. The term "co-crystal" means a physical association of two or more molecules which owe their stability through non-covalent interaction. One or more components of this molecular complex provide a stable framework in the crystalline lattice. In certain instances, the guest molecules are incorporated in the crystalline lattice as anhydrates or solvates, see e.g. "Crystal Engineering of the Composition of Pharmaceutical Phases. Do Pharmaceutical Co-crystals Represent a New Path to Improved Medicines?" Almarasson, O., et. al., The Royal Society of Chemistry, 1889-1896, 2004. Preferred co-crystals include p-toluenesulfonic acid and benzenesulfonic acid.

The term "pharmaceutically acceptable co-crystal" means one that is compatible with the other ingredients of the formulation and not deleterious to the recipient thereof.

In a further aspect, the disclosed compounds can be isolated as solvates and, in particular, as hydrates of a disclosed compound, which can be obtained, for example, by crystallization from a solvent or from aqueous solution. In this connection, one, two, three or any arbitrary number of solvate or water molecules can combine with the compounds according to the invention to form solvates and hydrates.

The disclosed compounds can be used in the form of salts derived from inorganic or organic acids. Pharmaceutically acceptable salts include salts of acidic or basic groups present in the disclosed compounds. Suitable pharmaceutically acceptable salts include base addition salts, including alkali metal salts, e.g., sodium or potassium salts; alkaline earth metal salts, e.g., calcium or magnesium salts; and salts formed with suitable organic ligands, e.g., quaternary ammonium salts, which may be similarly prepared by reacting the drug compound with a suitable pharmaceutically acceptable base. The salts can be prepared in situ during the final isolation and purification of the compounds of the present disclosure; or following final isolation by reacting a free base function, such as a secondary or tertiary amine, of a disclosed compound with a suitable inorganic or organic acid; or reacting a free acid function, such as a carboxylic acid, of a disclosed compound with a suitable inorganic or organic base.

Acidic addition salts can be prepared in situ during the final isolation and purification of a disclosed compound, or separately by reacting moieties comprising one or more nitrogen groups with a suitable acid. In various aspects, acids which may be employed to form pharmaceutically acceptable acid addition salts include such inorganic acids as hydrochloric acid, sulphuric acid and phosphoric acid and such organic acids as oxalic acid, maleic acid, succinic acid and citric acid. In a further aspect, salts further include, but are not limited to, the following: hydrochloride, hydrobromide, hydroiodide, nitrate, sulfate, bisulfate, phosphate, acid phosphate, isonicotinate, acetate, lactate, salicylate, citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzensulfonate, p-toluenesulfonate, butyrate, camphorate, camphorsulfonate, digluconate, glycerophosphate, hemisulfate, heptanoate, hexanoate, fumarate, hydrochloride, 2-hydroxyethanesulfonate (isethionate), nicotinate, 2-naphthalenesulfonate, oxalate, pectinate, persulfate, 3-phenylpropionate, picrate, pivalate, propionate, succinate, tartrate, thiocyanate, phosphate, glutamate, bicarbonate, undecanoate, and pamoate (i.e., 1,1'-methylene-bis-(2-hydroxy-3-naphthoate)) salts. Also, basic nitrogen-containing groups can be quaternized with such agents as lower alkyl halides, such as methyl, ethyl, propyl, and butyl chloride, bromides, and iodides; dialkyl sulfates like dimethyl, diethyl, dibutyl, and diamyl sulfates, long chain halides such as decyl, lauryl, myristyl and stearyl chlorides, bromides and iodides, aralkyl halides like benzyl and phenethyl bromides, and others.

Basic addition salts can be prepared in situ during the final isolation and purification of a disclosed compound, or separately by reacting carboxylic acid moieties with a suitable base such as the hydroxide, carbonate or bicarbonate of a pharmaceutical acceptable metal cation or with ammonia, or an organic primary, secondary or tertiary amine. Pharmaceutical acceptable salts include, but are not limited to, cations based on the alkali and alkaline earth metals, such as sodium, lithium, potassium, calcium, magnesium, aluminum salts and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine, and the like. Other representative organic amines useful for the formation of base addition salts include diethylamine, ethylenediamine, ethanolamine, diethanolamine, piperazine and the like. In further aspects, bases which may be used in the preparation of pharmaceutically acceptable salts include the following: ammonia, L-arginine, benethamine, benzathine, calcium hydroxide, choline, deanol, diethanolamine, diethylamine, 2-(diethylamino)-ethanol, ethanolamine, ethylenediamine, N-methylglucamine, hydrabamine, 1H-imidazole, L-lysine, magnesium hydroxide, 4-(2-hydroxyethyl)-morpholine, piperazine, potassium hydroxide, 1-(2-hydroxyethyl)-pyrrolidine, secondary amine, sodium hydroxide, triethanolamine, tromethamine and zinc hydroxide.

Pharmaceutical Compositions.

In various aspects, the present disclosure relates to pharmaceutical compositions comprising a therapeutically effective amount of at least one disclosed compound, at least one product of a disclosed method, or a pharmaceutically acceptable salt thereof. As used herein, "pharmaceutically-acceptable carriers" means one or more of a pharmaceutically acceptable diluents, preservatives, antioxidants, solubilizers, emulsifiers, coloring agents, releasing agents, coating agents, sweetening, flavoring and perfuming agents, and adjuvants. The disclosed pharmaceutical compositions can be conveniently presented in unit dosage form and prepared by any of the methods well known in the art of pharmacy and pharmaceutical sciences.

In a further aspect, the disclosed pharmaceutical compositions comprise a therapeutically effective amount of at least one disclosed compound, at least one product of a disclosed method, or a pharmaceutically acceptable salt thereof as an active ingredient, a pharmaceutically acceptable carrier, optionally one or more other therapeutic agent, and optionally one or more adjuvant. The disclosed pharmaceutical compositions include those suitable for oral, rectal, topical, pulmonary, nasal, and parenteral administration, although the most suitable route in any given case will depend on the particular host, and nature and severity of the conditions for which the active ingredient is being administered. In a further aspect, the disclosed pharmaceutical composition can be formulated to allow administration orally, nasally, via inhalation, parenterally, paracancerally, transmucosally, transdermally, intramuscularly, intravenously, intradermally, subcutaneously, intraperitonealy, intraventricularly, intracranially and intratumorally.

As used herein, "parenteral administration" includes administration by bolus injection or infusion, as well as administration by intravenous, intramuscular, intraarterial, intrathecal, intracapsular, intraorbital, intracardiac, intradermal, intraperitoneal, transtracheal, subcutaneous, subcuticular, intraarticular, subcapsular subarachnoid, intraspinal, epidural and intrasternal injection and infusion.

In various aspects, the present disclosure also relates to a pharmaceutical composition comprising a pharmaceutically acceptable carrier or diluent and, as active ingredient, a therapeutically effective amount of a disclosed compound, a product of a disclosed method of making, a pharmaceutically acceptable salt, a hydrate thereof, a solvate thereof, a polymorph thereof, or a stereochemically isomeric form thereof. In a further aspect, a disclosed compound, a product of a disclosed method of making, a pharmaceutically acceptable salt, a hydrate thereof, a solvate thereof, a polymorph thereof, or a stereochemically isomeric form thereof, or any subgroup or combination thereof may be formulated into various pharmaceutical forms for administration purposes.

Pharmaceutically acceptable salts can be prepared from pharmaceutically acceptable non-toxic bases or acids. For therapeutic use, salts of the disclosed compounds are those wherein the counter ion is pharmaceutically acceptable. However, salts of acids and bases which are non-pharmaceutically acceptable may also find use, for example, in the preparation or purification of a pharmaceutically acceptable compound. All salts, whether pharmaceutically acceptable or not, are contemplated by the present disclosure. Pharmaceutically acceptable acid and base addition salts are meant to comprise the therapeutically active non-toxic acid and base addition salt forms which the disclosed compounds are able to form.

In various aspects, a disclosed compound comprising an acidic group or moiety, e.g., a carboxylic acid group, can be used to prepare a pharmaceutically acceptable salt. For example, such a disclosed compound may comprise an isolation step comprising treatment with a suitable inorganic or organic base. In some cases, it may be desirable in practice to initially isolate a compound from the reaction mixture as a pharmaceutically unacceptable salt and then simply convert the latter back to the free acid compound by treatment with an acidic reagent, and subsequently convert the free acid to a pharmaceutically acceptable base addition salt. These base addition salts can be readily prepared using conventional techniques, e.g., by treating the corresponding acidic compounds with an aqueous solution containing the desired pharmacologically acceptable cations and then evaporating the resulting solution to dryness, preferably under reduced pressure. Alternatively, they also can be prepared by mixing lower alkanolic solutions of the acidic compounds and the desired alkali metal alkoxide together, and then evaporating the resulting solution to dryness in the same manner as before.

Bases which can be used to prepare the pharmaceutically acceptable base-addition salts of the base compounds are those which can form non-toxic base-addition salts, i.e., salts containing pharmacologically acceptable cations such as, alkali metal cations (e.g., lithium, potassium and sodium), alkaline earth metal cations (e.g., calcium and magnesium), ammonium or other water-soluble amine addition salts such as N-methylglucamine-(meglumine), lower alkanolammonium and other such bases of organic amines. In a further aspect, derived from pharmaceutically acceptable organic non-toxic bases include primary, secondary, and tertiary amines, as well as cyclic amines and substituted amines such as naturally occurring and synthesized substituted amines. In various aspects, such pharmaceutically acceptable organic non-toxic bases include, but are not limited to, ammonia, methylamine, ethylamine, propylamine, isopropylamine, any of the four butylamine isomers, betaine, caffeine, choline, dimethylamine, diethylamine, diethanolamine, dipropylamine, diisopropylamine, di-n-butylamine, N, N'-dibenzylethylenediamine, pyrrolidine, piperidine, morpholine, trimethylamine, triethylamine, tripropylamine, tromethamine, 2-diethylaminoethanol, 2-dimethylaminoethanol, ethanolamine, quinuclidine, pyridine, quinoline and isoquinoline; benzathine, N-methyl-D-glucamine, ethylenediamine, N-ethylmorpholine, N-ethylpiperidine, glucamine, glucosamine, methylglucamine, morpholine, piperazine, piperidine, polyamine resins, procaine, purines, theobromine, hydrabamine salts, and salts with amino acids such as, for example, histidine, arginine, lysine and the like. The foregoing salt forms can be converted by treatment with acid back into the free acid form.

In various aspects, a disclosed compound comprising a protonatable group or moiety, e.g., an amino group, can be used to prepare a pharmaceutically acceptable salt. For example, such a disclosed compound may comprise an isolation step comprising treatment with a suitable inorganic or organic acid. In some cases, it may be desirable in practice to initially isolate a compound from the reaction mixture as a pharmaceutically unacceptable salt and then simply convert the latter back to the free base compound by treatment with a basic reagent, and subsequently convert the free base to a pharmaceutically acceptable acid addition salt. These acid addition salts can be readily prepared using conventional techniques, e.g., by treating the corresponding basic compounds with an aqueous solution containing the desired pharmacologically acceptable anions and then evaporating the resulting solution to dryness, preferably under reduced pressure. Alternatively, they also can be prepared by treating the free base form of the disclosed compound with a suitable pharmaceutically acceptable non-toxic inorganic or organic acid.

Acids which can be used to prepare the pharmaceutically acceptable acid-addition salts of the base compounds are those which can form non-toxic acid-addition salts, i.e., salts containing pharmacologically acceptable anions formed from their corresponding inorganic and organic acids. Exemplary, but non-limiting, inorganic acids include hydrochloric hydrobromic, sulfuric, nitric, phosphoric and the like. Exemplary, but non-limiting, organic acids include acetic, benzenesulfonic, benzoic, camphorsulfonic, citric, ethanesulfonic, fumaric, gluconic, glutamic, isethionic, lactic, maleic, malic, mandelicmethanesulfonic, mucic, pamoic, pantothenic, succinic, tartaric, p-toluenesulfonic acid and the like. In a further aspect, the acid-addition salt comprises an anion formed from hydrobromic, hydrochloric, maleic, phosphoric, sulfuric, and tartaric acids.

In practice, the compounds of the present disclosure, or pharmaceutically acceptable salts thereof, of the present disclosure can be combined as the active ingredient in intimate admixture with a pharmaceutical carrier according to conventional pharmaceutical compounding techniques. The carrier can take a wide variety of forms depending on the form of preparation desired for administration, e.g., oral or parenteral (including intravenous). Thus, the pharmaceutical compositions of the present disclosure can be presented as discrete units suitable for oral administration such as capsules, cachets or tablets each containing a predetermined amount of the active ingredient. Further, the compositions can be presented as a powder, as granules, as a solution, as a suspension in an aqueous liquid, as a non-aqueous liquid, as an oil-in-water emulsion or as a water-in-oil liquid emulsion. In addition to the common dosage forms set out above, the compounds of the present disclosure, and/or pharmaceutically acceptable salt(s) thereof, can also be administered by controlled release means and/or delivery devices. The compositions can be prepared by any of the methods of pharmacy. In general, such methods include a step of bringing into association the active ingredient with the carrier that constitutes one or more necessary ingredients. In general, the compositions are prepared by uniformly and intimately admixing the active ingredient with liquid carriers or finely divided solid carriers or both. The product can then be conveniently shaped into the desired presentation.

It is especially advantageous to formulate the aforementioned pharmaceutical compositions in unit dosage form for ease of administration and uniformity of dosage. The term "unit dosage form," as used herein, refers to physically discrete units suitable as unitary dosages, each unit containing a predetermined quantity of active ingredient calculated to produce the desired therapeutic effect in association with the required pharmaceutical carrier. That is, a "unit dosage form" is taken to mean a single dose wherein all active and inactive ingredients are combined in a suitable system, such that the patient or person administering the drug to the patient can open a single container or package with the entire dose contained therein, and does not have to mix any components together from two or more containers or packages. Typical examples of unit dosage forms are tablets (including scored or coated tablets), capsules or pills for oral administration; single dose vials for injectable solutions or suspension; suppositories for rectal administration; powder packets; wafers; and segregated multiples thereof. This list of unit dosage forms is not intended to be limiting in any way, but merely to represent typical examples of unit dosage forms.

The pharmaceutical compositions disclosed herein comprise a compound of the present disclosure (or pharmaceutically acceptable salts thereof) as an active ingredient, a pharmaceutically acceptable carrier, and optionally one or more additional therapeutic agents. In various aspects, the disclosed pharmaceutical compositions can include a pharmaceutically acceptable carrier and a disclosed compound, or a pharmaceutically acceptable salt thereof. In a further aspect, a disclosed compound, or pharmaceutically acceptable salt thereof, can also be included in a pharmaceutical composition in combination with one or more other therapeutically active compounds. The instant compositions include compositions suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions can be conveniently presented in unit dosage form and prepared by any of the methods well known in the art of pharmacy.

Techniques and compositions for making dosage forms useful for materials and methods described herein are described, for example, in the following references: Modern Pharmaceutics, Chapters 9 and 10 (Banker & Rhodes, Editors, 1979); Pharmaceutical Dosage Forms: Tablets (Lieberman et al., 1981); Ansel, Introduction to Pharmaceutical Dosage Forms 2nd Edition (1976); Remington's Pharmaceutical Sciences, 17th ed. (Mack Publishing Company, Easton, Pa., 1985); Advances in Pharmaceutical Sciences (David Ganderton, Trevor Jones, Eds., 1992); Advances in Pharmaceutical Sciences Vol 7. (David Ganderton, Trevor Jones, James McGinity, Eds., 1995); Aqueous Polymeric Coatings for Pharmaceutical Dosage Forms (Drugs and the Pharmaceutical Sciences, Series 36 (James McGinity, Ed., 1989); Pharmaceutical Particulate Carriers: Therapeutic Applications: Drugs and the Pharmaceutical Sciences, Vol 61 (Alain Rolland, Ed., 1993); Drug Delivery to the Gastrointestinal Tract (Ellis Horwood Books in the Biological Sciences. Series in Pharmaceutical Technology; J. G. Hardy, S. S. Davis, Clive G. Wilson, Eds.); Modern Pharmaceutics Drugs and the Pharmaceutical Sciences, Vol 40 (Gilbert S. Banker, Christopher T. Rhodes, Eds.).

The compounds described herein are typically to be administered in admixture with suitable pharmaceutical diluents, excipients, extenders, or carriers (termed herein as a pharmaceutically acceptable carrier, or a carrier) suitably selected with respect to the intended form of administration and as consistent with conventional pharmaceutical practices. The deliverable compound will be in a form suitable for oral, rectal, topical, intravenous injection or parenteral administration. Carriers include solids or liquids, and the type of carrier is chosen based on the type of administration being used. The compounds may be administered as a dosage that has a known quantity of the compound.

Because of the ease in administration, oral administration can be a preferred dosage form, and tablets and capsules represent the most advantageous oral dosage unit forms in which case solid pharmaceutical carriers are obviously employed. However, other dosage forms may be suitable depending upon clinical population (e.g., age and severity of clinical condition), solubility properties of the specific disclosed compound used, and the like. Accordingly, the disclosed compounds can be used in oral dosage forms such as pills, powders, granules, elixirs, tinctures, suspensions, syrups, and emulsions. In preparing the compositions for oral dosage form, any convenient pharmaceutical media can be employed. For example, water, glycols, oils, alcohols, flavoring agents, preservatives, coloring agents and the like can be used to form oral liquid preparations such as suspensions, elixirs and solutions; while carriers such as starches, sugars, microcrystalline cellulose, diluents, granulating agents, lubricants, binders, disintegrating agents, and the like can be used to form oral solid preparations such as powders, capsules and tablets. Because of their ease of administration, tablets and capsules are the preferred oral dosage units whereby solid pharmaceutical carriers are employed. Optionally, tablets can be coated by standard aqueous or nonaqueous techniques.

The disclosed pharmaceutical compositions in an oral dosage form can comprise one or more pharmaceutical excipient and/or additive. Non-limiting examples of suitable excipients and additives include gelatin, natural sugars such as raw sugar or lactose, lecithin, pectin, starches (for example corn starch or amylose), dextran, polyvinyl pyrrolidone, polyvinyl acetate, gum arabic, alginic acid, tylose, talcum, lycopodium, silica gel (for example colloidal), cellulose, cellulose derivatives (for example cellulose ethers in which the cellulose hydroxy groups are partially etherified with lower saturated aliphatic alcohols and/or lower saturated, aliphatic oxyalcohols, for example methyl oxypropyl cellulose, methyl cellulose, hydroxypropyl methyl cellulose, hydroxypropyl methyl cellulose phthalate), fatty acids as well as magnesium, calcium or aluminum salts of fatty acids with 12 to 22 carbon atoms, in particular saturated (for example stearates), emulsifiers, oils and fats, in particular vegetable (for example, peanut oil, castor oil, olive oil, sesame oil, cottonseed oil, corn oil, wheat germ oil, sunflower seed oil, cod liver oil, in each case also optionally hydrated); glycerol esters and polyglycerol esters of saturated fatty acids $C_{12}H_{24}O_2$ to $C_{18}H_{36}O_2$ and their mixtures, it being possible for the glycerol hydroxy groups to be totally or also only partly esterified (for example mono-, di- and triglycerides); pharmaceutically acceptable mono- or multivalent alcohols and polyglycols such as polyethylene glycol and derivatives thereof, esters of aliphatic saturated or unsaturated fatty acids (2 to 22 carbon atoms, in particular 10-18 carbon atoms) with monovalent aliphatic alcohols (1 to 20 carbon atoms) or multivalent alcohols such as glycols, glycerol, diethylene glycol, pentacrythritol, sorbitol, mannitol and the like, which may optionally also be etherified, esters of citric acid with primary alcohols, acetic acid, urea, benzyl benzoate, dioxolanes, glyceroformals, tetrahydrofurfuryl alcohol, polyglycol ethers with 01-012-alcohols, dimethylacetamide, lactamides, lactates, ethylcarbonates, silicones (in particular medium-viscous polydimethyl siloxanes), calcium carbonate, sodium carbonate, calcium phosphate, sodium phosphate, magnesium carbonate and the like.

Other auxiliary substances useful in preparing an oral dosage form are those which cause disintegration (so-called disintegrants), such as: cross-linked polyvinyl pyrrolidone, sodium carboxymethyl starch, sodium carboxymethyl cellulose or microcrystalline cellulose. Conventional coating substances may also be used to produce the oral dosage form. Those that may for example be considered are: polymerizates as well as copolymerizates of acrylic acid and/or methacrylic acid and/or their esters; copolymerizates of acrylic and methacrylic acid esters with a lower ammonium group content (for example EudragitR RS), copolymerizates of acrylic and methacrylic acid esters and trimethyl ammonium methacrylate (for example EudragitR RL); polyvinyl acetate; fats, oils, waxes, fatty alcohols; hydroxypropyl methyl cellulose phthalate or acetate succinate; cellulose acetate phthalate, starch acetate phthalate as well as polyvinyl acetate phthalate, carboxy methyl cellulose; methyl cellulose phthalate, methyl cellulose succinate, -phthalate succinate as well as methyl cellulose phthalic acid half ester; zein; ethyl cellulose as well as ethyl cellulose succinate; shellac, gluten; ethylcarboxyethyl cellulose; ethacrylate-maleic acid anhydride copolymer; maleic acid anhydride-vinyl methyl ether copolymer; styrol-maleic acid copolymerizate; 2-ethyl-hexyl-acrylate maleic acid anhydride; crotonic acid-vinyl acetate copolymer; glutaminic acid/glutamic acid ester copolymer; carboxymethylethylcellulose glycerol monooctanoate; cellulose acetate succinate; polyarginine.

Plasticizing agents that may be considered as coating substances in the disclosed oral dosage forms are: citric and tartaric acid esters (acetyl-triethyl citrate, acetyl tributyl-, tributyl-, triethyl-citrate); glycerol and glycerol esters (glycerol diacetate, -triacetate, acetylated monoglycerides, castor oil); phthalic acid esters (dibutyl-, diamyl-, diethyl-, dimethyl-, dipropyl-phthalate), di-(2-methoxy- or 2-ethoxyethyl)-phthalate, ethylphthalyl glycolate, butylphthalylethyl glycolate and butylglycolate; alcohols (propylene glycol, polyethylene glycol of various chain lengths), adipates (diethyladipate, di-(2-methoxy- or 2-ethoxyethyl)-adipate; benzophenone; diethyl- and diburylsebacate, dibutylsuccinate, dibutyltartrate; diethylene glycol dipropionate; ethyleneglycol diacetate, -dibutyrate, -dipropionate; tributyl phosphate, tributyrin; polyethylene glycol sorbitan monooleate (polysorbates such as Polysorbar 50); sorbitan monooleate.

Moreover, suitable binders, lubricants, disintegrating agents, coloring agents, flavoring agents, flow-inducing agents, and melting agents may be included as carriers. The pharmaceutical carrier employed can be, for example, a solid, liquid, or gas. Examples of solid carriers include, but are not limited to, lactose, terra alba, sucrose, glucose, methylcellulose, dicalcium phosphate, calcium sulfate, mannitol, sorbitol talc, starch, gelatin, agar, pectin, acacia, magnesium stearate, and stearic acid. Examples of liquid carriers are sugar syrup, peanut oil, olive oil, and water. Examples of gaseous carriers include carbon dioxide and nitrogen.

In various aspects, a binder can include, for example, starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. In a further aspect, a disintegrator can include, for example, starch, methyl cellulose, agar, bentonite, xanthan gum, and the like.

In various aspects, an oral dosage form, such as a solid dosage form, can comprise a disclosed compound that is attached to polymers as targetable drug carriers or as a prodrug. Suitable biodegradable polymers useful in achieving controlled release of a drug include, for example, polylactic acid, polyglycolic acid, copolymers of polylactic and polyglycolic acid, caprolactones, polyhydroxy butyric acid, polyorthoesters, polyacetals, polydihydropyrans, polycyanoacylates, and hydrogels, preferably covalently crosslinked hydrogels.

Tablets may contain the active ingredient in admixture with non-toxic pharmaceutically acceptable excipients which are suitable for the manufacture of tablets. These excipients may be, for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period.

A tablet containing a disclosed compound can be prepared by compression or molding, optionally with one or more accessory ingredients or adjuvants. Compressed tablets can be prepared by compressing, in a suitable machine, the active ingredient in a free-flowing form such as powder or granules, optionally mixed with a binder, lubricant, inert diluent, surface active or dispersing agent. Molded tablets can be made by molding in a suitable machine, a mixture of the powdered compound moistened with an inert liquid diluent.

In various aspects, a solid oral dosage form, such as a tablet, can be coated with an enteric coating to prevent ready decomposition in the stomach. In various aspects, enteric coating agents include, but are not limited to, hydroxypropylmethylcellulose phthalate, methacrylic acid-methacrylic acid ester copolymer, polyvinyl acetate-phthalate and cellulose acetate phthalate. Akihiko Hasegawa "Application of solid dispersions of Nifedipine with enteric coating agent to prepare a sustained-release dosage form" Chem. Pharm. Bull. 33:1615-1619 (1985). Various enteric coating materials may be selected on the basis of testing to achieve an enteric coated dosage form designed ab initio to have a preferable combination of dissolution time, coating thicknesses and diametral crushing strength (e.g., see S. C. Porter et al. "The Properties of Enteric Tablet Coatings Made From Polyvinyl Acetate-phthalate and Cellulose acetate Phthalate", J. Pharm. Pharmacol. 22:42p (1970)). In a further aspect, the enteric coating may comprise hydroxypropylmethylcellulose phthalate, methacrylic acid-methacrylic acid ester copolymer, polyvinyl acetate-phthalate and cellulose acetate phthalate.

In various aspects, an oral dosage form can be a solid dispersion with a water soluble or a water insoluble carrier. Examples of water soluble or water insoluble carrier include, but are not limited to, polyethylene glycol, polyvinylpyrrolidone, hydroxypropylmethyl-cellulose, phosphatidylcholine, polyoxyethylene hydrogenated castor oil, hydroxypropylmethylcellulose phthalate, carboxymethylethylcellulose, or hydroxypropylmethylcellulose, ethyl cellulose, or stearic acid.

In various aspects, an oral dosage form can be in a liquid dosage form, including those that are ingested, or alternatively, administered as a mouth wash or gargle. For example, a liquid dosage form can include aqueous suspensions, which contain the active materials in admixture with excipients suitable for the manufacture of aqueous suspensions. In addition, oily suspensions may be formulated by suspending the active ingredient in a vegetable oil, for example *arachis* oil, olive oil, sesame oil or coconut oil, or in a mineral oil such as liquid paraffin. Oily suspensions may also contain various excipients. The pharmaceutical compositions of the present disclosure may also be in the form of oil-in-water emulsions, which may also contain excipients such as sweetening and flavoring agents.

For the preparation of solutions or suspensions it is, for example, possible to use water, particularly sterile water, or physiologically acceptable organic solvents, such as alcohols (ethanol, propanol, isopropanol, 1,2-propylene glycol, polyglycols and their derivatives, fatty alcohols, partial esters of glycerol), oils (for example peanut oil, olive oil, sesame oil, almond oil, sunflower oil, soya bean oil, castor oil, bovine hoof oil), paraffins, dimethyl sulphoxide, triglycerides and the like.

In the case of a liquid dosage form such as a drinkable solutions, the following substances may be used as stabilizers or solubilizers: lower aliphatic mono- and multivalent alcohols with 2-4 carbon atoms, such as ethanol, n-propanol, glycerol, polyethylene glycols with molecular weights between 200-600 (for example 1 to 40% aqueous solution), diethylene glycol monoethyl ether, 1,2-propylene glycol, organic amides, for example amides of aliphatic C1-C6-carboxylic acids with ammonia or primary, secondary or tertiary C1-C4-amines or C1-C4-hydroxy amines such as urea, urethane, acetamide, N-methyl acetamide, N,N-diethyl acetamide, N,N-dimethyl acetamide, lower aliphatic amines and diamines with 2-6 carbon atoms, such as ethylene diamine, hydroxyethyl theophylline, tromethamine (for example as 0.1 to 20% aqueous solution), aliphatic amino acids.

In preparing the disclosed liquid dosage form can comprise solubilizers and emulsifiers such as the following non-limiting examples can be used: polyvinyl pyrrolidone, sorbitan fatty acid esters such as sorbitan trioleate, phosphatides such as lecithin, acacia, tragacanth, polyoxyethylated sorbitan monooleate and other ethoxylated fatty acid esters of sorbitan, polyoxyethylated fats, polyoxyethylated oleotriglycerides, linolizated oleotriglycerides, polyethylene oxide condensation products of fatty alcohols, alkylphenols or fatty acids or also 1-methyl-3-(2-hydroxyethyl)imidazolidone-(2). In this context, polyoxyethylated means that the substances in question contain polyoxyethylene chains, the degree of polymerization of which generally lies between 2 and 40 and in particular between 10 and 20. Polyoxyethylated substances of this kind may for example be obtained by reaction of hydroxyl group-containing compounds (for example mono- or diglycerides or unsaturated compounds such as those containing oleic acid radicals) with ethylene oxide (for example 40 Mol ethylene oxide per 1 Mol glyceride). Examples of oleotriglycerides are olive oil, peanut oil, castor oil, sesame oil, cottonseed oil, corn oil. See also Dr. H. P. Fiedler "Lexikon der Hillsstoffe für Pharmazie, Kostnetik and angrenzende Gebiete" 1971, pages 191-195.

In various aspects, a liquid dosage form can further comprise preservatives, stabilizers, buffer substances, flavor correcting agents, sweeteners, colorants, antioxidants and complex formers and the like. Complex formers which may be for example be considered are: chelate formers such as ethylene diamine retrascetic acid, nitrilotriacetic acid, diethylene triamine pentacetic acid and their salts.

It may optionally be necessary to stabilize a liquid dosage form with physiologically acceptable bases or buffers to a pH range of approximately 6 to 9. Preference may be given to as neutral or weakly basic a pH value as possible (up to pH 8).

In order to enhance the solubility and/or the stability of a disclosed compound in a disclosed liquid dosage form, a parenteral injection form, or an intravenous injectable form, it can be advantageous to employ α-, β- or γ-cyclodextrins or their derivatives, in particular hydroxyalkyl substituted cyclodextrins, e.g. 2-hydroxypropyl-β-cyclodextrin or sulfobutyl-β-cyclodextrin. Also co-solvents such as alcohols may improve the solubility and/or the stability of the compounds according to the present disclosure in pharmaceutical compositions.

In various aspects, a disclosed liquid dosage form, a parenteral injection form, or an intravenous injectable form can further comprise liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

Pharmaceutical compositions of the present disclosure suitable injection, such as parenteral administration, such as intravenous, intramuscular, or subcutaneous administration. Pharmaceutical compositions for injection can be prepared as solutions or suspensions of the active compounds in water. A suitable surfactant can be included such as, for example, hydroxypropylcellulose. Dispersions can also be prepared in glycerol, liquid polyethylene glycols, and mixtures thereof in oils. Further, a preservative can be included to prevent the detrimental growth of microorganisms.

Pharmaceutical compositions of the present disclosure suitable for parenteral administration can include sterile aqueous or oleaginous solutions, suspensions, or dispersions. Furthermore, the compositions can be in the form of sterile powders for the extemporaneous preparation of such sterile injectable solutions or dispersions. In some aspects, the final injectable form is sterile and must be effectively fluid for use in a syringe. The pharmaceutical compositions should be stable under the conditions of manufacture and storage; thus, preferably should be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), vegetable oils, and suitable mixtures thereof.

Injectable solutions, for example, can be prepared in which the carrier comprises saline solution, glucose solution or a mixture of saline and glucose solution. Injectable suspensions may also be prepared in which case appropriate liquid carriers, suspending agents and the like may be employed. In some aspects, a disclosed parenteral formulation can comprise about 0.01-0.1 M, e.g. about 0.05 M, phosphate buffer. In a further aspect, a disclosed parenteral formulation can comprise about 0.9% saline.

In various aspects, a disclosed parenteral pharmaceutical composition can comprise pharmaceutically acceptable carriers such as aqueous or non-aqueous solutions, suspensions, and emulsions. Examples of non-aqueous solvents are propylene glycol, polyethylene glycol, vegetable oils such as olive oil, and injectable organic esters such as ethyl oleate.

Aqueous carriers include but not limited to water, alcoholic/aqueous solutions, emulsions or suspensions, including saline and buffered media. Parenteral vehicles can include mannitol, normal serum albumin, sodium chloride solution, Ringer's dextrose, dextrose and sodium chloride, lactated Ringer's and fixed oils. Intravenous vehicles include fluid and nutrient replenishers, electrolyte replenishers such as those based on Ringer's dextrose, and the like. Preservatives and other additives may also be present, such as, for example, antimicrobials, antioxidants, collating agents, inert gases and the like. In a further aspect, a disclosed parenteral pharmaceutical composition can comprise may contain minor amounts of additives such as substances that enhance isotonicity and chemical stability, e.g., buffers and preservatives. Also contemplated for injectable pharmaceutical compositions are solid form preparations that are intended to be converted, shortly before use, to liquid form preparations. Furthermore, other adjuvants can be included to render the formulation isotonic with the blood of the subject or patient.

In addition to the pharmaceutical compositions described herein above, the disclosed compounds can also be formulated as a depot preparation. Such long acting formulations can be administered by implantation (e.g., subcutaneously or intramuscularly) or by intramuscular injection. Thus, for example, the compounds can be formulated with suitable polymeric or hydrophobic materials (e.g., as an emulsion in an acceptable oil) or ion exchange resins, or as sparingly soluble derivatives, e.g., as a sparingly soluble salt.

Pharmaceutical compositions of the present disclosure can be in a form suitable for topical administration. As used herein, the phrase "topical application" means administration onto a biological surface, whereby the biological surface includes, for example, a skin area (e.g., hands, forearms, elbows, legs, face, nails, anus and genital areas) or a mucosal membrane. By selecting the appropriate carrier and optionally other ingredients that can be included in the composition, as is detailed herein below, the compositions of the present invention may be formulated into any form typically employed for topical application. A topical pharmaceutical composition can be in a form of a cream, an ointment, a paste, a gel, a lotion, milk, a suspension, an aerosol, a spray, foam, a dusting powder, a pad, and a patch. Further, the compositions can be in a form suitable for use in transdermal devices. These formulations can be prepared, utilizing a compound of the present disclosure, or pharmaceutically acceptable salts thereof, via conventional processing methods. As an example, a cream or ointment is prepared by mixing hydrophilic material and water, together with about 5 wt % to about 10 wt % of the compound, to produce a cream or ointment having a desired consistency.

In the compositions suitable for percutaneous administration, the carrier optionally comprises a penetration enhancing agent and/or a suitable wetting agent, optionally combined with suitable additives of any nature in minor proportions, which additives do not introduce a significant deleterious effect on the skin. Said additives may facilitate the administration to the skin and/or may be helpful for preparing the desired compositions. These compositions may be administered in various ways, e.g., as a transdermal patch, as a spot-on, as an ointment.

Ointments are semisolid preparations, typically based on petrolatum or petroleum derivatives. The specific ointment base to be used is one that provides for optimum delivery for the active agent chosen for a given formulation, and, preferably, provides for other desired characteristics as well (e.g., emollience). As with other carriers or vehicles, an ointment base should be inert, stable, nonirritating and nonsensitizing. As explained in Remington: The Science and Practice of Pharmacy, 19th Ed., Easton, Pa.: Mack Publishing Co. (1995), pp. 1399-1404, ointment bases may be grouped in four classes: oleaginous bases; emulsifiable bases; emulsion bases; and water-soluble bases. Oleaginous ointment bases include, for example, vegetable oils, fats obtained from animals, and semisolid hydrocarbons obtained from petroleum. Emulsifiable ointment bases, also known as absorbent ointment bases, contain little or no water and include, for example, hydroxystearin sulfate, anhydrous lanolin and hydrophilic petrolatum. Emulsion ointment bases are either water-in-oil (W/O) emulsions or oil-in-water (O/W) emulsions, and include, for example, cetyl alcohol, glyceryl monostearate, lanolin and stearic acid. Preferred water-soluble ointment bases are prepared from polyethylene glycols of varying molecular weight.

Lotions are preparations that are to be applied to the skin surface without friction. Lotions are typically liquid or semiliquid preparations in which solid particles, including the active agent, are present in a water or alcohol base. Lotions are typically preferred for treating large body areas, due to the ease of applying a more fluid composition. Lotions are typically suspensions of solids, and oftentimes comprise a liquid oily emulsion of the oil-in-water type. It is generally necessary that the insoluble matter in a lotion be finely divided. Lotions typically contain suspending agents to produce better dispersions as well as compounds useful for localizing and holding the active agent in contact with the skin, such as methylcellulose, sodium carboxymethylcellulose, and the like.

Creams are viscous liquids or semisolid emulsions, either oil-in-water or water-in-oil. Cream bases are typically water-washable, and contain an oil phase, an emulsifier and an aqueous phase. The oil phase, also called the "internal" phase, is generally comprised of petrolatum and/or a fatty alcohol such as cetyl or stearyl alcohol. The aqueous phase typically, although not necessarily, exceeds the oil phase in volume, and generally contains a humectant. The emulsifier in a cream formulation is generally a nonionic, anionic, cationic or amphoteric surfactant. Reference may be made to Remington: The Science and Practice of Pharmacy, supra, for further information.

Pastes are semisolid dosage forms in which the bioactive agent is suspended in a suitable base. Depending on the nature of the base, pastes are divided between fatty pastes or those made from a single-phase aqueous gel. The base in a fatty paste is generally petrolatum, hydrophilic petrolatum and the like. The pastes made from single-phase aqueous gels generally incorporate carboxymethylcellulose or the like as a base. Additional reference may be made to Remington: The Science and Practice of Pharmacy, for further information.

Gel formulations are semisolid, suspension-type systems. Single-phase gels contain organic macromolecules distributed substantially uniformly throughout the carrier liquid, which is typically aqueous, but also, preferably, contain an alcohol and, optionally, an oil. Preferred organic macromolecules, i.e., gelling agents, are crosslinked acrylic acid polymers such as the family of carbomer polymers, e.g., carboxypolyalkylenes that may be obtained commercially under the trademark Carbopol™. Other types of preferred polymers in this context are hydrophilic polymers such as polyethylene oxides, polyoxyethylene-polyoxypropylene copolymers and polyvinylalcohol; modified cellulose, such as hydroxypropyl cellulose, hydroxyethyl cellulose, hydroxypropyl methylcellulose, hydroxypropyl methylcellulose phthalate, and methyl cellulose; gums such as tragacanth and xanthan gum; sodium alginate; and gelatin. In order to prepare a uniform gel, dispersing agents such as alcohol or glycerin can be added, or the gelling agent can be dispersed by trituration, mechanical mixing or stirring, or combinations thereof.

Sprays generally provide the active agent in an aqueous and/or alcoholic solution which can be misted onto the skin for delivery. Such sprays include those formulated to provide for concentration of the active agent solution at the site of administration following delivery, e.g., the spray solution can be primarily composed of alcohol or other like volatile liquid in which the active agent can be dissolved. Upon delivery to the skin, the carrier evaporates, leaving concentrated active agent at the site of administration.

Foam compositions are typically formulated in a single or multiple phase liquid form and housed in a suitable container, optionally together with a propellant which facilitates the expulsion of the composition from the container, thus transforming it into a foam upon application. Other foam forming techniques include, for example the "Bag-in-a-can" formulation technique. Compositions thus formulated typically contain a low-boiling hydrocarbon, e.g., isopropane. Application and agitation of such a composition at the body temperature cause the isopropane to vaporize and generate the foam, in a manner similar to a pressurized aerosol foaming system. Foams can be water-based or aqueous alkanolic, but are typically formulated with high alcohol content which, upon application to the skin of a user, quickly evaporates, driving the active ingredient through the upper skin layers to the site of treatment.

Skin patches typically comprise a backing, to which a reservoir containing the active agent is attached. The reservoir can be, for example, a pad in which the active agent or composition is dispersed or soaked, or a liquid reservoir. Patches typically further include a frontal water permeable adhesive, which adheres and secures the device to the treated region. Silicone rubbers with self-adhesiveness can alternatively be used. In both cases, a protective permeable layer can be used to protect the adhesive side of the patch prior to its use. Skin patches may further comprise a removable cover, which serves for protecting it upon storage.

Examples of patch configuration which can be utilized with the present invention include a single-layer or multi-layer drug-in-adhesive systems which are characterized by the inclusion of the drug directly within the skin-contacting adhesive. In such a transdermal patch design, the adhesive not only serves to affix the patch to the skin, but also serves as the formulation foundation, containing the drug and all the excipients under a single backing film. In the multi-layer drug-in-adhesive patch a membrane is disposed between two distinct drug-in-adhesive layers or multiple drug-in-adhesive layers are incorporated under a single backing film.

Examples of pharmaceutically acceptable carriers that are suitable for pharmaceutical compositions for topical applications include carrier materials that are well-known for use in the cosmetic and medical arts as bases for e.g., emulsions, creams, aqueous solutions, oils, ointments, pastes, gels, lotions, milks, foams, suspensions, aerosols and the like, depending on the final form of the composition. Representative examples of suitable carriers according to the present invention therefore include, without limitation, water, liquid alcohols, liquid glycols, liquid polyalkylene glycols, liquid esters, liquid amides, liquid protein hydrolysates, liquid alkylated protein hydrolysates, liquid lanolin and lanolin derivatives, and like materials commonly employed in cosmetic and medicinal compositions. Other suitable carriers according to the present invention include, without limitation, alcohols, such as, for example, monohydric and polyhydric alcohols, e.g., ethanol, isopropanol, glycerol, sorbitol, 2-methoxyethanol, diethyleneglycol, ethylene glycol, hexyleneglycol, mannitol, and propylene glycol; ethers such as diethyl or dipropyl ether; polyethylene glycols and methoxypolyoxyethylenes (carbowaxes having molecular weight ranging from 200 to 20,000); polyoxyethylene glycerols, polyoxyethylene sorbitols, stearoyl diacetin, and the like.

Topical compositions of the present disclosure can, if desired, be presented in a pack or dispenser device, such as an FDA-approved kit, which may contain one or more unit dosage forms containing the active ingredient. The dispenser device may, for example, comprise a tube. The pack or dispenser device may be accompanied by instructions for administration. The pack or dispenser device may also be accompanied by a notice in a form prescribed by a governmental agency regulating the manufacture, use, or sale of pharmaceuticals, which notice is reflective of approval by the agency of the form of the compositions for human or veterinary administration. Such notice, for example, may include labeling approved by the U.S. Food and Drug Administration for prescription drugs or of an approved product insert. Compositions comprising the topical composition of the invention formulated in a pharmaceutically acceptable carrier may also be prepared, placed in an appropriate container, and labeled for treatment of an indicated condition.

Another patch system configuration which can be used by the present invention is a reservoir transdermal system design which is characterized by the inclusion of a liquid compartment containing a drug solution or suspension separated from the release liner by a semi-permeable membrane and adhesive. The adhesive component of this patch system can either be incorporated as a continuous layer between the membrane and the release liner or in a concentric configuration around the membrane. Yet another patch system configuration which can be utilized by the present invention is a matrix system design which is characterized by the inclusion of a semisolid matrix containing a drug solution or suspension which is in direct contact with the release liner. The component responsible for skin adhesion is incorporated in an overlay and forms a concentric configuration around the semisolid matrix.

Pharmaceutical compositions of the present disclosure can be in a form suitable for rectal administration wherein the carrier is a solid. It is preferable that the mixture forms unit dose suppositories. Suitable carriers include cocoa butter and other materials commonly used in the art. The suppositories can be conveniently formed by first admixing the composition with the softened or melted carrier(s) followed by chilling and shaping in molds.

Pharmaceutical compositions containing a compound of the present disclosure, and/or pharmaceutically acceptable salts thereof, can also be prepared in powder or liquid concentrate form.

The pharmaceutical composition (or formulation) may be packaged in a variety of ways. Generally, an article for distribution includes a container that contains the pharmaceutical composition in an appropriate form. Suitable containers are well known to those skilled in the art and include materials such as bottles (plastic and glass), sachets, foil blister packs, and the like. The container may also include a tamper proof assemblage to prevent indiscreet access to the contents of the package. In addition, the container typically has deposited thereon a label that describes the contents of the container and any appropriate warnings or instructions.

The disclosed pharmaceutical compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration. The pack or dispenser may also be accompanied with a notice associated with the container in form prescribed by a governmental agency regulating the manufacture, use, or sale of pharmaceuticals, which notice is reflective of approval by the agency of the form of the drug for human or veterinary administration. Such notice, for example, may be the labeling approved by the U.S. Food and Drug Administration for prescription drugs, or the approved product insert. Pharmaceutical compositions comprising a disclosed compound formulated in a compatible pharmaceutical carrier may also be prepared, placed in an appropriate container, and labeled for treatment of an indicated condition.

The exact dosage and frequency of administration depends on the particular disclosed compound, a product of a disclosed method of making, a pharmaceutically acceptable salt, solvate, or polymorph thereof, a hydrate thereof, a solvate thereof, a polymorph thereof, or a stereochemically isomeric form thereof; the particular condition being treated and the severity of the condition being treated; various factors specific to the medical history of the subject to whom the dosage is administered such as the age; weight, sex, extent of disorder and general physical condition of the particular subject, as well as other medication the individual may be taking; as is well known to those skilled in the art. Furthermore, it is evident that said effective daily amount may be lowered or increased depending on the response of the treated subject and/or depending on the evaluation of the physician prescribing the compounds of the present disclosure.

Depending on the mode of administration, the pharmaceutical composition will comprise from 0.05 to 99% by weight, preferably from 0.1 to 70% by weight, more preferably from 0.1 to 50% by weight of the active ingredient, and, from 1 to 99.95% by weight, preferably from 30 to 99.9% by weight, more preferably from 50 to 99.9% by weight of a pharmaceutically acceptable carrier, all percentages being based on the total weight of the composition.

In the treatment conditions which require regulation, limitation, or inhibition of AVIL activity an appropriate dosage level will generally be about 0.01 to 1000 mg per kg patient body weight per day and can be administered in single or multiple doses. In various aspects, the dosage level will be about 0.1 to about 500 mg/kg per day, about 0.1 to 250 mg/kg per day, or about 0.5 to 100 mg/kg per day. A suitable dosage level can be about 0.01 to 1000 mg/kg per day, about 0.01 to 500 mg/kg per day, about 0.01 to 250 mg/kg per day, about 0.05 to 100 mg/kg per day, or about 0.1 to 50 mg/kg per day. Within this range the dosage can be 0.05 to 0.5, 0.5 to 5.0 or 5.0 to 50 mg/kg per day. For oral administration, the compositions are preferably provided in the form of tablets containing 1.0 to 1000 mg of the active ingredient, particularly 1.0, 5.0, 10, 15, 20, 25, 50, 75, 100, 150, 200, 250, 300, 400, 500, 600, 750, 800, 900 and 1000 mg of the active ingredient for the symptomatic adjustment of the dosage of the patient to be treated. The compound can be administered on a regimen of 1 to 4 times per day, preferably once or twice per day. This dosing regimen can be adjusted to provide the optimal therapeutic response.

Such unit doses as described hereinabove and hereinafter can be administered more than once a day, for example, 2, 3, 4, 5 or 6 times a day. In various aspects, such unit doses can be administered 1 or 2 times per day, so that the total dosage for a 70 kg adult is in the range of 0.001 to about 15 mg per kg weight of subject per administration. In a further aspect, dosage is 0.01 to about 1.5 mg per kg weight of subject per administration, and such therapy can extend for a number of weeks or months, and in some cases, years. It will be understood, however, that the specific dose level for any particular patient will depend on a variety of factors including the activity of the specific compound employed; the age, body weight, general health, sex and diet of the individual being treated; the time and route of administration; the rate of excretion; other drugs that have previously been administered; and the severity of the particular disease undergoing therapy, as is well understood by those of skill in the area.

A typical dosage can be one 1 mg to about 100 mg tablet or 1 mg to about 300 mg taken once a day, or, multiple times per day, or one time-release capsule or tablet taken once a day and containing a proportionally higher content of active ingredient. The time-release effect can be obtained by capsule materials that dissolve at different pH values, by capsules that release slowly by osmotic pressure, or by any other known means of controlled release.

It can be necessary to use dosages outside these ranges in some cases as will be apparent to those skilled in the art. Further, it is noted that the clinician or treating physician will know how and when to start, interrupt, adjust, or terminate therapy in conjunction with individual patient response.

The present disclosure is further directed to a method for the manufacture of a medicament for regulating, limiting or inhibiting AVIL activity (e.g., treatment of one or more disorders associated with AVIL dysfunction) in mammals (e.g., humans) comprising combining one or more disclosed compounds, products, or compositions with a pharmaceutically acceptable carrier or diluent. Thus, in one aspect, the present disclosure further relates to a method for manufacturing a medicament comprising combining at least one disclosed compound or at least one disclosed product with a pharmaceutically acceptable carrier or diluent.

The disclosed pharmaceutical compositions can further comprise other therapeutically active compounds, which are usually applied in the treatment of the above mentioned pathological or clinical conditions.

It is understood that the disclosed compositions can be prepared from the disclosed compounds. It is also understood that the disclosed compositions can be employed in the disclosed methods of using.

As already mentioned, the present disclosure relates to a pharmaceutical composition comprising a therapeutically effective amount of a disclosed compound, a product of a disclosed method of making, a pharmaceutically acceptable salt, a hydrate thereof, a solvate thereof, a polymorph thereof, and a pharmaceutically acceptable carrier. Additionally, the present disclosure relates to a process for preparing such a pharmaceutical composition, characterized in that a pharmaceutically acceptable carrier is intimately mixed with a therapeutically effective amount of a compound according to the present disclosure.

As already mentioned, the present disclosure also relates to a pharmaceutical composition comprising a disclosed compound, a product of a disclosed method of making, a pharmaceutically acceptable salt, a hydrate thereof, a solvate thereof, a polymorph thereof, and one or more other drugs in the treatment, prevention, control, amelioration, or reduction of risk of diseases or conditions for a disclosed compound or the other drugs may have utility as well as to the use of such a composition for the manufacture of a medicament. The present disclosure also relates to a combination of disclosed compound, a product of a disclosed method of making, a pharmaceutically acceptable salt, a hydrate thereof, a solvate thereof, a polymorph thereof, and a therapeutic agent that can be used to treat disorders or diseases. The present disclosure also relates to such a combination for use as a medicine. The present disclosure also relates to a product comprising (a) disclosed compound, a product of a disclosed method of making, a pharmaceutically acceptable salt, a hydrate thereof, a solvate thereof, a polymorph thereof, and (b) an additional therapeutic agent, as a combined preparation for simultaneous, separate or sequential use in the treatment or prevention of a condition in a mammal, including a human, the treatment or prevention of which is affected or facilitated by the modulatory effect of the disclosed compound and the additional therapeutic agent. The different drugs of such a combination or product may be combined in a single preparation together with pharmaceutically acceptable carriers or diluents, or they may each be present in a separate preparation together with pharmaceutically acceptable carriers or diluents.

Methods of Using the Compounds.

In a further aspect, the present disclosure provides methods of treatment comprising administration of a therapeutically effective amount of a disclosed compound or pharmaceutical composition as disclosed herein above to a subject in need thereof. In particular, the disclosed compounds and disclosed pharmaceutical compositions can be used in methods of treating a disease or disorder that is associated with increased, aberrant, or dysfunctional levels of advillin (AVIL) activity in a cell, tissue, or organism. That is, the disclosed compounds and disclosed pharmaceutical compositions can be used to regulate, limit, or inhibit AVIL activity in a cell, tissue, or organism to provide a clinical or therapeutic benefit to a subject which has been determined to or been diagnosed to have with increased, aberrant, or dysfunctional levels of AVIL activity.

Adult cancers often have complex genomic landscapes, making it challenging to identify key cancer-driving events. As disclosed herein below, a pediatric rhabdomyosarcoma was identified as having a gene fusion, AVIL fused to a house-keeping gene, MARS. In adults, AVIL was overexpressed in all of the glioblastomas tested herein below. Tumors were addicted to AVIL dysregulation: silencing the MARS-AVIL fusion in rhabdomyosarcoma, or silencing AVIL in glioblastoma nearly eradicated the cells in culture, and dramatically inhibited in vivo xenografts in mice. Conversely, overexpressing AVIL promoted tumorigenesis. GBM and lower-grade glioma patients with increased AVIL expression had worse prognosis. The effect of AVIL was partly mediated by LIN28B, whose expression also correlated with clinical prognosis. High levels of AVIL expression were also associated with poor patient outcomes in several other cancers. High throughput small molecule screening has yielded several lead compounds (Compounds A-L), all of which have the phenotypic effect similar to inhibition with siAVIL. One was also tested effective in xenografts.

Oncogene addiction describes a phenomenon according to which tumor cells become reliant on the activity of a particular oncogene and die once this activity is inhibited. (Vivanco, 2014; Weinstein, 2002; Weinstein and Joe, 2006). Many of the targeted cancer therapies exploit this concept (Lord and Ashworth, 2013; Luo et al., 2009). It is perhaps best exemplified by the successful use of imatinib in the therapy of chronic myelogenous leukemia (CML) (Druker et al., 2001). In CML, the major driver of tumorigenesis is the BCR-ABL fusion oncogene; imatinib inhibits the constitutively active BCR-ABL protein kinase, to which leukemic cells become addicted. Other successful examples include trastuzumab targeting ERBB2 addiction (Paik et al., 2008), and vemurafenib targeting BRAF addiction (Bollag et al., 2010; Chapman et al., 2011; Davies et al., 2002). The challenge is to find such key oncogenes. Even though large sets of genome and transcriptome data are available to facilitate the identification of driver mutations in cancer, true signals are often buried in a large number of passenger events.

Glioblastoma (GBM) is the most common primary brain tumor and among the deadliest of human cancers. Despite advances in surgery, radiation and chemotherapy, survival of patients affected by GBM remains dismal (~15 months after diagnosis). (Prados and Levin, 2000; Castro et al., 2003; King et al., 2005; Stupp et al., 2005). Clearly, better treatment options, and identification of novel therapeutic targets are urgently needed.

Tumor cells use multiple "tricks" to dysregulate some oncogenes, which at the same time give credence to the genes as key players in tumorigenesis and malignancy. However, this knowledge is usually accumulated over a long period of time and often involves different laboratories examining various types of cancer. Our strategy is to use this concept proactively to find key oncogenes that are dysregulated by multiple mechanisms in different types of cancer. Most adult solid tumors have a complex landscape of genetic lesions, impeding analysis. In contrast, pediatric tumors tend to have fewer point mutations and structural changes. Our study was initiated in the pediatric tumor, rhabdomyosarcoma. As disclosed herein below, a gene fusion has been described which results in the juxtaposition of a house-keeping gene next to the AVIL gene, in particular, it is disclosed herein below that a subset of GBMs retain AVIL amplification. Interestingly, at RNA and protein levels, all of the GBM cases in our collection overexpress AVIL. Loss-of-function experiments proved the dependency of tumor growth on AVIL dysregulation, yet no effect on non-cancer astrocytes was observed. Consistently, forced overexpression of AVIL resulted in enhanced tumorigenesis. Clinically, higher expression of AVIL correlates with worse patient outcome in GBMs as well as in lower-grade gliomas. The oncogenic effect is at least partly mediated by LIN28B in gliomas. In addition to gliomas, lung cancer, bladder cancer, and renal cancer patients with high level of AVIL expression also had worse prognosis. GBM cells treated with the disclosed compounds have a phenotype similar to the siAVIL transfected cells. One compound was also tested effective in xenografts. AVIL, as disclosed herein, is surprisingly an oncogene and an effective therapeutic target.

Glioblastoma (GBM), WHO classification Grade IV Astrocytoma, is the most common, and most aggressive malignant primary brain tumor in humans (Dunn et al., 2012). Survival of patients affected by GBM has remained low, despite advances in surgery, radiation, and chemotherapy (Castro et al., 2003; King et al., 2005; Prados and Levin, 2000; Stupp et al., 2005). About 50% of patients diagnosed with GBM die within one year, and 90% die within three years (American Brain Tumor Association, 2014). The disclosure herein below shows that AVIL is overexpressed in the vast majority, if not all of human glioblastomas. Moreover, it was found that GBM cells depend on the overexpression of AVIL for increased survival and migration. Silencing AVIL induced GBM cell death in vitro, and prevented GBM xenograft formation and growth in animal models. Silencing AVIL also dramatically changed cell morphology, and reduced cell migration/invasion ability. In contrast, normal astrocytes express very low levels of AVIL, and silencing AVIL had no obvious effect on cell growth, or morphology. Taken together, this demonstrates that AVIL is a new and promising selective therapeutic target, inhibition of which may effectively suppress GBM growth and invasion, yet spare normal brain cells. Indeed, all the three lead compounds had significantly different $IC_{50}$ values in GBMs versus in astrocytes. In vivo, with only three injections for compound A, smaller tumors were observed as compared to the solvent control. We did not observe any obvious side effect in the animals. Optimization for chemicals that are more potent, stable, water soluble, and capable of crossing the blood-brain barrier is of course needed for practical usage, but our data unambiguously demonstrated that AVIL is a critical oncogene, which GBMs are addicted to, and is a viable drug target.

In some aspects, the method includes diagnosis of the subject's need for treatment prior to administration of the compound or pharmaceutical composition. In some aspects, the subject has been diagnosed with a disorder treatable by regulation, limitation, or inhibition of AVIL prior to administering. In some aspects, the subject has been diagnosed with a cancer. In some aspects, the method includes identifying a subject's need for treatment prior to the administering step.

The disclosed compounds can be used as single agents or in combination with one or more other drugs in the treatment, prevention, control, amelioration or reduction of risk of the aforementioned diseases, disorders and conditions for which compounds or the other drugs have utility, where the combination of drugs together are safer or more effective than either drug alone. The other drug(s) can be administered by a route and in an amount commonly used therefore, contemporaneously or sequentially with a disclosed compound. When a disclosed compound is used contemporaneously with one or more other drugs, a pharmaceutical composition in unit dosage form containing such drugs and the disclosed compound is preferred. However, the combination therapy can also be administered on overlapping schedules. It is also envisioned that the combination of one or more active ingredients and a disclosed compound will be more efficacious than either as a single agent.

AVIL is known as a member of the vilin/gelsolin family, which regulates actin filament reorganization (Marks et al., 1998). In encodes a protein also called advillin, which is known to affect cell movement and has been reported to be involved in the formation of filopedia-like structures in fibroblasts, as well as a role in ciliogenesis (Morin et al., 2010). AVIL is overexpressed in in many, if not all, glioblastomas. GBM cells depend on the overexpression of AVIL for increased survival and migration. Silencing AVIL induced GBM cell death in vitro, and can prevent GBM xenograft formation and growth in animal models. Silencing AVIL can also change cell morphology in GBM cells, and reduce cell migration/invasion ability. In contrast, normal astrocytes express very low levels of AVIL, and silencing AVIL had no obvious effect on cell growth, or morphology.

Therefore, compounds that regulate, limit, or inhibit AVIL expression show improved prognosis in the treatment of cancers in which there is an inverse correlation between AVIL expression and patient prognosis, such as, but not limited to, brain cancer and cancerous tumors such as glioblastomas, rhabdosarcomas, gliomas, lung cancer, bladder cancer including bladder urothelial carcinoma, and renal cancer including kidney clear cell carcinoma.

Accordingly, in various aspects, the present disclosure pertains to methods of targeting AVIL with the disclosed compounds. The disclosed compounds or disclosed pharmaceutical compositions can act as regulators of AVIL expression in cells having increased, aberrant, or dysfunctional levels of AVIL, and accordingly can be useful in the treatment of cancer (including but not limited to those types mentioned herein).

The compositions can be administered alone or combination with a chemotherapeutic drug. Combination therapy can present advantages over single-agent therapies: lower treatment failure rate, lower case-fatality ratios, slower development of resistance and consequently, less money needed for the development of new drugs. Chemotherapeutic drugs include conventional chemotherapeutic reagents such as alkylating agents, anti-metabolites, anti-mitototics, plant alkaloids, antibiotics, and miscellaneous compounds. Examples of these drugs include CDDP, methotrexate, vincristine, adriamycin, bleomycin, carmustine, hydroxyurea, hydrazine, nitrosoureas, triazenes such as dacarabzine and temozolomide, nitrogen mustards such as chlorambucil, cyclophosphamide, isofamide, mechlorethamine, melphalan, uracil mustard; aziridine such as thiotepa; methanesulphonate esters such as busulfan; platinum complexes such as cisplatin, carboplatin; bioreductive alkylators, such as mitomycin and and altretemine. Chemotherapeutic drugs also include proteasome inhibitors such as salinosporamides, bortezomib, PS-519, and omuralide. The disclosed compounds can also be administered in combination with surgery. For example, the disclosed compounds can be administered prior to, during or after surgery or radiotherapy. Adminstration during surgery can be as a bathing solution for the operation site. The resected tumor can also be bathed in the disclosed compounds.

In further aspects, the disclosed compounds can be utilized in combination with one or more chemotherapeutic agents. For example, the one or more chemotherapeutic agent can be a chemotherapeutic agent selected from alkylating agents, antimetabolites, platinating agents, toxoids, EGFR inhibitors, anti-hormonal agents, topoisomerase inhibitors, tubulin agents, signaling inhibitors (e.g., kinase inhibitors), and other chemotherapeutic agents.

A "chemotherapeutic agent" is a chemical compound useful in the treatment of cancer. Examples of chemotherapeutic agents include alkylating agents such as thiotepa and cyclosphosphamide (CYTOXAN®); alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); delta-9-tetrahydrocannabinol (dronabinol, MARINOL®); beta-lapachone; lapachol; colchicines; betulinic acid; a camptothecin (including the synthetic analogue topotecan (HYCAMTIN®), CPT-11 (irinotecan, CAMPTOSAR®), acetylcamptothecin, scopolectin, and 9-aminocamptothecin); bryostatin; callystatin; CC-1065 (including its adozelesin, carzelesin and bizelesin synthetic analogues); podophyllotoxin; podophyllinic acid; teniposide; cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e. g., calicheamicin, especially calicheamicin gamma1I and calicheamicin omegaI1 (see, e.g., Agnew, Chem Intl. Ed. Engl., 33:183-186 (1994)); dynemicin, including dynemicin A; an esperamicin; as well as neocarzinostatin chromophore and related chromoprotein enediyne antiobiotic chromophores), aclacinomysins, actinomycin, authramycin, azaserine, bleomycins, cactinomycin, carabicin, carminomycin, carzinophilin, chromomycinis, dactinomycin, daunorubicin, detorubicin, 6-diazo-5-oxo-L-norleucine, doxorubicin (including ADRIAMYCIN®, morpholino-doxorubicin, cyanomorpholino-doxorubicin, 2-pyrrolino-doxorubicin, doxorubicin HCl liposome injection (DOXIL®), liposomal doxorubicin TLC D-99 (MYOCET®), peglylated liposomal doxorubicin (CAELYX®), and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate, gemcitabine (GEMZAR®), tegafur (UFTORAL®), capecitabine (XELODA®), an epothilone, and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfornithine; elliptinium acetate; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; 2-ethylhydrazide; procarbazine; PSK® polysaccharide complex (JHS Natural Products, Eugene, Oreg.); razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; dacarbazine; mannomustine; mitobronitol; mitolactol; pipobroman; gacytosine; arabinoside ("Ara-C"); thiotepa; taxoid, e.g., paclitaxel (TAXOL®), albumin-engineered nanoparticle formulation of paclitaxel (ABRAXANE™), and docetaxel (TAXOTERE®); chloranbucil; 6-thioguanine; mercaptopurine; methotrexate; platinum agents such as cisplatin, oxaliplatin, and carboplatin; vincas, which prevent tubulin polymerization from forming microtubules, including vinblastine (VELBAN®), vincristine (ONCOVIN®), vindesine (ELDISINE®, FILDESIN®), and vinorelbine (NAVELBINE®); etoposide (VP-16); ifosfamide; mitoxantrone; leucovovin; novantrone; edatrexate; daunomycin; aminopterin; ibandronate; topoisomerase inhibitor RFS 2000; difluorometlhylornithine (DMFO); retinoids such as retinoic acid, including bexarotene (TARGRETIN®); bisphosphonates such as clodronate (for example, BONEFOSO® or OSTAC®), etidronate (DIDROCAL®), NE-58095, zoledronic acid/zoledronate (ZOMETA®), alendronate (FOSAMAX®), pamidronate (AREDIA®), tiludronate (SKELID®), or risedronate (ACTONEL®); troxacitabine (a 1,3-dioxolane nucleoside cytosine analog); antisense oligonucleotides, particularly those that inhibit expression of genes in signaling pathways implicated in aberrant cell proliferation, such as, for example, PKC-alpha, Raf, H-Ras, and epidermal growth factor receptor (EGF-R); vaccines such as THERATOPE® vaccine and gene therapy vaccines, for example, ALLOVECTIN® vaccine, LEUVECTIN® vaccine, and VAXID® vaccine; topoisomerase 1 inhibitor (e.g., LURTOTECAN®); rmRH (e.g., ABARELIX®); BAY439006 (sorafenib; Bayer); SU-11248 (Pfizer); perifosine, COX-2 inhibitor (e.g., celecoxib or etoricoxib), proteosome inhibitor (e.g., PS341); bortezomib (VELCADE®); CCI-779; tipifarnib (R11577); orafenib, ABT510; Bcl-2 inhibitor such as oblimersen sodium (GENASENSE®); pixantrone; EGFR inhibitors (see definition below); tyrosine kinase inhibitors (see definition below); and pharmaceutically acceptable salts, acids or derivatives of any of the above; as well as combinations of two or more of the above such as CHOP, an abbreviation for a combined therapy of cyclophosphamide, doxorubicin, vincristine, and prednisolone, and FOLFOX, an abbreviation for a treatment regimen with oxaliplatin (ELOXATIN™) combined with 5-FU and leucovovin.

Herein, chemotherapeutic agents include "anti-hormonal agents" or "endocrine therapeutics" which act to regulate, reduce, block, or inhibit the effects of hormones that can promote the growth of cancer. They may be hormones themselves, including, but not limited to: anti-estrogens with mixed agonist/antagonist profile, including, tamoxifen (NOLVADEX®), 4-hydroxytamoxifen, toremifene (FARESTON®), idoxifene, droloxifene, raloxifene (EVISTA®), trioxifene, keoxifene, and selective estrogen receptor modulators (SERMs) such as SERM3; pure anti-estrogens without agonist properties, such as fulvestrant (FASLODEX®), and EM800 (such agents may block estrogen receptor (ER) dimerization, inhibit DNA binding, increase ER turnover, and/or suppress ER levels); aromatase inhibitors, including steroidal aromatase inhibitors such as formestane and exemestane (AROMASIN®), and non-steroidal aromatase inhibitors such as anastrazole (ARIMIDEX®), letrozole (FEMARA®) and aminoglutethimide, and other aromatase inhibitors include vorozole (RIVISOR®), megestrol acetate (MEGASE®), fadrozole, and 4(5)-imidazoles; lutenizing hormone-releaseing hormone agonists, including leuprolide (LUPRON® and ELIGARD®), goserelin, buserelin, and tripterelin; sex steroids, including progestines such as megestrol acetate and medroxyprogesterone acetate, estrogens such as diethylstilbestrol and premarin, and androgens/retinoids such as fluoxymesterone, all transretionic acid and fenretinide; onapristone; anti-progesterones; estrogen receptor down-regulators (ERDs); anti-androgens such as flutamide, nilutamide and bicalutamide; and pharmaceutically acceptable salts, acids or derivatives of any of the above; as well as combinations of two or more of the above.

Herein, a "taxoid" is a chemotherapeutic agent that functions to inhibit microtubule depolymerization. Examples include paclitaxel (TAXOL®), albumin-engineered nanoparticle formulation of paclitaxel (ABRAXANE™), and docetaxel (TAXOTERE®). The preferred taxoid is paclitaxel.

As used herein, the term "EGFR inhibitor" refers to compounds that bind to or otherwise interact directly with EGFR and prevent or reduce its signaling activity, and is alternatively referred to as an "EGFR antagonist." Examples of such agents include antibodies and small molecules that bind to EGFR. Examples of antibodies which bind to EGFR include MAb 579 (ATCC CRL HB 8506), MAb 455 (ATCC CRL HB8507), MAb 225 (ATCC CRL 8508), MAb 528 (ATCC CRL 8509) (see, U.S. Pat. No. 4,943,533, Mendelsohn et al.) and variants thereof, such as chimerized 225

(C225 or Cetuximab; ERBUTIX®) and reshaped human 225 (H225) (see, WO 96/40210, Imclone Systems Inc.); IMC-11F8, a fully human, EGFR-targeted antibody (Imclone); antibodies that bind type II mutant EGFR (U.S. Pat. No. 5,212,290); humanized and chimeric antibodies that bind EGFR as described in U.S. Pat. No. 5,891,996; and human antibodies that bind EGFR, such as ABX-EGF or Panitumumab (see WO98/50433, Abgenix/Amgen); EMD 55900 (Stragliotto et al., Eur. J. Cancer, 32A:636-640 (1996)); EMD7200 (matuzumab) a humanized EGFR antibody directed against EGFR that competes with both EGF and TGF-alpha for EGFR binding (EMD/Merck); human EGFR antibody, HuMax-EGFR (GenMab); fully human antibodies known as E1.1, E2.4, E2.5, E6.2, E6.4, E2.11, E6.3 and E7.6.3 and described in U.S. Pat. No. 6,235,883; MDX-447 (Medarex Inc); and mAb 806 or humanized mAb 806 (Johns et al., J. Biol. Chem., 279(29):30375-30384 (2004)). The anti-EGFR antibody may be conjugated with a cytotoxic agent, thus generating an immunoconjugate (see, e.g., EP659,439A2, Merck Patent GmbH). EGFR antagonists include small molecules such as compounds described in U.S. Pat. Nos. 5,616,582, 5,457,105, 5,475,001, 5,654, 307, 5,679,683, 6,084,095, 6,265,410, 6,455,534, 6,521,620, 6,596,726, 6,713,484, 5,770,599, 6,140,332, 5,866,572, 6,399,602, 6,344,459, 6,602,863, 6,391,874, 6,344,455, 5,760,041, 6,002,008, and 5,747,498, as well as the following PCT publications: WO98/14451, WO98/50038, WO99/09016, and WO99/24037. Particular small molecule EGFR antagonists include OSI-774 (CP-358774, erlotinib, TARCEVA® Genentech/OSI Pharmaceuticals); PD 183805 (CI 1033, 2-propenamide, N-[4-[(3-chloro-4-fluorophenyl)amino]-7-[3-(4-morpholinyl)propoxy]-6-quinazolinyl]-, dihydrochloride, Pfizer Inc.); ZD1839, gefitinib (IRESSA J) 4-(3'-Chloro-4'-fluoroanilino)-7-methoxy-6-(3-morpholino propoxy)quinazoline, AstraZeneca); ZM 105180 ((6-amino-4-(3-methylphenyl-amino)-quinazoline, Zeneca); BIBX-1382 (N8-(3-chloro-4-fluoro-phenyl)-N2-(1-methyl-piperidin-4-yl)-pyrimido[5,4-d]pyrimidine-2,8-diamine, Boehringer Ingelheim); PKI-166 ((R)-4-[4-[(1-phenylethyl)amino]-1H-pyrrolo[2,3-d]pyrimidin-6-yl]-phenol); (R)-6-(4-hydroxyphenyl)-4-[(1-phenylethyl)amino]-7H-pyrrolo[2,3-d]pyrimidine); CL-387785 (N-[4-[(3-bromophenyl)amino]-6-quinazolinyl]-2-butynamide); EKB-569 (N-[4-[(3-chloro-4-fluorophenyl)amino]-3-cyano-7-ethoxy-6-quinolinyl]-4-(di-methylamino)-2-butenamide) (Wyeth); AG1478 (Sugen); AG1571 (SU 5271; Sugen); dual EGFR/HER2 tyrosine kinase inhibitors such as lapatinib (GW 572016 or N-[3-chloro-4-[(3fluorophenyl)methoxy]phenyl]6[5[[[2methyl-sulfonyl) ethyl]amino]methyl]-2-furanyl]-4-quinazolinamine; Glaxo-SmithKline).

A "tyrosine kinase inhibitor" is a molecule which inhibits tyrosine kinase activity of a tyrosine kinase such as a HER receptor. Examples of such inhibitors include the EGFR-targeted drugs noted in the preceding paragraph; small molecule HER2 tyrosine kinase inhibitor such as TAK165 available from Takeda; CP-724,714, an oral selective inhibitor of the ErbB2 receptor tyrosine kinase (Pfizer and OSI); dual-HER inhibitors such as EKB-569 (available from Wyeth) which preferentially binds EGFR but inhibits both HER2 and EGFR-overexpressing cells; lapatinib (GW572016; available from Glaxo-SmithKline) an oral HER2 and EGFR tyrosine kinase inhibitor; PKI-166 (available from Novartis); pan-HER inhibitors such as canertinib (C1-1033; Pharmacia); Raf-1 inhibitors such as antisense agent ISIS-5132 available from ISIS Pharmaceuticals which inhibits Raf-1 signaling; non-HER targeted TK inhibitors such as Imatinib mesylate (GLEEVAC J) available from Glaxo; MAPK extracellular regulated kinase I inhibitor C1-1040 (available from Pharmacia); quinazolines, such as PD 153035,4-(3-chloroanilino) quinazoline; pyridopyrimidines; pyrimidopyrimidines; pyrrolopyrimidines, such as CGP 59326, CGP 60261 and CGP 62706; pyrazolopyrimidines, 4-(phenylamino)-7H-pyrrolo[2,3-d]pyrimidines; curcumin (diferuloyl methane, 4,5-bis(4-fluoroanilino)phthalimide); tyrphostines containing nitrothiophene moieties; PD-0183805 (Warner-Lamber); antisense molecules (e.g., those that bind to HER-encoding nucleic acid); quinoxalines (U.S. Pat. No. 5,804,396); tryphostins (U.S. Pat. No. 5,804, 396); ZD6474 (Astra Zeneca); PTK-787 (Novartis/Schering AG); pan-HER inhibitors such as C1-1033 (Pfizer); Affinitac (ISIS 3521; Isis/Lilly); Imatinib mesylate (Gleevac; Novartis); PKI 166 (Novartis); GW2016 (Glaxo SmithKline); C1-1033 (Pfizer); EKB-569 (Wyeth); Semaxinib (Sugen); ZD6474 (AstraZeneca); PTK-787 (Novartis/Schering AG); INC-1C11 (Imclone); or as described in any of the following patent publications: U.S. Pat. No. 5,804,396; WO99/09016 (American Cyanamid); WO98/43960 (American Cyanamid); WO97/38983 (Warner Lambert); WO99/06378 (Warner Lambert); WO99/06396 (Warner Lambert); WO96/30347 (Pfizer, Inc); WO96/33978 (Zeneca); WO96/3397 (Zeneca); and WO96/33980 (Zeneca).

Thus in various further aspects, the disclosed compounds can be administered to subjects in combination with one or more chemotherapeutic drugs. For example, treating a subject with a glioma can be effected by a method comprising administering to the subject a disclosed compound or a pharmaceutically acceptable salt or hydrate thereof in combination with one or more chemotherapeutic drugs. For example, inhibiting intracranial metastasis of gliomal cancer cells in a subject can be effected by a method comprising administering to the subject a disclosed compound or a pharmaceutically acceptable salt or hydrate thereof in combination with one or more chemotherapeutic drugs. For example, preventing relapse of glioma in a subject can be effected by a method comprising administering to the subject a disclosed compound or a pharmaceutically acceptable salt or hydrate thereof in combination with one or more chemotherapeutic drugs.

It is contemplated that the disclosed compounds can be administered before, simultaneously, or after the administration of one or more chemotherapeutic drugs. While not wishing to be bound by theory, it is believed that the disclosed compounds, in combination with one or more chemotherapeutic drugs, can have an augmented or synergistic effect on the subject. Further, disclosed compounds, in combination with one or more chemotherapeutic drugs, can be individually given in dosages lower than the one or more chemotherapeutic drugs would be typically administered as single-agent therapies.

In further aspects, the invention relates to administration of the disclosed compounds to subjects in combination with temozolomide (4-methyl-5-oxo-2,3,4,6,8-pentazabicyclo [4.3.0] nona-2,7,9-triene-9-carboxamide). For example, treating a subject with a glioma can be effected by a method comprising administering to the subject a disclosed compound or a pharmaceutically acceptable salt or hydrate thereof in combination with temozolomide. For example, inhibiting intracranial metastasis of gliomal cancer cells in a subject can be effected by a method comprising administering to the subject a disclosed compound or a pharmaceutically acceptable salt or hydrate thereof in combination with temozolomide. For example, preventing relapse of glioma in a subject can be effected by a method comprising administering to the subject a disclosed compound or a pharmaceutically acceptable salt or hydrate thereof in combination with Temozolomide.

It is also understood that the disclosed compounds, when administered to subjects in combination with one or more chemotherapeutic drugs, can also be employed in connection with radiation therapy and/or surgical therapy.

Radiation therapy (Radiotherapy), including brachytherapy, can be used to treat gliomas. In one aspect, the invention realtes to the administration of the disclosed compounds to subjects in connection with radiation therapy. It is contemplated that the disclosed compounds can be administered before, during, or after the radiation therapy. For example, treating a subject with a glioma can be effected by a method comprising administering to the subject a disclosed compound or a pharmaceutically acceptable salt or hydrate thereof in connection with radiation therapy. For example, inhibiting intracranial metastasis of gliomal cancer cells in a subject can be effected by a method comprising administering to the subject a disclosed compound or a pharmaceutically acceptable salt or hydrate thereof in connection with radiation therapy. For example, preventing relapse of glioma in a subject can be effected by a method comprising administering to the subject a disclosed compound or a pharmaceutically acceptable salt or hydrate thereof in connection with radiation therapy.

While not wishing to be bound by theory, it is believed that the disclosed compounds, in combination with radiotherapy, can have an augmented or synergistic effect in a subject. Further, the disclosed compounds, when used in combination with radiotherapy, can lower a subject's need for radiotherapy (e.g., less radiation need be used) and/or can lower a subject's need for disclosed compounds (e.g., disclosed compounds can be given in dosages lower than would be typically administered as single-agent therapies).

It is also understood that the disclosed compounds, when administered to subjects in connection with radiation therapy, can also be employed in combination with one or more chemotherapeutic drugs and/or in connection surgical therapy.

Surgery can be used to treat gliomas. In one aspect, the invention relates to the administration of the disclosed compounds to subjects in connection with surgical treatment. For example, treating a subject with a glioma can be effected by a method comprising administering to the subject a disclosed compound or a pharmaceutically acceptable salt or hydrate thereof in connection with surgery. For example, inhibiting intracranial metastasis of gliomal cancer cells in a subject can be effected by a method comprising administering to the subject a disclosed compound or a pharmaceutically acceptable salt or hydrate thereof in connection with surgery. For example, preventing relapse of glioma in a subject can be effected by a method comprising administering to the subject a disclosed compound or a pharmaceutically acceptable salt or hydrate thereof in connection with surgery.

It is contemplated that the disclosed compounds can be administered before, during, or after surgical treatment. While not wishing to be bound by theory, it is believed that the disclosed compounds, in combination with surgery, can have an augmented or synergystic effect on the subject. Further, disclosed compounds, when used in combination with surgery, can lower a subject's need for surgery (e.g., less tissue need be removed) and/or can lower a subject's need for disclosed compounds (e.g., disclosed compounds can be given in dosages lower than would be typically administered as single-agent therapies).

It is also understood that the disclosed compounds, when administered to subjects in connection with surgical therapy, can also be employed in connection with radiation therapy and/or surgical therapy.

The disclosed compositions can also be employed to prevent relapse in a subject previously treated for a glioma. In one aspect, such a method comprises administering to the subject a prophylactically effective amount of a disclosed compound or a pharmaceutically acceptable salt or hydrate thereof. It is understood that the dosage needed to prevent relapse (i.e. maintenance dose) may be less (e.g., half) of the dosage needed to effect treatment of a glioma. Thus, in maintenance, a suitable dosage of the disclosed compound or a pharmaceutically acceptable salt or hydrate thereof can be from 0.5 to about 250 mg/kg of the subject, can be administered at a dosage of from 5 to about 100 mg/kg of the subject, can be administered at a dosage of from 5 to about 50 mg/kg of the subject, or can be administered at a dosage of from 10 to about 250 mg/kg of the subject.

It is also understood that when using the disclosed compounds for preventing of relapse of glioma, in either single agent therapy or in combination therapy, can be also administered to subjects in connection with surgical therapy and/or surgical therapy.

In a further aspect, the present disclosure pertains to methods of inhibiting AVIL activity in a subject, comprising administering to the subject a disclosed compound, or a pharmaceutically acceptable salt thereof, wherein the disclosed compound comprises one or more of Compounds A-L:

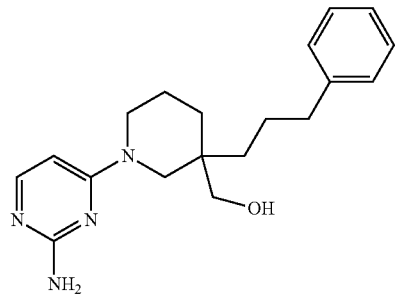

Compound A:
(1-(2-aminopyrimidin-4-yl)-3-(3-phenylpropyl)piperidin-3-yl)methanol

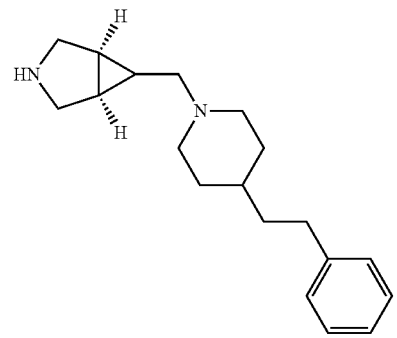

Compound B:
(1R,5S)-6-((4-phenethylpiperidin-1-yl)methyl)-3-azabicyclo[3.1.0]hexane

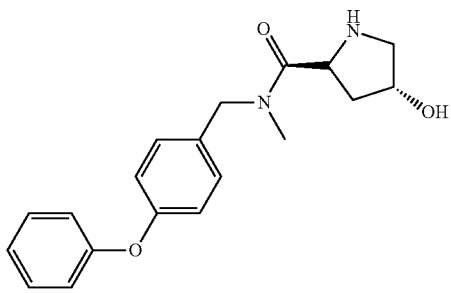

Compound C:
(2S,4R)-4-hydroxy-N-methyl-N-(4-phenoxybenzyl)pyrrolidine-2-carboxamide

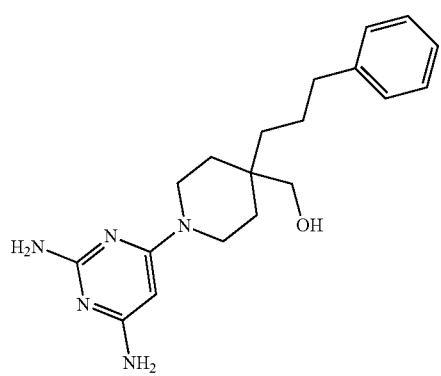

Compound D:
(1-(2,6-diaminopyrimidin-4-yl)-4-(3-phenylpropyl)piperidin-4-yl)methanol

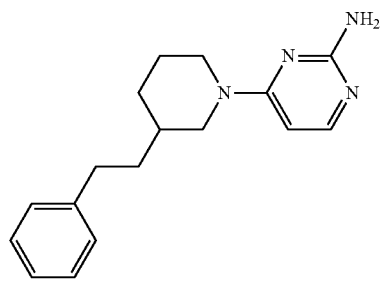

Compound E:
4-(3-phenethylpiperidin-1-yl)pyrimidin-2-amine

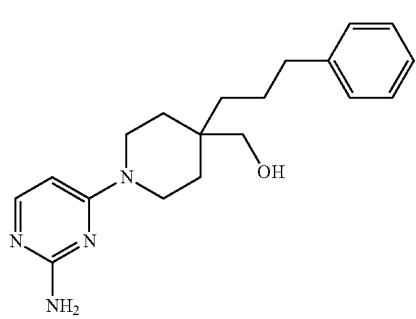

Compound F:
(1-(2-aminopyrimidin-4-yl)-4-(3-phenylpropyl)piperidin-4-yl)methanol

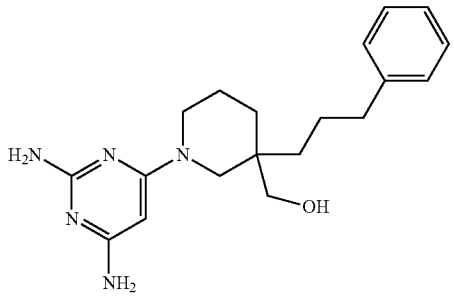

Compound G:
(1-(2,6-diaminopyrimidin-4-yl)-3-(3-phenylpropyl)piperidin-3-yl)methanol

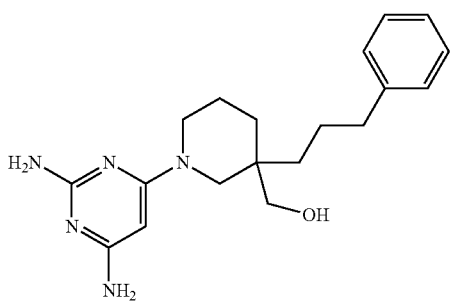

Compound H:
(1-(2,6-diaminopyrimidin-4-yl)-3-(3-phenylpropyl)piperidin-3-yl)methanol

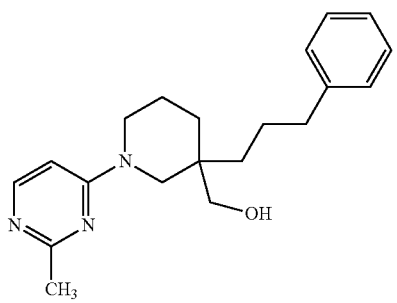

Compound I:
(1-(2,6-methylpyrimidin-4-yl)-3-(3-phenylpropyl)piperidin-3-yl)methanol

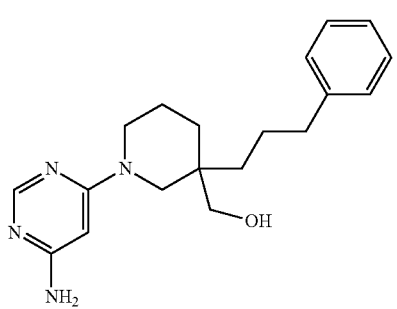

Compound J:
(1-(6-aminopyrimidin-4-yl)-3-(3-phenylpropyl)piperidin-3-yl)methanol -continued

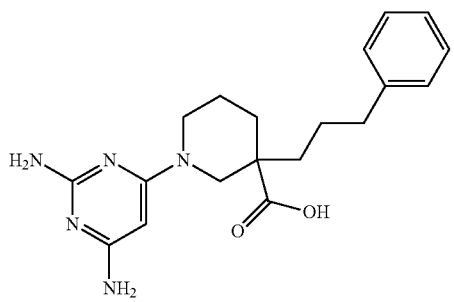

Compound K:
1-(2,6-diaminopyrimidin-4-yl)-3-(3-phenylpropyl)piperidine-3-carboxylic acid

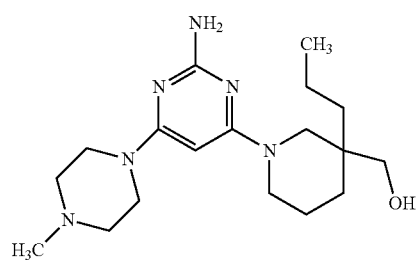

Compound L:
(1-(2-amino-6-(4-methylpiperazin-1-yl)pyrimidin-4-yl)-3-propylpiperidin-3-yl)methanol In a further aspect, the present disclosure pertains to methods of treating a subject with a glioma, comprising administering to the subject a disclosed compound, or a pharmaceutically acceptable salt thereof, wherein the disclosed compound comprises one or more of Compounds A-L:

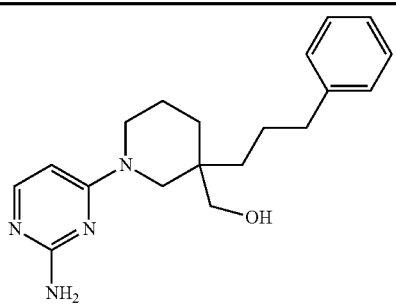

Compound A:
(1-(2-aminopyrimidin-4-yl)-3-(3-phenylpropyl)piperidin-3-yl)methanol -continued

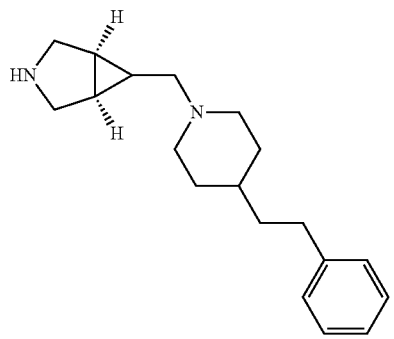

Compound B:
(1R,5S)-6-((4-phenethylpiperidin-1-yl)methyl)-3-azabicyclo[3.1.0]hexane

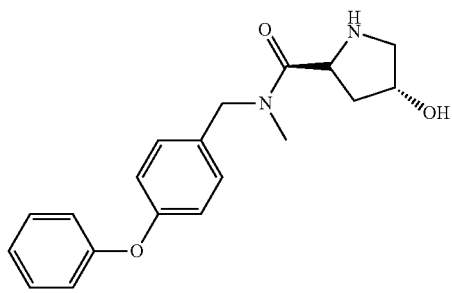

Compound C:
(2S,4R)-4-hydroxy-N-methyl-N-(4-phenoxybenzyl)pyrrolidine-2-carboxamide

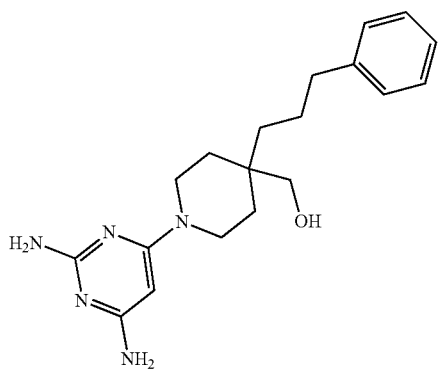

Compound D:
(1-(2,6-diaminopyrimidin-4-yl)-4-(3-phenylpropyl)piperidin-4-yl)methanol

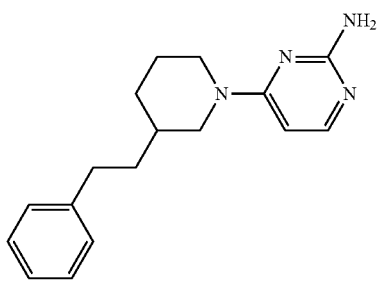

Compound E:
4-(3-phenethylpiperidin-1-yl)pyrimidin-2-amine

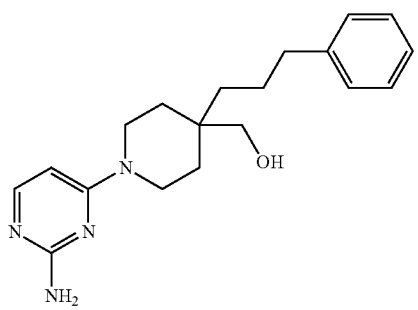

Compound F:
(1-(2-aminopyrimidin-4-yl)-4-(3-phenylpropyl)piperidin-4-yl)methanol

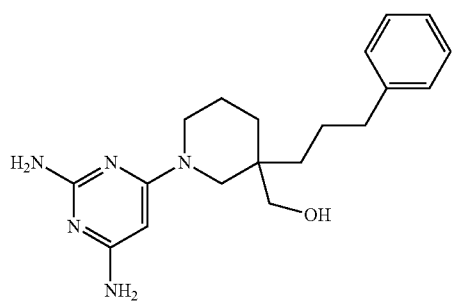

Compound G:
(1-(2,6-diaminopyrimidin-4-yl)-3-(3-phenylpropyl)piperidin-3-yl)methanol

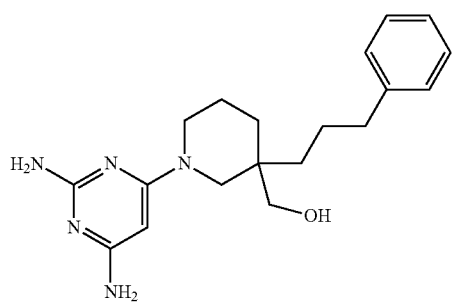

Compound H:
(1-(2,6-diaminopyrimidin-4-yl)-3-(3-phenylpropyl)piperidin-3-yl)methanol

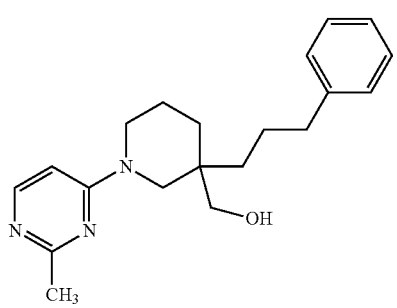

Compound I:
(1-(2,6-methylpyrimidin-4-yl)-3-(3-phenylpropyl)piperidin-3-yl)methanol

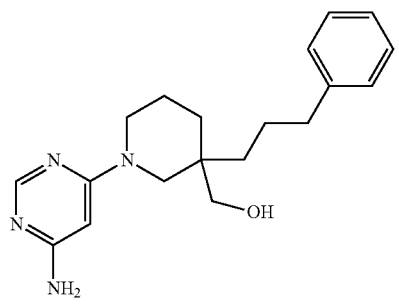

Compound J:
(1-(6-aminopyrimidin-4-yl)-3-(3-phenylpropyl)piperidin-3-yl)methanol

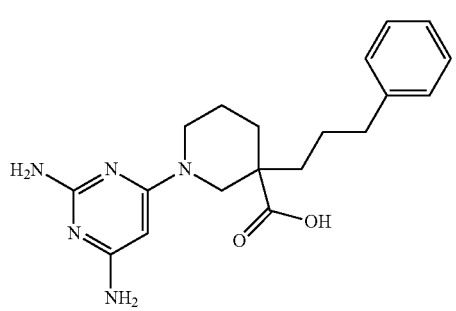

Compound K:
1-(2,6-diaminopyrimidin-4-yl)-3-(3-phenylpropyl)piperidine-3-carboxylic acid

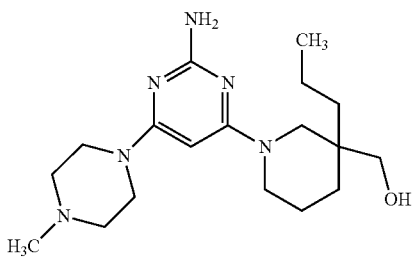

Compound L:
(1-(2-amino-6-(4-methylpiperazin-1-yl)pyrimidin-4-yl)-3-propylpiperidin-3-yl)methanol In a further aspect, the present disclosure pertains to methods of inhibiting intracranial metastasis of gliomal cancer cells in a subject, comprising administering to the subject a disclosed compound, or a pharmaceutically acceptable salt thereof, wherein the disclosed compound comprises one or more of Compounds A-L:

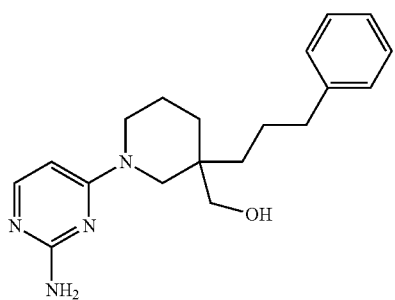

Compound A:
(1-(2-aminopyrimidin-4-yl)-3-(3-phenylpropyl)piperidin-3-yl)methanol

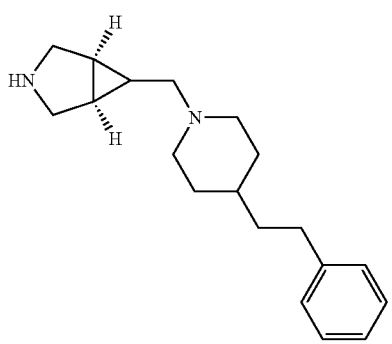

Compound B:
(1R,5S)-6-((4-phenethylpiperidin-1-yl)methyl)-3-azabicyclo[3.1.0]hexane

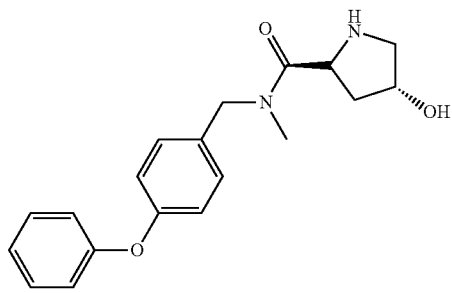

Compound C:
(2S,4R)-4-hydroxy-N-methyl-N-(4-phenoxybenzyl)pyrrolidine-2-carboxamide

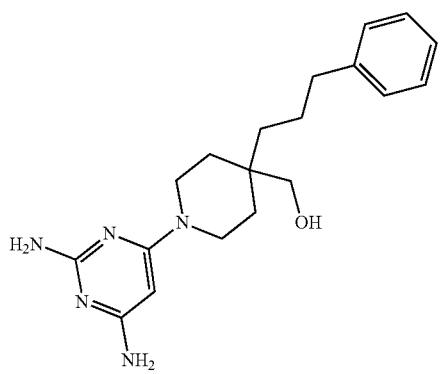

Compound D:
(1-(2,6-diaminopyrimidin-4-yl)-4-(3-phenylpropyl)piperidin-4-yl)methanol

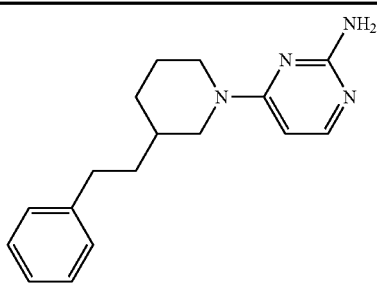

Compound E:
4-(3-phenethylpiperidin-1-yl)pyrimidin-2-amine

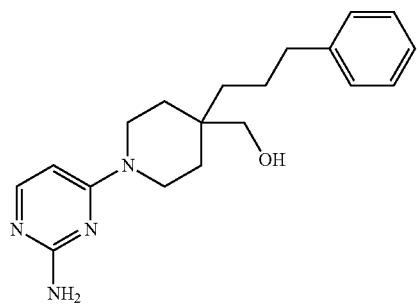

Compound F:
(1-(2-aminopyrimidin-4-yl)-4-(3-phenylpropyl)piperidin-4-yl)methanol

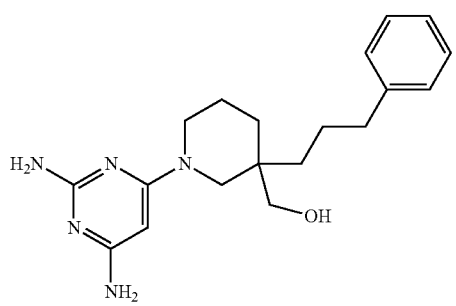

Compound G:
(1-(2,6-diaminopyrimidin-4-yl)-3-(3-phenylpropyl)piperidin-3-yl)methanol

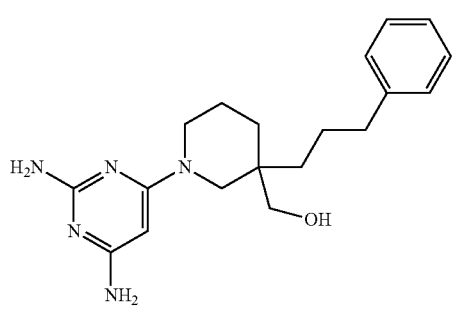

Compound H:
(1-(2,6-diaminopyrimidin-4-yl)-3-(3-phenylpropyl)piperidin-3-yl)methanol -continued

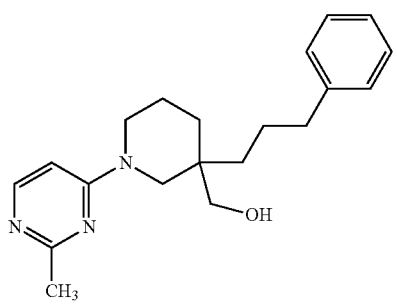

Compound I:
(1-(2,6-methylpyrimidin-4-yl)-3-(3-phenylpropyl)piperidin-3-yl)methanol

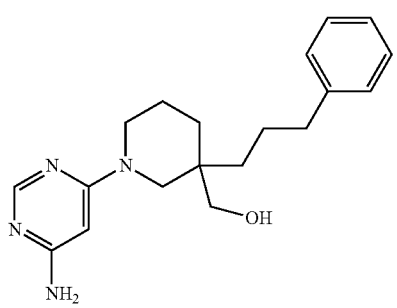

Compound J:
(1-(6-aminopyrimidin-4-yl)-3-(3-phenylpropyl)piperidin-3-yl)methanol

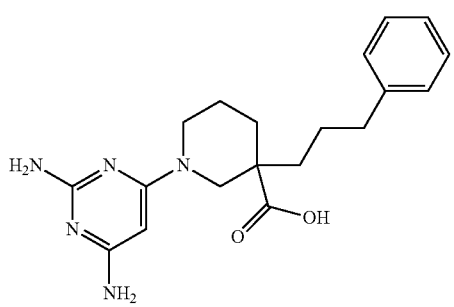

Compound K:
1-(2,6-diaminopyrimidin-4-yl)-3-(3-phenylpropyl)piperidine-3-carboxylic acid

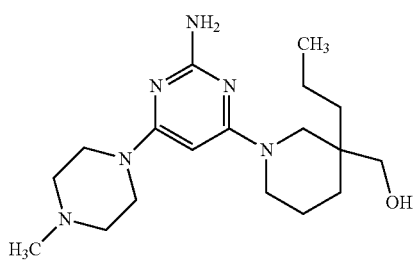

Compound L:
(1-(2-amino-6-(4-methylpiperazin-1-yl)pyrimidin-4-yl)-3-propylpiperidin-3-yl)methanol In a further aspect, the present disclosure pertains to methods of preventing relapse in a subject previously treated for a glioma, comprising administering to the subject a disclosed compound, or a pharmaceutically acceptable salt thereof, wherein the disclosed compound comprises one or more of Compounds A-L:

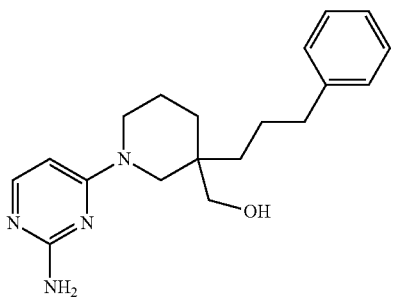

Compound A:
(1-(2-aminopyrimidin-4-yl)-3-(3-phenylpropyl)piperidin-3-yl)methanol

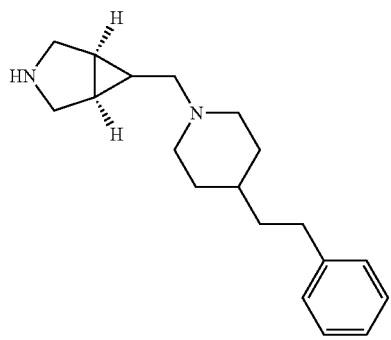

Compound B:
(1R,5S)-6-((4-phenethylpiperidin-1-yl)methyl)-3-azabicyclo[3.1.0]hexane

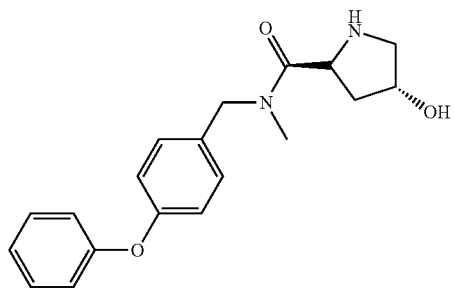

Compound C:
(2S,4R)-4-hydroxy-N-methyl-N-(4-phenoxybenzyl)pyrrolidine-2-carboxamide

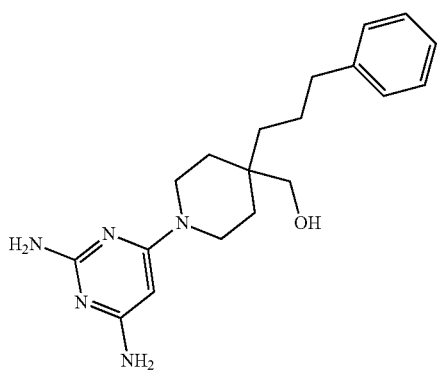

Compound D:
(1-(2,6-diaminopyrimidin-4-yl)-4-(3-phenylpropyl)piperidin-4-yl)methanol

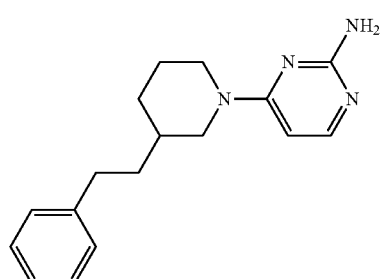

Compound E:
4-(3-phenethylpiperidin-1-yl)pyrimidin-2-amine

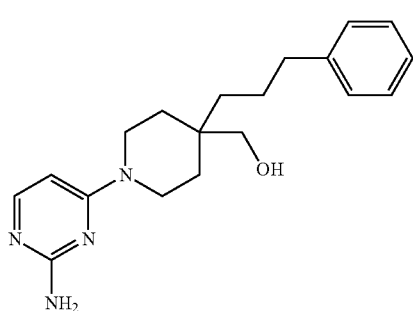

Compound F:
(1-(2-aminopyrimidin-4-yl)-4-(3-phenylpropyl)piperidin-4-yl)methanol

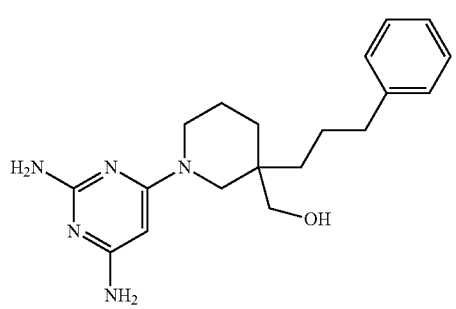

Compound G:
(1-(2,6-diaminopyrimidin-4-yl)-3-(3-phenylpropyl)piperidin-3-yl)methanol

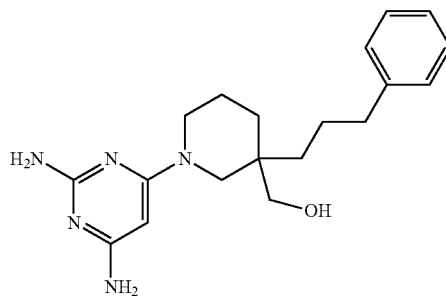

Compound H:
(1-(2,6-diaminopyrimidin-4-yl)-3-(3-phenylpropyl)piperidin-3-yl)methanol

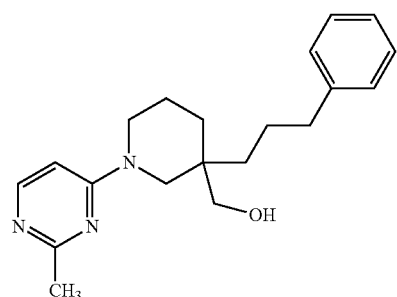

Compound I:
(1-(2,6-methylpyrimidin-4-yl)-3-(3-phenylpropyl)piperidin-3-yl)methanol

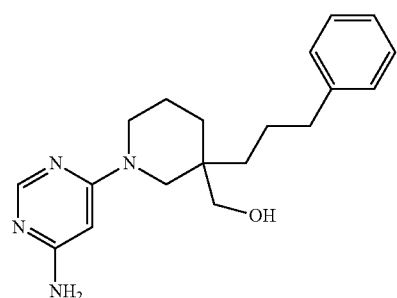

Compound J:
(1-(6-aminopyrimidin-4-yl)-3-(3-phenylpropyl)piperidin-3-yl)methanol

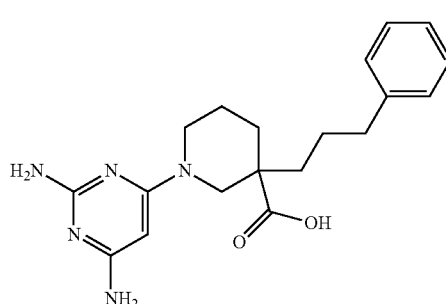

Compound K:
1-(2,6-diaminopyrimidin-4-yl)-3-(3-phenylpropyl)piperidine-3-carboxylic acid

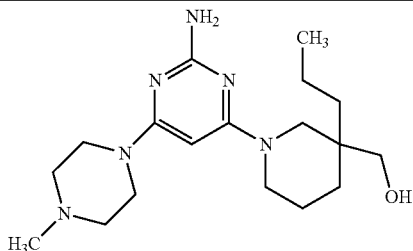

Compound L:
(1-(2-amino-6-(4-methylpiperazin-1-yl)
pyrimidin-4-yl)-3-propylpiperidin-3-yl)
methanol In a further aspect, the cancer is a cancer of the brain. In a still further aspect, the cancer is selected from acoustic neuroma, glioma, meningioma, pituitary adenoma, schwannoma, CNS lymphoma, primitive neuroectodermal tumor, craniopharyngioma, chordoma, medulloblastoma, cerebral neuroblastoma, central neurocytoma, pineocytoma, pineoblastoma, atypical teratoid rhabdoid tumor, chondrosarcoma, chondroma, choroid plexus carcinoma, choroid plexus papilloma, craniopharyngioma, dysembryoplastic neuroepithelial tumor, gangliocytoma, germinoma, hemangioblastoma, hemangiopercytoma, and metastatic brain tumor cell.

In a further aspect, the cancer is a glioma. In a still further aspect, the glioma is glioblastoma multiforme. In a yet further aspect, the glioma is selected from is selected from a ependymoma, astrocytoma, oligodendroglioma, and oligoastrocytoma. In a yet further aspect, the glioma is selected from a juvenile pilocytic astrocytoma, subependymal giant cell astrocytoma, ganglioglioma, subependymoma, pleomorphic xanthoastrocytom, anaplastic astrocytoma, glioblastoma multiforme, brain stem glioma, oligodendroglioma, ependymoma, oligoastrocytoma, cerebellar astrocytoma, desmoplastic infantile astrocytoma, subependymal giant cell astrocytoma, diffuse astrocytoma, mixed glioma, optic glioma, gliomatosis cerebri, paraganglioma, and ganglioglioma cell.

Cancers that may be treated by a disclosed compound include, but are not limited to: cardiac; sarcoma (angiosarcoma, fibrosarcoma, rhabdomyosarcoma, liposarcoma); myxoma; rhabdomyoma; fibroma; lipoma and teratoma; lung, e.g., non-small cell lung, bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hamartoma, mesothelioma; gastrointestinal, e.g., esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Karposi's sarcoma, leiomyoma, hemangioma, lipoma, neurofibroma, fibroma), large bowel (adenocarcinoma, tubular adenoma, villous adenoma, hamartoma, leiomyoma), colon, colorectal, rectal; genitourinary tract, e.g., kidney (adenocarcinoma, Wilm's tumor [nephroblastoma], lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); liver, e.g., hepatoma (hepatocellular carcinoma), cholangiocarcinoma, hepatoblastoma, angiosarcoma, hepatocellular adenoma, hemangioma; bone, e.g., osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; nervous system, e.g., skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma [pinealoma], glioblastoma multiform, oligodendroglioma, schwannoma, retinoblastoma, congenital tumors), spinal cord neurofibroma, meningioma, glioma, sarcoma); gynecological, e.g., uterus (endometrial carcinoma), cervix (cervical carcinoma, pre-tumor cervical dysplasia), ovaries (ovarian carcinoma [serous cystadenocarcinoma, mucinous cystadenocarcinoma, unclassified carcinoma], granulosathecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), fallopian tubes (carcinoma); hematologic, e.g., blood (myeloid leukemia [acute and chronic], acute lymphoblastic leukemia, chronic lymphocytic leukemia, myeloproliferative diseases, multiple myeloma, myelodysplastic syndrome), Hodgkin's disease, non-Hodgkin's lymphoma [malignant lymphoma]; skin, e.g., malignant melanoma, basal cell carcinoma, squamous cell carcinoma, Karposi's sarcoma, moles dysplastic nevi, lipoma, angioma, dermatofibroma, keloids, psoriasis; and adrenal glands, e.g., a neuroblastoma. Thus, the term "cancerous cell" as provided herein, includes a cell afflicted by any one of the above-identified conditions.

Cancers that may be treated by a disclosed compound include, but are not limited to, any of the following cancers in which it has been determined that the cancer is associated with aberrant expression of AVIL: cardiac; sarcoma (angiosarcoma, fibrosarcoma, rhabdomyosarcoma, liposarcoma); myxoma; rhabdomyoma; fibroma; lipoma and teratoma; lung, e.g., non-small cell lung, bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hamartoma, mesothelioma; gastrointestinal, e.g., esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Karposi's sarcoma, leiomyoma, hemangioma, lipoma, neurofibroma, fibroma), large bowel (adenocarcinoma, tubular adenoma, villous adenoma, hamartoma, leiomyoma), colon, colorectal, rectal; genitourinary tract, e.g., kidney (adenocarcinoma, Wilm's tumor [nephroblastoma], lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); liver, e.g., hepatoma (hepatocellular carcinoma), cholangiocarcinoma, hepatoblastoma, angiosarcoma, hepatocellular adenoma, hemangioma; bone, e.g., osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; nervous system, e.g., skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma [pinealoma], glioblastoma multiform, oligodendroglioma, schwannoma, retinoblastoma, congenital tumors), spinal cord neurofibroma, meningioma, glioma, sarcoma); gynecological, e.g., uterus (endometrial carcinoma), cervix (cervical carcinoma, pre-tumor cervical dysplasia), ovaries (ovarian carcinoma [serous cystadenocarcinoma, mucinous cystadenocarcinoma, unclassified carcinoma], granulosathecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), fallopian tubes (carcinoma); hematologic, e.g., blood (myeloid leukemia [acute and chronic], acute lymphoblastic leukemia, chronic lymphocytic leukemia, myeloproliferative diseases, multiple myeloma, myelodysplastic syndrome), Hodgkin's disease, non-Hodgkin's lymphoma [malignant lymphoma]; skin, e.g., malignant melanoma, basal cell carcinoma, squamous cell carcinoma, Karposi's sarcoma, moles dysplastic nevi, lipoma, angioma, dermatofibroma, keloids, psoriasis; and adrenal glands, e.g., a neuroblastoma. Thus, the term "cancerous cell" as provided herein, includes a cell afflicted by any one of the above-identified conditions.

Methods of Treating a Cancer.

In various aspects, the present disclosure pertains to functional nucleic acids that are useful to regulate, limit, or inhibit the expression of AVIL (advillin) in cells of a mammal having increased, aberrant, or dysfunctional levels of AVIL, which will have use as therapeutic agents in a variety of clinical conditions such as cancer. Functional nucleic acids include antisense molecules, aptamers, ribozymes, triplex forming molecules, RNAi, external guide sequences, gene editing compositions such as CRISPR/Cas, zinc finger nuclease, or TALEN.

Thus, in various aspects, a disclosed cancer can be treated using a functional nucleic acid is capable of silencing AVIL or the MARS-AVIL fusion.

Thus, in various aspects, the functional nucleic acid targets a region with the nucleic acid sequence:

```
                                (MARS-AVIL, SEQ ID NO: 1)
ATGAGACTGTTCGTGAGTGATGGCGTCCCGGGTTGCTTGCCGGTGCTGGC

CGCCGCCGGGAGAGCCCGGGCAGAGCAGAGGTGCTCATCAGCACTGTAG

GCCCGGAAGATTGTGTGGTCCCGTTCCTGACCCGGCCTAAGGTCCCTGTC

TTGCAGCTGGATAGCGGCAACTACCTCTTCTCCACTAGTGCAATCTGCCG

ATATTTTTTTTGTTATCTGGCTGGGAGCAAGATGACCTCACTAACCAGT

GGCTGGAATGGGAAGCGACAGAGCTGCAGCCAGCTTTGTCTGCTGCCCTG

TACTATTTAGTGGTCCAAGGCAAGAAGGGGAAGATGTTCTTGGTTCAGT

GCGGAGAGCCCTGACTCACATTGACCACAGCTTGAGTCGTCAGAACTGTC

CTTTCCTGGCTGGGGAGACAGAATCTCTAGCCGACATTGTTTTGTGGGA

GCCCTATACCCATTACTGCAAGATCCCGCCTACCTCCCTGAGGAGCTGAG

TGCCCTGCACAGCTGGTTCCAGACACTGAGTACCCAGGAACCATGTCAGC

GAGCTGCAGAGACTGTACTGAAACAGCAAGGTGTCCTGGCTCTCCGGCCT

TACCTCCAAAAGCAGCCCCAGCCCAGCCCCGCTGAGGGAAGGGCTGTCAC

CAATGAGCCTGAGGAGGAGGAGCTGGCTACCCTATCTGAGGAGGAGATTG

CTATGGCTGTTACTGCTTGGGAGAAGGGCCTAGAAAGTTTGCCCCCGCTG

CGGCCCCAGCAGAATCCAGTGTTGCCTGTGGCTGGAGAAAGGAATGTGCT

CATCACCAGTGCCCTCCCTTACGTCAACAATGTCCCCCACCTTGGGAACA

TCATTGGTTGTGTGCTCAGTGCCGATGTCTTTGCCAGGTACTCTCGCCTC

CGCCAGTGGAACACCCTCTATCTGTGTGGGACAGATGAGTATGGTACAGC

AACAGAGACCAAGGCTCTGGAGGAGGGACTAACCCCCCAGGAGATCTGCG

ACAAGTACCACATCATCCATGCTGACATCTACCGCTGGTTTAACATTTCG

TTTGATATTTTTGGTCGCACCACCACTCCACAGCAGACCAAAATCACCCA

GGACATTTTCCAGCAGTTGCTGAAACGAGGTTTTGTGCTGCAAGATACTG

TGGAGCAACTGCGATGTGAGCACTGTGCTCGCTTCCTGGCTGACCGCTTC

GTGGAGGGCGTGTGTCCCTTCTGTGGCTATGAGGAGGCTCGGGGTGACCA

GTGTGACAAGTGTGGCAAGCTCATCAATGCTGTCGAGCTTAAGAAAATGG

AGCTGGCGCTGGTGCCTGTGAGCGCCCACGGCAACTTCTATGAGGGGGAC

TGCTACGTCATCCTCTCGACCCGGAGAGTGGCCAGTCTCCTATCCCAGGA

CATCCACTTCTGGATCGGGAAGGACTCCTCCCAGGATGAGCAAAGCTGCG

CAGCCATATATACCACACAGCTGGACGACTACCTGGGAGGCAGCCCTGTG

CAGCACCGAGAGGTCCAGTACCATGAGTCAGACACTTTCCGTGGCTACTT

CAAGCAGGGCATCATCTACAAGCAGGGGGGTGTCGCCTCTGGGATGAAGC

ACGTGGAGACCAATACCTACGACGTGAAGCGGCTGCTACATGTGAAAGGG

AAAAGAAACATCAGGGCTACCGAGGTGGAAATGAGCTGGGACAGTTTCAA

CCGAGGTGATGTCTTCTTGCTGGACCTTGGGAAAGTCATCATCCAATGGA

ATGGCCCAGAGAGCAACAGTGGGGAGCGCCTGAAGGCTATGCTTCTGGCA

AAGGATATTCGAGACAGGGAGCGAGGGGGCCGTGCTAAAATAGGAGTGAT

CGAGGGAGACAAGGAGGCAGCCAGCCCAGAGCTGATGAAGGTCCTTCAGG

ACACCCTTGGCCGACGCTCCATTATCAAGCCTAGAGTCCCTGATGAGATC

ATAGATCAGAAGCAGAAATCAACTATCATGTTGTATCATATCTCAGATTC

AGCTGGGCAGCTGGCAGTCACAGAGGTAGCAACAAGGCCTCTGGTCCAGG

ACTTACTGAACCATGATGACTGCTACATCCTGGACCAAAGTGGAACCAAA

ATCTACGTGTGGAAAGGAAAAGGAGCCACAAAGGCTGAAAAACAGGCAGC

CATGTCTAAAGCGCTGGGCTTCATCAAGATGAAGAGCTACCCCAGCAGCA

CCAATGTGGAGACCGTCAACGATGGTGCTGAGTCGGCCATGTTCAAGCAG

CTGTTCCAGAAGTGGTCAGTAAAGGACCAGACCATGGGCCTGGGGAAAAC

GTTCAGCATTGTAAAATTGCTAAAGTTTTCCAGGATAAATTTGATGTGA

CTCTGCTACACACCAAGCCAGAGGTAGCTGCCCAGGAAAGAATGGTCGAT
```

```
GATGGCAACGGAAAAGTTGAGGTCTGGAGAATTGAGAACCTGGAGCTGGT
CCCTGTGGAGTATCAATGGTATGGCTTCTTTTATGGGGGAGACTGTTATC
TGGTCCTCTACACATACGAGGTAAATGGGAAGCCACATCACATCTTGTAC
ATCTGGCAGGGCCGCCACGCCTCACAGGATGAGCTGGCAGCCTCAGCATA
CCAGGCAGTGGAGGTGGATCGGCAGTTTGATGGGGCTGCTGTGCAGGTTC
GAGTCAGGATGGGAACGGAGCCACGCCACTTCATGGCCATCTTCAAAGGG
AAGCTAGTTATCTTTGAGGGTGGGACTTCCAGGAAGGGAAATGCCGAGCC
TGACCCTCCAGTAAGACTCTTCCAAATTCATGGAAATGACAAATCTAACA
CCAAAGCAGTGGAAGTTCCAGCCTTTGCCTCCTCCCTAAACTCCAATGAT
GTCTTTCTGCTGCGAACTCAGGCAGAGCACTACCTGTGGTATGGCAAGGG
GTCTAGTGGGGATGAGCGGGCAATGGCTAAGGAGCTGGCCAGCCTTCTCT
GTGATGGCAGCGAGAACACTGTGGCCGAGGGCCAGGAGCCAGCCGAGTTC
TGGGACCTACTGGGAGGGAAAACTCCCTATGCCAATGATAAAAGACTTCA
GCAGGAAATCCTAGATGTCCAGTCTCGTCTCTTTGAATGTTCCAATAAGA
CCGGCCAATTCGTTGTCACTGAGATCACAGACTTCACCCAGGATGACCTG
AACCCTACTGACGTGATGCTCCTAGATACCTGGGACCAGGTGTTCTTGTG
GATTGGGGCTGAGGCCAATGCCACGGAGAAGGAGAGTGCCCTTGCCACAG
CACAGCAGTACCTGCACACTCACCCCAGCGGCCGAGATCCCGACACACCA
ATCCTGATCATTAAGCAGGGGTTTGAGCCTCCCATCTTCACAGGCTGGTT
CCTAGCCTGGGACCCTAACATTTGGAGTGCAGGAAAAACATATGAACAAT
TAAAAGAAGAGCTGGGAGATGCTGCTGCTATCATGCGAATCACTGCTGAC
ATGAAGAATGCAACCCTCTCCCTGAATTCTAATGACAGTGAGCCAAAATA
TTACCCTATAGCAGTTCTGTTGAAAAACCAGAATCAGGAGCTGCCTGAGG
ATGTAAACCCTGCCAAAAAGGAGAATTACCTCTCTGAACAGGACTTTGTG
TCTGTGTTTGGCATCACAAGAGGGCAATTTGCAGCTCTGCCTGGCTGGAA
ACAGCTCCAAATGAAGAAGAAAAGGGGCTTTTCTAA.
```

Thus, in various aspects, the functional nucleic acid targets a region with the nucleic acid sequence:

```
                                     (AVIL, SEQ ID NO: 2)
ATGCCTCTGACCAGTGCCTTCAGGGCTGTGGACAACGACCCTGGGATCAT
TGTCTGGAGAATAGAGAAAATGGAGCTGGCGCTGGTGCCTGTGAGCGCCC
ACGGCAACTTCTATGAGGGGGACTGCTACGTCATCCTCTCGACCCGGAGA
GTGGCCAGTCTCCTATCCCAGGACATCCACTTCTGGATCGGGAAGGACTC
CTCCCAGGATGAGCAAAGCTGCGCAGCCATATATACCACACAGCTGGACG
ACTACCTGGGAGGCAGCCCTGTGCAGCACCGAGAGGTCCAGTACCATGAG
TCAGACACTTTCCGTGGCTACTTCAAGCAGGGCATCATCTACAAGCAGGG
GGGTGTCGCCTCTGGGATGAAGCACGTGGAGACCAATACCTACGACGTGA
AGCGGCTGCTACATGTGAAAGGGAAAGAAACATCAGGGCTACCGAGGTG
GAAATGAGCTGGGACAGTTTCAACCGAGGTGATGTCTTCTTGCTGGACCT
TGGGAAAGTCATCATCCAATGGAATGGCCCAGAGAGCAACAGTGGGGAGC
GCCTGAAGGCTATGCTTCTGGCAAAGGATATTCGAGACAGGGAGCGAGGG
GGCCGTGCTAAAATAGGAGTGATCGAGGGAGACAAGGAGGCAGCCAGCCC
AGAGCTGATGAAGGTCCTTCAGGACACCCTTGGCCGACGCTCCATTATCA
AGCCTACAGTCCCTGATGAGATCATAGATCAGAAGCAGAAATCAACTATC
ATGTTGTATCATATCTCAGATTCAGCTGGGCAGCTGGCAGTCACAGAGGT
AGCAACAAGGCCTCTGGTCCAGGACTTACTGAACCATGATGACTGCTACA
TCCTGGACCAAAGTGGAACCAAAATCTACGTGTGGAAAGGAAAAGGAGCC
ACAAAGGCTGAAAAACAGGCAGCCATGTCTAAAGCGCTGGGCTTCATCAA
GATGAAGAGCTACCCCAGCAGCACCAATGTGGAGACCGTCAACGATGGTG
CTGAGTCGGCCATGTTCAAGCAGCTGTTCCAGAAGTGGTCAGTAAAGGAC
CAGACCATGGGCCTGGGGAAAACGTTCAGCATTGGTAAAATTGCTAAAGT
TTTCCAGGATAAATTTGATGTGACTCTGCTACACACCAAGCCAGAGGTAG
CTGCCCAGGAAAGAATGGTCGATGATGGCAACGAAAAGTTGAGGTCTGG
AGAATTGAGAACCTGGAGCTGGTCCCTGTGGAGTATCAATGGTATGGCTT
CTTTTATGGGGAGACTGTTATCTGGTCCTCTACACATACGAGGTAAATG
GGAAGCCACATCACATCTTGTACATCTGGCAGGGCCGCCACGCCTCACAG
GATGAGCTGGCAGCCTCAGCATACCAGGCAGTGGAGGTGGATCGGCAGTT
TGATGGGGCTGCTGTGCAGGTTCGAGTCAGGATGGGAACGGAGCCACGCC
ACTTCATGGCCATCTTCAAAGGGAAGCTAGTTATCTTTGAGGGTGGGACT
TCCAGGAAGGGAAATGCCGAGCCTGACCCTCCAGTAAGACTCTTCCAAAT
TCATGGAAATGACAAATCTAACACCAAAGCAGTGGAAGTTCCAGCCTTTG
CCTCCTCCCTAAACTCCAATGATGTCTTTCTGCTGCGAACTCAGGCAGAG
CACTACCTGTGGTATGGCAAGGGGTCTAGTGGGGATGAGCGGGCAATGGC
TAAGGAGCTGGCCAGCCTTCTCTGTGATGGCAGCGAGAACACTGTGGCCG
AGGGCCAGGAGCCAGCCGAGTTCTGGGACCTACTGGGAGGGAAAACTCCC
TATGCCAATGATAAAAGACTTCAGCAGGAAATCCTAGATGTCCAGTCTCG
TCTCTTTGAATGTTCCAATAAGACCGGCCAATTCGTTGTCACTGAGATCA
CAGACTTCACCGAGGATGAGCTGAACCCTACTGACGTGATGCTCCTAGAT
ACCTGGGACCAGGTGTTCTTGTGGATTGGGGCTGAGGCCAATGCCACGGA
GAAGGAGAGTGCCCTTGCCACAGCACAGCAGTACCTGCACACTCACCCCA
GCGGCCGAGATCCCGACACACCAATCCTGATCATTAAGCAGGGGTTTGAG
CCTCCCATCTTCACAGGCTGGTTCCTAGCCTGGGACCCTAACATTTGGAG
TGCAGGAAAAACATATGAACAATTAAAAGAAGAGCTGGGAGATGCTGCTG
CTATCATGCGAATCACTGCTGACATGAAGAATGCAACCCTCTCCCTGAAT
TCTAATGACAGTGAGCCAAAATATTACCCTATAGCAGTTCTGTTGAAAAA
CCAGAATCAGGAGCTGCCTGAGGATGTAAACCCTGCCAAAAAGGAGAATT
ACCTCTCTGAACAGGACTTTGTGTCTGTGTTTGGCATCACAAGAGGGCAA
TTTGCAGCTCTGCCTGGCTGGAAACAGCTCCAAATGAAGAAAGAAAAGGG
GCTTTTCTAA.
```

Examples of gen silencing functional nucleic acids include antisense molecules, shRNA, miRNA, siRNA, and oligonucleotides used with gene editing techniques, such as CRISPR or TALON. In some cases, the functional nucleic acid is an siRNA. Therefore, in various aspects the functional nucleic acid is an siRNA comprising the nucleic acid sequence GCUUCUGGCAAAGGAUAUU (siAVIL 593, SEQ ID NO:3). In various aspects the functional nucleic acid is an siRNA comprising the nucleic acid sequence CCACACAGCUGGACGACUA (siAVIL265, SEQ ID NO:4). In various aspects, the functional nucleic acid is an siRNA comprising the nucleic acid sequence GCAAAGGAUAUUCGAGACA (siAVIL600, SEQ ID NO:5). In various aspects, the functional nucleic acid is an siRNA comprising the nucleic acid sequence GCACCAAUGUGGAGACCGU (siAVIL1000, SEQ ID NO:6). In various aspects, the functional nucleic acid is an siRNA comprising the nucleic acid sequence GGAAAGAAUGGUCGAUGAU (siAVIL1187, SEQ ID NO:7). In various aspects, the functional nucleic acid is an siRNA comprising the nucleic acid sequence GCAUUCCUUGCUUGUUAUA (siAVIL2651, SEQ ID NO:8). In various aspects, the functional nucleic acid is an siRNA comprising the nucleic acid sequence GAGCUUAAGAAAAUGGAGC (siMARS-AVIL, SEQ ID NO:9). In some embodiments, the siRNA has a nucleic acid sequence complementary to the nucleic acid sequence of any one of SEQ ID Nos:3 to 9.

Kits.

In a further aspect, the present disclosure relates to kits comprising at least one disclosed compound, or a pharmaceutically acceptable salt, hydrate, solvate, or polymorph thereof, and one or more of: (a) at least one agent known to treat a cancer; (b) instructions for treating a cancer and/or instructions for administering the compound in connection with the treatment of cancer. The disclosed compounds and/or pharmaceutical compositions comprising the disclosed compounds can conveniently be presented as a kit, whereby two or more components, which may be active or inactive ingredients, carriers, diluents, and the like, are provided with instructions for preparation of the actual dosage form by the patient or person administering the drug to the patient. Such kits may be provided with all necessary materials and ingredients contained therein, or they may contain instructions for using or making materials or components that must be obtained independently by the patient or person administering the drug to the patient. In further aspects, a kit can include optional components that aid in the administration of the unit dose to patients, such as vials for reconstituting powder forms, syringes for injection, customized IV delivery systems, inhalers, etc. Additionally, a kit can contain instructions for preparation and administration of the compositions. The kit can be manufactured as a single use unit dose for one patient, multiple uses for a particular patient (at a constant dose or in which the individual compounds may vary in potency as therapy progresses); or the kit may contain multiple doses suitable for administration to multiple patients ("bulk packaging"). The kit components may be assembled in cartons, blister packs, bottles, tubes, and the like.

In a further aspect, the disclosed kits can be packaged in a daily dosing regimen (e.g., packaged on cards, packaged with dosing cards, packaged on blisters or blow-molded plastics, etc.). Such packaging promotes products and increases patient compliance with drug regimens. Such packaging can also reduce patient confusion. The present invention also features such kits further containing instructions for use.

In a further aspect, the present disclosure also provides a pharmaceutical pack or kit comprising one or more containers filled with one or more of the ingredients of the pharmaceutical compositions of the invention. Associated with such container(s) can be a notice in the form prescribed by a governmental agency regulating the manufacture, use or sale of pharmaceuticals or biological products, which notice reflects approval by the agency of manufacture, use or sale for human administration.

In various aspects, the disclosed kits can also comprise compounds and/or products co-packaged, co-formulated, and/or co-delivered with other components. For example, a drug manufacturer, a drug reseller, a physician, a compounding shop, or a pharmacist can provide a kit comprising a disclosed compound and/or product and another component for delivery to a patient.

It is contemplated that the disclosed kits can be used in connection with the disclosed methods of making, the disclosed methods of using or treating, and/or the disclosed compositions.

Research Tools.

The disclosed compounds and pharmaceutical compositions have activity as inhibitors of AVIL expression. As such, the disclosed compounds are also useful as research tools. Accordingly, one aspect of the present disclosure relates to a method of using a compound of the invention as a research tool, the method comprising conducting a biological assay using a compound of the invention. Compounds of the invention can also be used to evaluate new chemical compounds. Thus another aspect of the invention relates to a method of evaluating a test compound in a biological assay, comprising: (a) conducting a biological assay with a test compound to provide a first assay value; (b) conducting the biological assay with a compound of the invention to provide a second assay value; wherein step (a) is conducted either before, after or concurrently with step (b); and (c) comparing the first assay value from step (a) with the second assay value from step (b). Exemplary biological assays include an assay that can be conducted in vitro or in a cell culture system. Still another aspect of the invention relates to a method of studying a biological system, e.g., a model animal for a clinical condition, or biological sample having increased, aberrant, or dysfunctional levels of AVIL, the method comprising: (a) contacting the biological system or sample with a compound of the invention; and (b) determining the effects caused by the compound on the biological system or sample.

Now having described the aspects of the present disclosure, in general, the following Examples describe some additional aspects of the present disclosure. While aspects of the present disclosure are described in connection with the following examples and the corresponding text and figures, there is no intent to limit aspects of the present disclosure to this description. On the contrary, the intent is to cover all alternatives, modifications, and equivalents included within the spirit and scope of the present disclosure.

EXAMPLES

The following examples are put forth so as to provide those of ordinary skill in the art with a complete disclosure and description of how the compounds, compositions, articles, devices and/or methods claimed herein are made and evaluated, and are intended to be purely exemplary of the disclosure and are not intended to limit the scope of what the inventors regard as their disclosure. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

The various testing methods and procedures referenced in the examples described herein are discussed in more detail below.

Example 1. Materials and Methods

Cell Culture. The rhabdomyosarcoma cell lines RH30, RH18, and RD were cultured in RPMI-1640 medium with 10% FBS. RH18 was a gift from Dr. P. J. Houghton. Glioblastoma cell line U87 cells were cultured in Minimum Essential Medium Eagle (MEM), supplemented with 1 mM sodium pyruvate, 1% nonessential amino acids, 0.15% sodium bicarbonate, and 10% fetal bovine serum (FBS); T98G cells were cultured in MEM with 10% FBS; A172 cells were cultured in Dulbecco's modified Eagle's medium (DMEM) with 4.5 g/L glucose, and supplemented with 10% FBS; U251 cells were cultured in Roswell Park Memorial Institute medium with 5% FBS. Immortalized human astrocytes (a kind gift from Dr. Russ Pieper, University of California San Francisco) were grown in DMEM/F12 with 4.5 g/L of glucose, supplemented with 10% FBS. All cells were grown at 37° C. in 5% $CO_2$-95% $O_2$. All cell lines unless specified were originally obtained from ATCC. They were not further authenticated.

Clinical Samples. Fresh-frozen samples of normal brain and tumors were collected under an approved University of Virginia Institutional Review Board protocol. Tumors were macrodissected, and RNA and protein were extracted according to well-established protocols.

AVIL overexpression and silencing. The MARS-AVIL coding region was amplified from RH30. An AVIL cDNA clone was purchased from GeneCopoeia (GC-0G11537), and was cloned into the Retrovirus vector pQCXIH. Stable cells that overexpresss MARS-AVIL, or AVIL were selected via hygromycin. For siRNA treatments, siAVIL1 (targeting 5'-GCTTCTGGCAAAGGATATT-3'), siAVIL2 (targeting 5'-GCATTCCTTGCTTGTTATA-3'), and control siRNA (siGL2) were purchased from Life Technologies. RNAimax (Invitrogen) was used for siRNA transfection, which was performed according to the manufacturer's instructions.

Polymerase chain reaction (PCR) and Real-time PCR. RNA was extracted using TRIzol reagent (Invitrogen), and quantified with Nanodrop (Thermo). cDNA was generated by AMV-RT kit (NEB), and a random hexamer primer. Real-time qPCR was carried out on the StepOne Plus system from Applied Biosystems using SYBR mix (Thermo). Primer sequences are listed here:

```
MARS-AVIL-S    5'-CCCTTCTGTGGCTATGAGGA-3',
MARS-AVIL-AS   5'-TGGATGTCCTGGGATAGGAG-3';
AVIL-S,        5'-TGCGAACTCAGGCAGAGCACTA-3',
AVIL-AS        5'-CAGTGTTCTCGCTGCCATCACA-3'.
```

Western blotting. To measure protein levels, cell lysates were resolved by denaturing gel electrophoresis, before electrotransfer to a Protran nitrocellulose membrane. The membrane was subjected to western blot analysis with antibodies against the proteins of interest. The following antibodies and dilutions were used: rabbit anti-MARS (1:2000; Sigma HPA004125), rabbit anti-AVIL (1:2000; Sigma SAB2100191), rabbit anti-PARP (1:1000; Cell Signaling 9542), rabbit anti-Cleaved Caspase-3 (1:1000; Cell Signaling 9664), and mouse anti-GAPDH (1:10000; Ambion Am4300).

Fluorescence In Situ Hybridization (FISH). DNA probes for fluorescence in situ hybridization (FISH) were labeled by nick translation with SpectrumGreen or SpectrumRed 2'-deoxyuridine-5'-triphosphate (Abbott). Cells were grown in 8-chamber slides and fixed with methanol:acetone=1:1 fixation solution for 10 minutes at 4° C. BAC Fish clone, RP11-143123 was purchased from BACPAC.

Protein purification. The sequence for human Advillin (AVIL) was cloned into the pMAL-c4x vector. The corresponding plasmid was transformed into BL21 (DE3) cells. Expression of MBP-AVIL was induced at $OD_{600} \approx 0.7$ by the addition of 1 mM IPTG, and continued for 18 hrs at 23° C. Harvested cells were subsequently resuspended in 20 mM Tris-HCl pH 7.4, 200 mM NaCl, 1 mM EDTA, 1 mM DTT (Wash Buffer), supplemented with Complete Protease Inhibitor Cocktail (Roche), lysed in Emulsiflex C3 (AVESTIN) and cell debris was removed by centrifugation. MBP-AVIL was immobilized on Amylose Resin (New England BioLabs) followed by extensive washing (>50 column volumes) with Wash Buffer. Protein was eluted with Wash Buffer supplemented with 10 mM Maltose. After overnight incubation with TEV protease, MBP-tag was removed by size exclusion on HiLoad 16/600 Superdex 200 pg columns, previously equilibrated to 20 mM HEPES, pH 7.4, 50 mM NaCl, 1 mM DTT (Protein Buffer). Recombinant AVIL was flash-frozen in liquid nitrogen and stored in −80° C.

Electron microscopy. Stock solution of G-actin in G-buffer (5 mM Hepes, pH 7.5, 0.1 mM $CaCl_2$), 1% sodium azide) was diluted to 5 µM by F-buffer (10 mM MOPS buffer, pH 7.2, 50 mM KCL, 2 mM $MgCl_2$, 0.5 mM ATP), and polymerized for 1-2 hours. F-actin was diluted to 2 µM by F-buffer, and incubated with 20 µM of recombinant advillin with 0.1 mM $CaCl_2$. Incubation time was 10-30 minutes at room temperature. 5 µl of complex was applied to glow-discharged carbon coated grids, and stained by 2% uranyl acetate. The samples were examined on a Tecnai T12 microscope operated at 80 keV at a magnification of 30,000. The images were recorded on 1K×1K CCD-camera.

Cell morphology assessment. All materials were from Life Technologies unless otherwise indicated. In-house-made dishes with glass coverslip bottoms were pre-adsorbed with 2 µg/ml fibronectin overnight. Cells were stained with 5 µM Dil in OptiMEM for 15 minutes, then rinsed with PBS and returned to normal growth medium until the experiment. Cells were seeded on glass-bottomed dishes in serum-free, 002-independent medium (CCM1, Hyclone), and cultured for 1.5 hours. Each sample was imaged live on an Olympus Fluoview 1000 laser scanning confocal microscope with a 10× (0.3 NA) objective. The samples were maintained at 37° C. with a stage heater. The Dil-stained cells were excited using the 543 nm line of a HeNe laser. Images were acquired at a resolution of 0.795 µm/pixel. Settings were adjusted to minimize photodamage. Cell area measurements were automated using custom MATLAB scripts. Briefly, cell images were subjected to an interactive threshold, resulting in silhouettes, which were then automatically quantified using MATLAB's built-in region properties function. Cell areas ($µm^2$) of the control and AVIL knock-down groups were compared using the Rank-Sum test for non-normally distributed data. The sample sizes for the control and knock-down groups were 55 and 51 cells, respectively.

Cell migration and invasion assay. The effect of AVIL on cell migration was assayed by a wound-healing assay. Briefly, cells were cultured to confluency. A wound was created by scraping the cells using a 10 ul plastic pipette tip, and the medium was replaced with fresh medium. Images were captured immediately after the scratch, and again six hours later. Cell migration was qualitatively assessed by the size of the gap within the confluent monolayer culture at the end of the experiment. Eight gaps were measured.

The effect of AVIL on cell invasion was assessed by a transwell invasion assay. siAVIL or siGL2 transfected glioblastoma cells ($1 \times 10^5$) were suspended in 300 μL 0.1% FBS medium, and added to the upper chamber of the wells. The lower chamber contained 600 μL of 10% FBS medium. The plate was kept in air with 5% $CO_2$ for 8 h at 37° C. The cells on the upper membrane surface were then mechanically removed. The cells that had migrated to the lower side of the collagen IV-coated membrane were fixed and stained with 0.1% crystal violet. Migrated cells were counted in five randomly chosen fields under a microscope, and the average number of these cells per field was calculated.

Tumor formation in vivo. U251 cells were transfected with control shRNA, or shAVIL1 for 12 h. The transfected cells were then counted, and $2 \times 10^5$ were stereotactically (Stoelting) implanted into the right corpus striatum of immunocompromised SCID/NCr BALB/c adult male mice (6-8 weeks old) (n=7 for each condition). Cerebral magnetic resonance imaging was performed on anesthetized mice at 4 weeks post implantation. Ten to fifteen minutes before scanning, 30 ul of Magnevist brand gadopentetate dimeglumine was injected intraperitoneally. T1-weighted serial coronal images of each brain were acquired at 1 mm intervals with a 5×5 mm field, and a 256×256 pixel resolution. For image analysis and tumor volume quantification, a luminosity histogram was first generated for a selected area of the left cerebrum that was grossly tumor-free. This served as an internal control. Pixel luminosity mean and SD were noted. Histogram generation was repeated on a similar selection from the right cerebrum that contained all enhanced tumor. Pixels in the right cerebrum, greater than two SDs above the left cerebrum control luminosity mean, were recorded as representing enhanced tumor for a given image. This procedure was then repeated for of all the images showing an enhanced tumor for a given brain, thus generating a sum of enhanced tumor pixels for each brain. Tumor volume relates to tumor pixels in a linear manner, and was calculated based on the image acquisition, interval distance, and resolution.

Astrocytes stably expressing AVIL or an empty vector were injected subcutaneously into the flanks of NIH-III Nude mice. Around 2 million cells were used per injection. The animals were monitored twice a week. For drug treatment, 1.5 million U87 cells were injected subcutaneously into the flanks of NIH-III Nude mice. Compound 56750508 was dissolved in 50% DMSO, 15% ethanol, and 35% water. After tumors became visible (around 2 weeks), 50 ul drug solution or solvent was injected intra-tumorly. Three injections were performed with two day intervals.

Small molecule microarray (SMM) screening. Each SMM slide contained approximately 5000 printed features in duplicate and was prepared as described previously (Bradner et al., 2006a; Bradner et al., 2006b). In total 50,000 compounds were screened. The collection contained computationally selected commercially available compounds, as well as products of diversity-oriented synthesis and known bioactive compounds. Each sample was screened against two replicate SMMs. Each slide was incubated with 3 mL of a solution of 0.5 μg/ml recombinant AVIL-His protein in TBS-T buffer for 1 hour at room temperature. The slides were then incubated with a 3 ml solution of anti-His mouse monoclonal antibody conjugated to AlexaFluor 647 (Qiagen) at a concentration of 1:1000. Each incubation step was followed by three washes in TBS-T. Finally the slides were briefly rinsed in distilled water and spin-dried (Bradner et al., 2006b). The slides were immediately scanned using a GenePix 4000B fluorescence scanner (Molecular Devices). The image was analyzed using GenePix Pro software (Axon Instruments) and the raw data was analyzed based on the signal-to-noise ratio and reproducibility. For each slide an average Robust-Z score was calculated for each distinct feature. The refined data was visualized using Spotfire software (Spotfire TIBCO Software). Assay positives with a Robust Z score greater than 3-sigma from the median were compared to the control screen, and all other SMM screens within the Koehler Lab SMM database to filter nonspecific binders.

Thermal shift assay. SYPRO Orange (ThermoFisher Scientific) was added to 0.5 mg/ml AVIL (in Protein Buffer) in a 1:4500 ratio. 2.5 uL increasing concentrations of candidate compounds were added to 22.5 μL of AVIL/SYPRO Orange mixture on a 96 well plate (10% final concentration of DMSO). Protein unfolding was measured in a CFX96 qPCR (Bio-Rad) instrument with 0.2° C./15 sec steps, over the range of 20-90° C.

Example 2. MARS-AVIL Fusion in Rhabdomyosarcoma

Figure 1B:
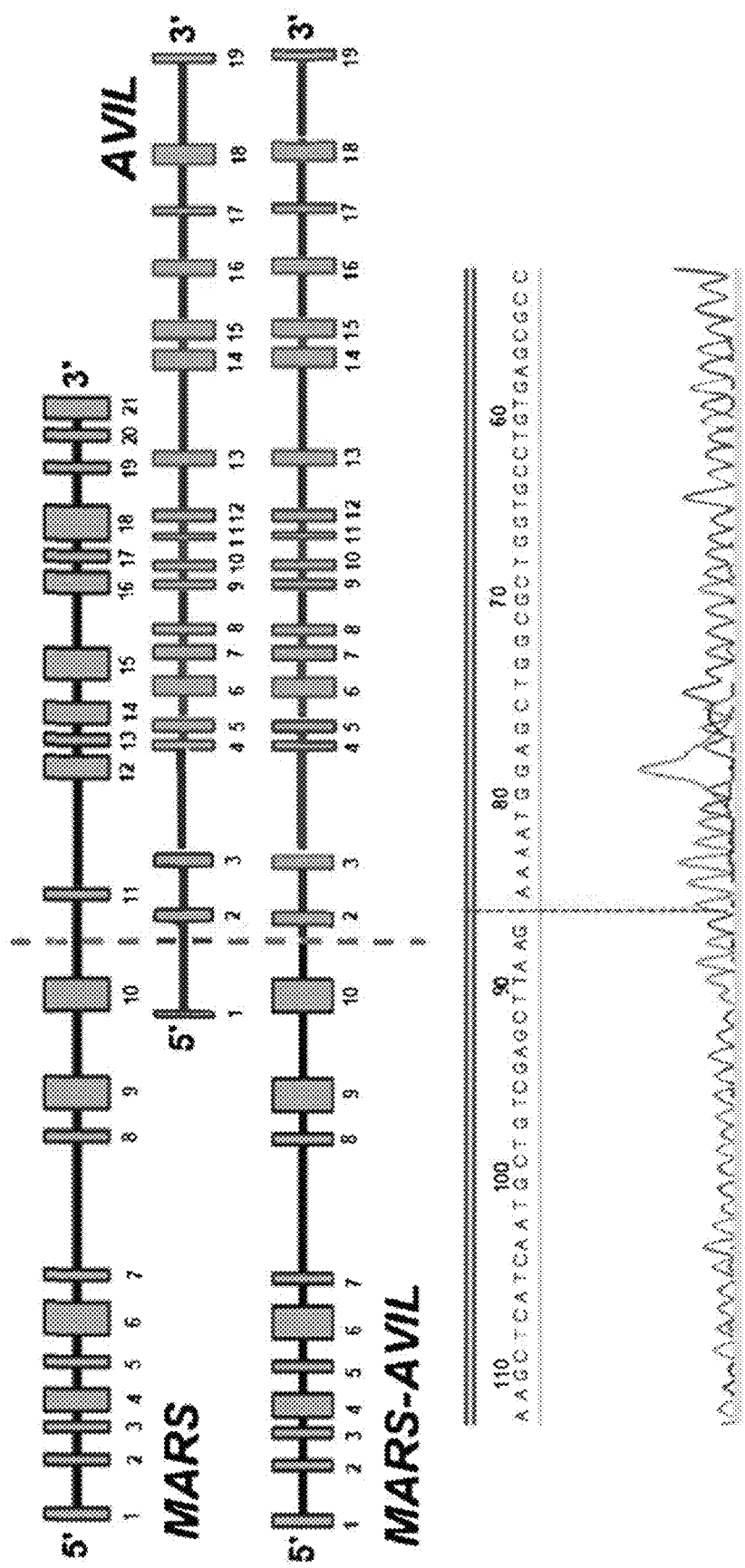
Figure 1C:
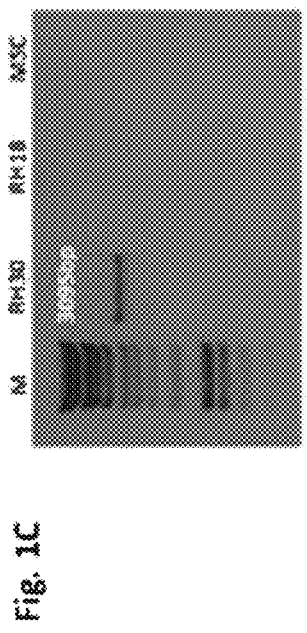
Figure 8A:
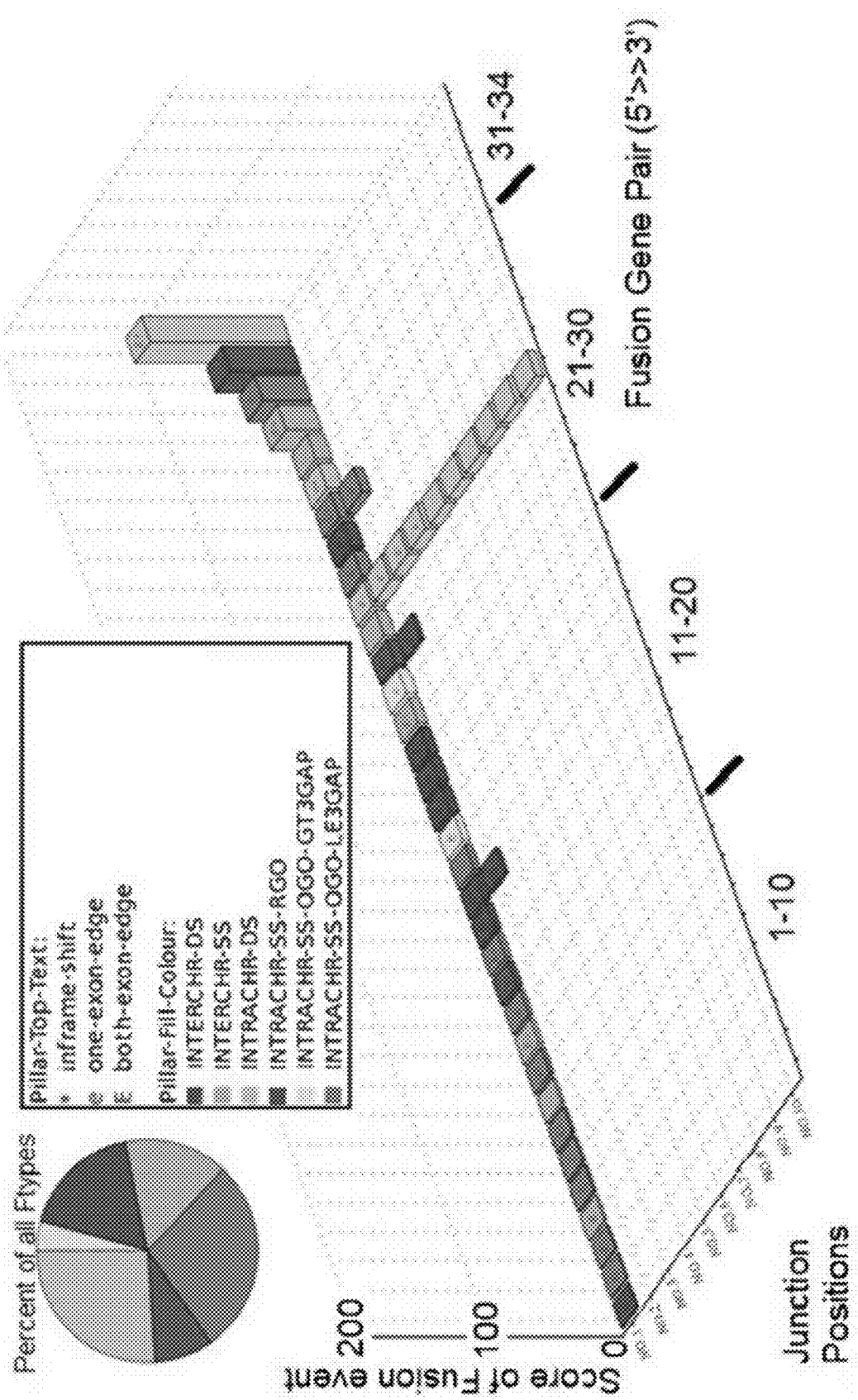
FIG. 8A shows representative data demonstrating the landscape of fusion RNAs in RH30 RNA-sequencing. MARS-AVIL fusion has the highest number of reads.

RNA-Sequencing was performed on a rhabdomyosarcoma cell line, RH30. The data were analyzed using publically available RNA-Sequencing datasets for rhabdomyosarcoma, which include RNA-Seq data for additional rhabdomyosarcoma lines, RMS-13 and A-673 (FIG. 1A). Using the Soapfuse software, a common, abundant fusion transcript was identified, joining the first 10 exons of MARS (methionyl-tRNAsynthetase) to the last 18 exons of AVIL (advillin) in both RH30 and RMS-13 cells (FIG. 8A) (of note, A-673 is now proved to be a Ewing sarcoma instead). Even though PAX3-FOXO1 is the most well-known fusion in this type of rhabdomyosarcoma, MARS-AVIL has the highest number of reads in the RNA-Seq data (FIG. 8A). The MARS and AVIL genes are located in the same chromosomal region, 12q14, with 300 kb and are separated by approximately 15 genes. They transcribe in a head-to-head configuration. Using long range PCR, it was determined that the fusion results from an inversion of a fragment covering exon10 of MARS and exon1 of AVIL (FIGS. 1B and 10), yielding a head to tail configuration. With Sanger sequencing, the break site was identified, which is located in intron9 of MARS and intron1 of AVIL (FIG. 8B). This fusion was not present in another rhabdomyosarcoma cell line, RH18, or a mesenchymal stem cell culture (MSC). Interestingly, an Image clone, BC004134 (Strausbert et al., 2002) with a 100% identical match around the fusion junction has been deposited in the human non-reference RNA database. It is labeled as an "mRNA similar to advillin", and the tissue source was "rhabdomyosarcoma", indicating that the chimeric transcript was found independently before, but was not recognized as a gene fusion product.

Figure 1D:
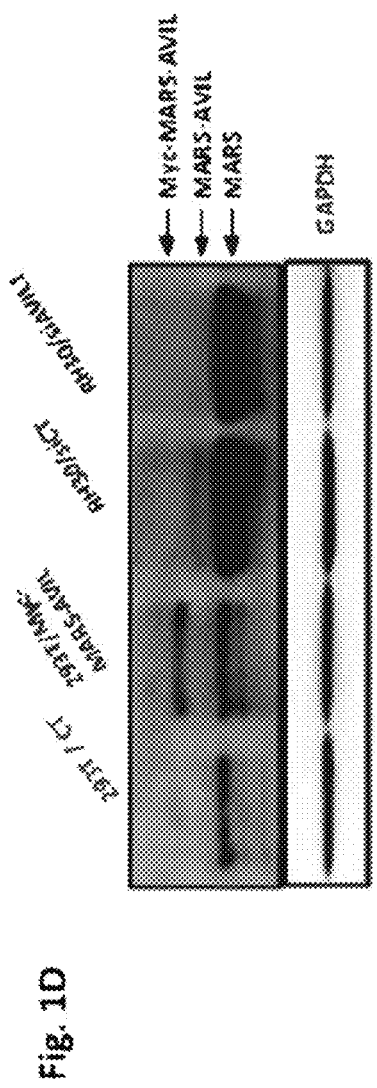
Figure 1E:

The reading frame of the AVIL portion is the same as the MARS portion, predicting that the fusion transcript will translate into an in-frame chimeric protein. Using a MARS antibody, a correctly-sized protein was detected as the possible fusion protein. To prove the identity of the band, an siRNA targeting the 3' of AVIL was prepared to silence both AVIL and MARS-AVIL. With the MARS antibody, a reduction of the MARS-AVIL protein signal was detected. As a positive control, the same antibody detected a Myc-tagged MARS-AVIL fusion in a 293T system (FIG. 1D). Importantly, in the collection of 14 clinical cases of rhabdomyosarcoma examined, the fusion transcript was detected in eight—more than half of the cases (FIG. 1E).

Example 3. MARS-AVIL Fusion is Important for Rhabdomyosarcoma Tumorigenesis

Figure 2A:
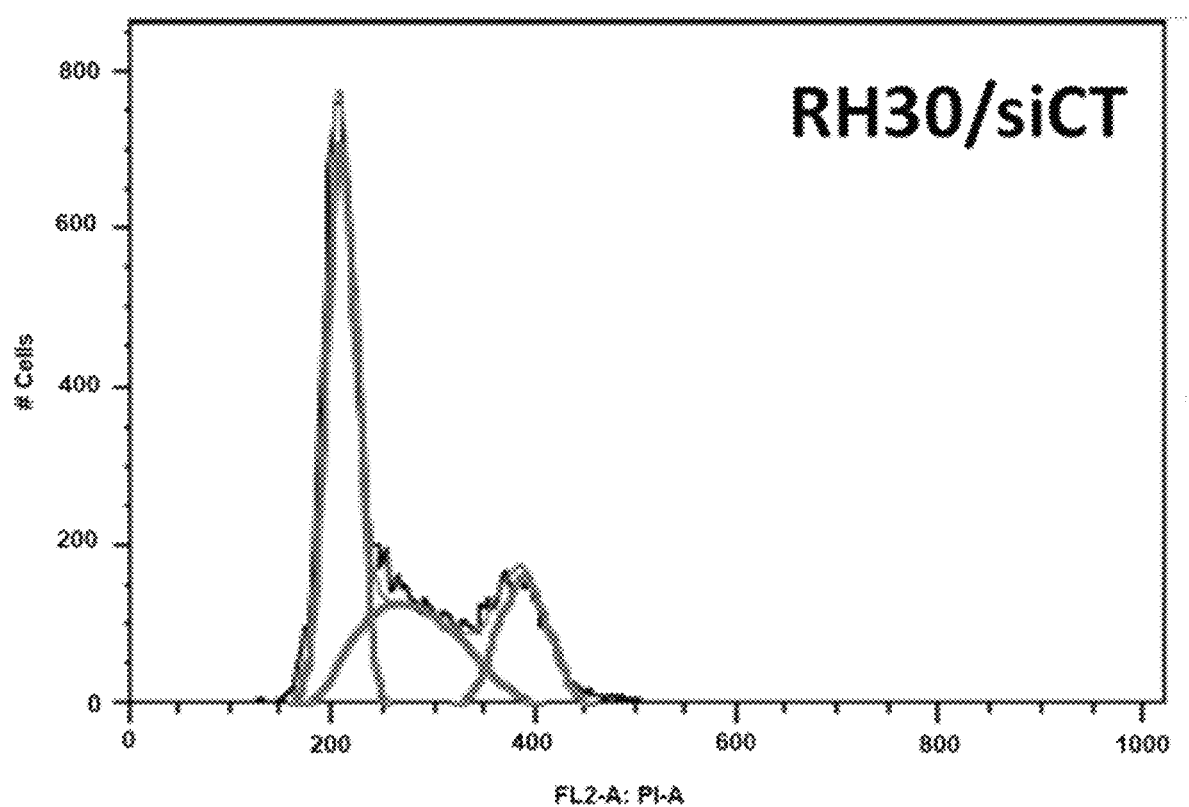
Figure 2B:
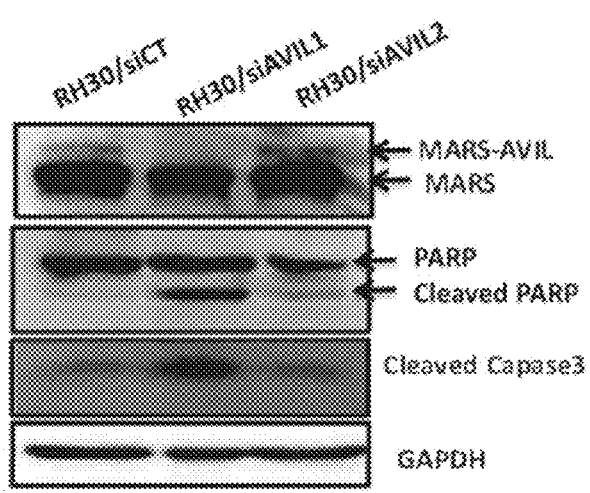
Figure 2C:
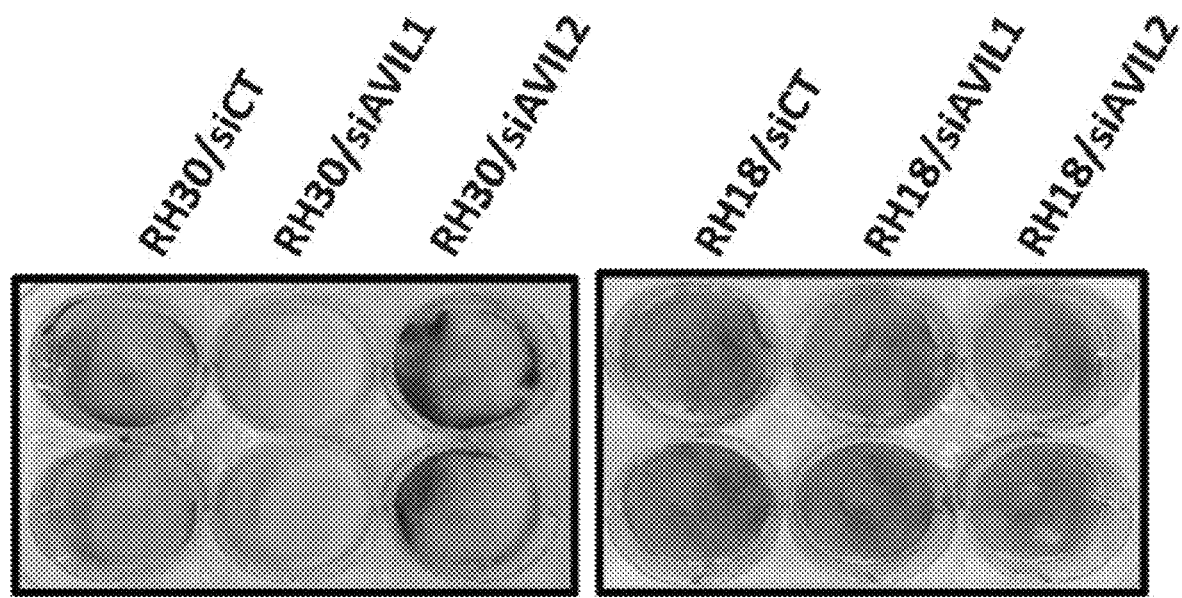
Figure 8C:
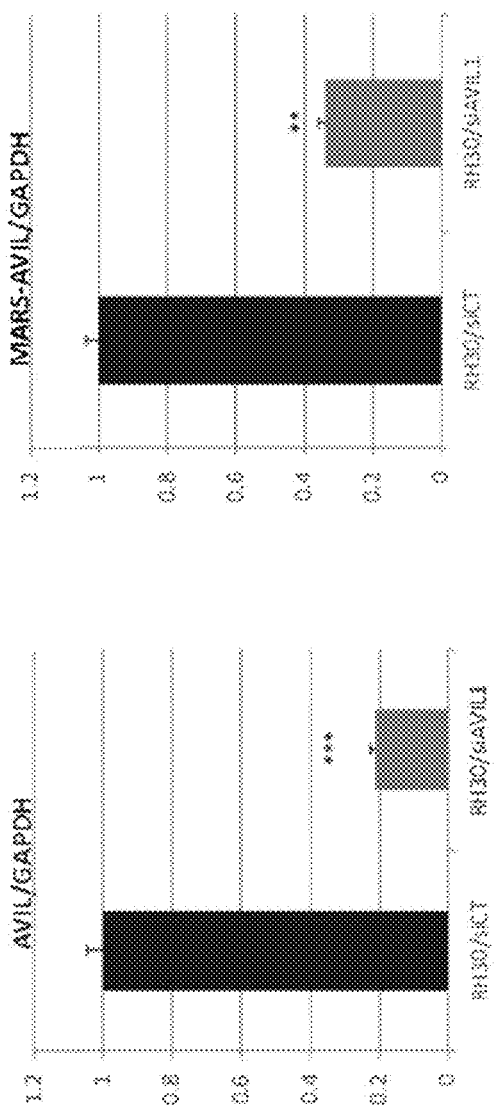
FIG. 8C-D show representative data demonstrating siRNA effect on MARS-AVIL and wild type AVIL transcripts measured by qRT-PCR. (C) siAVIL1 silences both MARS-AVIL, and wild type AVIL transcripts. (D) siAVIL2 only silences wide type AVIL. RH30 cells were transfected with siCT, siAVIL1, or siAVIL2. qRT-PCR measuring MARS-AVIL, and wild type AVIL, that were normalized against the level of GAPDH.
Figure 8D:
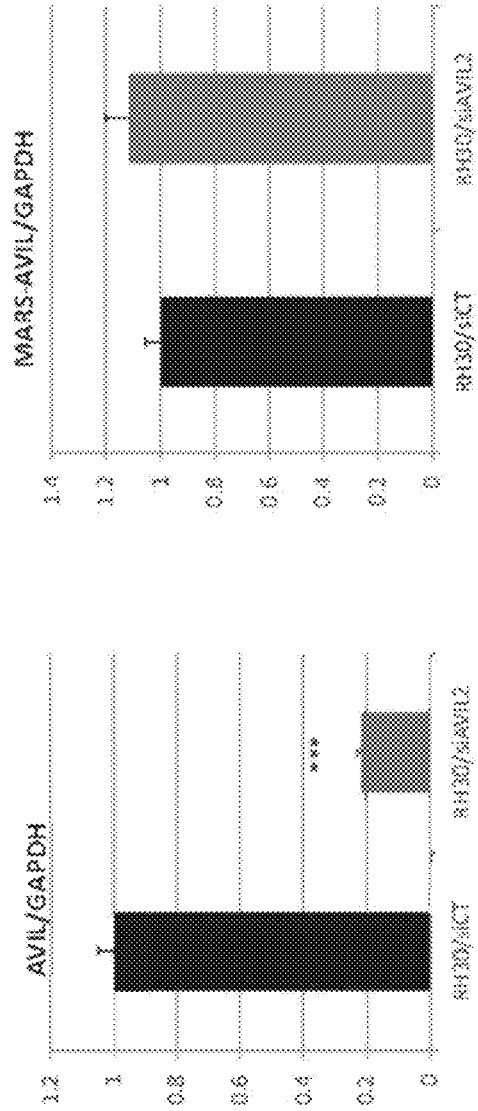
Figure 8E:
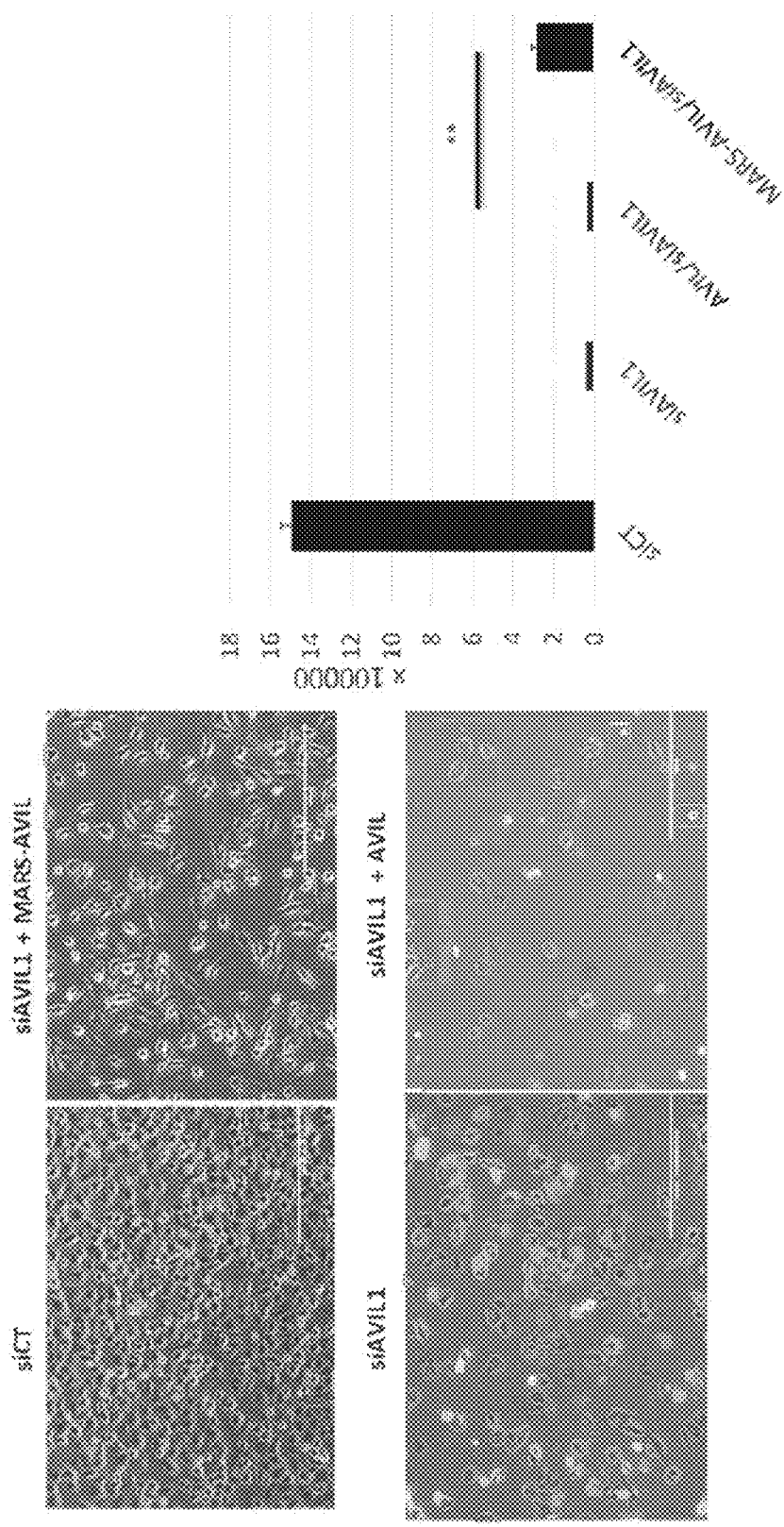
FIG. 8E shows representative data demonstrating MARS-AVIL, but not AVIL can rescue the phenotype caused by siAVIL1. On the left, images of cells were taken four days after the siRNA and plasmid transfection. On the right, cell numbers are plotted.

In order to investigate the implications of the MARS-AVIL fusion in the tumorigenesis of rhabdomyosarcoma, both loss- and gain-of-function approaches were utilized. For loss-of-function, two siRNAs were designed: one targeting both the fusion and wild type AVIL (siAVIL1) (FIG. 8C), and the other only targeting wild type AVIL (siAVIL2) (FIG. 8D). When RH30 cells were transfected with siAVIL1, but not siAVIL2, it was determined that a dramatic reduction in cell number, which is reflected by a significant increase in the subG1 peak in cell cycle analysis (FIG. 2A). Consistently, increased cleaved PARP was observed, and cleaved Caspase3 signals in cells transfected with siAVIL1, but not with siAVIL2 (FIG. 2B). The cell death was due to silencing the MARS-AVIL fusion, rather than silencing AVIL, or some off-target effect, as no effect was observed in RH18 (MARS-AVIL fusion-negative) with either siRNA. In contrast, most RH30 cells died when transfected with siAVIL1 (FIG. 2C). Also, rescue experiments were performed by transfecting various expression plasmids in RH30 cells that were transfected with siAVIL1. Transfecting MARS-AVIL, but not AVIL-expression vector resulted a partial rescue of cell growth (FIG. 8E).

Figure 2D:
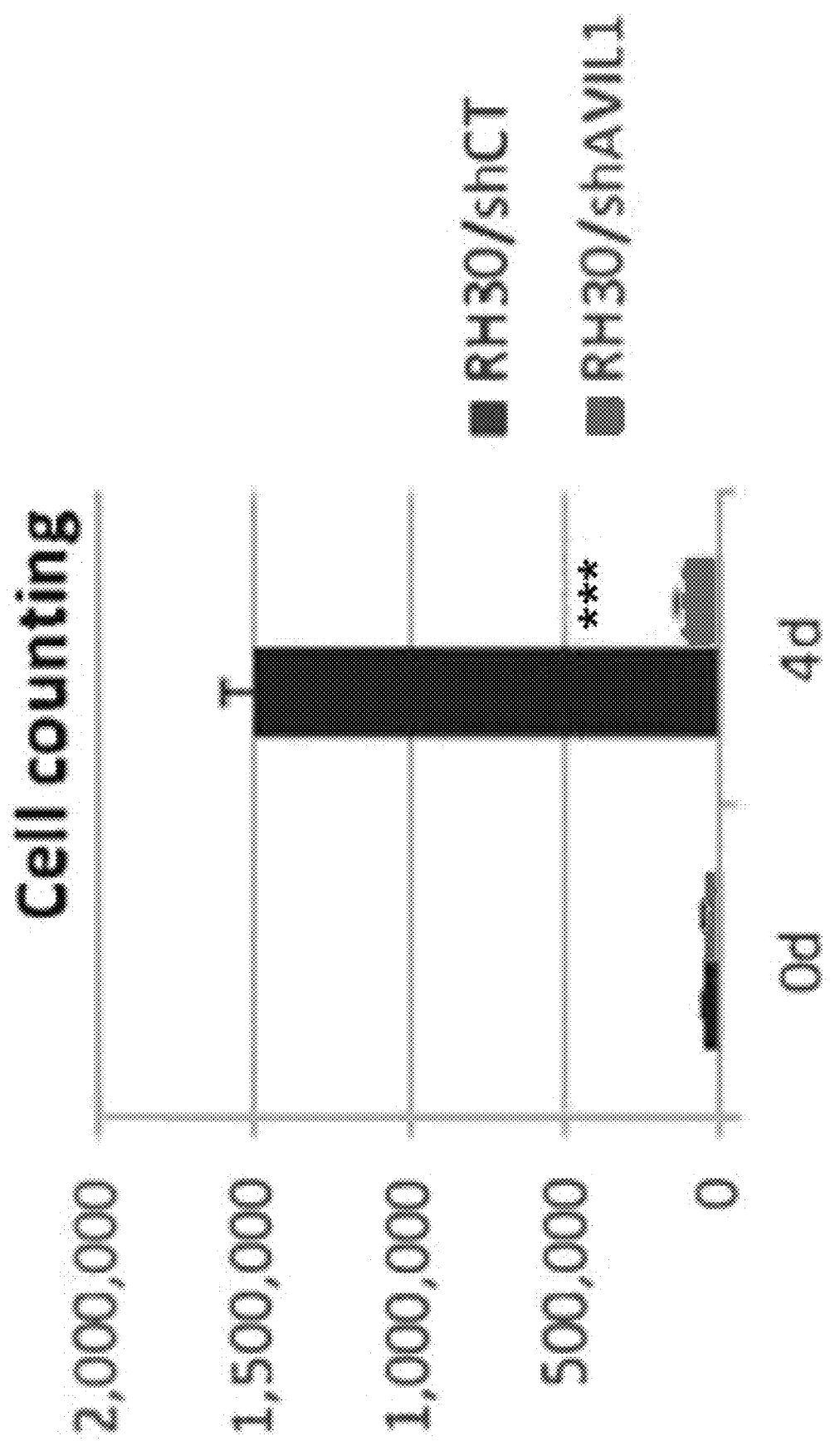
Figure 8G:
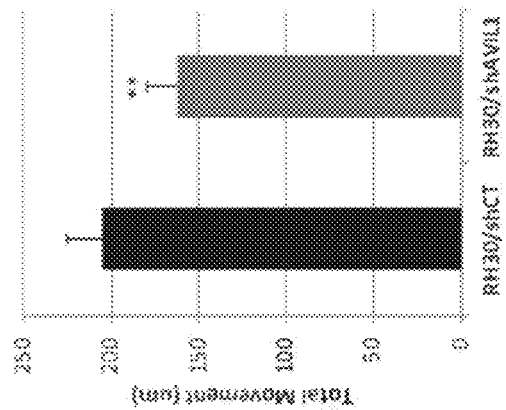
FIGS. 8F-G show representative data demonstrating Wound-healing assay measuring cell migration. (F) RH30 cells were transfected with siCT, siAVIL1, or siAVIL2. (G) Stable cells expressing shRNA constructs, shCT, or shAVIL1 were selected and tested.
Figure 8F:
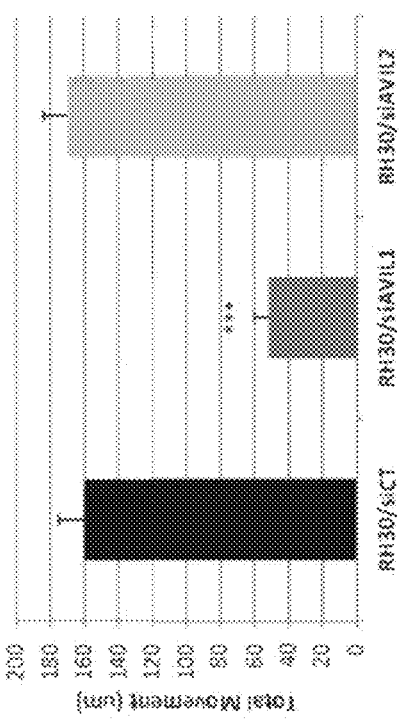

In addition to cell death, short-term treatment of the RH30 cells with siAVIL1 resulted in slower migration, as demonstrated by a wound-healing assay (FIG. 8F). The same effect on cell number and motility was also seen with an shRNA targeting the same region as siAVIL1 (FIG. 2D and FIG. 8G).

Figure 2E:
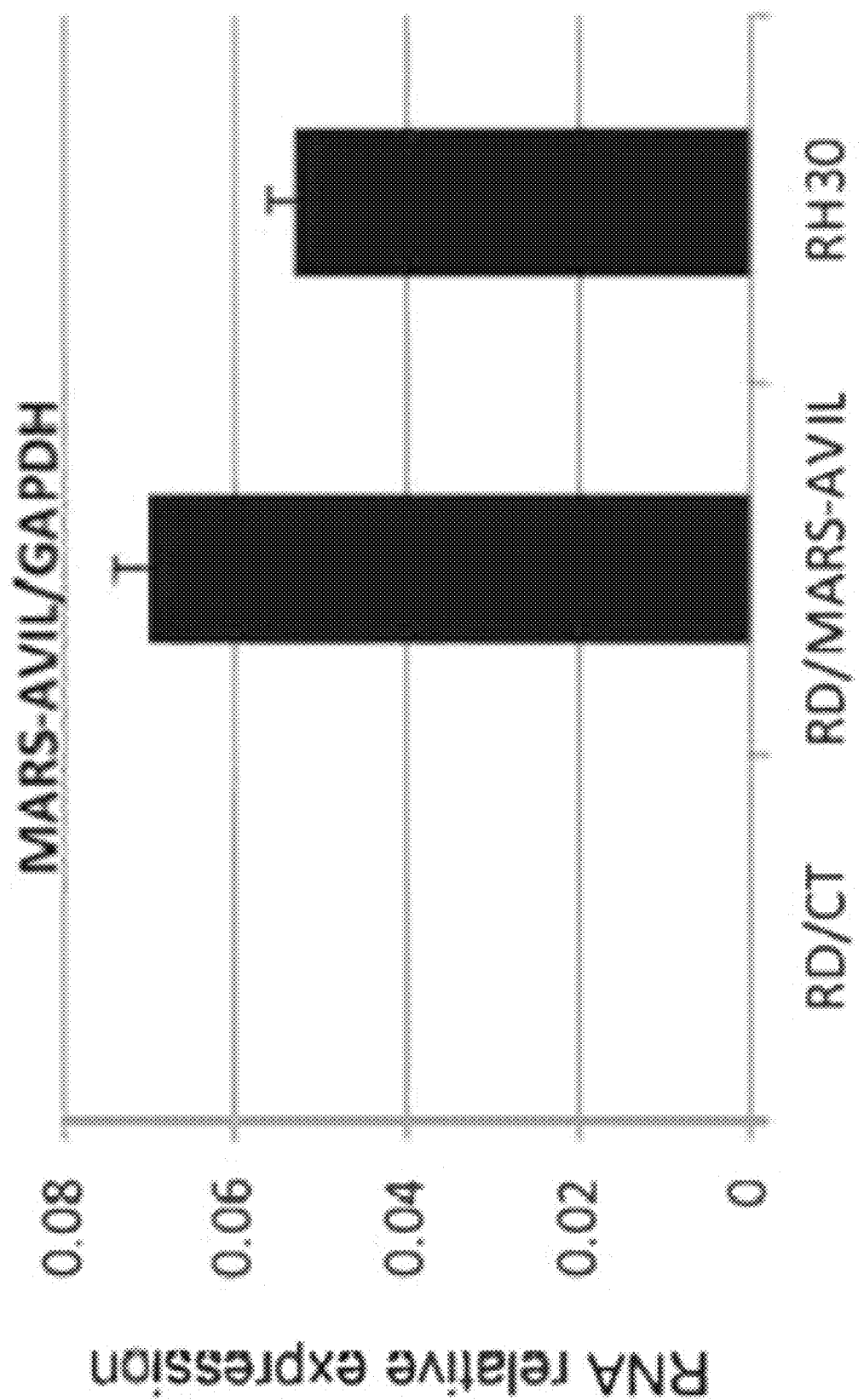
Figure 2F:
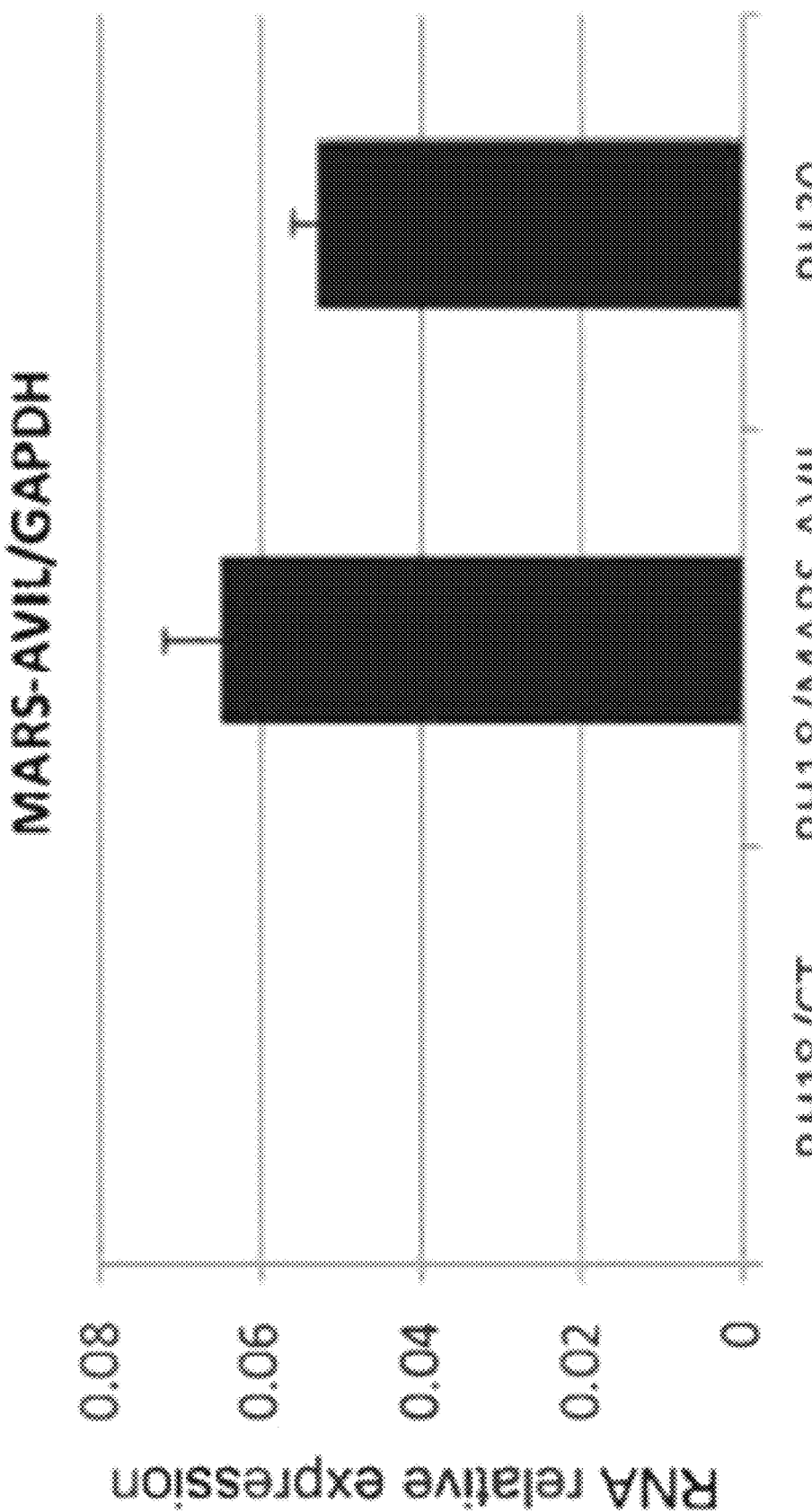

For gain-of-function experiments, RH18 and RD cells (both MARS-AVIL fusion negative) that stably express the fusion to a level similar to that of RH30 were generated. Consistent with the loss-of-function results, the fusion-transfected cells had significantly higher growth rates and motility (FIGS. 2E and 2F).

Figure 2G:
Figure 2H:
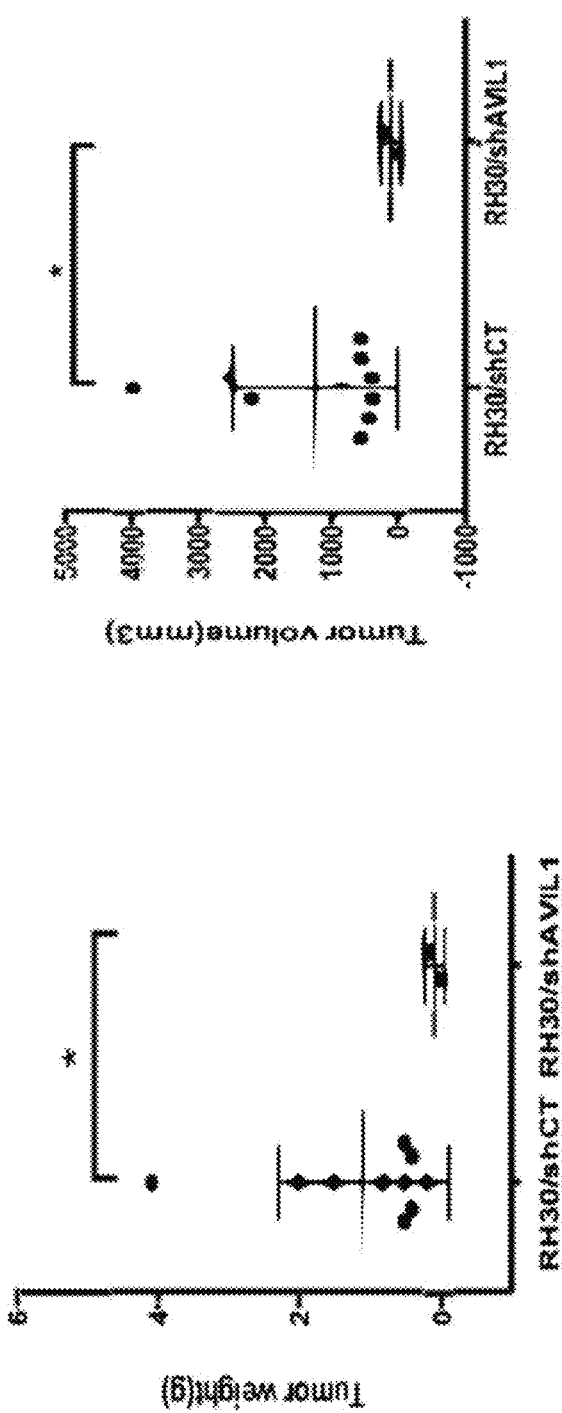
Figure 21:
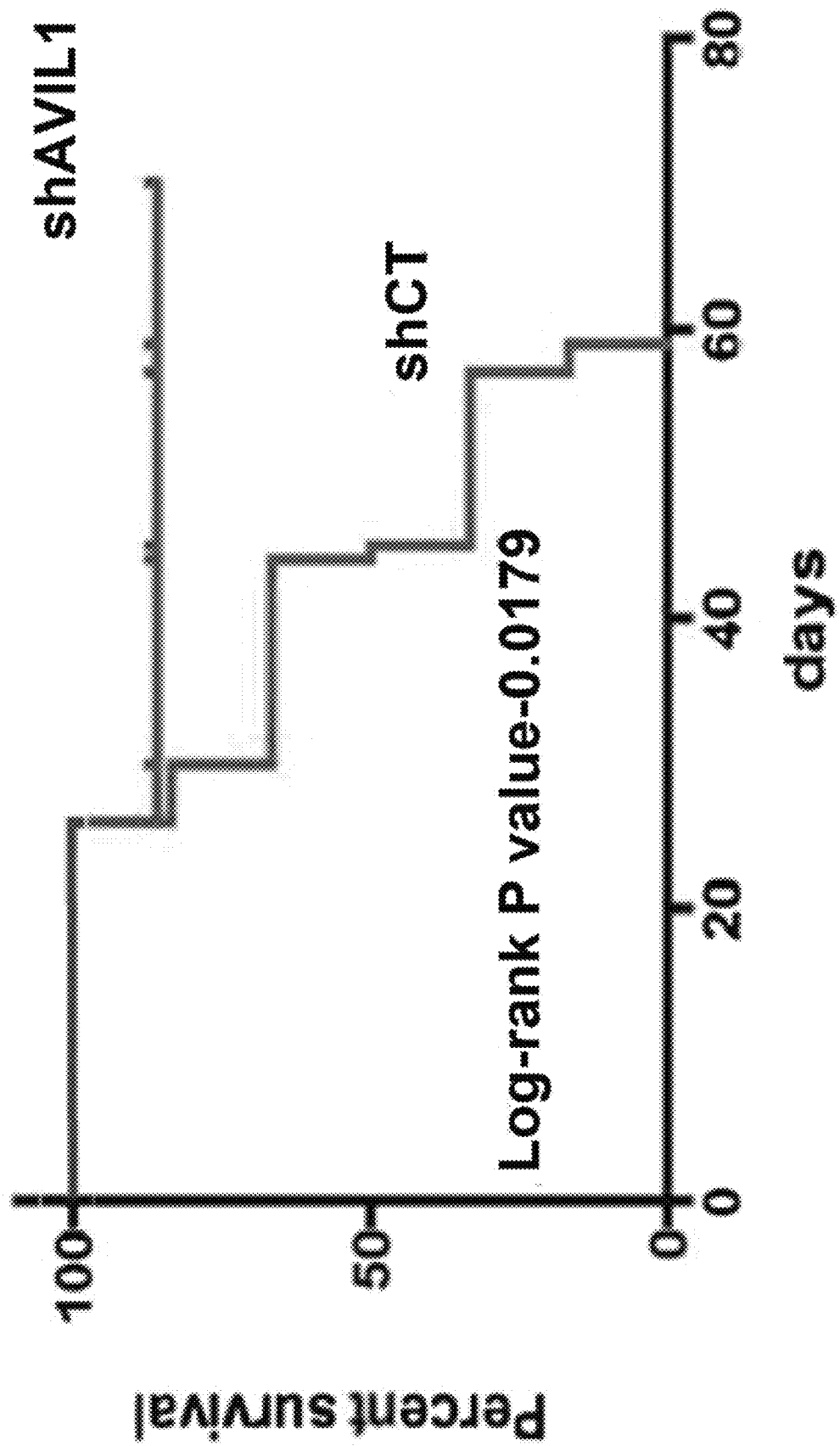

To investigate the role of MARS-AVIL in rhabdomyosarcoma tumorigenesis in vivo, xenografts with cells stably expressing shAVIL1 or a control shRNA were generated. All control mice (10/10) developed tumors. In contrast, only one very small tumor (1/10) was found in the shAVIL1 group (FIG. 2G, 2H). All of the mice in the control group died, or reached the limit for tumor burden, and had to be euthanized within 60 days. None of the mice in the shAVIL1 group died as a direct result of tumors, nor did they reach the tumor size limit (one mouse was euthanized as a control when the first shCT mice were terminated) (FIG. 2I).

Example 4. AVIL is Frequently Up-Regulated in Glioblastomas

Figure 3A:
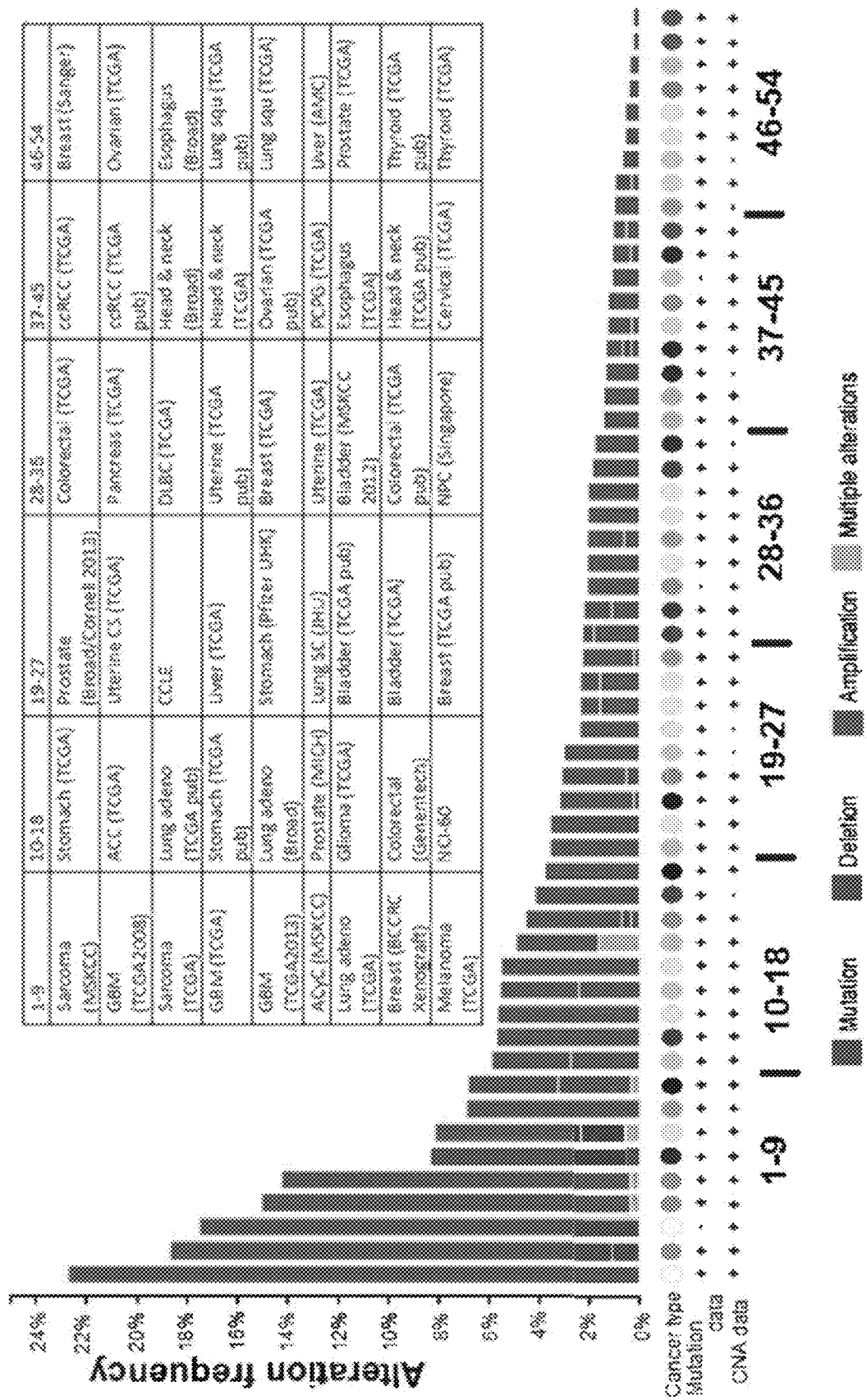
Figure 8H:
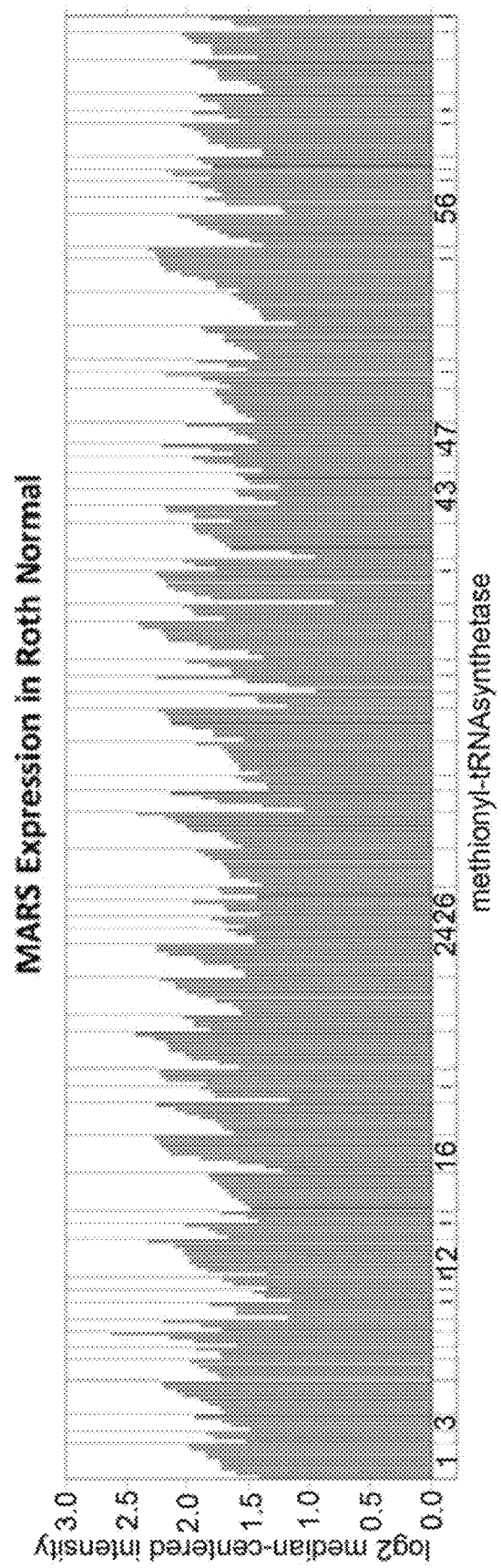
Figure 81:
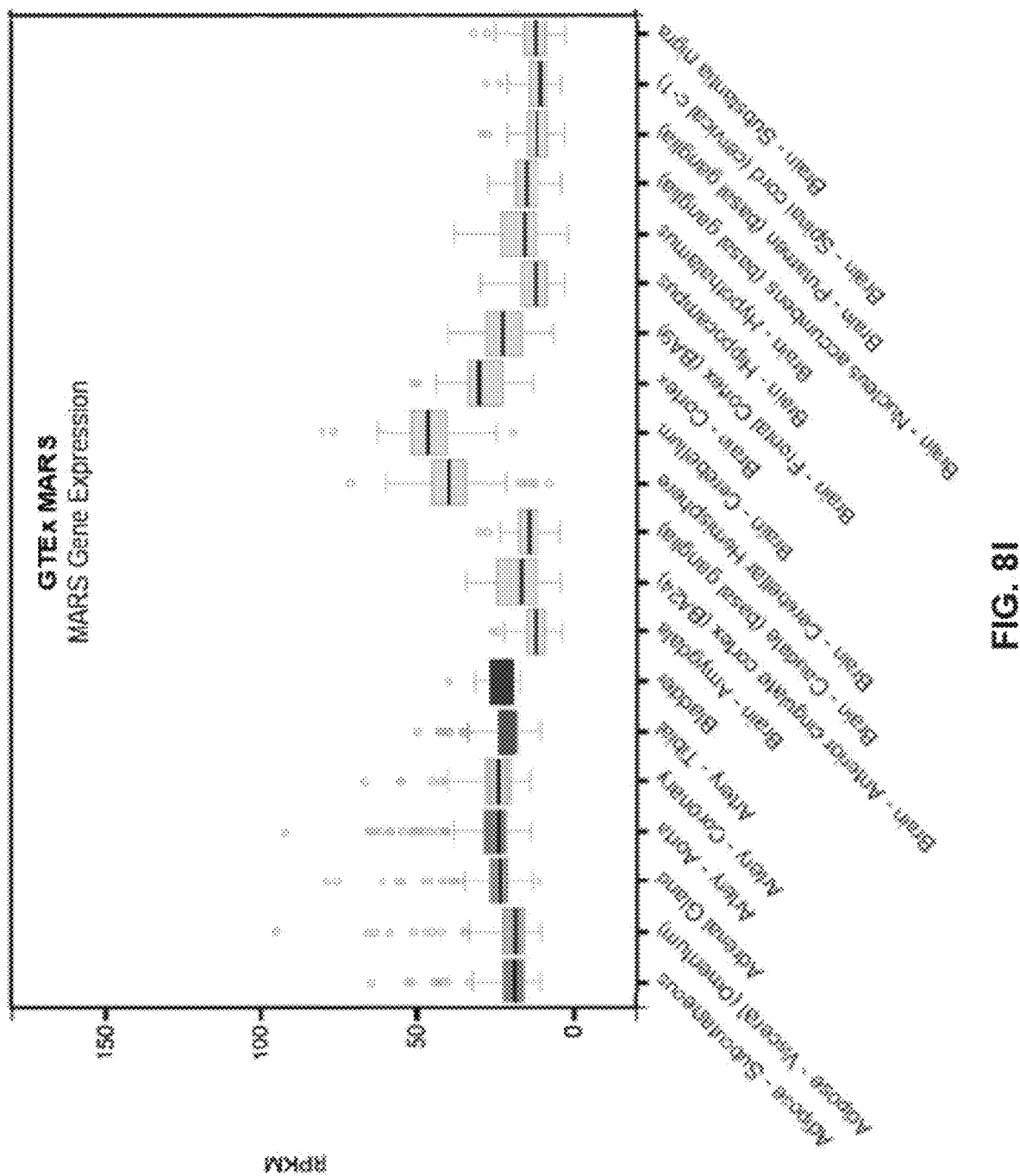

MARS is a house-keeping gene, expressed in all examined tissues (Roth et al., 2006). AVIL is differentially expressed among tissues; high in brain, but low in most other tissues (Rhodes et al., 2007; Roth et al., 2006) (FIG. 8H-1). Without wishing to be bound by a particular theory, it is possible that via fusing to MARS, AVIL is overexpressed in rhabdomyosarcomas; although it seems that the fusion has some unique properties, which wide-type AVIL does not retain. Further, without wishing to be bound by a particular theory, it is possible that the dysregulation of AVIL expression can contribute to the tumorigenesis of other cancers. It was determined that the AVIL locus is amplified in 15-18% of glioblastoma cases in The Cancer Genome Atlas (TOGA) studies via cBioPortal analysis (Cerami et al., 2012; Gao et al., 2013) (FIG. 3A). The copy number gain was verified by FISH analyses, using a probe covering the AVIL locus (FIG. 3B). The AVIL locus is amplified in two glioblastoma cell lines, SF767 and A172, but not in three other glioblastoma lines, U87, U251, T98G, or in an immortalized astrocyte culture. However, at the RNA level, U251 and T98G have higher levels of AVIL expression than the normal astrocyte cell line (FIG. 3C). The difference became even more dramatic when AVIL protein levels were measured; hardly any signal was detected in the normal astrocytes. In contrast, all of the tumor cell lines had higher AVIL protein expression (FIG. 3D). These results suggest that in addition to copy number gain, a higher percentage of glioblastomas may use transcriptional, and/or translational mechanisms to up-regulate AVIL expression.

Figure 3E:
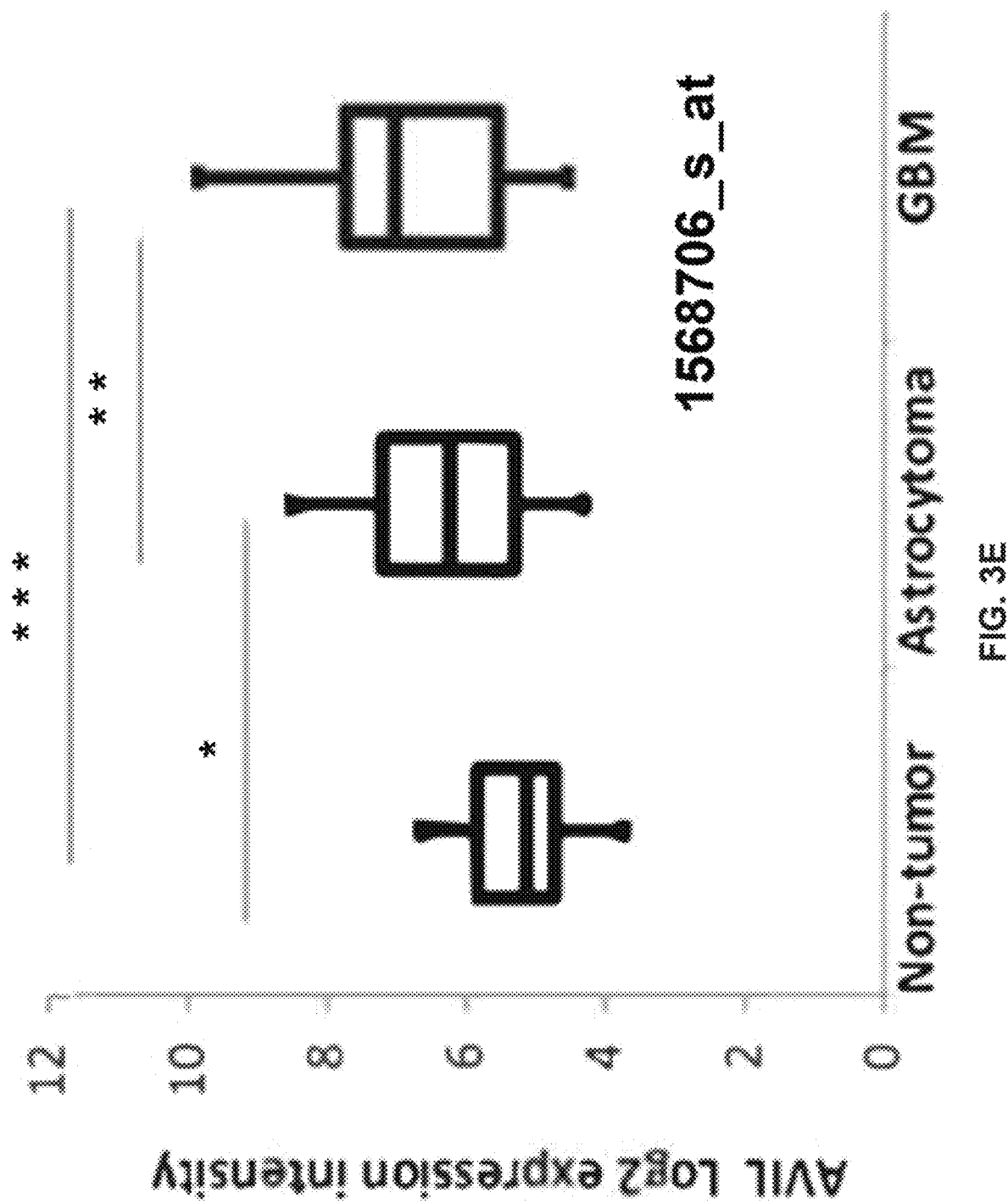
Figure 3F:
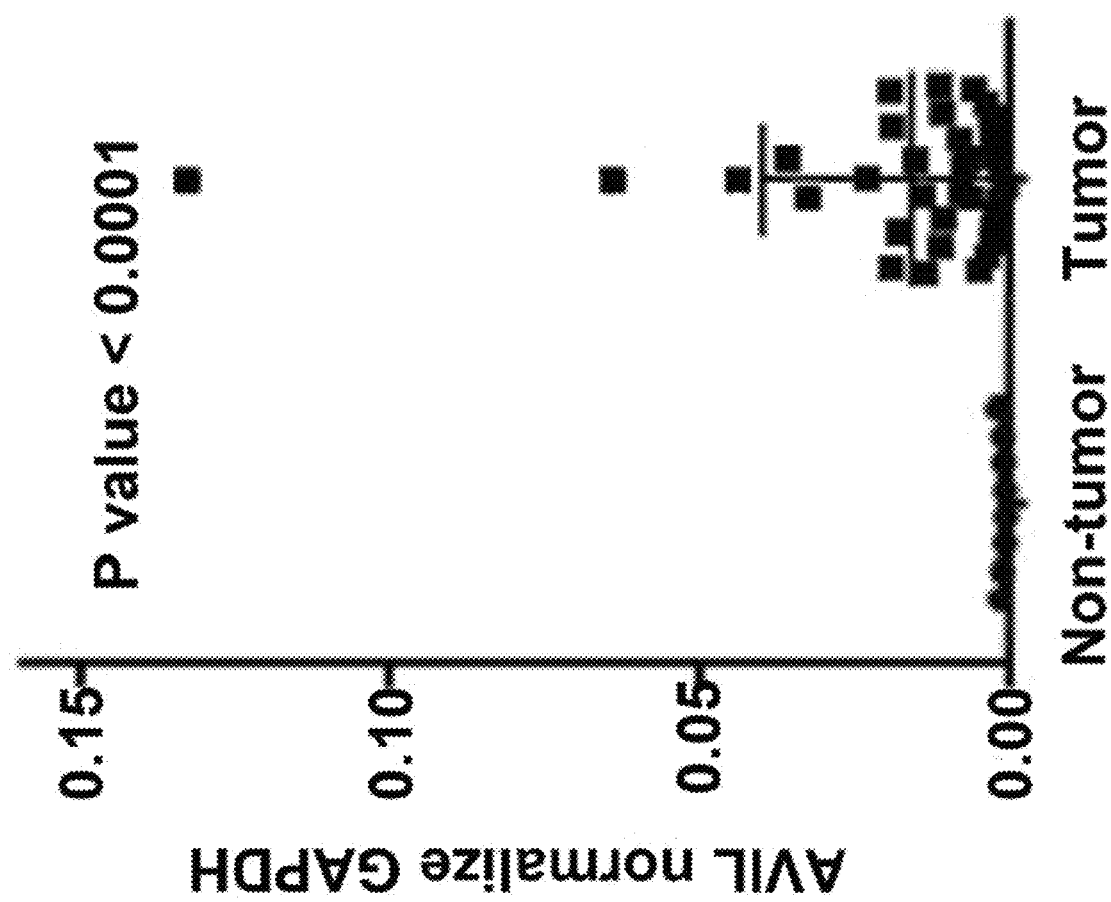
Figure 3G:
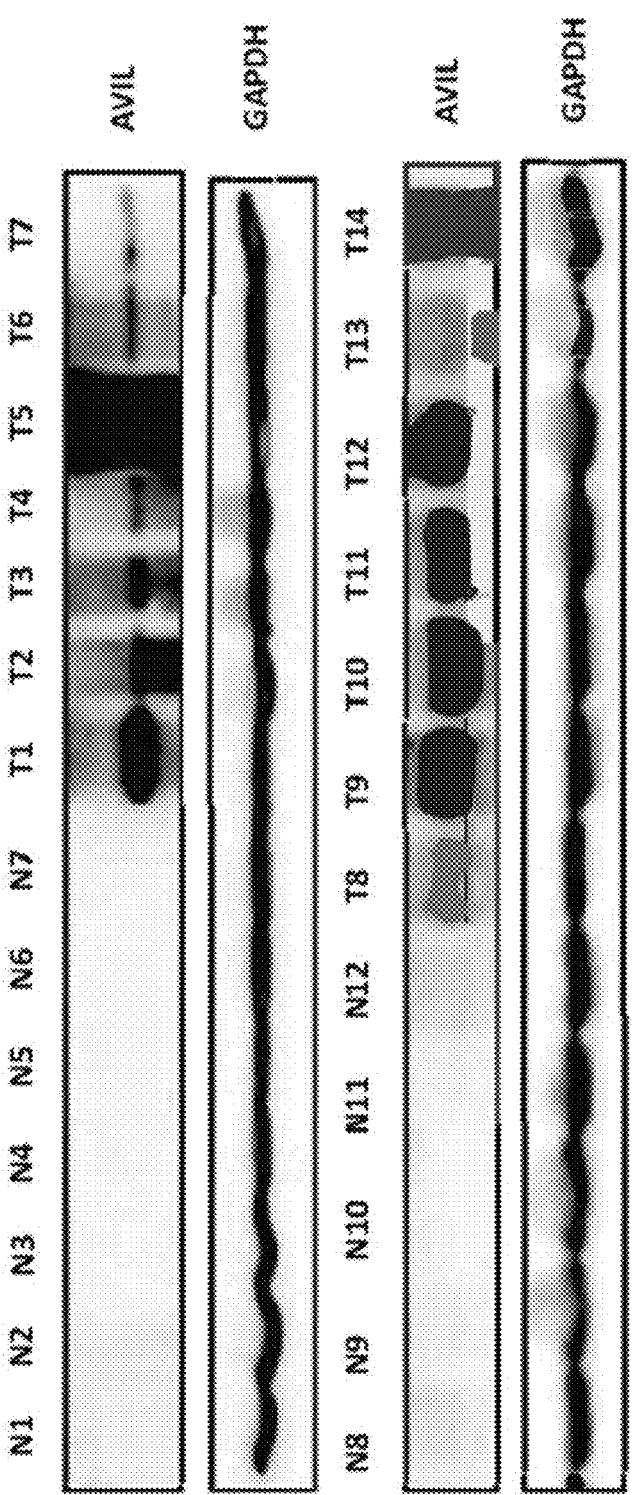

The REMBRANDT database was examined, which has microarray data for 28 non-tumor brain tissues, 148 astrocytomas (WHO grade II or III), and 228 GBM (WHO grade IV) cases (Madhavan et al., 2009). Two different microarray probes showed that AVIL expression correlates with tumor grade, with the highest levels in GBMs (FIG. 3E). In the inventor's collection of eight non-tumor brain tissues, and 36 glioblastoma cases, it was also confirmed that there is a significant difference in AVIL RNA expression levels between the two groups (FIG. 3F). Next, the expression levels of the AVIL protein was determined in 12 non-tumor brain tissues, and 14 GBMs. The data show that AVIL protein was absent, or barely detected in any of the non-tumor cases, but higher levels of AVIL protein expression were seen in all of the GBM cases (FIG. 3G).

Example 5. AVIL Overexpression is Important for Glioblastoma Tumorigenesis

Figure 8J:
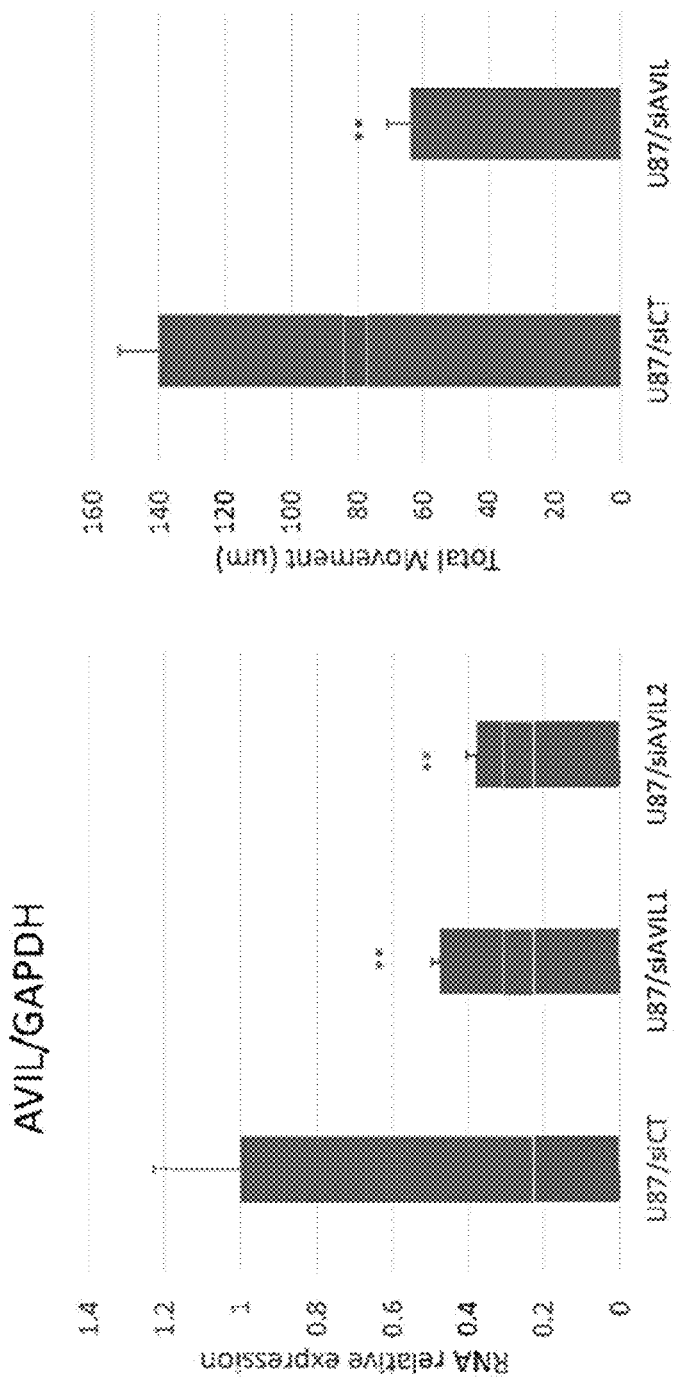
FIG. 8J shows representative data demonstrating that silencing AVIL resulted in reduced migration in U87 cells. AVIL level was measured by qRT-PCR, and normalized to GAPDH (left). Wound-healing, measuring cell migration at an earlier time point after siRNA transfection in U87 cells (right).

Both siAVIL1 and siAVIL2 effectively silenced AVIL expression in A172 GBM cells (FIG. 4A). These cells almost completely died out when transfected with either siRNA (FIG. 4B). Consistently, it was observed that there is a significant induction of cleaved Caspase3 in the cells (FIG. 4C). Obvious reduction of cell migration was also seen at an earlier time point (FIG. 4D). The same effect was seen in U251 (FIG. 4E), and U87 cells (FIG. 8J). In contrast, no growth inhibition was seen in the astrocyte cultures (FIG. 4F). As A172 and U251 are highly invasive, the effect of silencing AVIL on the invasiveness of the cells was assessed. The data show that when AVIL was silenced, a dramatic reduction in the number of cells that invaded through trans-well was observed in both cell lines (FIG. 4G).

Figure 4H:
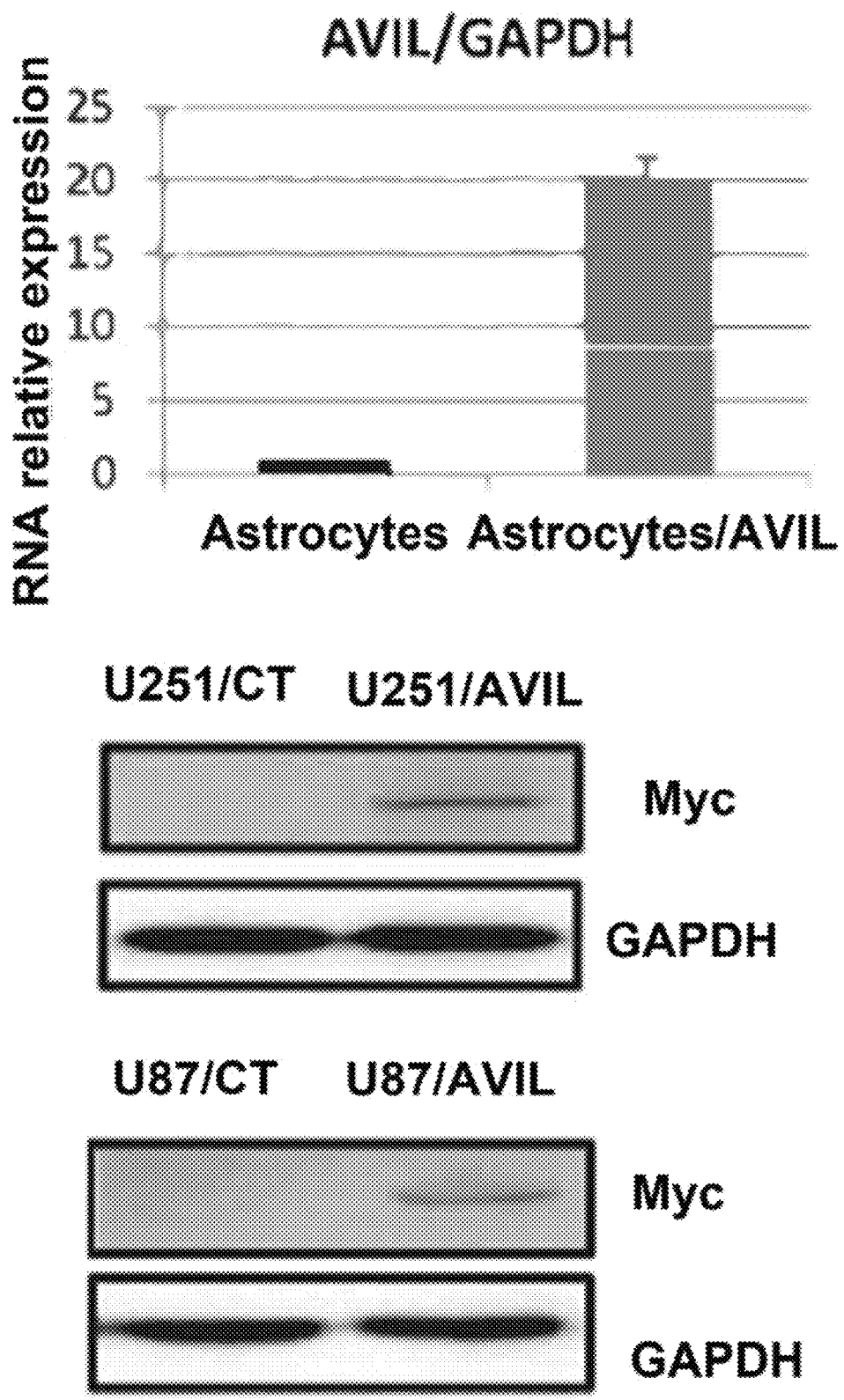
FIGS. 4A-4N show representative data demonstrating that AVIL overexpression is important for GBM tumorigenesis, as described further in Example 1. (A) Relative expression of siCT, SIAVIL1 and siAVIL2 in A172 cells. siAVIL1 and siAVIL2 effectively silenced AVIL in A172 cells. AVIL level as measured by qRT-PCR, and normalized to GAPDH. (B) Crystal violet staining of A172 cells transfected with siAVIL1, siAVIL2, or siCT. (C) Western blot measuring cleaved Caspase3 in A172 cells transfected with the siRNAs. (D) Wound-healing measuring cell migration at 48 hrs after siRNA transfection in A172 cells. (E) Effect of AVIL-silencing in U251 cells. Shown are Western blot analysis (left), crystal violet staining (middle), and wound healing assay (right). (F) Effect of AVIL-silencing in astrocytes. Shown are qRT-PCR analysis (left), and crystal violet staining (right). (G) Tumor cell invasiveness was measured by matrigel-coated transwell assay. (H) Overexpressing AVIL in astrocytes (upper), U251 (middle), and U87 (lower) resulted in increased cell proliferation, assayed by MTT (middle), or cell motility, assayed by wound-healing (right). (I) Three representative MRI brain images of mice injected with U251 cells stably expressing shCT or shAVIL. Arrows point to the area of tumor. (J) Tumor volume comparison between the two groups. (K) Percent of survival of the animals was plotted according to Kaplan-Meier analysis. (L) Focus assay. NIH-3T3 cells were transfected with AVIL-expressing (AVIL) or control empty plasmid (CT). Representative image is shown. (M) Quantitative difference of the foci number between two groups. (N) Astrocytes expressing AVIL or control plasmid were injected subcutaneously into the flanks of immunodeficient mice. Representative images showing the absence (CT) and presence (AVIL) of tumor. (* $p<0.05$,  $p<0.01$, * $p<0.001$).

In gain-of-function systems, the AVIL gene was overexpressed in astrocyte, U251, and U87 cells. The data show that AVIL overexpression led to increased proliferation rates, and migration in all three cell lines (FIG. 4H).

To confirm whether AVIL plays an important role in tumorigenesis in vivo, the effect of silencing AVIL in tumor initiation with a widely used U251 intracranial xenograft model was assessed. In this model, tumor-bearing animals usually die in about one month (Candolfi et al., 2007). Briefly, U251 cells that were freshly infected with lentivirus expressing shAVIL1 or shCT were implanted in the brains of immune deficient mice. After four weeks, all control mice had reached significant tumor volumes, detected by MRI (FIG. 4I). In contrast, hardly any tumor formation was observed in the shAVIL1 group by MRI. Consistently, dramatic differences in tumor volumes were observed between the two groups (FIG. 4J). All of the shCT group animals died within 35 days, or had to be euthanized due to abnormal behavior caused by tumor burden. All of the shAVIL1 group animals displayed no sign of disease, until the day the study animals were terminated in the experiment, with the exception of two (i.e., one shAVIL1 mouse was euthanized at the same time as a shCT mouse as a control, whereas another shAVIL1 mouse developed an infection after the MRI imaging, requiring euthanasia) (FIG. 4K). These results support the crucial role that the overexpression of AVIL plays in tumor initiation in vivo.

Example 6. AVIL is an Oncogene

To test whether AVIL functions as a bona fide oncogene, a classic focus assay on NIH3T3 cells was carried out. It was observed that significantly larger and higher numbers of foci were evident in cells transfected with AVIL compared to those infected with an empty vector control (FIGS. 4L and 4M).

It was then assessed whether the overexpression of AVIL can transform astrocytes in vivo. Briefly, 2 million astrocyte cells stably expressing AVIL or a control plasmid were injected subcutaneously into the flanks of NIH-III nude mice. No tumor was seen in any of the ten injections for the control group. In contrast, four out of eight injections of the AVIL overexpression group had visible tumors within ten days of injection (representative images in FIG. 4N).

Example 7. AVIL Effect can be Mediated at Least in Part by LIN28B

Figure 5A:
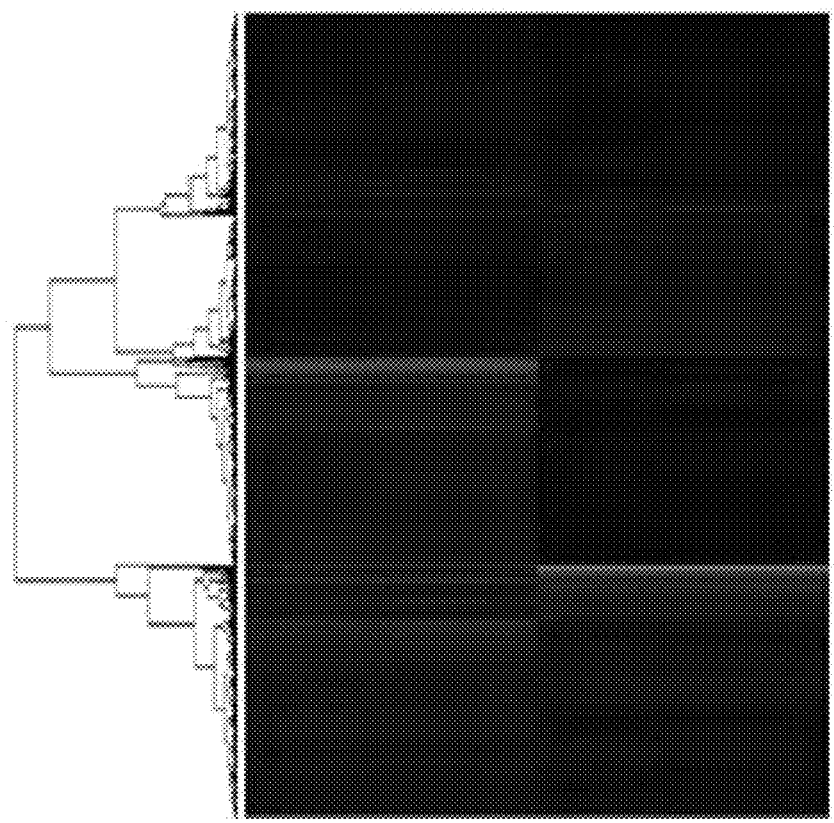
Figure 5B:
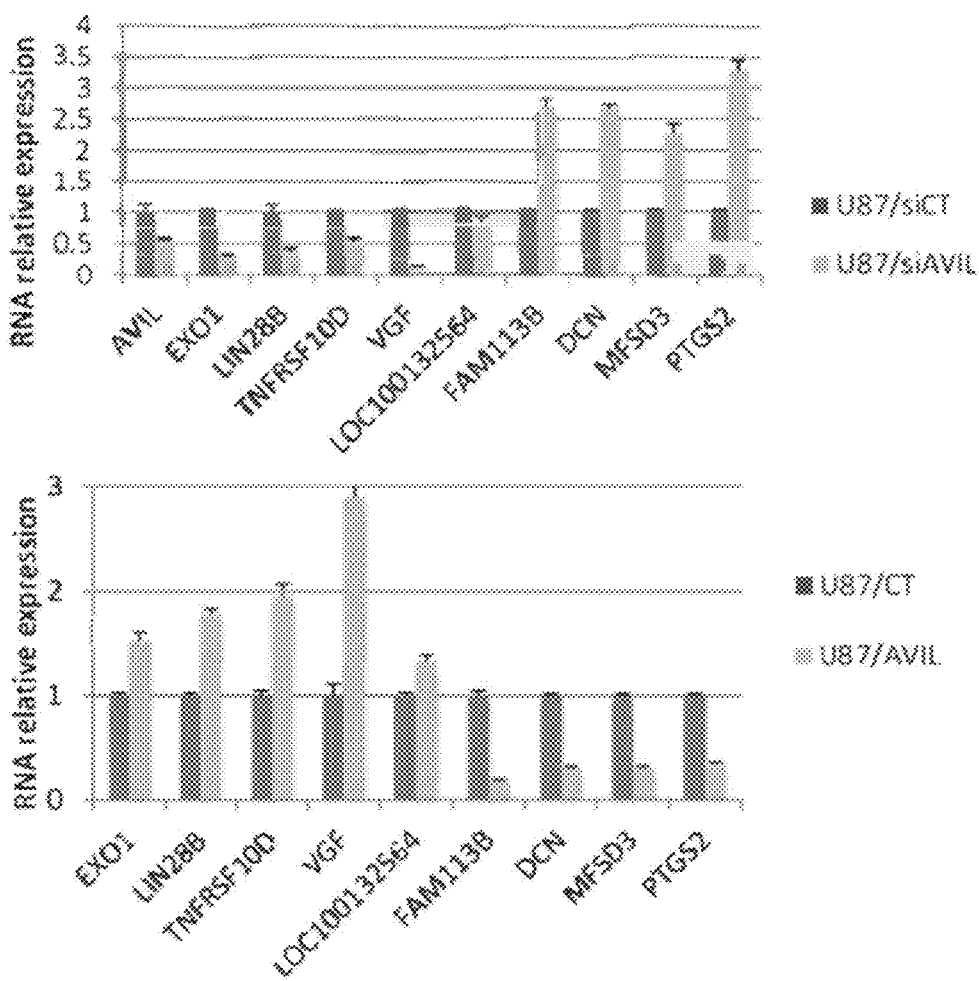
Figure 5C:
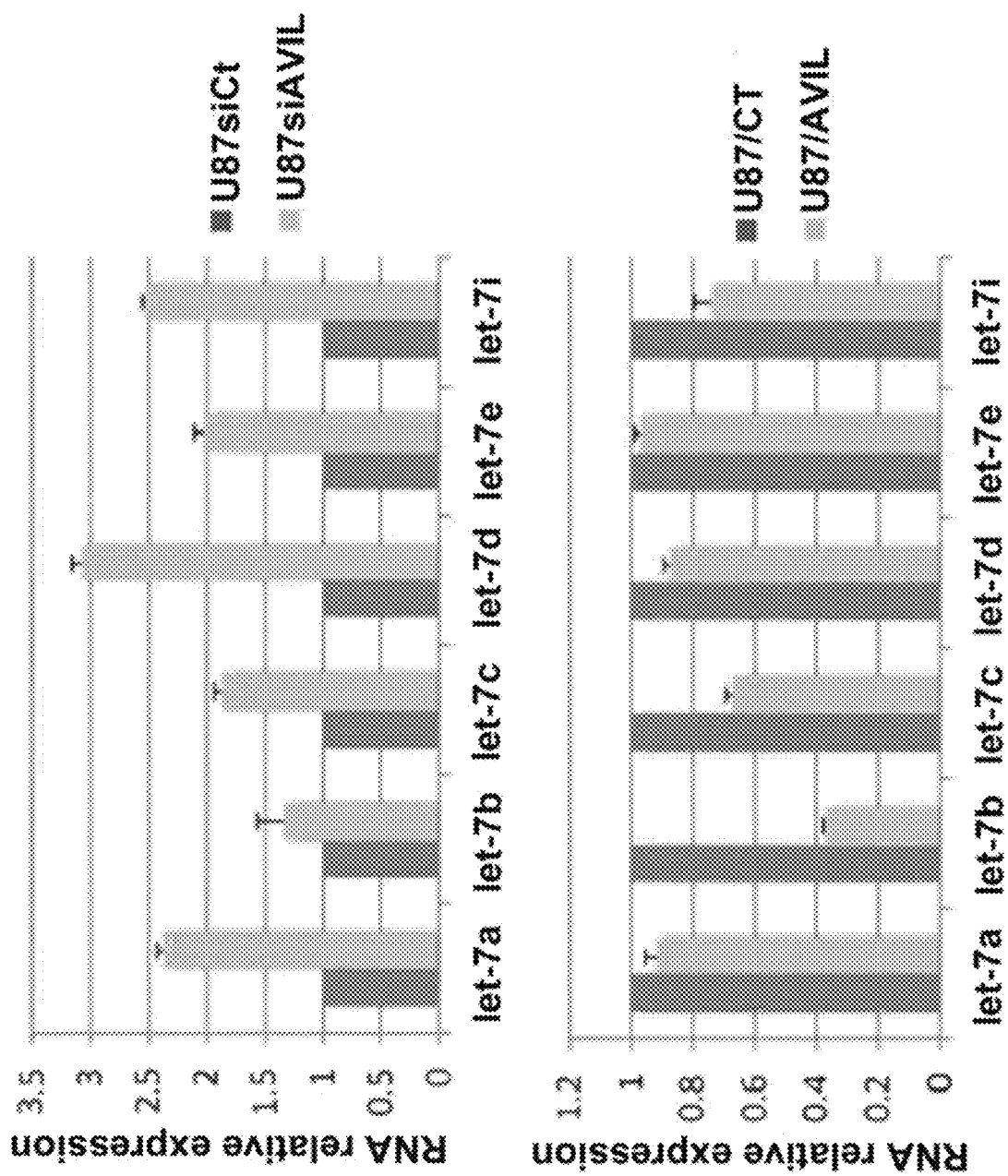
Figure 8K:
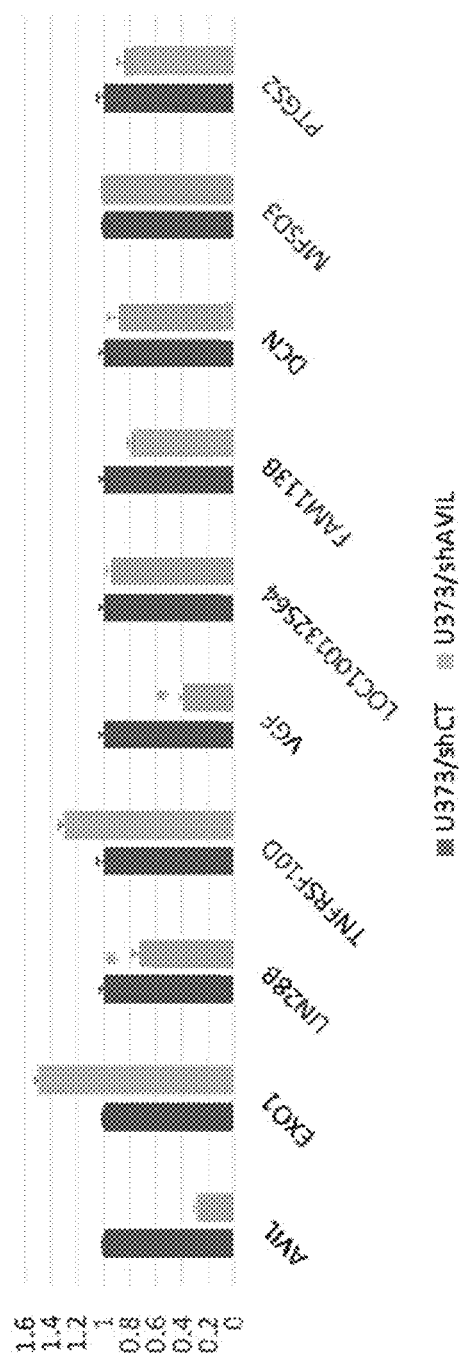
FIG. 8K shows representative data demonstrating that nine targets of AVIL were measured in U373 cells. Silencing AVIL in U373 confirmed LIN28B and VGF changes associated with AVIL silencing.

Microarray analyses were carried out on U87 cells transfected with siAVIL or an AVIL expression vector, along with control transfections (FIG. 5A). Nine candidates, whose expressions were inversely changed over two-fold when AVIL was silenced and overexpressed, were examined. All candidates, except LOC100132564, were validated via qRT-PCR (FIG. 5B). Among the nine, only LIN28B and VGF were consistently down-regulated when AVIL was silenced in another GBM cell line, U373 (FIG. 8K). VGF is a gene up-regulated by nerve growth factor (Canu et al., 1997), but its exact function is unknown. LIN28B belongs to the group of RNA-binding proteins that play critical roles in embryonic development, as well as tumorigenesis. Its family member, LIN28A has been used together with OCT4, SOX2, and NANOG to induce pluripotency (OSNA) (Park et al., 2008; Yu et al., 2007). Both LIN28A and LIN28B have been demonstrated to be aberrantly expressed in various types of cancer, and are associated with advanced diseases (Viswanathan et al., 2009). LIN28B is best known to negatively regulate the biogenesis of tumor suppressive microR-NAs, let-7. Consistently it was observed that silencing AVIL induced all of the members of let-7 that are expressed (let7-f, let7-g, and mir-98 are not expressed in U87 cells). Conversely, overexpression of AVIL resulted in the down-regulation for most let-7 members (FIG. 5C).

Several studies have demonstrated that LIN28B can promote growth, and invasion of cancer cells. (Guo et al., 2006; Liang et al., 2010; Nguyen et al., 2014). It was then tested whether some of the oncogenic effect of AVIL is mediated, in part, by LIN28B. In both U87 and U373 cells, silencing AVIL resulted in a dramatic reduction in cell growth. This reduction can be partially rescued by introducing LIN28B (FIG. 5D). This is not due to the forced expression of this oncogenic protein alone, as expressing LIN28B in control cells had no effect on cell growth rate. Similarly, a reduced cell migration rate was also rescued by LIN28B in in both lines transfected with siAVIL (FIG. 5E), suggesting that at least some oncogenic effects of AVIL are mediated by LIN28B.

Example 8. Advillin Binds to F-Actin, and Regulates Cell Shape and Spreading

Figure 5G:
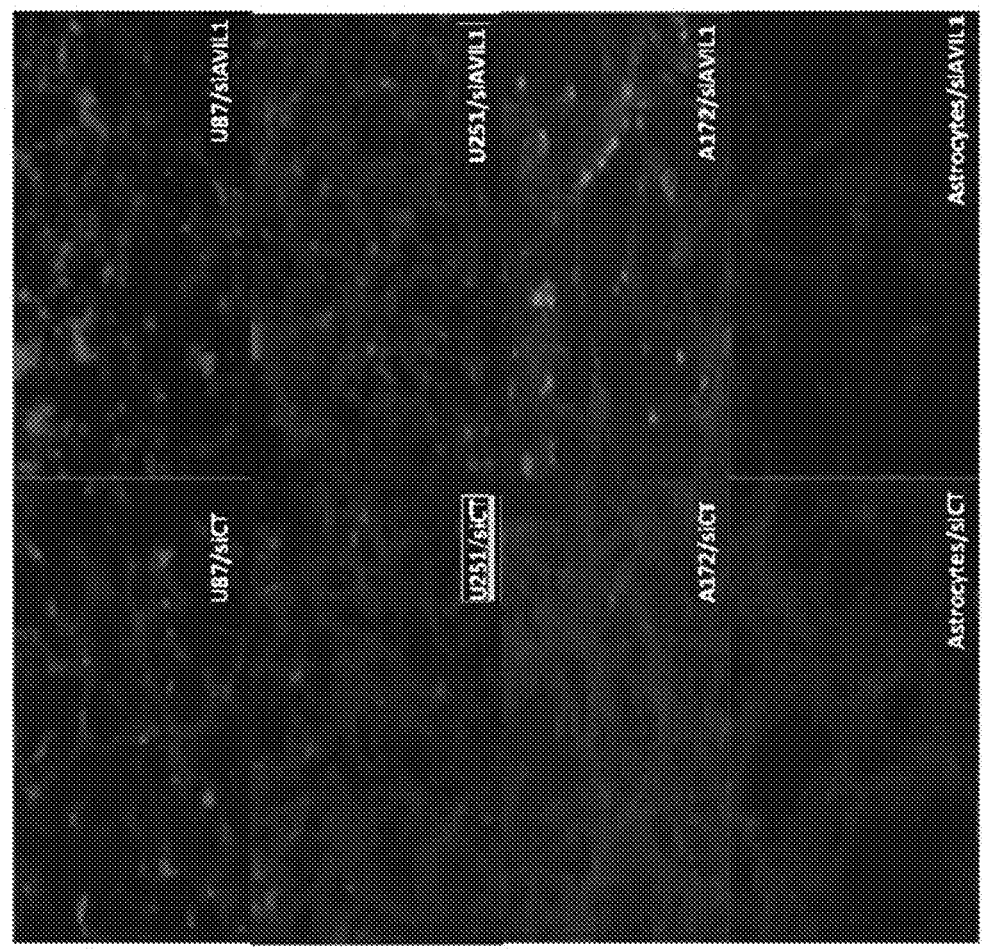
Figure 5F:
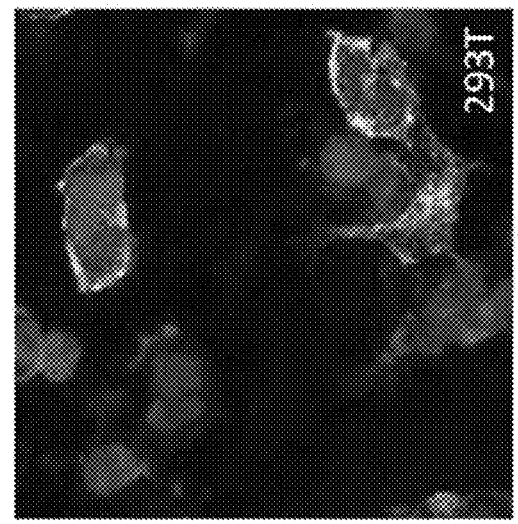

AVIL is known as a member of the villin/gelsolin family, which regulates actin filament reorganization. (Marks et al., 1998). It encodes a protein also called advillin, which is known to affect cell movement, and has been reported to be involved in the formation of filopodia-like structures in fibroblasts, as well as a role in ciliogenesis (Morin et al., 2010). Consistently it was observed that silencing AVIL resulted in reduced cell migration, and that overexpressing AVIL enhanced migration (FIG. 4). GFP-AVIL was then expressed in 293T and HeLa cells to further assess the interaction with actin filament reorganization. Using phalloidin to stain F-actin, the colocalization of advillin and actin filaments in both lines was observed (FIG. 5F). When AVIL was silenced in three different GBM cell lines (A172, U251, and U87), a dramatic cell shape change was observed. Cells retracted from an expanding spindle shape, and became small and round (FIG. 5G), followed by apoptosis. In the case of A172, accumulation of actin ruffles became abundant. However, no obvious cell shape changes were seen when non-neoplastic astrocyte cultures were transfected with the AVIL siRNA.

Figure 5I:
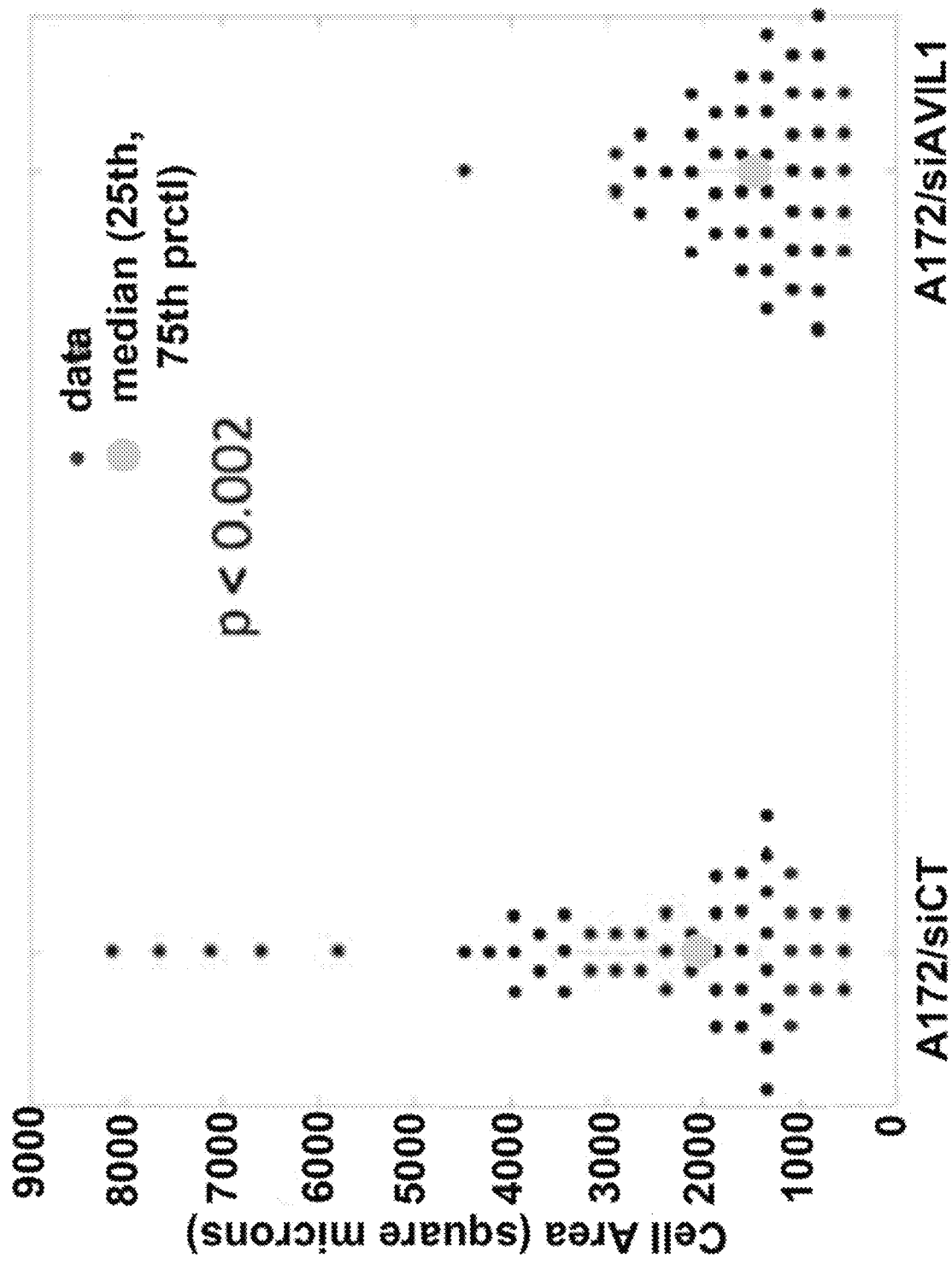

The dependence of GBM cells on AVIL to attach and spread was further evidenced when the cell shape and area was monitored after cells were plated onto a fibronectin substrate. Control cells spread much more than the siAVIL1 transfected cells, as reflected by overall silhouettes of the cells (FIG. 5H), and the areas the cells occupied (FIG. 5I).

Figure 5J:
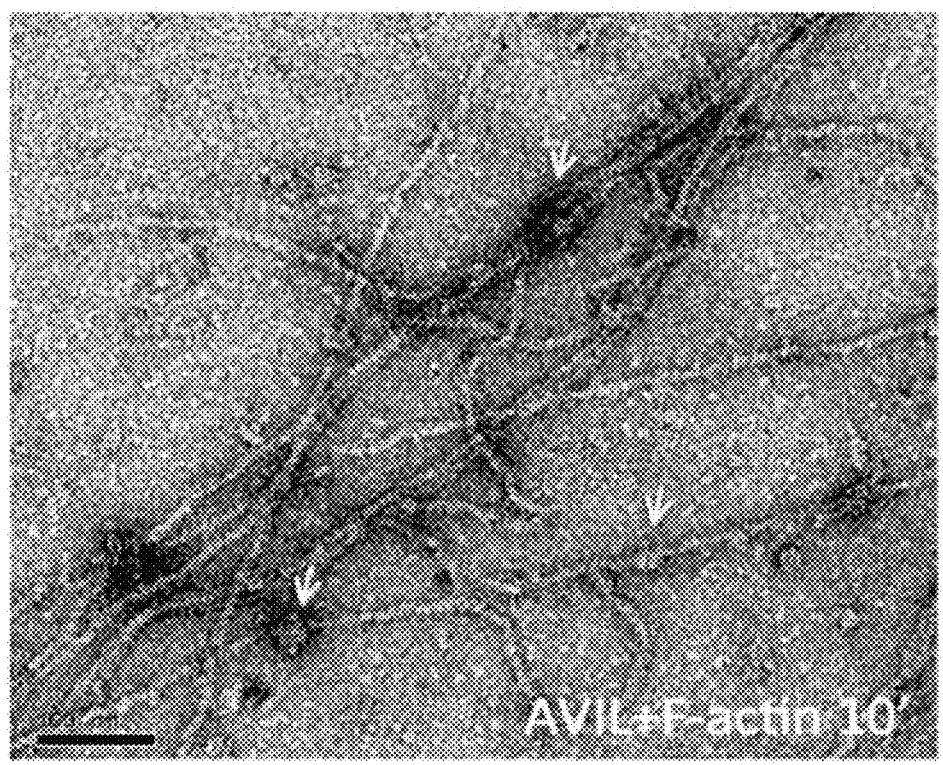

Recombinant advillin was prepared and used for electron microscopy experiments. The data show that similar to villin, advillin forms oligomers and binds to F-actin within 10 minutes of incubation (FIG. 5J).

Figure 6A:
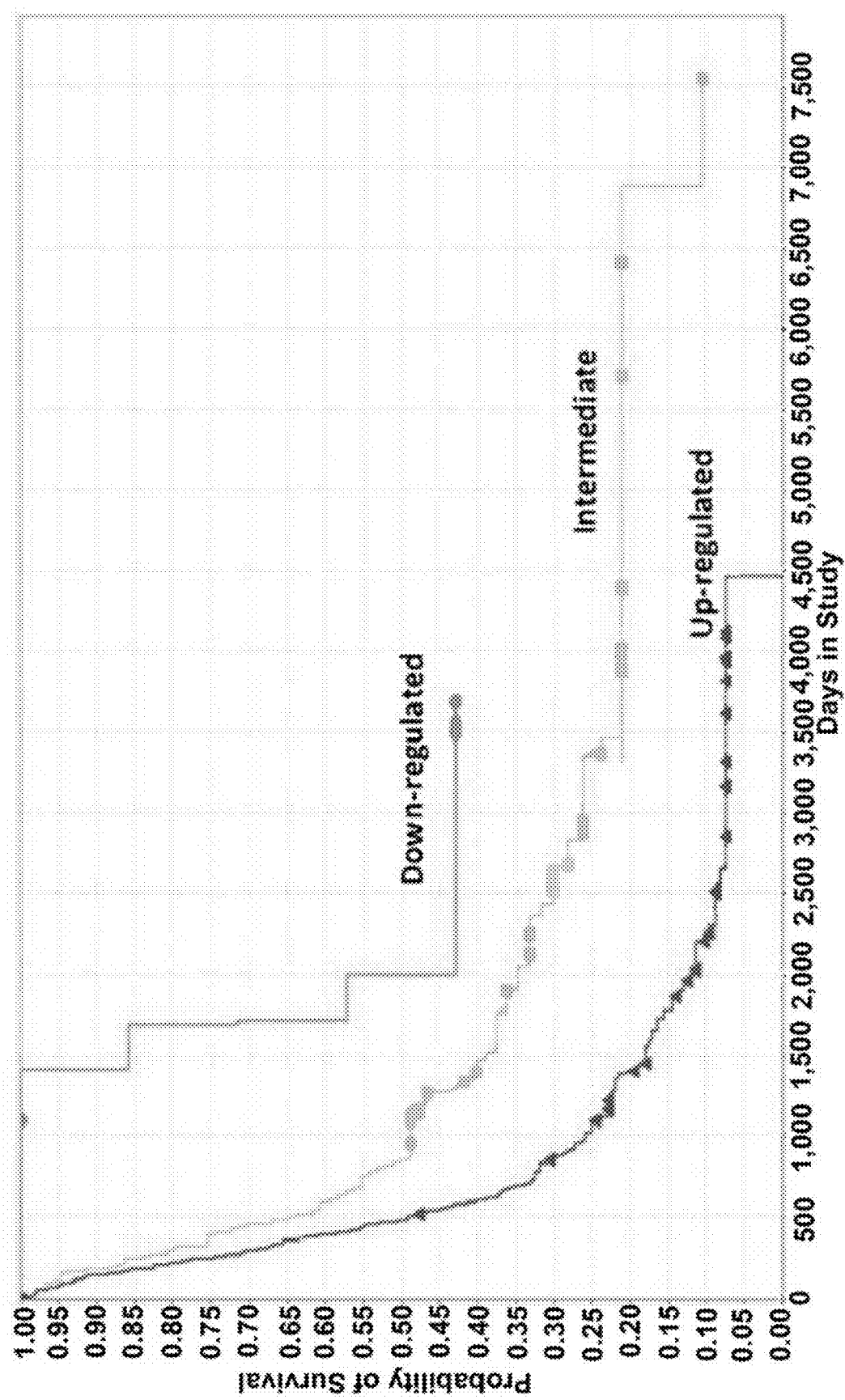
FIGS. 6A-6H show representative data demonstrating that AVIL expression inversely correlates with cancer patient survival, as described further in Example 1. (A) Clinical analysis using the REMBRANDT dataset. A three-class model, stratified by AVIL RNA expression in 343 glioma cases. Higher expression of AVIL correlates with worse overall patient survival. (B) Clinical analysis using TCGA lower grade glioma dataset. A two-class model stratified by AVIL RNA expression in 286 samples that have RNA-sequencing data. The high AVIL group (two fold or higher) has a much shorter overall survival than the low AVIL group ($p=1\times10^{-5}$, log-rank test). The median survival for the high AVIL group is 23.1 months, versus 75.1 months for the low AVIL group. (C) Disease-free survival between the two groups was also significantly different ($p<0.01$). (D) A two-class model, stratified by LIN28B expression using TOGA GBM data. The high LIN28B group has a significantly worse survival ($p=0.03$, log-rank test). (E) With TOGA lower grade glioma data, the high LIN28B group is found to have worse survival ($p=0.0001$, log-rank test). (F), (G), and (H) Higher AVIL expression correlates with worse overall survival for lung adenocarcinoma ($p=1E-6$), bladder cancer ($p<0.05$), and renal cell carcinoma ($p<0.05$).
Figure 8L:
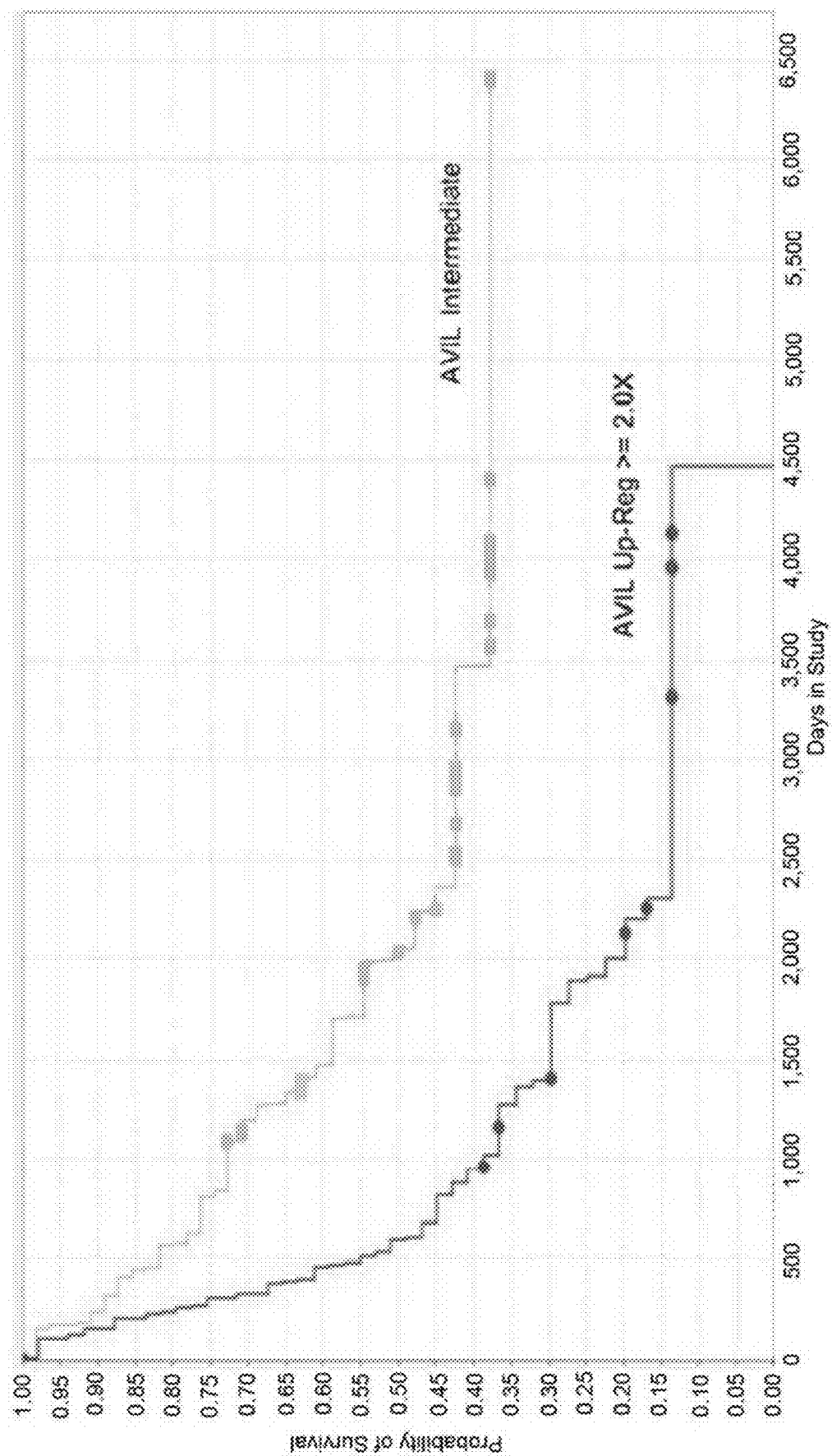
FIG. 8L shows representative data demonstrating that a two-class model stratified by AVIL expression in 104 glioma cases that had microarray probe 1568706 signal. Higher AVIL expression correlates with poor patient prognosis ($p=2\times10^{-4}$).

Example 9. High Level AVIL Expression is a Poor Prognostic Indicator in Multiple Cancers To validate the clinical significance of AVIL in human gliomas, the relationship between AVIL expression and patient survival was examined in 343 glioma cases in the REMBRANDT project (Madhavan et al., 2009). A three-class model, in which patients were stratified according to AVIL expression showed a clear positive correlation between higher AVIL expression, and shorter survival (up-regulated vs. intermediate, $p=1\times10^{-5}$; up-regulated vs. all other, $p=4\times10^{-7}$, log-rank test) (FIG. 6A). The same trend was also observed with a different microarray probe (FIG. 8L).

Figure 6B:
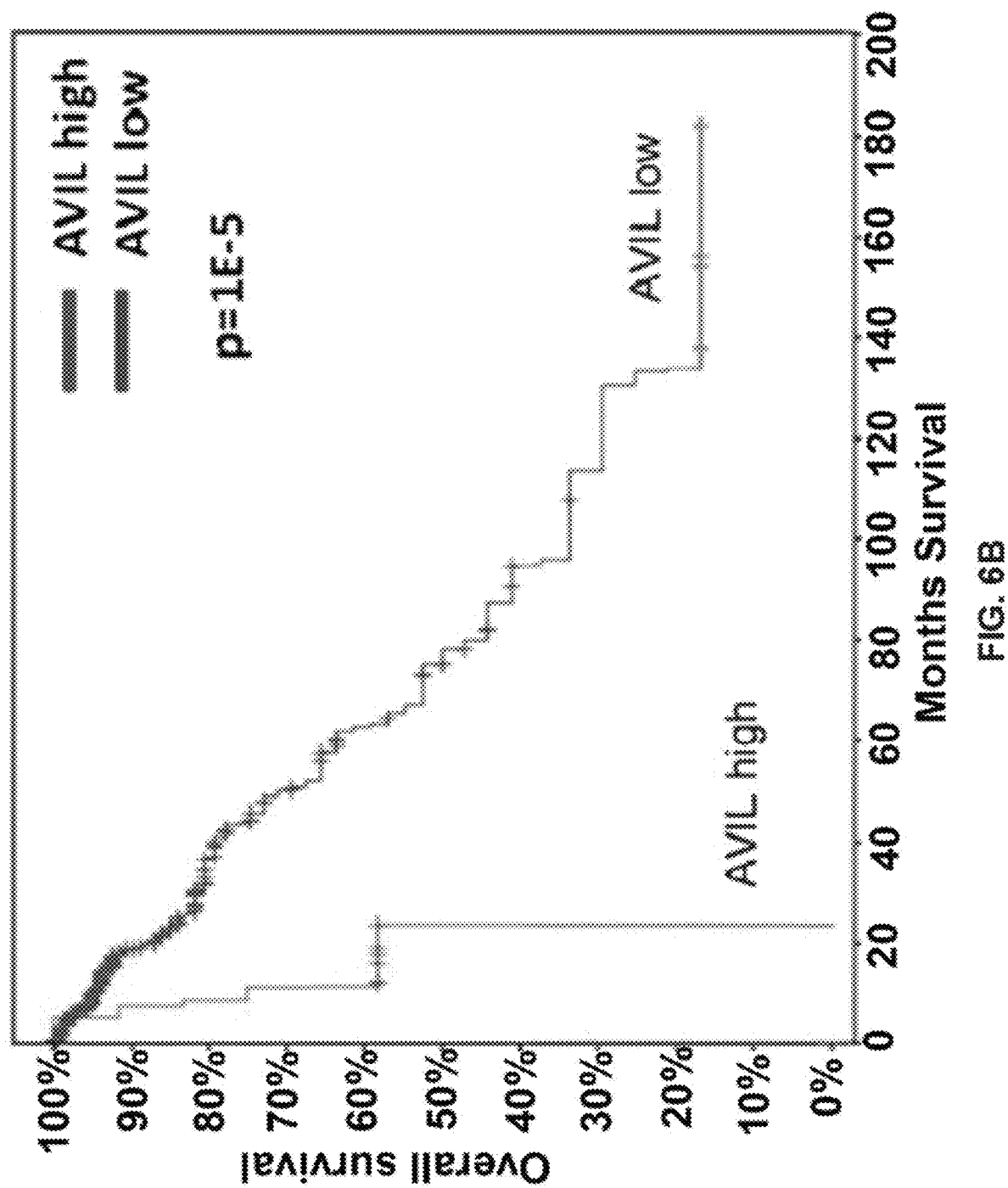
Figure 6C:
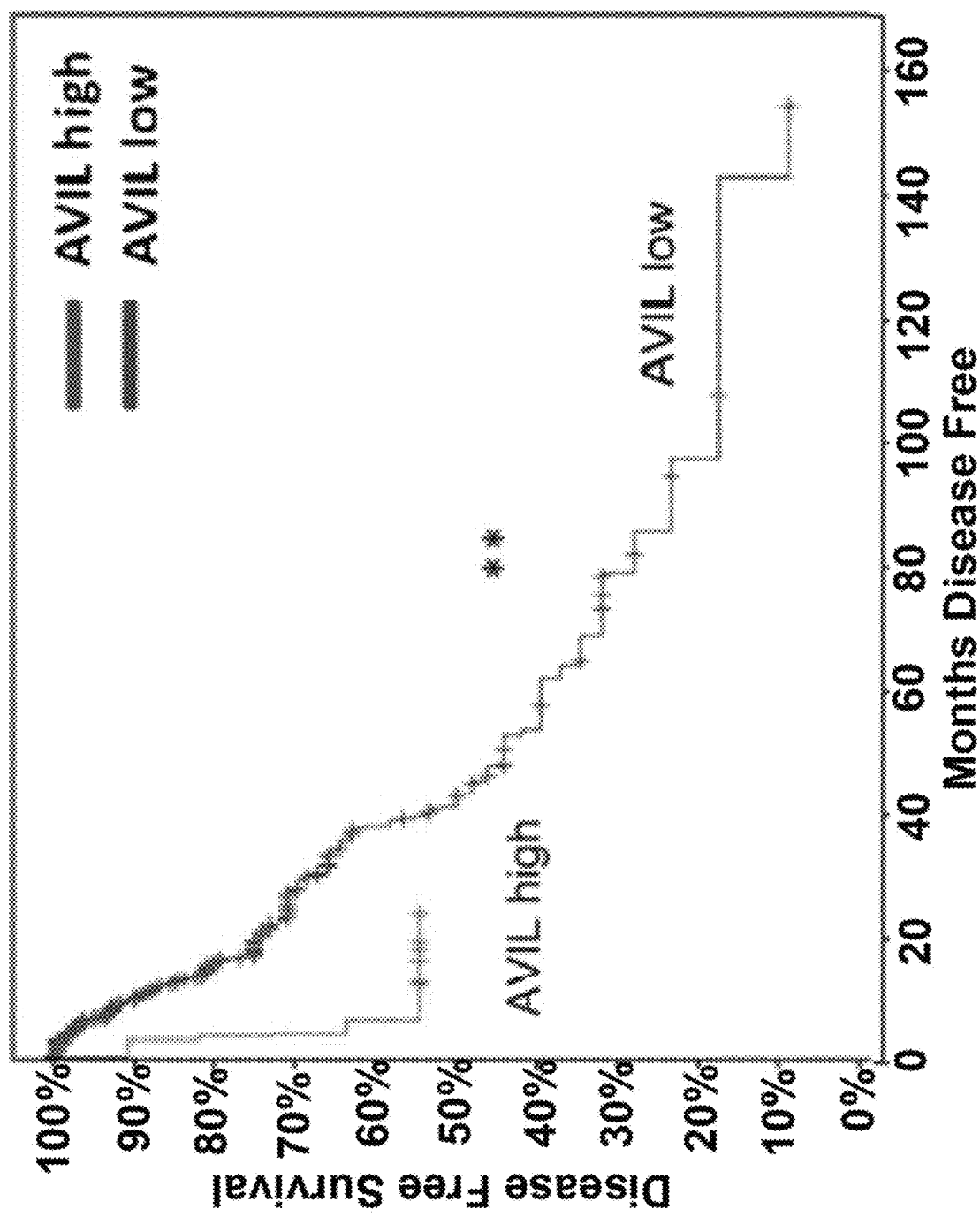
Figure 8M:
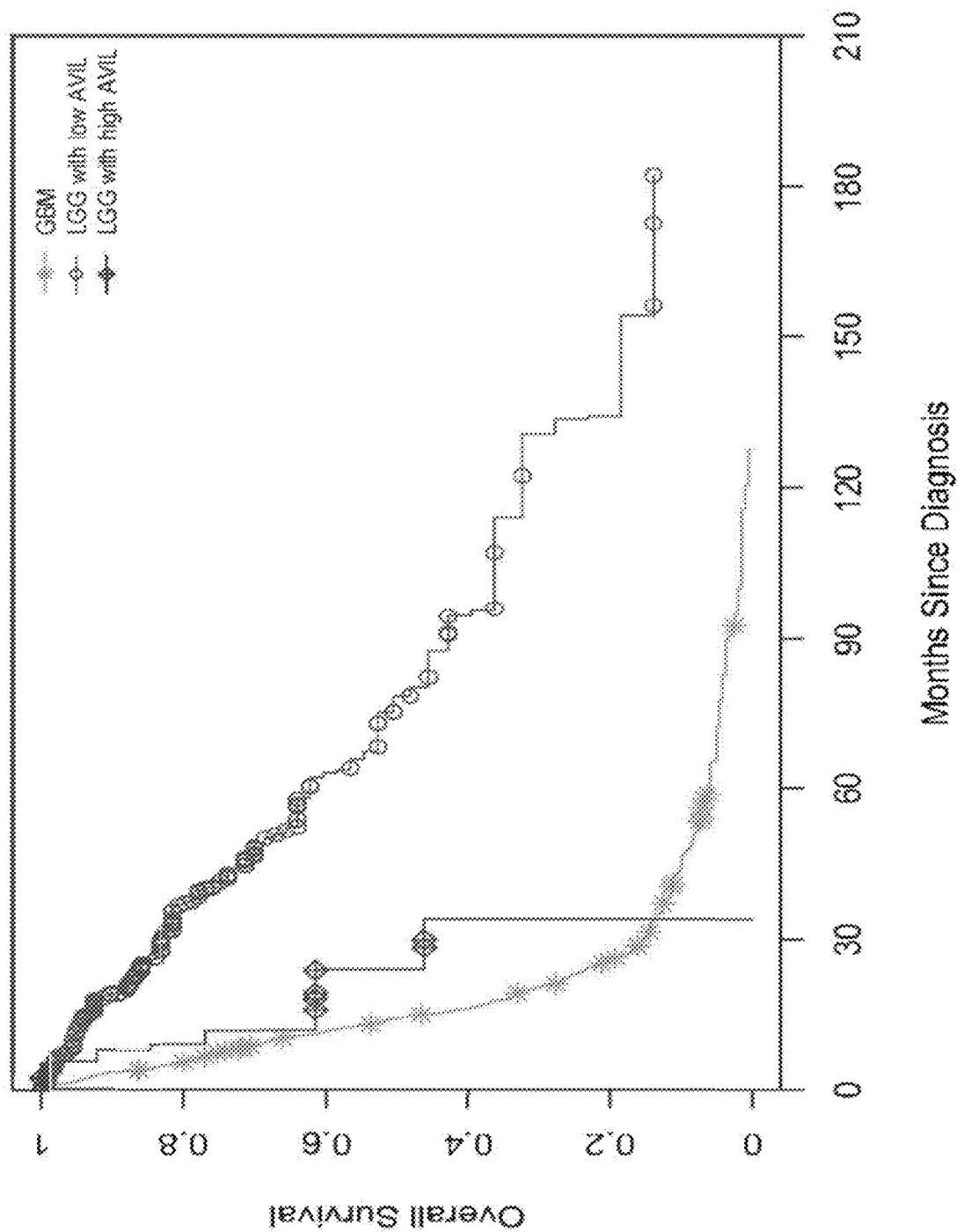
FIG. 8M shows representative data demonstrating a two-class model stratified by AVIL expression in 283 lower grade gliomas (LGG). The overall survival for the group with higher AVIL expression is significantly shorter than the group with lower AVIL expression (p=1E-5), and not significant different from the survival of GBM patients (p=0.08).

The term lower-grade glioma (LGG) includes the grade II and III gliomas. However, the management of LGG is one of the most controversial areas in clinical neuro-oncology, with survival ranges from 1 to 15 years. A recent TOGA lower-grade glioma dataset (Cancer Genome Atlas Research et al., 2015) was also queried for AVIL expression. Out of 286 samples that had RNA-sequencing data, the high AVIL group (two fold or higher than average) had a much shorter overall survival than the low AVIL group ($p=1\times10^{-5}$, log-rank test). The median survival for the low AVIL group was 75.1 months. In contrast, the high AVIL group only had a median survival of 23.1 months, comparable to those of GBM patients (FIG. 6B and FIG. 8M). Consistently, the two groups also had a significant difference in disease-free survival (p<0.01) (FIG. 6C). The difference in patient survival based on AVIL expression is more significant than that based on traditional histopathologic classification and grading.

Figure 6D:
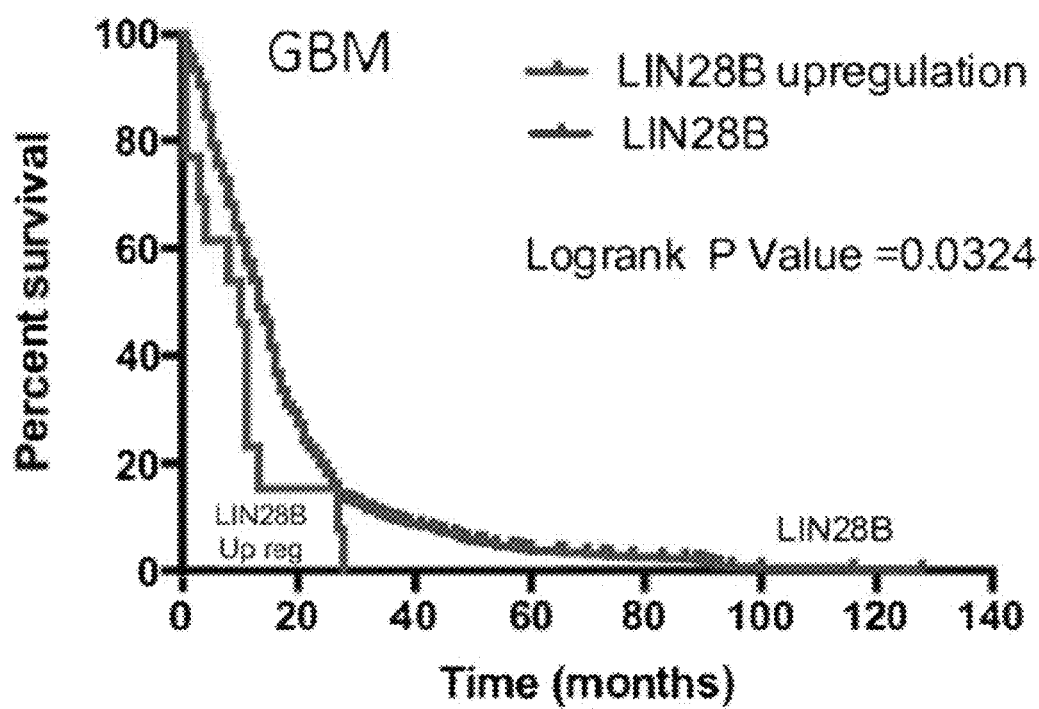
Figure 6E:
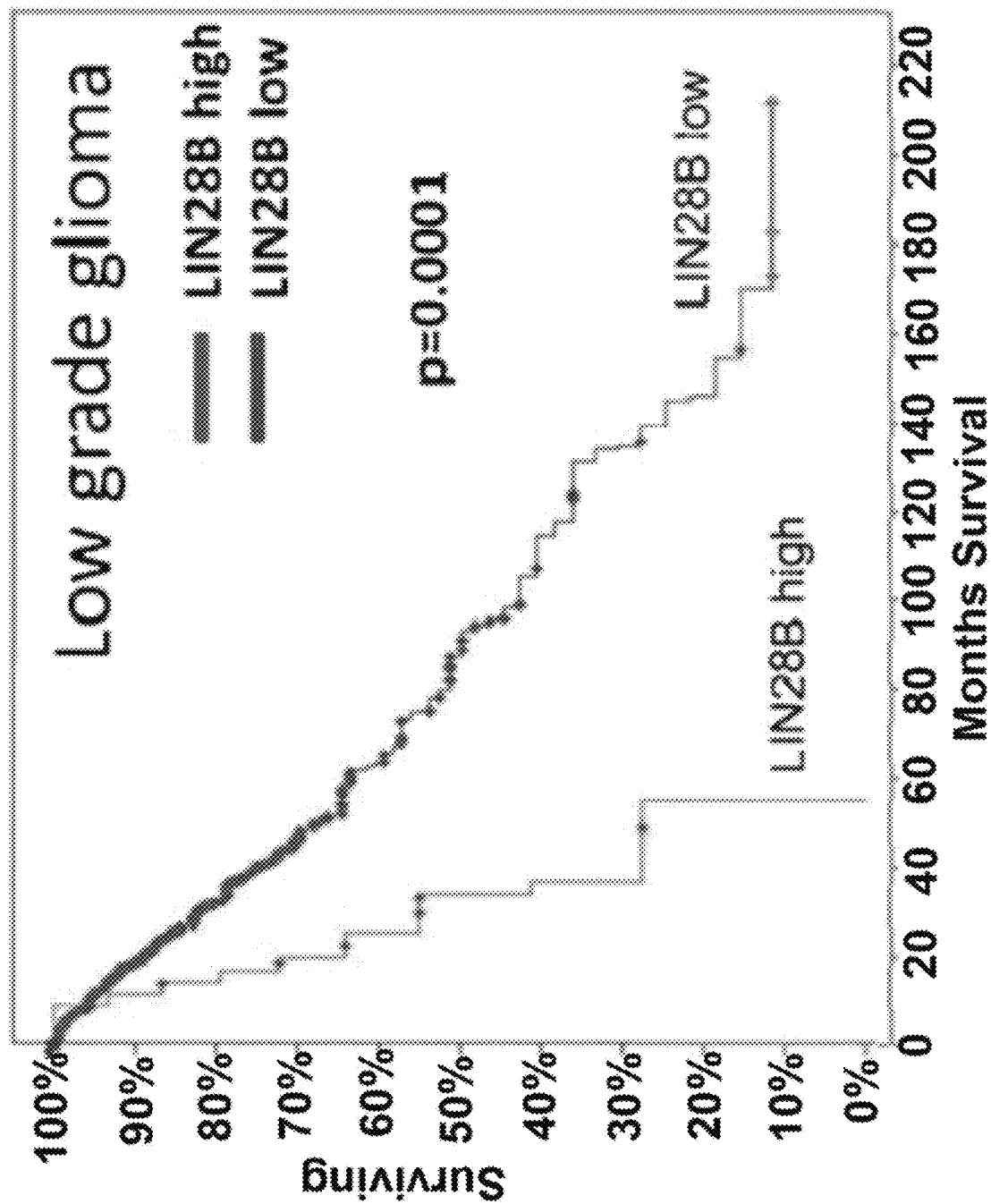

The data herein show that LIN28B is a downstream mediator of AVIL activity. In view of this finding, the correlation of LIN28B expression with clinical outcome was assessed. In GBMs, it was observed that high LIN28B levels correlated with poorer patient survival (p=0.03) (FIG. 6D). In lower-grade gliomas, the expression level of LIN28B had a stronger inverse correlation with patient survival (p=0.0001) (FIG. 6E).

Figure 6F:
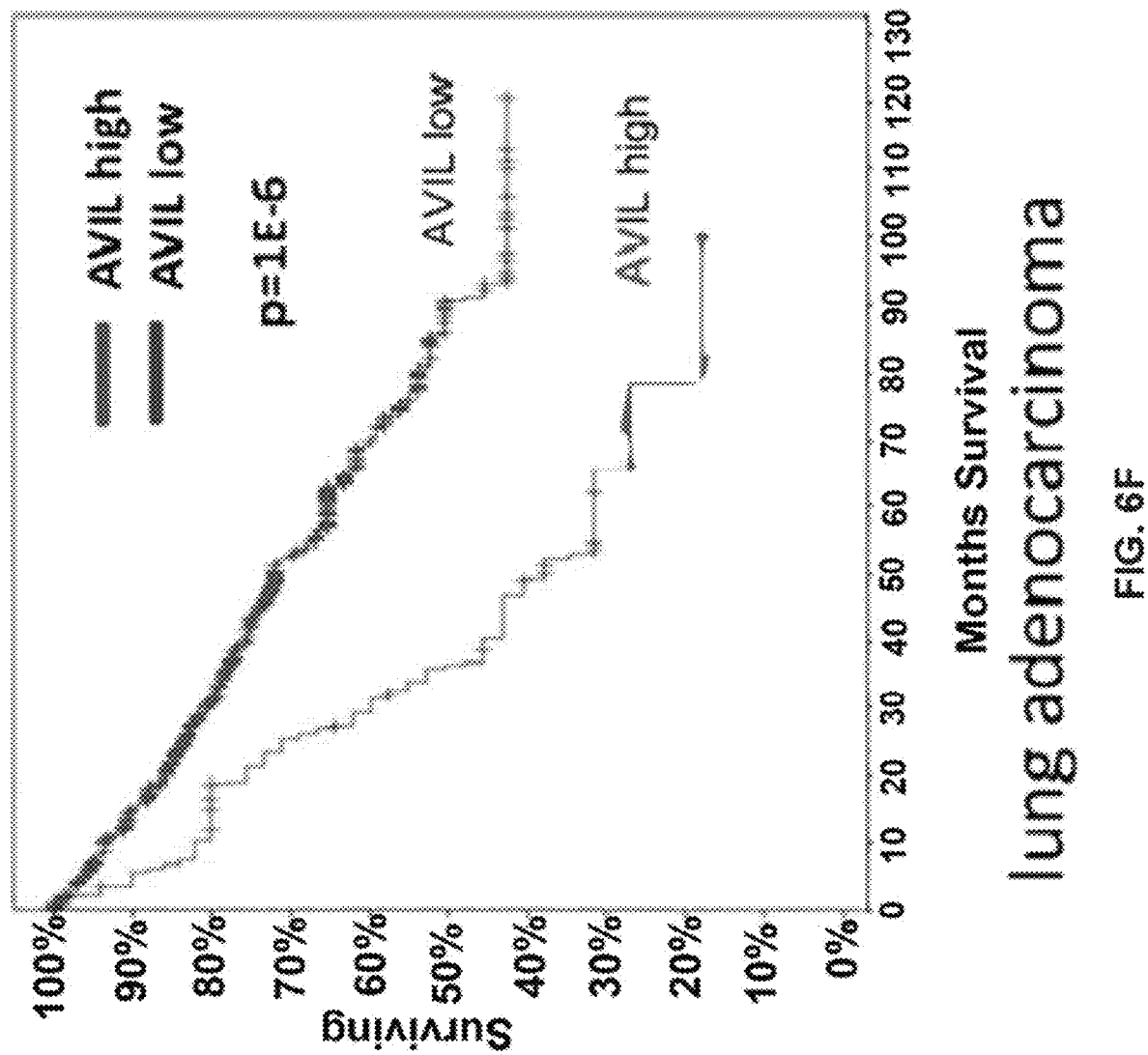
Figure 6G:
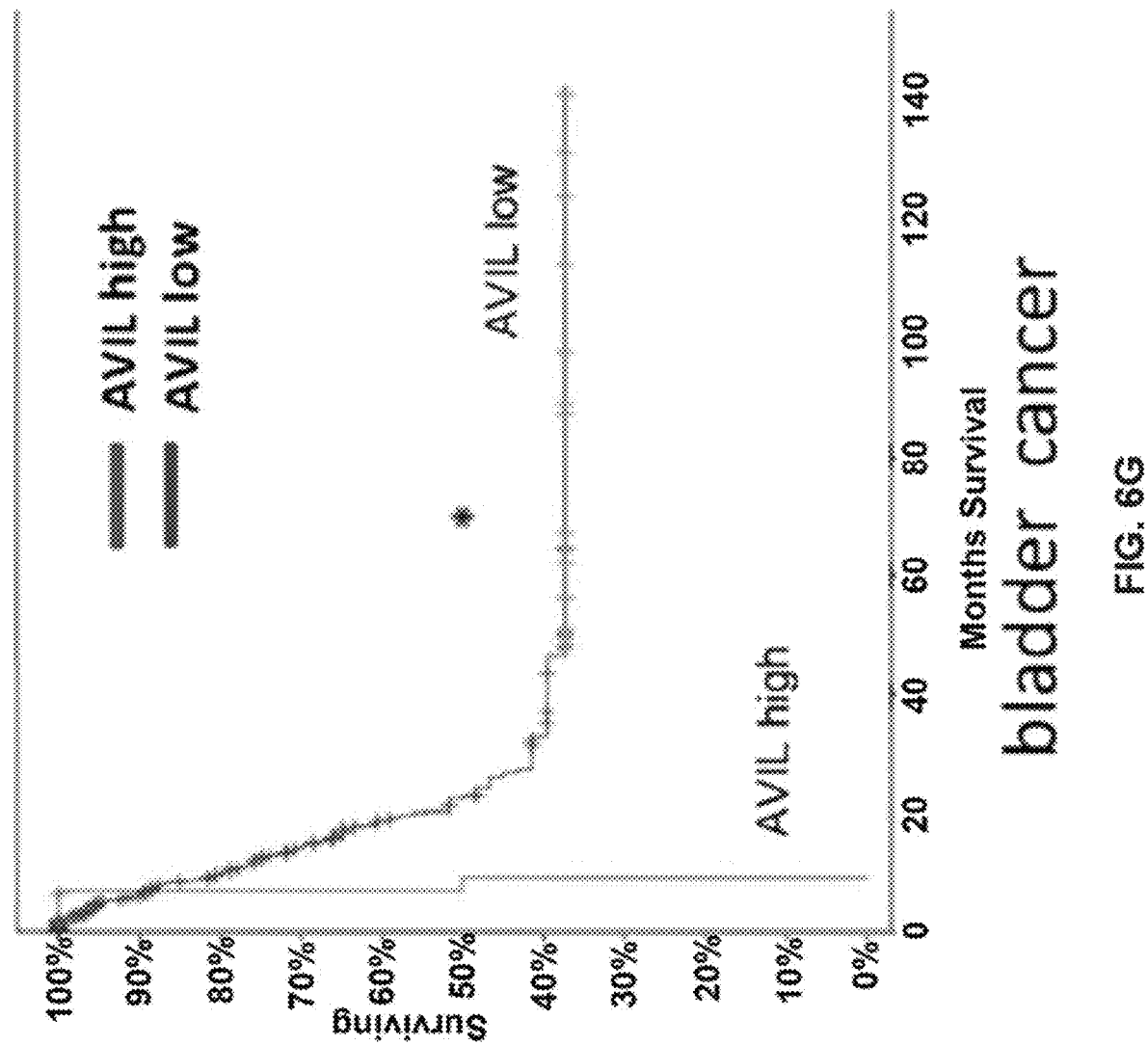
Figure 6H:
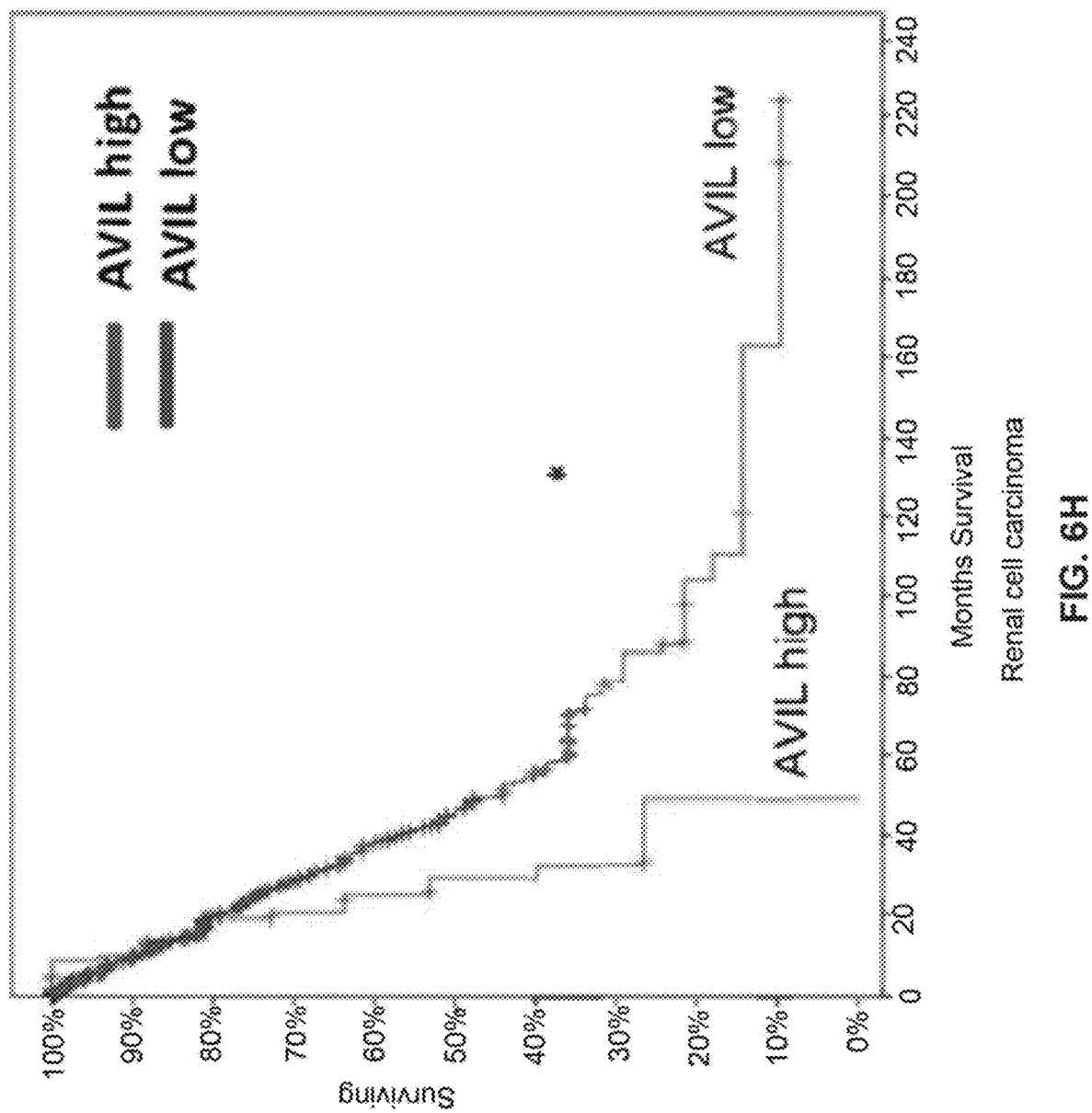

Aside from gliomas, other TOGA cancer RNA-Sequencing datasets were queried, and it was found that high levels of AVIL expression are associated with poor prognosis in bladder urothelial carcinoma, and kidney clear cell carcinoma (FIGS. 6F, 6G, and 6H).

Example 10. Targeting AVIL in GBM

Figure 7A:
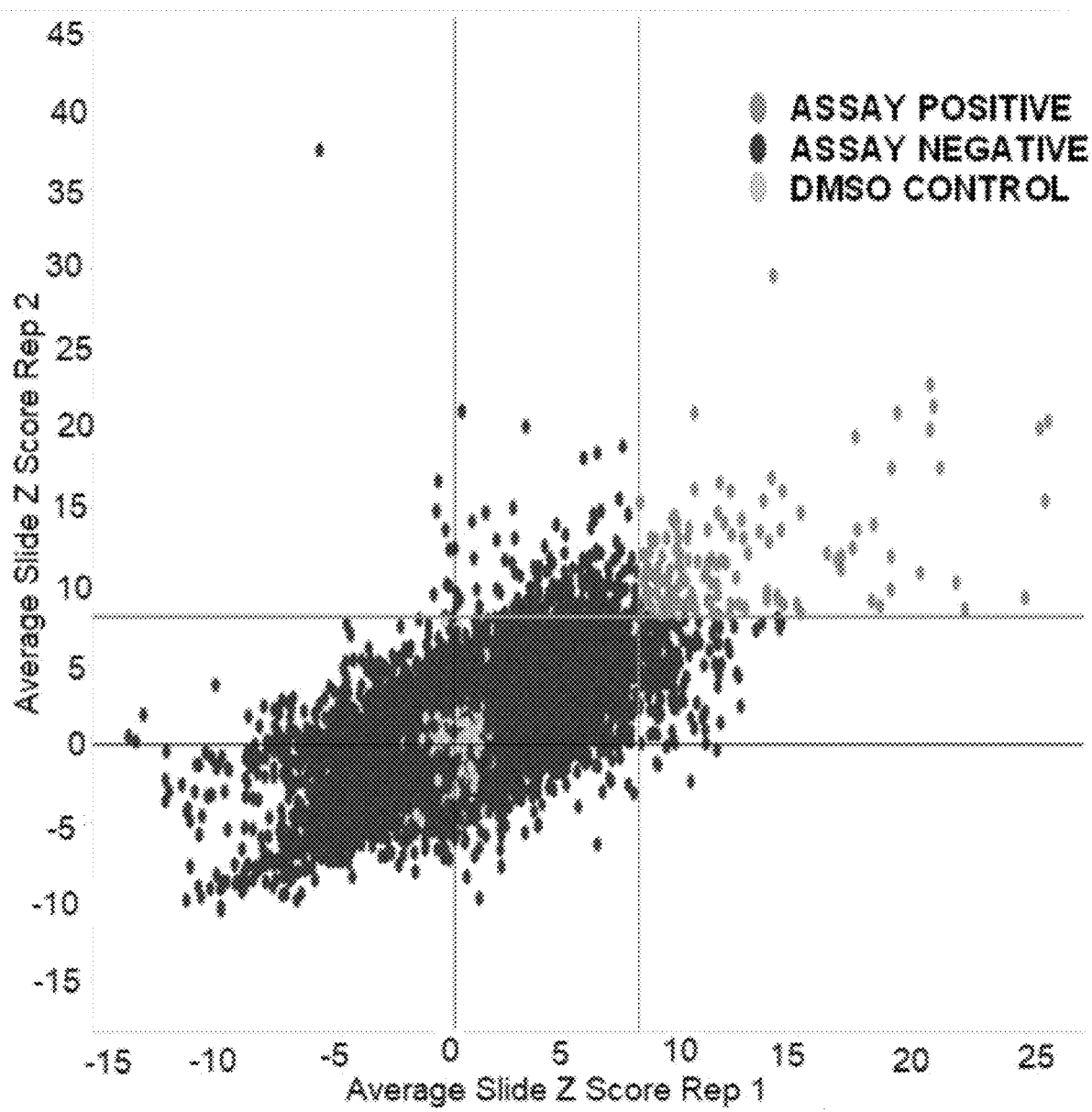
FIGS. 7A-7H show representative data demonstrating the targeting of AVIL in GBMs as described further in Example 1. (A) Small Molecule microarray screening. Assay positives with a Robust Z score greater than 3-sigma from the median are highlighted. (B) $IC_{50}$ values of three of the disclosed compounds (Compounds A, B, and C) in four GBM lines and astrocytes. (C) Representative images of U251, U87 and astrocytes treated with Compound A. (D) Thermal shift assay demonstrated a dose-dependent melting temperature (Tm) shift upon the binding of Compound A to AVIL protein. Graphs representing negative of the first derivatives of melting curves between 30-50° C. of AVIL incubated with increasing concentrations of Compound A. Small inserts represent full melting curves (20-90° C.). Melting temperature ($T_m$) was determined as the lowest point of the curve. (E) LIN28B gene expression was downregulated with all three compounds measured by qRT-PCR. (F) Similar set of gene ontology terms is enriched in the genes downregulated by the drug (compound A as an example), and siRNA targeting AVIL. Plotted are statistical significance ($-\text{Log} 10(p\text{-value})$) of each term. (G) Significant enrichment of the gene set downregulated by siAVIL was seen in Compound A downregulated genes. (H) U87 xenograft model. Compound A injection resulted in significantly smaller tumor, both measured by tumor volume and tumor weight.
Figure 7B:
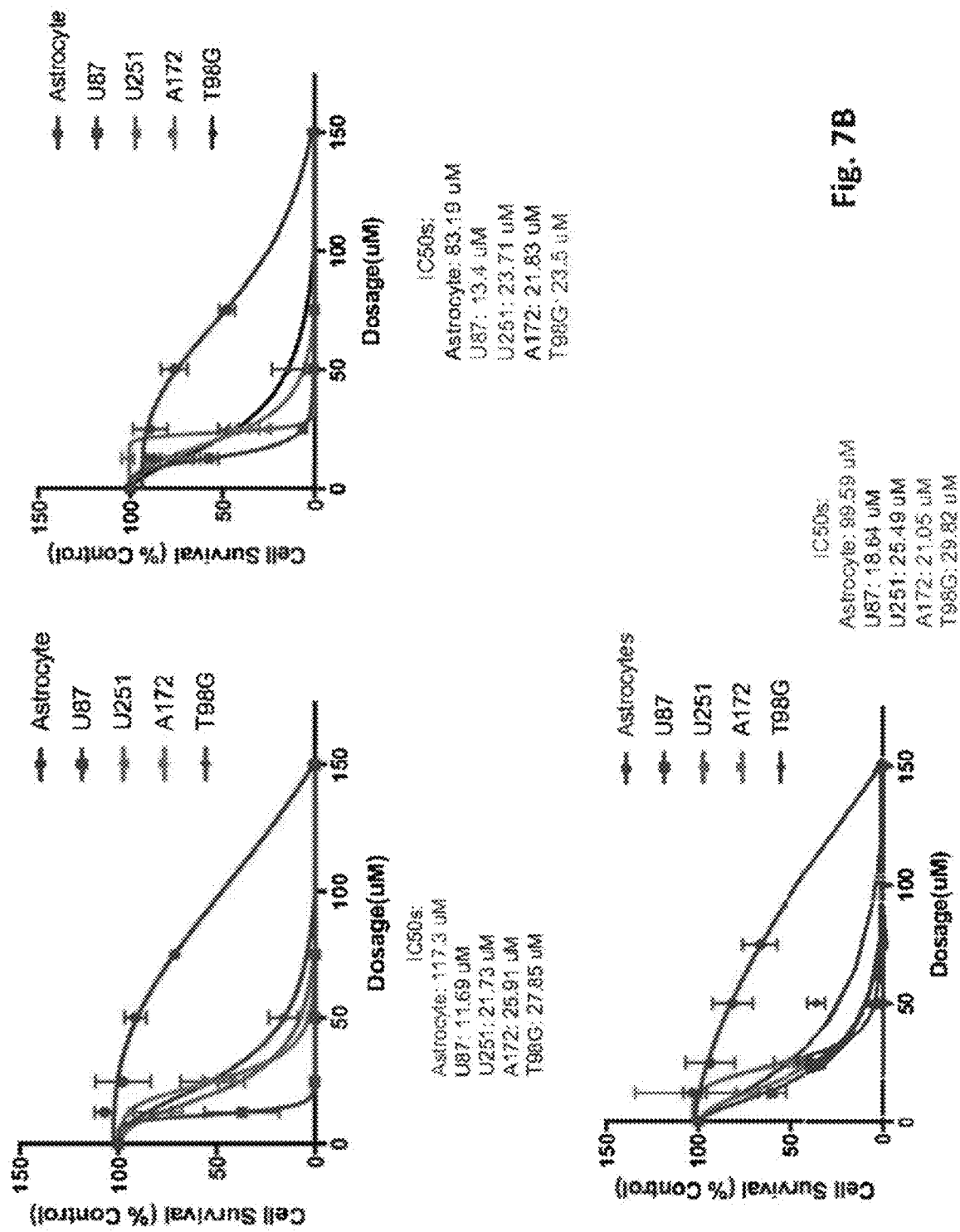
Figure 7C:
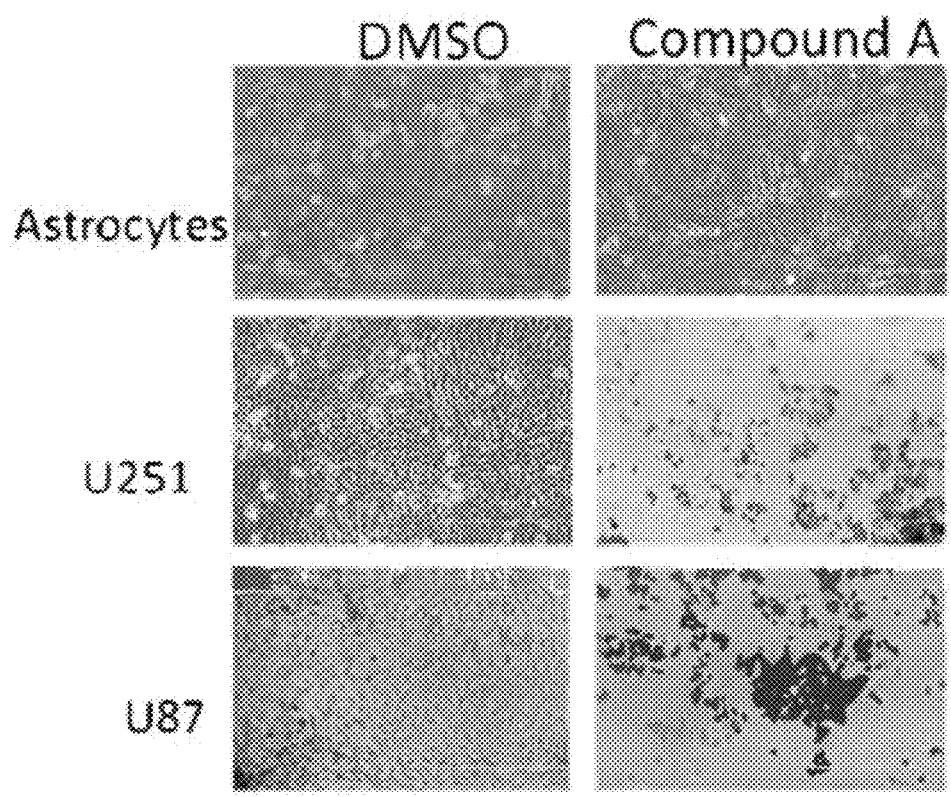
Figure 7D:
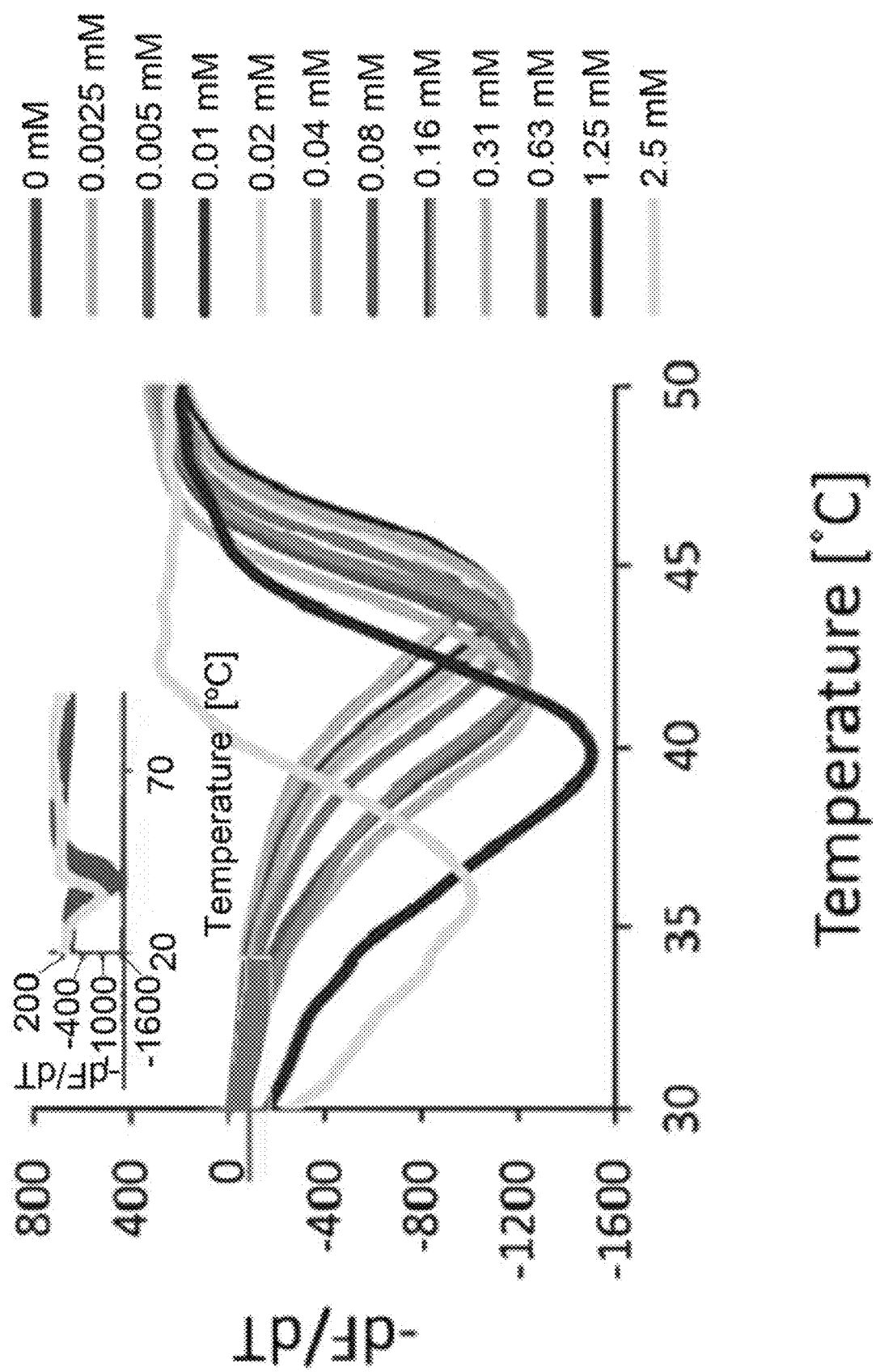

To investigate whether AVIL is a viable drug target, a platform of small-molecule microarray was utilized (Bradner et al., 2006a; Bradner et al., 2006b) in order to identify compounds that interact with the AVIL protein. 50,000 small molecules were screened with recombinant advillin protein, including commercially available compounds, products of diversity-oriented synthesis, and known bioactive compounds. From these compounds, 82 advillin-interacting compounds were identified (FIG. 7A). Cellular assays using GBM cell lines immortalized astrocytes were conducted, and it was found that three lead compounds (A, B, and C) were associated with significantly different $IC_{50}$ values in four GBM lines (U87, A172, U251, and T98G) compared to activity in astrocytes (FIGS. 7B and 7C). Pubchem ID for the three compounds are as follows: Compound A is CID 56750508, Compound B is CID 56890068, and Compound C is CID 70768068. Thermal shift assay data confirmed binding of these compounds with advillin recombinant protein (example in FIG. 7D).

Figure 7E:
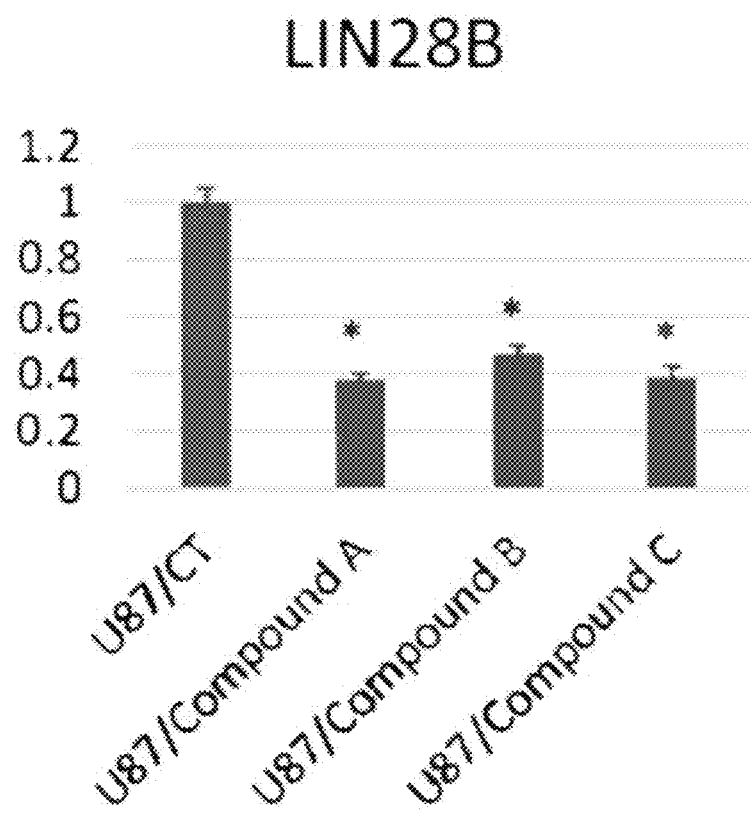
Figure 7F:
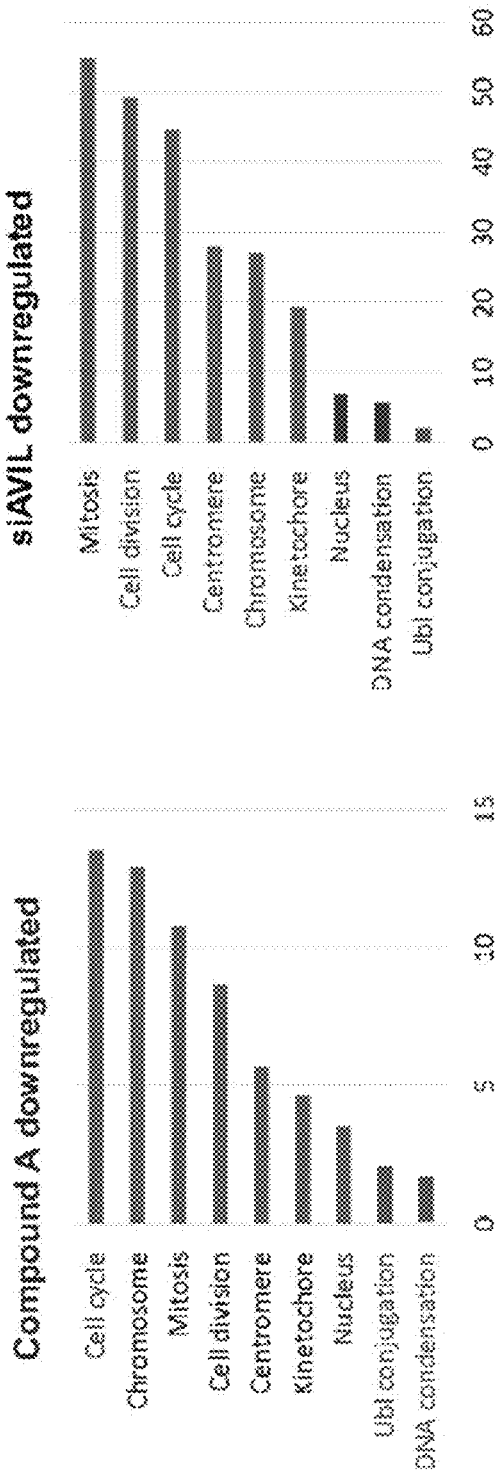
Figure 7G:
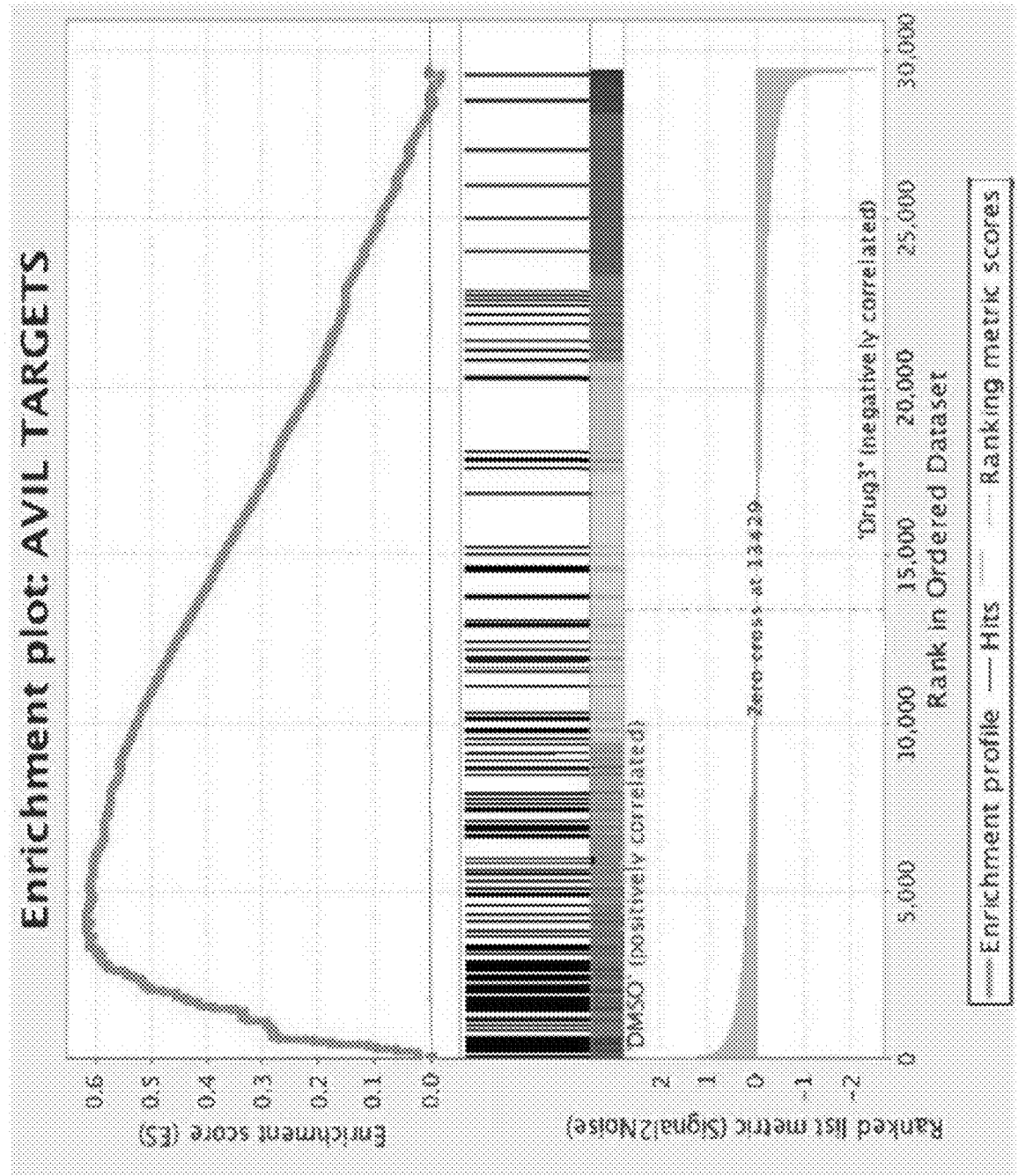
Figure 7H:
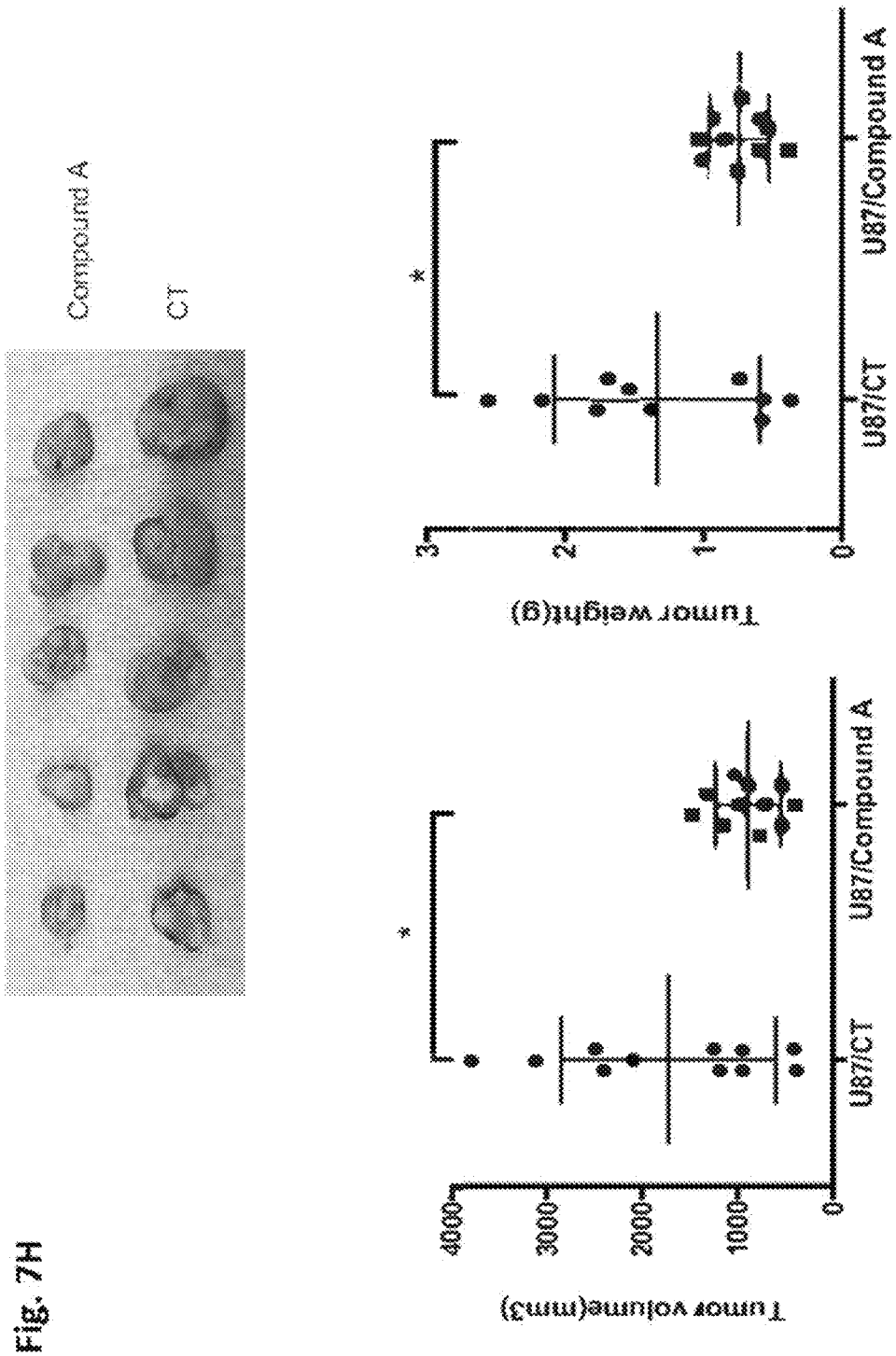

The effect of the three compounds on LIN28B expression was tested. As shown in FIG. 7E, all three compounds downregulated LIN28B expression similar to siAVIL. To test whether the compounds can trigger transcriptome response similar to siAVIL, a microarray analysis of the U87 cells treated with these compounds was performed. Strikingly, cells treated with all three compounds had similar transcriptome profiles when compared to that of the siAVIL transfected cells, by both gene ontology and Gene Set Enrichment analyses (example in FIGS. 7F and 7G). The one with the highest GSEA enrichment score, Compound A, was then selected for injection into a U87 xenograft model. By the time of harvest, animals injected with this chemical had significantly smaller tumor volumes and tumor weights compared with the control group injected only with solvent (FIG. 7H).

Figure 8N:
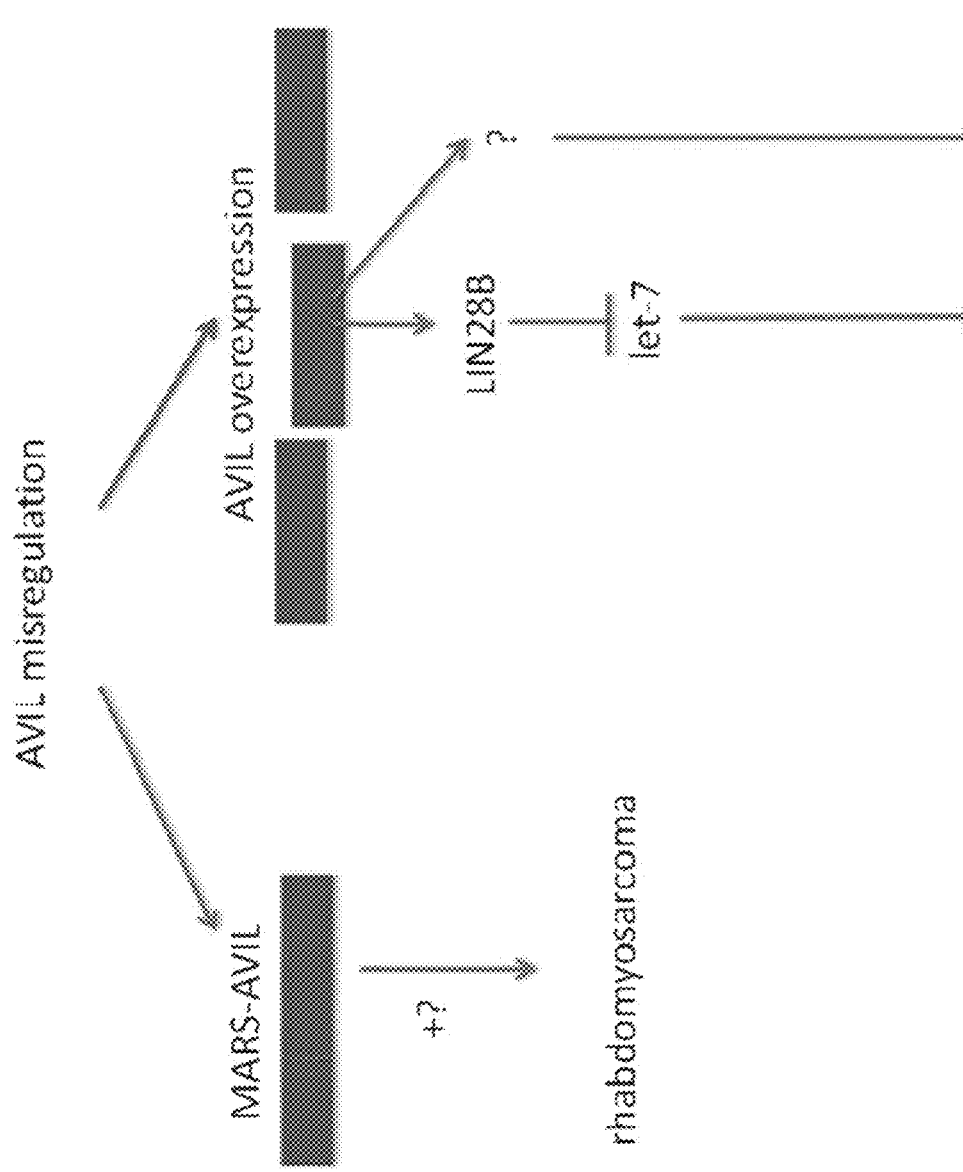
FIG. 8N shows a Schematic representation of the misregulation of AVIL in rhabdomyosarcoma and glioma.

Without wishing to be bound by a particular theory, it is possible that in rhabdomyosarcomas, AVIL forms a fusion with a house-keeping gene MARS, which is critical for the tumorigenesis of this tumor. In gliomas, it is overexpressed due to copy number gain, transcription level, and/or translation level. It up-regulates LIN28B, which is a negative regulator of let-7, the tumor suppressive microRNAs (FIG. 8N). The overexpression of AVIL, and LIN28B, are all correlated with aggressive gliomas. Patients of lower grade gliomas with high levels of AVIL expression have a prognosis similar to those with malignant GBMs. Consistently, let-7 members have been shown to inhibit glioma cell malignancy (Lee et al., 2011; Wang et al., 2013), and are expressed at lower levels in high-grade gliomas, than in low-grade gliomas (Wang et al., 2013).

Example 11. Compound $IC_{50}$ Values in Glioblastoma Cells

In this example, samples of glioblastoma cells (U87) and astrocyte cells (non-cancer control) were exposed various disclosed compounds to determine the effectiveness of the compounds for inhibiting cell growth. The $IC_{50}$ for each combination was measured, and is reported in the Table 1 below. The results show that the disclosed compounds are effective in inhibiting cell growth

TABLE 1

| Compound | $IC_{50}$ - U87 (µM) | $IC_{50}$ - Astrocyte (µM) |
|---|---|---|
| A | 9 | 55 |
| D | 2.5 | 51 |
| E | 1 | 30 |
| F | 4 | 28 |
| G | 10 | >80 |
| H | 8 | 59 |
| I | 19 | 80 |
| J | 20 | >80 |
| K | 39 | 34 |
| L | >80 | >80 |

Figure 9A:
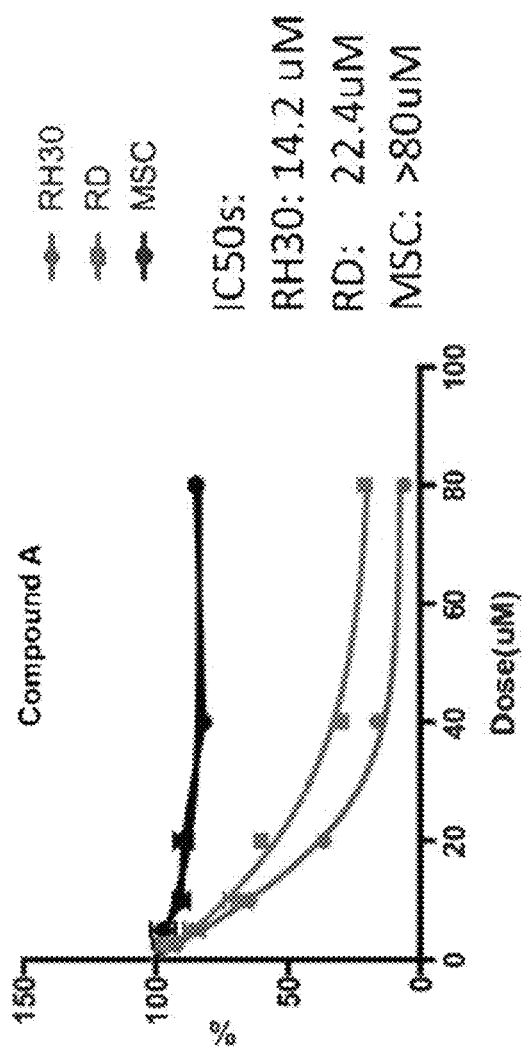
FIG. 9A shows representative data demonstrating cell survival curves comparing the effect of Compound A on RH30, RD and MSC cells at different doses.
Figure 9B:
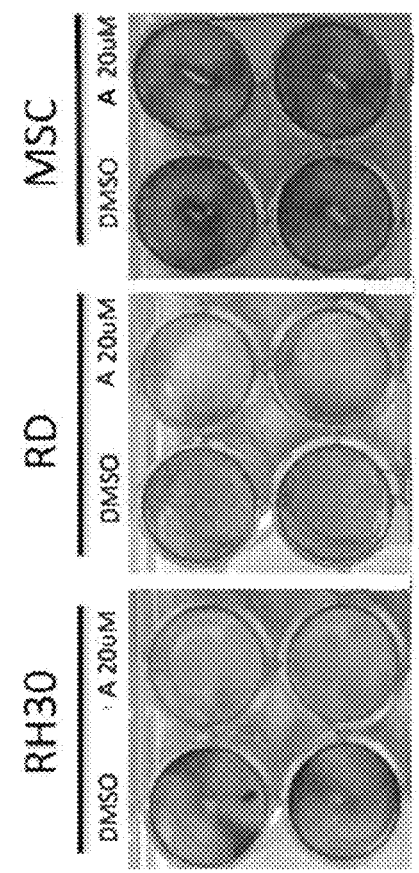
FIG. 9B shows Crystal violet staining of RH30 RD and MSC cells. RH30 and RD are rhabdomyosarcoma cells. MSC is mesenchymal stem cells, as a non-cancer control. The results demonstrate that most if not all of the RH30 and RD cells were wiped out with 20 µM, whereas no significant effect was seen in MSC cells.

FIG. 9A shows cell survival curves comparing the effect of Compound A on RH30, RD and MSC cells at varied doses. RH30 and RD are rhabdomyosarcoma cells. MSC is mesenchymal stem cells, as a non-cancer control. FIG. 9B shows Crystal violet staining of RH30, RD and MSC cells. The results demonstrate that most if not all of the RH30 and RD cells were wiped out with 20 µM of Compound A, whereas no significant effect was seen in MSC cells.

REFERENCES

The following references which are cited herein are incorporated by reference in their entirety, to the extent they are consistent with the present invention.
1. Bollag, G., Hirth, P., Tsai, J., Zhang, J., Ibrahim, P. N., Cho, H., Spevak, W., Zhang, C., Zhang, Y., Habets, G., et al. (2010). Clinical efficacy of a RAF inhibitor needs broad target blockade in BRAF-mutant melanoma. Nature 467, 596-599.
2. Bradner, J. E., McPherson, O. M., and Koehler, A. N. (2006a). A method for the covalent capture and screening of diverse small molecules in a microarray format. Nat Protoc 1, 2344-2352.
3. Bradner, J. E., McPherson, O. M., Mazitschek, R., Barnes-Seeman, D., Shen, J. P., Dhaliwal, J., Stevenson, K. E., Duffner, J. L., Park, S. B., Neuberg, D. S., et al. (2006b). A robust small-molecule microarray platform for screening cell lysates. Chem Biol 13, 493-504.
4. Cancer Genome Atlas Research, N., Brat, D. J., Verhaak, R. G., Aldape, K. D., Yung, W. K., Salama, S. R., Cooper, L. A., Rheinbay, E., Miller, C. R., Vitucci, M., et al. (2015). Comprehensive, Integrative Genomic Analysis of Diffuse Lower-Grade Gliomas. N Engl J Med 372, 2481-2498.
5. Candolfi, M., Curtin, J. F., Nichols, W. S., Muhammad, A. G., King, G. D., Pluhar, G. E., McNiel, E. A., Ohlfest, J.

R., Freese, A. B., Moore, P. F., et al. (2007). Intracranial glioblastoma models in preclinical neuro-oncology: neuropathological characterization and tumor progression. J Neurooncol 85, 133-148.
6. Canu, N., Possenti, R., Ricco, A. S., Rocchi, M., and Levi, A. (1997). Cloning, structural organization analysis, and chromosomal assignment of the human gene for the neurosecretory protein VGF. Genomics 45, 443-446.
7. Castro, M. G., Cowen, R., Williamson, I. K., David, A., Jimenez-Dalmaroni, M. J., Yuan, X., Bigliari, A., Williams, J. C., Hu, J., and Lowenstein, P. R. (2003). Current and future strategies for the treatment of malignant brain tumors. Pharmacol Ther 98, 71-108.
8. Cavenee, W. K., Dryja, T. P., Phillips, R. A., Benedict, W. F., Godbout, R., Gallie, B. L., Murphree, A. L., Strong, L. C., and White, R. L. (1983). Expression of recessive alleles by chromosomal mechanisms in retinoblastoma. Nature 305, 779-784.
9. Cerami, E., Gao, J., Dogrusoz, U., Gross, B. E., Sumer, S. O., Aksoy, B. A., Jacobsen, A., Byrne, C. J., Heuer, M. L., Larsson, E., et al. (2012). The cBio cancer genomics portal: an open platform for exploring multidimensional cancer genomics data. Cancer Discov 2, 401-404.
10. Chapman, P. B., Hauschild, A., Robert, C., Haanen, J. B., Ascierto, P., Larkin, J., Dummer, R., Garbe, C., Testori, A., Maio, M., et al. (2011). Improved survival with vemurafenib in melanoma with BRAF V600E mutation. N Engl J Med 364, 2507-2516.
11. Chen, Y., Takita, J., Choi, Y. L., Kato, M., Ohira, M., Sanada, M., Wang, L., Soda, M., Kikuchi, A., Igarashi, T., et al. (2008). Oncogenic mutations of ALK kinase in neuroblastoma. Nature 455, 971-974.
12. Davies, H., Bignell, G. R., Cox, C., Stephens, P., Edkins, S., Clegg, S., Teague, J., Woffendin, H., Garnett, M. J., Bottomley, W., et al. (2002). Mutations of the BRAF gene in human cancer. Nature 417, 949-954.
13. Druker, B. J., Talpaz, M., Resta, D. J., Peng, B., Buchdunger, E., Ford, J. M., Lydon, N. B., Kantarjian, H., Capdeville, R., Ohno-Jones, S., et al. (2001). Efficacy and safety of a specific inhibitor of the BCR-ABL tyrosine kinase in chronic myeloid leukemia. N Engl J Med 344, 1031-1037.
14. Dunn, G. P., Rinne, M. L., Wykosky, J., Genovese, G., Quayle, S. N., Dunn, I. F., Agarwalla, P. K., Chheda, M. G., Campos, B., Wang, A., et al. (2012). Emerging insights into the molecular and cellular basis of glioblastoma. Genes Dev 26, 756-784.
15. Gao, J., Aksoy, B. A., Dogrusoz, U., Dresdner, G., Gross, B., Sumer, S. O., Sun, Y., Jacobsen, A., Sinha, R., Larsson, E., et al. (2013). Integrative analysis of complex cancer genomics and clinical profiles using the cBioPortal. Sci Signal 6, pl1.
16. Guo, Y., Chen, Y., Ito, H., Watanabe, A., Ge, X., Kodama, T., and Aburatani, H. (2006). Identification and characterization of lin-28 homolog B (LIN28B) in human hepatocellular carcinoma. Gene 384, 51-61.
17. Janoueix-Lerosey, I., Lequin, D., Brugieres, L., Ribeiro, A., de Pontual, L., Combaret, V., Raynal, V., Puisieux, A., Schleiermacher, G., Pierron, G., et al. (2008). Somatic and germline activating mutations of the ALK kinase receptor in neuroblastoma. Nature 455, 967-970.
18. King, G. D., Curtin, J. F., Candolfi, M., Kroeger, K., Lowenstein, P. R., and Castro, M. G. (2005). Gene therapy and targeted toxins for glioma. Curr Gene Ther 5, 535-557.
19. Knudson, A. G., Jr. (1971). Mutation and cancer: statistical study of retinoblastoma. Proc Natl Acad Sci USA 68, 820-823.
20. Lee, S. T., Chu, K., Oh, H. J., Im, W. S., Lim, J. Y., Kim, S. K., Park, C. K., Jung, K. H., Lee, S. K., Kim, M., et al. (2011). Let-7 microRNA inhibits the proliferation of human glioblastoma cells. J Neurooncol 102, 19-24.
21. Liang, L., Wong, C. M., Ying, Q., Fan, D. N., Huang, S., Ding, J., Yao, J., Yan, M., Li, J., Yao, M., et al. (2010). MicroRNA-125b suppressed human liver cancer cell proliferation and metastasis by directly targeting oncogene LIN28B2. Hepatology 52, 1731-1740.
22. Lord, C. J., and Ashworth, A. (2013). Mechanisms of resistance to therapies targeting BRCA-mutant cancers. Nat Med 19, 1381-1388.
23. Luo, J., Solimini, N. L., and Elledge, S. J. (2009). Principles of cancer therapy: oncogene and non-oncogene addiction. Cell 136, 823-837.
24. Madhavan, S., Zenklusen, J. C., Kotliarov, Y., Sahni, H., Fine, H. A., and Buetow, K. (2009). Rembrandt: helping personalized medicine become a reality through integrative translational research. Mol Cancer Res 7, 157-167.
25. Marino-Enriquez, A., and Dal Cin, P. (2013). ALK as a paradigm of oncogenic promiscuity: different mechanisms of activation and different fusion partners drive tumors of different lineages. Cancer Genet 206, 357-373.
26. Marks, P. W., Arai, M., Bandura, J. L., and Kwiatkowski, D. J. (1998). Advillin (p92): a new member of the gelsolin/villin family of actin regulatory proteins. J Cell Sci 111 (Pt 15), 2129-2136.
27. Morin, R. D., Johnson, N. A., Severson, T. M., Mungall, A. J., An, J., Goya, R., Paul, J. E., Boyle, M., Woolcock, B. W., Kuchenbauer, F., et al. (2010). Somatic mutations altering EZH2 (Tyr641) in follicular and diffuse large B-cell lymphomas of germinal-center origin. Nat Genet 42, 181-185.
28. Morris, S. W., Kirstein, M. N., Valentine, M. B., Dittmer, K. G., Shapiro, D. N., Saltman, D. L., and Look, A. T. (1994). Fusion of a kinase gene, ALK, to a nucleolar protein gene, NPM, in non-Hodgkin's lymphoma. Science 263, 1281-1284.
29. Mosse, Y. P., Laudenslager, M., Longo, L., Cole, K. A., Wood, A., Attiyeh, E. F., Laquaglia, M. J., Sennett, R., Lynch, J. E., Perri, P., et al. (2008). Identification of ALK as a major familial neuroblastoma predisposition gene. Nature 455, 930-935.
30. Nguyen, L. H., Robinton, D. A., Seligson, M. T., Wu, L., Li, L., Rakheja, D., Cornerford, S. A., Ramezani, S., Sun, X., Parikh, M. S., et al. (2014). Lin28b is sufficient to drive liver cancer and necessary for its maintenance in murine models. Cancer Cell 26, 248-261.
31. Paik, S., Kim, C., and Wolmark, N. (2008). HER2 status and benefit from adjuvant trastuzumab in breast cancer. N Engl J Med 358, 1409-1411.
32. Park, I. H., Zhao, R., West, J. A., Yabuuchi, A., Huo, H., Ince, T. A., Lerou, P. H., Lensch, M. W., and Daley, G. Q. (2008). Reprogramming of human somatic cells to pluripotency with defined factors. Nature 451, 141-146.
33. Prados, M. D., and Levin, V. (2000). Biology and treatment of malignant glioma. Semin Oncol 27, 1-10.
34. Ren, H., Tan, Z. P., Zhu, X., Crosby, K., Haack, H., Ren, J. M., Beausoleil, S., Moritz, A., Innocenti, G., Rush, J., et al. (2012). Identification of anaplastic lymphoma kinase as a potential therapeutic target in ovarian cancer. Cancer Res 72, 3312-3323.
35. Rhodes, D. R., Kalyana-Sundaram, S., Mahavisno, V., Varambally, R., Yu, J., Briggs, B. B., Barrette, T. R., Anstet, M. J., Kincead-Beal, C., Kulkarni, P., et al. (2007). Oncomine 3.0: genes, pathways, and networks in a collection of 18,000 cancer gene expression profiles. Neoplasia 9, 166-180.
36. Roth, R. B., Hevezi, P., Lee, J., Willhite, D., Lechner, S. M., Foster, A. C., and Zlotnik, A. (2006). Gene expression analyses reveal molecular relationships among 20 regions of the human CNS. Neurogenetics 7, 67-80.
37. Shaw, A. T., Yeap, B. Y., Solomon, B. J., Riely, G. J., Gainor, J., Engelman, J. A., Shapiro, G. I., Costa, D. B., Ou, S. H., Butaney, M., et al. (2011). Effect of crizotinib on overall survival in patients with advanced non-small-cell lung cancer harbouring ALK gene rearrangement: a retrospective analysis. Lancet Oncol 12, 1004-1012.
38. Soda, M., Choi, Y. L., Enomoto, M., Takada, S., Yamashita, Y., Ishikawa, S., Fujiwara, S., Watanabe, H., Kurashina, K., Hatanaka, H., et al. (2007). Identification of the transforming EML4-ALK fusion gene in non-small-cell lung cancer. Nature 448, 561-566.
39. Strausberg, R. L., Feingold, E. A., Grouse, L. H., Derge, J. G., Klausner, R. D., Collins, F. S., Wagner, L., Shenmen, C. M., Schuler, G. D., Altschul, S. F., et al. (2002). Generation and initial analysis of more than 15,000 full-length human and mouse cDNA sequences. Proc Natl Acad Sci USA 99, 16899-16903.
40. Stupp, R., Mason, W. P., van den Bent, M. J., Weller, M., Fisher, B., Taphoorn, M. J., Belanger, K., Brandes, A. A., Marosi, C., Bogdahn, U., et al. (2005). Radiotherapy plus concomitant and adjuvant temozolomide for glioblastoma. N Engl J Med 352, 987-996.
41. van Gaal, J. C., Flucke, U. E., Roeffen, M. H., de Bont, E. S., Sleijfer, S., Mavinkurve-Groothuis, A. M., Suurmeijer, A. J., van der Graaf, W. T., and Versleijen-Jonkers, Y. M. (2012). Anaplastic lymphoma kinase aberrations in rhabdomyosarcoma: clinical and prognostic implications. J Clin Oncol 30, 308-315.
42. Viswanathan, S. R., Powers, J. T., Einhorn, W., Hoshida, Y., Ng, T. L., Toffanin, S., O'Sullivan, M., Lu, J., Phillips, L. A., Lockhart, V. L., et al. (2009). Lin28 promotes transformation and is associated with advanced human malignancies. Nat Genet 41, 843-848.
43. Vivanco, I. (2014). Targeting molecular addictions in cancer. Br J Cancer 111, 2033-2038.
44. Vivoli, M., Novak, H. R., Littlechild, J. A., and Harmer, N. J. (2014). Determination of protein-ligand interactions using differential scanning fluorimetry. J Vis Exp, 51809.
45. Wang, X. R., Luo, H., Li, H. L., Cao, L., Wang, X. F., Yan, W., Wang, Y. Y., Zhang, J. X., Jiang, T., Kang, C. S., et al. (2013). Overexpressed let-7a inhibits glioma cell malignancy by directly targeting K-ras, independently of PTEN. Neuro Oncol 15, 1491-1501.
46. Weinstein, I. B. (2002). Cancer. Addiction to oncogenes—the Achilles heal of cancer. Science 297, 63-64.
47. Weinstein, I. B., and Joe, A. K. (2006). Mechanisms of disease: Oncogene addiction—a rationale for molecular targeting in cancer therapy. Nat Clin Pract Oncol 3, 448-457.
48. Yu, J., Vodyanik, M. A., Smuga-Otto, K., Antosiewicz-Bourget, J., Frane, J. L., Tian, S., Nie, J., Jonsdottir, G. A., Ruotti, V., Stewart, R., et al. (2007). Induced pluripotent stem cell lines derived from human somatic cells. Science 318, 1917-1920.

It will be apparent to those skilled in the art that various modifications and variations can be made in the present disclosure without departing from the scope or spirit of the disclosure. Other embodiments of the disclosure will be apparent to those skilled in the art from consideration of the specification and practice of the disclosure disclosed herein. It is intended that the specification and examples be considered as exemplary only, with a true scope and spirit of the disclosure being indicated by the following claims.

What is claimed is:

1. A pharmaceutical composition comprising a therapeutically effective amount of at least one compound having a structure associated with a formula:

Compound A

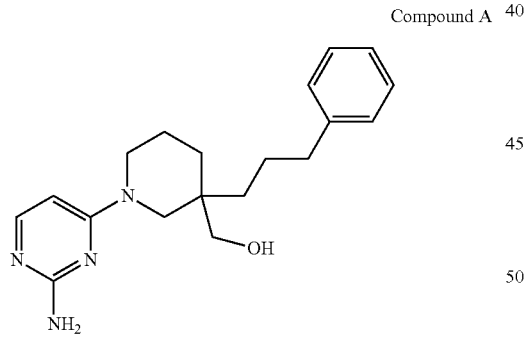

Compound B

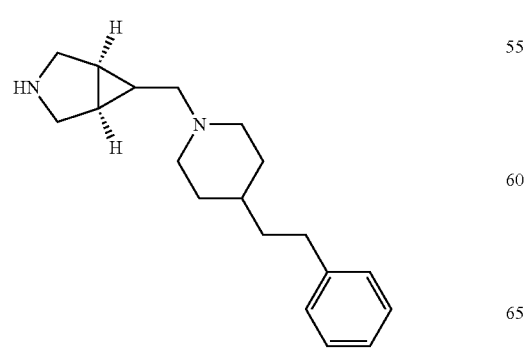

Compound C

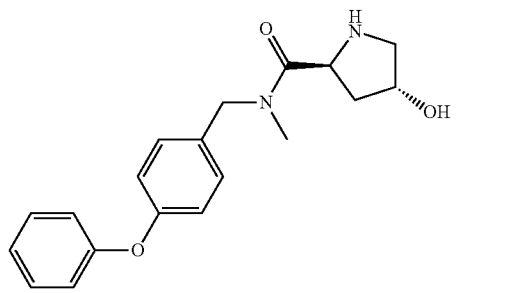

Compound D

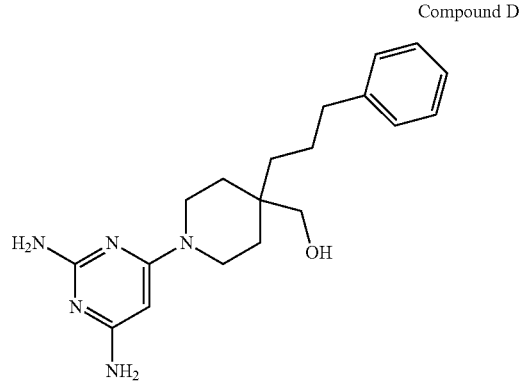

-continued

Compound E
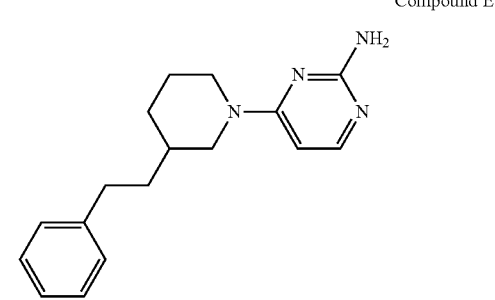

Compound F
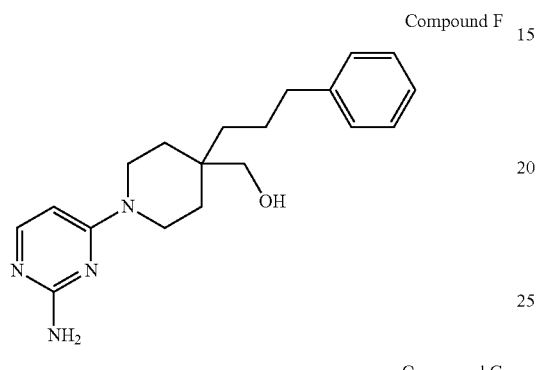

Compound G
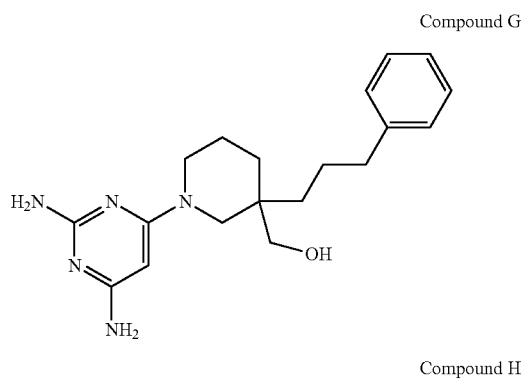

Compound H

Compound I
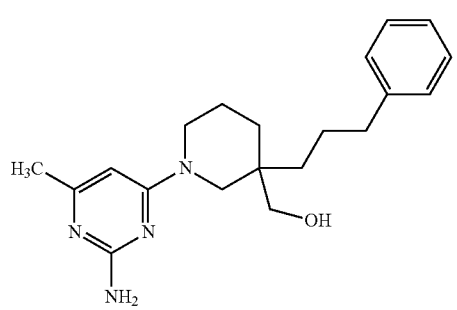

-continued

Compound J
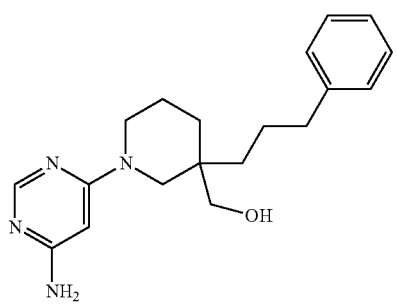

Compound K
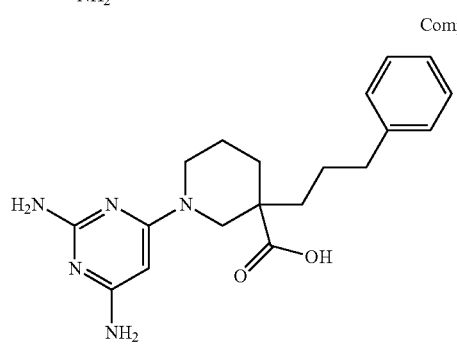

Compound L
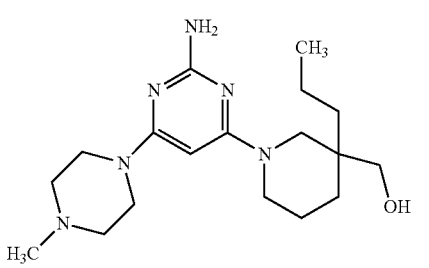

or a pharmaceutically acceptable salt thereof; and a pharmaceutically acceptable carrier.

2. The pharmaceutical composition of claim 1, further comprising at least one agent known to treat a cancer.

3. The pharmaceutical composition of claim 2, wherein the at least one agent known to treat a cancer is a hormone therapy agent; an alkylating agent, an antimetabolite agent, an antineoplastic antibiotic agent, a mitotic inhibitor agent, a mTor inhibitor agent, other chemotherapeutic agent, or combinations thereof.

4. The pharmaceutical composition of claim 2, wherein the at least one agent known to treat a cancer is a hormone therapy agent is selected from one or more of the group consisting of leuprolide, tamoxifen, raloxifene, megestrol, fulvestrant, triptorelin, medroxyprogesterone, letrozole, anastrozole, exemestane, bicalutamide, goserelin, histrelin, fluoxymesterone, estramustine, flutamide, toremifene, degarelix, nilutamide, abarelix, and testolactone, or a pharmaceutically acceptable salt thereof.

5. The pharmaceutical composition of claim 2, wherein the at least one agent known to treat a cancer is a antineoplastic antibiotic agent is selected from one or more of the group consisting of doxorubicin, mitoxantrone, bleomycin, daunorubicin, dactinomycin, epirubicin, idarubicin, plicamycin, mitomycin, pentostatin, and valrubicin, or a pharmaceutically acceptable salt thereof.

6. The pharmaceutical composition of claim 2, wherein the at least one agent known to treat a cancer is an antimetabolite agent is selected from one or more of the group consisting of gemcitabine, 5-fluorouracil, capecitabine, hydroxyurea, mercaptopurine, pemetrexed, fludarabine, nelarabine, cladribine, clofarabine, cytarabine, decitabine, pralatrexate, floxuridine, methotrexate, and thioguanine, or a pharmaceutically acceptable salt thereof.

7. The pharmaceutical composition of claim 2, wherein the at least one agent known to treat a cancer is an alkylating agent is selected from one or more of the group consisting of carboplatin, cisplatin, cyclophosphamide, chlorambucil, melphalan, carmustine, busulfan, lomustine, dacarbazine, oxaliplatin, ifosfamide, mechlorethamine, temozolomide, thiotepa, bendamustine, and streptozocin, or a pharmaceutically acceptable salt.

8. The pharmaceutical composition of claim 2, wherein the at least one agent known to treat a cancer is a mitotic inhibitor agent is selected from one or more of the group consisting of irinotecan, topotecan, rubitecan, cabazitaxel, docetaxel, paclitaxel, etopside, vincristine, ixabepilone, vinorelbine, vinblastine, and teniposide, or a pharmaceutically acceptable salt.

9. The pharmaceutical composition of claim 2, wherein the at least one agent known to treat a cancer is a mTor inhibitor agent is selected from one or more of the group consisting of everolimus, siroliumus, and temsirolimus, or a pharmaceutically acceptable salt thereof.

10. The pharmaceutical composition of claim 2, wherein the at least one agent known to treat a cancer is selected from uracil mustard, chlormethine, cyclophosphamide, ifosfamide, melphalan, chlorambucil, pipobroman, triethylenemelamine, triethylenethiophosphoramine, busulfan, carmustine, lomustine, streptozocin, dacarbazine, temozolomide, thiotepa, altretamine, methotrexate, 5-fluorouracil, floxuridine, cytarabine, 6-mercaptopurine, 6-thioguanine, fludarabine phosphate, pentostatin, bortezomib, vinblastine, vincristine, vinorelbine, vindesine, bleomycin, dactinomycin, daunorubicin, doxorubicin, epirubicin, dexamethasone, clofarabine, cladribine, pemextresed, idarubicin, paclitaxel, docetaxel, ixabepilone, mithramycin, topotecan, irinotecan, deoxycoformycin, mitomycin-C, L-asparaginase, interferons, etoposide, teniposide 17a-ethinylestradiol, diethylstilbestrol, testosterone, prednisone, fluoxymesterone, dromostanolone propionate, testolactone, megestrolacetate, tamoxifen, methylprednisolone, methyltestosterone, prednisolone, triamcinolone, chlorotrianisene, hydroxyprogesterone, aminoglutethimide, estramustine, medroxyprogesteroneacetate, leuprolide, flutamide, toremifene, goserelin, cisplatin, carboplatin, hydroxyurea, amsacrine, procarbazine, mitotane, mitoxantrone, levamisole, navelbene, anastrazole, letrazole, capecitabine, reloxafine, droloxafine, hexamethylmelamine, oxaliplatin, iressa (gefinitib, Zd1839), capecitabine, erlotinib, azacitidine (5-Azacytidine; 5-AzaC), temozolomide, gemcitabine gemcitabine HCl, vasostatin, and combinations thereof.

11. The pharmaceutical composition of claim 1, wherein the at least one compound and the at least one agent known to treat a cancer are co-formulated.

12. A method for the regulation, control or limitation of the expression of advillin (AVIL) in at least one target cell, comprising:
   contacting the at least one target cell with an effective amount of a pharmaceutical composition of claim 1 or at least one compound comprising:

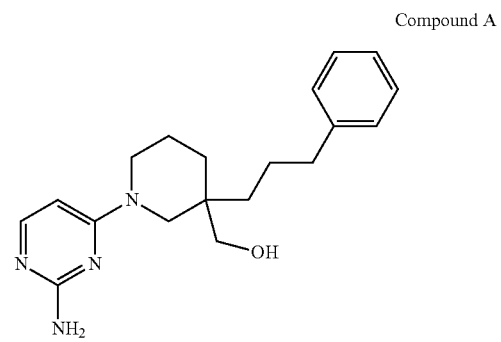

Compound A

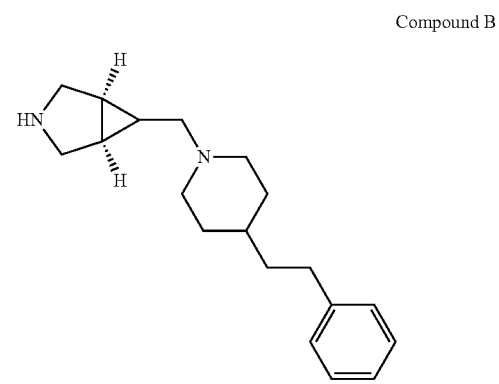

Compound B

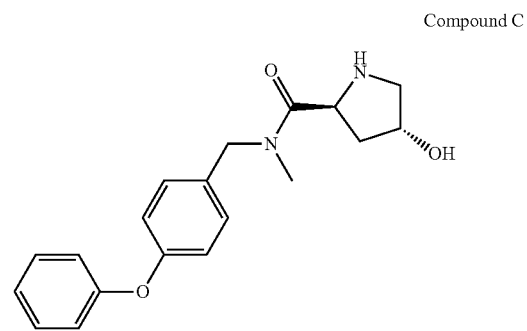

Compound C

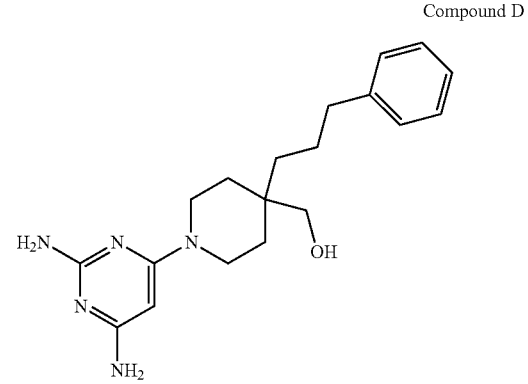

Compound D

Compound E

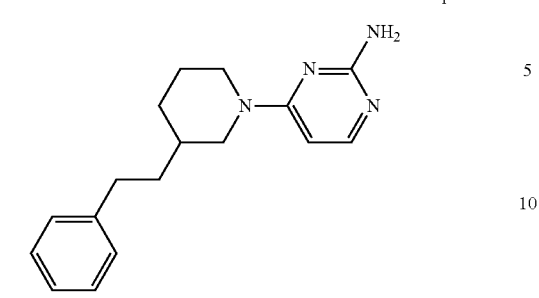

Compound F

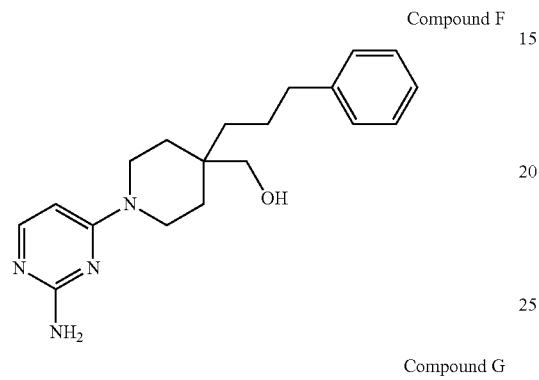

Compound G

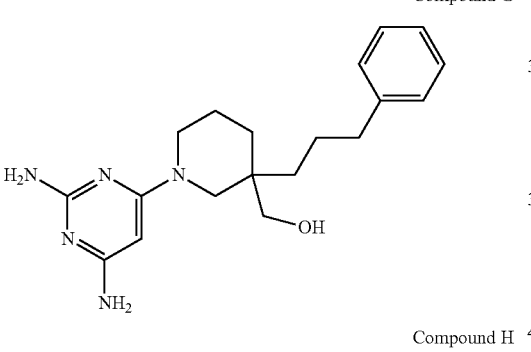

Compound H

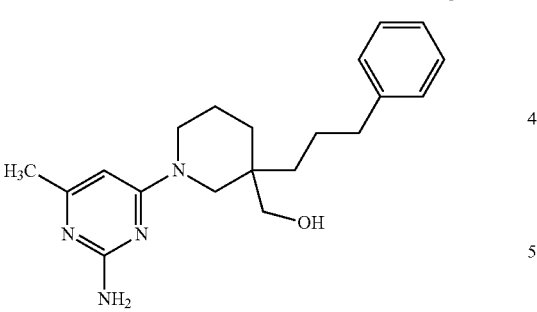

Compound I

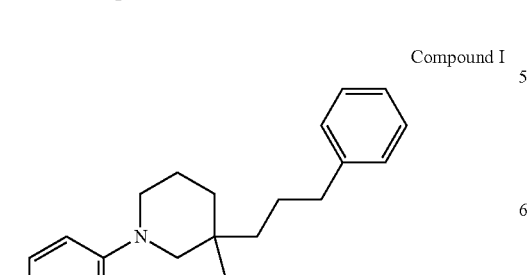

Compound J

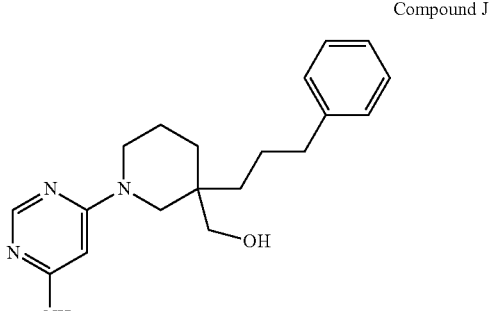

Compound K

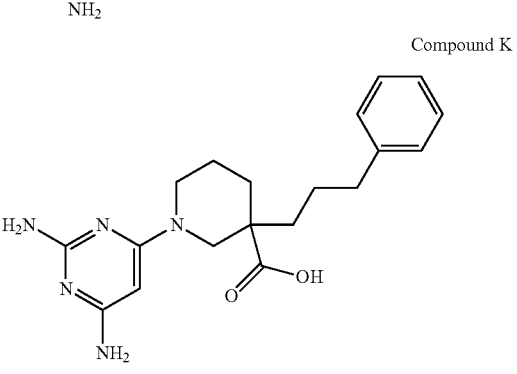

Compound L

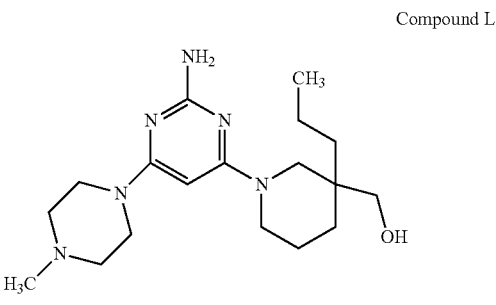 [SMILES: CCCC1(CO)CCCN(c2cc(N3CCN(C)CC3)nc(N)n2)C1]

or a pharmaceutically-acceptable salt thereof.

13. The method of claim 12, wherein the expression of advillin (AVIL) is the result of a disease or disorder associated with increased, aberrant, or dysfunctional levels of AVIL.

14. The method of claim 13, wherein the disease or disorder is cancer.

15. The method of claim 14, wherein the cancer is selected from brain cancer and cancerous tumors such as glioblastomas, rhabdosarcomas, gliomas, lung cancer, bladder cancer including bladder urothelial carcinoma, and renal cancer including kidney clear cell carcinoma.

16. The method of claim 12, wherein the compound exhibits an IC50 of less than about 40 uM on the at least one target cell.

17. The method of claim 12, wherein the compound exhibits an $IC_{50}$ of greater than about 50 uM on non-target cells having normal AVIL function.

18. A method for the treatment of an oncological disorder or disease associated with increased, aberrant, or dysfunctional levels of AVIL in a mammal comprising the step of administering to the mammal a therapeutically effective amount of a pharmaceutical composition of claim 1 or at least one compound comprising:

Compound A
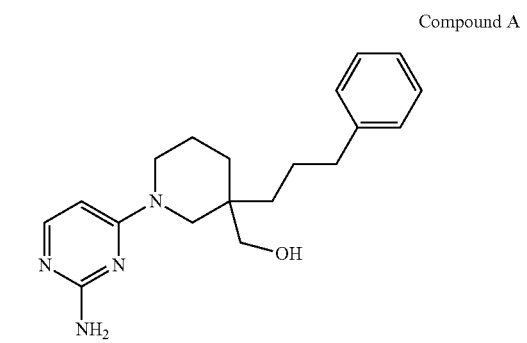
Compound B
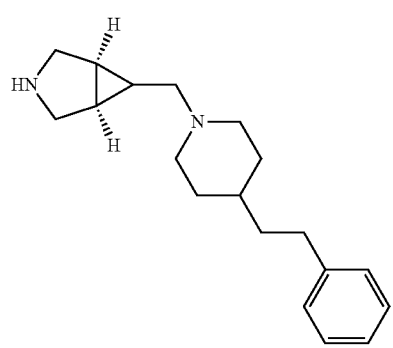
Compound C
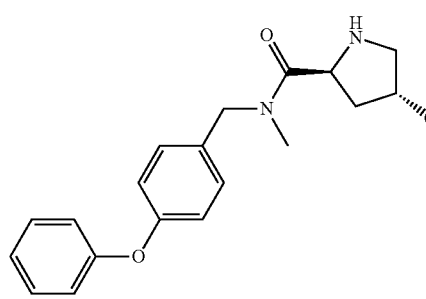
Compound D
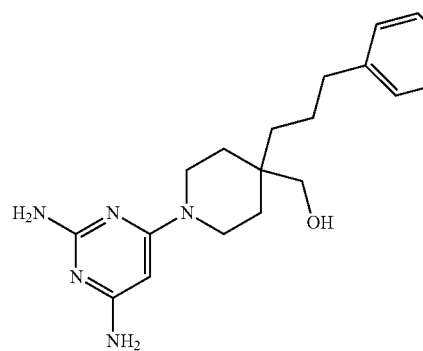
-continued
Compound E
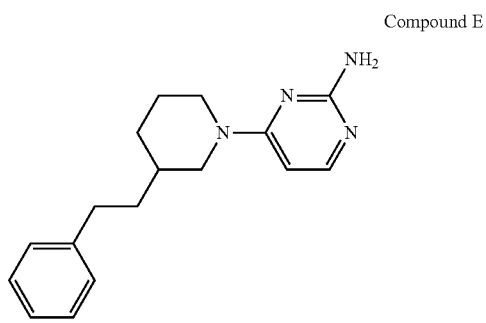
Compound F
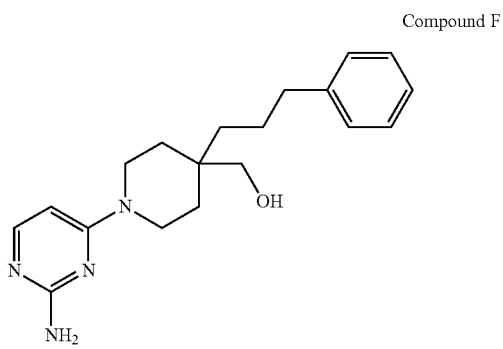
Compound G
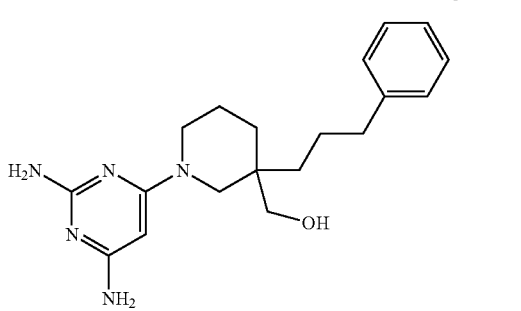
Compound H
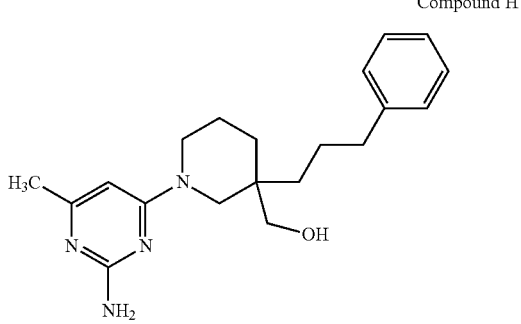
Compound I
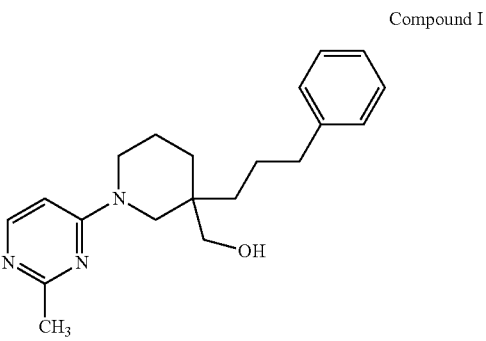

Compound J

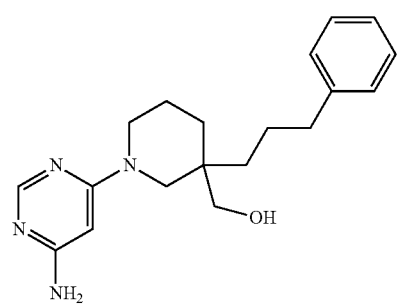

Compound K

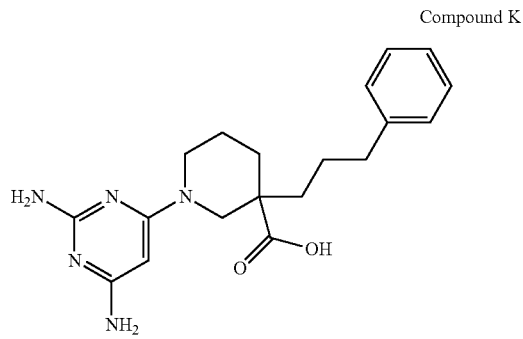

Compound L

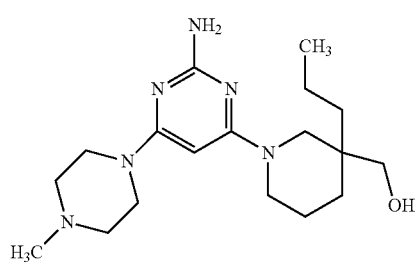

or pharmaceutically acceptable salt thereof.

19. A method for regulating, limiting, or inhibiting AVIL expression in a mammal comprising the step of administering to the mammal a therapeutically effective amount of a pharmaceutical composition of claim 1 or at least one compound comprising:

Compound A

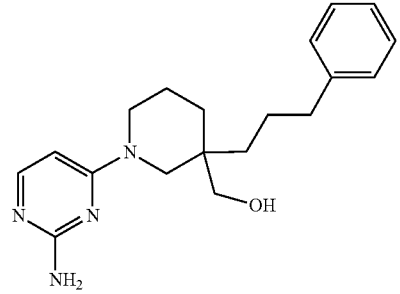

Compound B

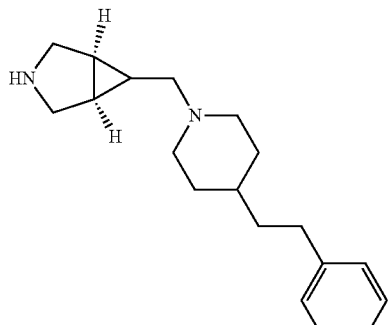

Compound C

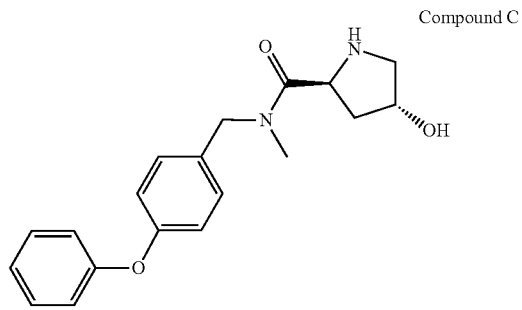

Compound D

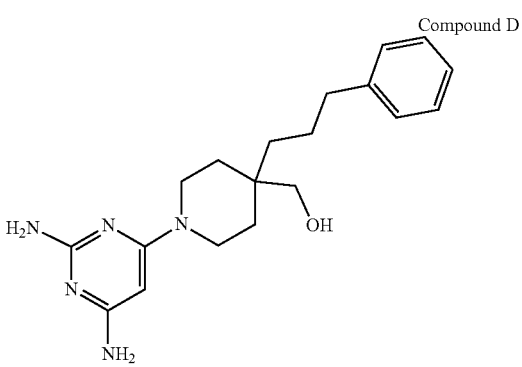

Compound E

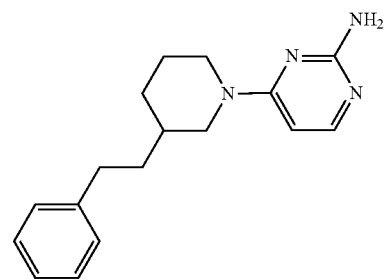

Compound F

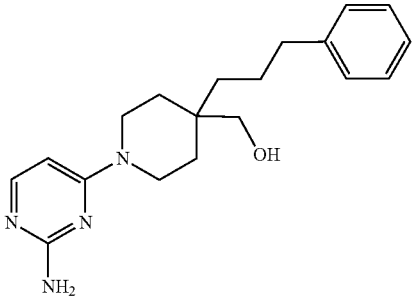

-continued
Compound G
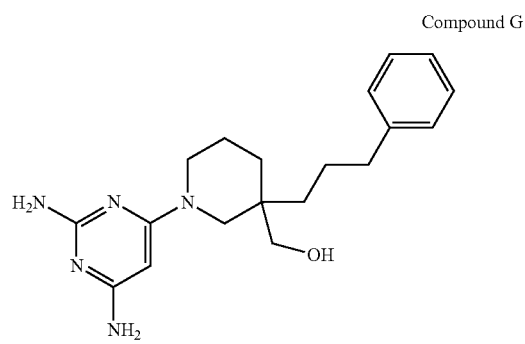
Compound H
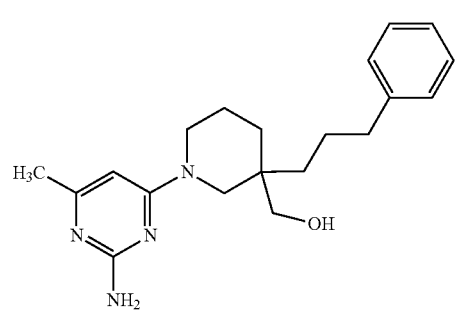
Compound I
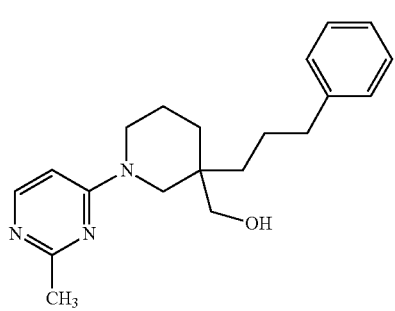
-continued
Compound J
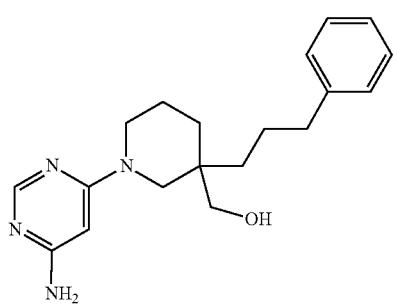
Compound K
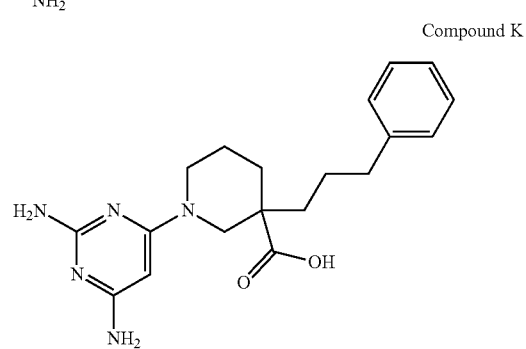
Compound L
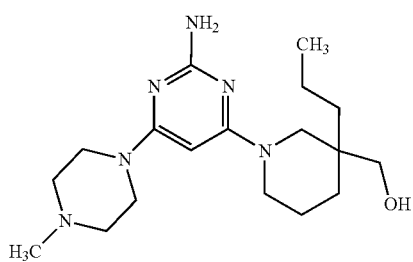
or pharmaceutically acceptable salt thereof.
* * * * *